US009296722B2

(12) United States Patent
Liu

(10) Patent No.: US 9,296,722 B2
(45) Date of Patent: Mar. 29, 2016

(54) AZOLYL UREA COMPOUNDS AND METHODS OF USE THEREOF

(75) Inventor: Gang Liu, San Diego, CA (US)

(73) Assignee: Ambit Biosciences Corporation, San Diego, CA (US)

( * ) Notice: Subject to any disclaimer, the term of this patent is extended or adjusted under 35 U.S.C. 154(b) by 0 days.

(21) Appl. No.: 13/700,121

(22) PCT Filed: May 26, 2011

(86) PCT No.: PCT/US2011/038123
§ 371 (c)(1),
(2), (4) Date: Jul. 31, 2013

(87) PCT Pub. No.: WO2011/150198
PCT Pub. Date: Dec. 1, 2011

(65) Prior Publication Data

US 2013/0310357 A1 Nov. 21, 2013

Related U.S. Application Data

(60) Provisional application No. 61/349,110, filed on May 27, 2010.

(51) Int. Cl.

| | |
|---|---|
| ***C07D 401/14*** | (2006.01) |
| ***C07D 413/14*** | (2006.01) |
| ***C07D 451/02*** | (2006.01) |
| ***C07D 455/02*** | (2006.01) |
| ***A61K 31/5377*** | (2006.01) |
| ***A61K 31/4545*** | (2006.01) |
| ***A61K 31/46*** | (2006.01) |
| ***A61K 31/4439*** | (2006.01) |
| ***A61K 31/4375*** | (2006.01) |
| ***A61K 31/439*** | (2006.01) |
| ***A61K 31/496*** | (2006.01) |
| ***A61K 31/497*** | (2006.01) |
| ***A61K 31/501*** | (2006.01) |
| ***A61K 45/06*** | (2006.01) |
| ***C07D 413/12*** | (2006.01) |
| ***C07D 453/02*** | (2006.01) |

(52) U.S. Cl.
CPC ............ *C07D 401/14* (2013.01); *A61K 31/439* (2013.01); *A61K 31/4375* (2013.01); *A61K 31/4439* (2013.01); *A61K 31/4545* (2013.01); *A61K 31/496* (2013.01); *A61K 31/497* (2013.01); *A61K 31/501* (2013.01); *A61K 31/5377* (2013.01); *A61K 45/06* (2013.01); *C07D 413/12* (2013.01); *C07D 413/14* (2013.01); *C07D 451/02* (2013.01); *C07D 453/02* (2013.01); *C07D 455/02* (2013.01)

(58) Field of Classification Search
None
See application file for complete search history.

(56) References Cited

U.S. PATENT DOCUMENTS

| | | | |
|---|---|---|---|
| 3,536,809 | A | 10/1970 | Applezweig |
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 4,014,887 | A | 3/1977 | Randell et al. |
| 4,728,743 | A | 3/1988 | Drauz et al. |
| 5,059,595 | A | 10/1991 | Le Grazie |
| 5,073,543 | A | 12/1991 | Marshall et al. |
| 5,120,548 | A | 6/1992 | McClelland et al. |
| 5,354,556 | A | 10/1994 | Sparks et al. |
| 5,405,829 | A | 4/1995 | Hartfiel et al. |
| 5,591,767 | A | 1/1997 | Mohr et al. |
| 5,639,476 | A | 6/1997 | Oshlack et al. |
| 5,639,480 | A | 6/1997 | Bodmer et al. |
| 5,674,533 | A | 10/1997 | Santus et al. |
| 5,709,874 | A | 1/1998 | Hanson et al. |
| 5,733,566 | A | 3/1998 | Lewis |
| 5,739,108 | A | 4/1998 | Mitchell |
| 5,759,542 | A | 6/1998 | Gurewich |
| 5,840,674 | A | 11/1998 | Yatvin et al. |
| 5,891,474 | A | 4/1999 | Busetti et al. |
| 5,900,252 | A | 5/1999 | Calanchi et al. |
| 5,922,356 | A | 7/1999 | Koseki et al. |
| 5,972,366 | A | 10/1999 | Haynes et al. |
| 5,972,891 | A | 10/1999 | Kamei et al. |
| 5,980,945 | A | 11/1999 | Ruiz |
| 5,985,307 | A | 11/1999 | Hanson et al. |
| 5,993,855 | A | 11/1999 | Yoshimoto et al. |
| 6,004,534 | A | 12/1999 | Langer et al. |
| 6,039,975 | A | 3/2000 | Shah et al. |
| 6,045,830 | A | 4/2000 | Igari et al. |
| 6,048,736 | A | 4/2000 | Kosak |

(Continued)

FOREIGN PATENT DOCUMENTS

| | | | |
|---|---|---|---|
| CN | 101440062 | B | 9/2011 |
| EP | 0220947 | B1 | 6/1994 |

(Continued)

OTHER PUBLICATIONS

Amato et al., "Synthesis of 1-tert-Butyl-4-cholorpiperidine: Generation of an N-tert-Butyl Group by the Reaction of a Dimethyliminium Salt with Methylmagnesium Chloride," *J. Org. Chem.*, 70(5):1930-1933 (2005).

Baiocchi et al., "Expression of the macrophage colony-stimulating factor and its receptor in gynecologic malignancies," *Cancer*, 67(4):990-996 (1991).

Bauknecht et al., "Expression of transcripts for CSF-1 and for the "macrophage" and "epithelial" isoforms of the CSF-1R transcripts in human ovarian carcinomas," *Cancer Detect. Prev.*, 18(3): 231-239 (1994).

Blume-Jensen and Hunter, "Oncogenic kinase signaling," *Nature* 411(6835):355-365 (2001).

(Continued)

*Primary Examiner* — Alicia L Otton
(74) *Attorney, Agent, or Firm* — Jones Day

(57) ABSTRACT

Provided herein are azolyl urea compounds for treatment of CSF-1R kinase mediated diseases. Also provided are pharmaceutical compositions comprising the compounds and methods of using the compounds and compositions.

16 Claims, 1 Drawing Sheet

(56) References Cited

U.S. PATENT DOCUMENTS

| | | | |
|---|---|---|---|
| 6,060,082 A | 5/2000 | Chen et al. |
| 6,071,495 A | 6/2000 | Unger et al. |
| 6,087,324 A | 7/2000 | Igari et al. |
| 6,113,943 A | 9/2000 | Okada et al. |
| 6,120,751 A | 9/2000 | Unger |
| 6,131,570 A | 10/2000 | Schuster et al. |
| 6,139,865 A | 10/2000 | Friend et al. |
| 6,197,350 B1 | 3/2001 | Yamagata et al. |
| 6,248,363 B1 | 6/2001 | Patel et al. |
| 6,253,872 B1 | 7/2001 | Neumann |
| 6,264,970 B1 | 7/2001 | Hata et al. |
| 6,267,981 B1 | 7/2001 | Okamoto et al. |
| 6,271,359 B1 | 8/2001 | Norris et al. |
| 6,274,552 B1 | 8/2001 | Tamarkin et al. |
| 6,316,652 B1 | 11/2001 | Steliou |
| 6,333,325 B1 | 12/2001 | Cirillo et al. |
| 6,376,461 B1 | 4/2002 | Igari et al. |
| 6,419,961 B1 | 7/2002 | Igari et al. |
| 6,525,046 B1 | 2/2003 | Cirillo et al. |
| 6,589,548 B1 | 7/2003 | Oh et al. |
| 6,613,358 B2 | 9/2003 | Randolph et al. |
| 6,699,500 B2 | 3/2004 | Okada et al. |
| 6,740,634 B1 | 5/2004 | Saikawa et al. |
| 7,144,911 B2 | 12/2006 | Flynn et al. |
| 7,202,257 B2 | 4/2007 | Flynn et al. |
| 7,320,989 B2 | 1/2008 | Anderson et al. |
| 7,326,712 B2 | 2/2008 | Hurley et al. |
| 7,531,566 B2 | 5/2009 | Flynn et al. |
| 2003/0236287 A1 | 12/2003 | Piotrowski et al. |
| 2009/0012091 A1 | 1/2009 | Yu |

FOREIGN PATENT DOCUMENTS

| | | | |
|---|---|---|---|
| WO | WO 03/068229 A1 | 8/2003 |
| WO | WO 2004/015142 A1 | 2/2004 |
| WO | WO 2005/042502 A1 | 5/2005 |
| WO | WO 2005/048948 * | 6/2005 |
| WO | WO 2005/048948 A2 | 6/2005 |
| WO | WO 2005/048953 A2 | 6/2005 |
| WO | WO 2007/055941 A2 | 5/2007 |
| WO | WO 2008/005310 A2 | 1/2008 |
| WO | WO 2008/046003 A2 | 4/2008 |
| WO | WO 2009/006389 A2 | 1/2009 |

OTHER PUBLICATIONS

Conway et al., "Effects of the cFMS Kinase Inhibitor 5-(3-Methoxy-4-((4-methoxybenzyl)oxy)benzyl)pyrimidine-2,4-diamine (GW2580) in Normal and Arthritic Rats," *J. Pharmacol. Exp. Ther.*, 326(1):41-50 (2008).(Epub Apr. 23, 2008).

Curtain et al., "Somatic activation of KIT in distinct subtypes of melanoma," *J. Clin. Oncol.*, 24(26):4340-4346 (2006).

De Giorgi and Verweij, "Imatinib and gastrointestinal stromal tumors: Where do we go from here?" *Mol. Cancer Ther.*, 4(3):495-501 (2005).

Duensing et al., "Biology of gastrointestinal stromal tumors: KIT mutations and beyond," *Cancer Invest.*, 22(1):106-116 (2004).

Eddington et al., "Synthesis and anticonvulsant activity of enaminones. 4. Investigations on isoxazole derivatives," *Eur. J. Med. Chem.*, 37:635-648 (2002).

Fabian et al., "A small molecule-kinase interaction map for clinical kinase inhibitors," *Nat. Biotechnol.*, 23(3):329-336 (2005).

Foster, "Deuterium Isotope Effects in the Metabolism of Drugs and Xenobiotics: Implications for Drug Design," *Adv. Drug Res.*, 14:1-36 (1985).

Gan et al., "A Sterically Conrolled Recyclable System: Reversible Photoredox Reactions between Anthraquinone and Hindered Tertiary Amines," *J. Amer. Chem. Soc.*, 115(18):8031-8037 (1993).

Gatley et al., "Deuterioglucose: Alteration of Biodistribution by an Isotope Effect," *J. Nucl. Med.*, 27:388-394 (1986).

Gordon et al., "The metabolism of the abortifacient terpene, (R)-(+)-pulegone, to a proximate toxin, menthofuran," *Drug Metab. Dispos.*, 15(5):589-594 (1987).

IUPAC-IUB Commission on Biochemical Nomenclature Abbreviated Nomeclature of Synthetic Polypeptides, *Biochem.*, 11(5):942-944 (1972).

Kirma et al., "Elevated expression of the oncogene c-fms and its ligand, the macrophage colony-stimulating factor-1, in cervical cancer and the role of transforming growth factor-beta1 in inducing c-fms expression," *Cancer Res.*, 67(5):1918-1926 (2007).

Kluger et al., "Macrophage colony-stimulating factor-1 receptor expression is associated with poor outcome in breast cancer by large cohort tissue microarray analysis," *Clin. Canc. Res.*, 10(1 Pt 1):173-177 (2004).

Krause and Van Etten, "Tyrosine kinases as targets for cancer therapy," *N. Engl. J. Med.*, 353(2):172-187 (2005).

Kushner et al., "Pharmacological uses and perspectives of heavy water and deuterated compounds," *Can. J. Physiol. Pharmacol.*, 77:79-88 (1999).

Kyne et al., "Enantioselective amino acid recognition using acyclic thiourea receptors," *J. Chem. Soc., Perkin Trans.*, 1:1258-1263 (2001).

Lijinsky et. al., "Dose-response studies in carcinogenesis by nitroso-n-methyl-n-(2-phenyl)ethylamine in rats and the effects of deuterium substituion," *Fd. Chem. Toxic.*, 20:393-399 (1982).

Lijinsky et. al., "Dose-response studies with nitrosoheptamethyleneimine and its α-deuterium-labeled derivative in F344 rats," *J. Nat. Cancer Inst.*, 69(5):1127-1133 (1982).

Lipton, "Pathophysiology of bone metastases: how this knowledge may lead to therapeutic intervention," *J. Support Oncol.*, 2(3):205-220 (2004).

Mangold et. al., "Effects of deuterium labeling on azido amino acid mutagenicity in *Salmonella typhimurium*," *Mutation Res.*, 308:33-42 (1994).

Mroczko et al., "Hematopoietic cytokines in the sera of patients with pancreatic cancer," *Clin. Chem. Lab. Med.*, 43(2):146-150 (2005).

Mroczko et al., "Serum macrophage-colony stimulating factor levels in colorectal cancer patients correlate with lymph node metastasis and poor prognosis," *Clin. Chim. Acta* 380(1-2):208-212 (2007). (Epub Feb. 27, 2007).

Müller-Tidow et al., "High-throughput analysis of genome-wide receptor tyrosine kinase expression in human cancers identifies potential novel drug targets," *Clin. Cancer Res.*, 10(4):1241-1249 (2004).

Ohno et al., "The orally-active and selective c-Fms tyrosine kinase inhibitor Ki20227 inhibits disease progression in a collagen-induced arthritis mouse model," *Eur. J. Immunol.*, 38(1):283-291 (2008).

Patel et al., "Arylcarboxyamino-substituted diaryl ureas as potent and selective FLT3 Inhibitors" *Bioorg.Med. Chem. Letters*, 19(17):5182-5185 (2009).

Plowman et al., "Receptor Tyosine Kinases as Targets for Drug Intervention," *DN&P*, 7(6):334-339 (1994).

Priceman et al., "Targeting distinct tumor-infiltrating myeloid cells by inhibiting CSF-1 receptor: combating tumor evasion of antiangiogenic therapy," *Blood*, 115(7):1461-1471 (2010). (Epub Dec. 11, 2009).

Ritchlin et al., "Mechanisms of TNF-α- and RANKL-mediated osteoclastogenesis and bone resorption in psoriatic arthritis," *J. Clin. Invest.* 111(6):821-831 (2003).

Sapi, "The Role of CSF-1 in Normal Physiology of Mammary Gland and Breast Cancer: An Update," *Exp. Biol. Med.*, (Maywood) 229(1):1-11 (2004).

Scholl et al., "Anti-colony-stimulating factor-1 antibody staining in primary breast adenocarcinomas correlates with marked inflammatory cell infiltrates and prognosis," *J. Natl. Cancer Inst.*, 86(2):120-126 (1994).

Scott et al., "The links between joint damage and disability in rheumatoid arthritis," *Rheumatology* (Oxford) 39(2):122-132 (2000).

Still et al. "Rapid Chromatographic Technique for Preparative Separations iwth Moderate Resolution," *J. Org. Chem.*, 43(14):2923-2925 (1978).

Takase et al. "Practical synthesis of 3-amino-5-tert-butylisoxazole from 4,4-dimethyl-3-oxopentanenitrile with hydroxylamine," *Heterocycles*, 32(6):1153-1158 (1991).

(56) References Cited

OTHER PUBLICATIONS

Wade, "Deuterium isostope effects on noncovalent interactions between molecules," *Chem. Biol. Interact.*, 117:191-217 (1999).

Zello et. al., "Plasma and urine enrichments following infusion of L-[1-$^{13}$C]phenylalanine and L-[ring-$^{2}$H$_5$]phenylalanine in humans: evidence for an isotope effect in renal tubular reabsorption," *Metabolism*, 43: 487-491 (1994).

\* cited by examiner

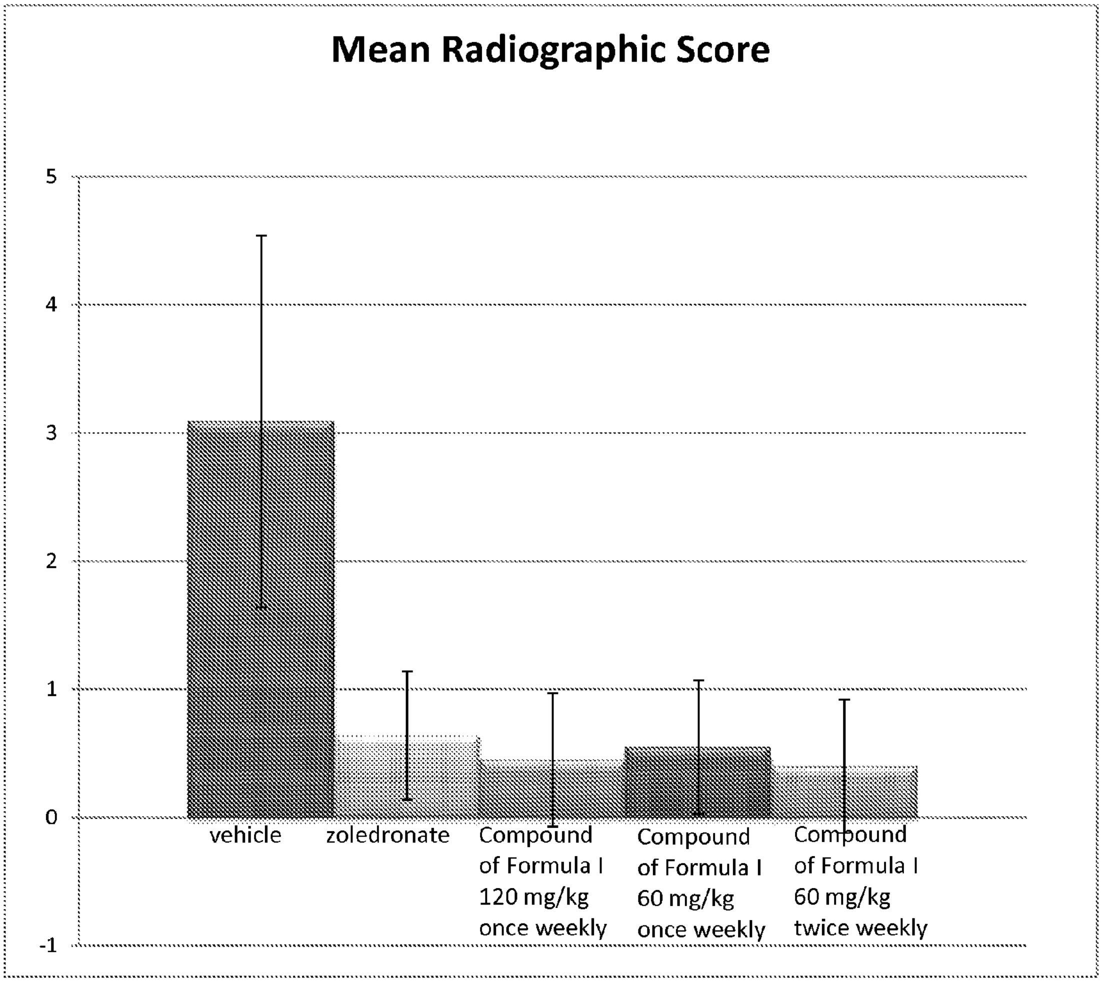
Mean Radiographic Score
5
4
3
2
1
0
-1
vehicle
zoledronate
Compound of Formula I 120 mg/kg once weekly
Compound of Formula I 60 mg/kg once weekly
Compound of Formula I 60 mg/kg twice weekly

AZOLYL UREA COMPOUNDS AND METHODS OF USE THEREOF

RELATED APPLICATIONS

This application is a National stage under 35 U.S.C. §371 (c) of International Application No. PCT/US2011/038123 filed May 26, 2011, which claims priority to U.S. provisional application No. 61/349,110, filed May 27, 2010. The disclosures of the above referenced applications are incorporated by reference herein in their entireties.

FIELD

Provided herein are azolyl urea compounds. In certain embodiments, the compounds are modulators of type III receptor tyrosine kinase family. In other embodiments, the compounds are modulators of CSF-1R kinases. Also provided are compositions comprising the compounds and methods of use thereof. The compounds provided are useful in the treatment, prevention, or amelioration of a disease or disorder related to CSF-1R kinase activity or one or more symptoms associated with such diseases or disorders.

BACKGROUND

Protein kinases (PKs) are enzymes that catalyze the phosphorylation of hydroxy groups on tyrosine, serine and threonine residues of proteins. Receptor tyrosine kinases (RTKs) are a sub-family of protein kinases that play a critical role in cell signaling and are involved in the process of tumorigenesis including cell proliferation, survival, angiogenesis, invasion and metastasis. A class of RTK known as the type III receptor tyrosine kinase family, which includes the receptors PDGFR α, PDGFR β, FLT3, KIT, VEGFR and CSF-1R, has been implicated in various proliferative and inflammatory diseases.

CSF-1R (also known as macrophage colony stimulating factor receptor (M-CSFR) or fms) is a receptor for the macrophage colony stimulating factor (M-CSF or CSF-1). Binding of the CSF-1 ligand to its receptor results in dimerization and auto-phosphorylation of the receptor and leads to activation of downstream signal transduction pathways including the PI3K/Akt and the mitogen activating protein kinase MAPK pathways. Activation of CSF-1R leads to the proliferation, survival, motility and differentiation of cells of the monocyte/macrophage lineage and hence plays a role in normal tissue development and immune defense. Activation of CSF-1R also leads to the proliferation and differentiation of osteoclast precursors and therefore mediates the process of bone resorption.

Because of its role in osteoclast biology, CSF-1R is believed to be an important therapeutic target for osteoporosis and inflammatory arthritis. For example, elevated M-CFS signaling leads to elevated osteoclast activity, which leads to bone loss attending arthritis and other inflammatory bone erosion. (See Scott et al. *Rheumatology* 2000, 39: 122-132, Ritchlin et al. *J. Clin. Invest.* 2003, 111:821-831). Inhibition of CSF-1R therefore represents a promising therapeutic approach for arthritis and other inflammatory bone erosion which is further supported by the efficacy data of known CSF-1R inhibitors such as Ki20227 and GW2580 in arthritic animal models (See Conwat et al. *JPET* 2008, 326:41-50 and Ohno et al. *Eur. J. Immunol.* 2008, 38:283-291). Dysregulation of osteoclast development and disruption in the balance of bone resorption and bone formation that underlie osteoporosis might also be treated with a modulator of CSF-1R.

Elevated expression or activation of CSF-1R and/or its ligand have been found in patients with acute myeloid leukemia, prostate, breast, ovarian, endometrial, colorectal, pancreatic and a variety of other cancers, and elevated levels of M-CSF is associated with poor prognosis in certain cancers (See, Muller-Tidow et al. *Clin Cancer Res,* 2004, 10:1241-1249, Bauknecht et al. *Cancer Detect. Prev.,* 1994, 18: 231-239; Baiocchi G et al. *Cancer* 1991, 67:990-996; Kirma et al *Cancer Res.* 2007; Sapi et al. *Exp. Biol. Med.,* 2004, 229:1-11; Kluger et al. *Clin. Canc. Res.* 2004 10:173-177; Mroczko et al., *Clin. Chem. Lab. Med.* 2005 43:146-50 and Mroczko et al., *Clin. Chim. Acta* 2007, 380:208-212). The data suggests that CSF-1R may be a valuable therapeutic target for these solid tumors.

Early studies have associated elevated expression of M-CSF with increased leukocyte infiltration of solid tumors in human breast and ovarian cancers (Scholl et al. *J. Natl. Cancer Inst.* 1994, 86:120-126, Tang et al. *J. Cell. Biochem.* 1990, 44:189-198). Further studies have shown that M-CSF is one of several cytokines implicated in the recruitment of tumor-associated macrophages (TAMs) that contribute to tumor angiogenesis and tumor progression to metastasis, and more recently, that the preclinical inhibitor GW2580 inhibits tumor metastasis and angiogenesis in mice tumor xenograft experiments (Priceman et al. *Blood* 2010 115(7):1461-1471). Stimulated osteoclast activity is also believed to underlie the pathophysiology of bone metastases. (Lipton, *J. Support. Oncol.* 2004 2:205-220). Metastatic bone lesions results in significant localized bone loss and lead to skeletal morbidity, symptoms which include bone pain, bone fractures and hypercalcemia. Inhibition of CSF-1R therefore may therefore provide therapy for solid tumors and metastatic cancer including metastases to the bone.

KIT (or stem cell factor receptor, or SCFR) is another member of the RTK family, and the presence of kit mutations is a key diagnostic marker for gastrointestinal stromal tumors (GIST) (Duensing et al. *Cancer Investigation* 2004, 22(1): 106-116). Gleevec® (imatinib mesylate or STI571), the first FDA-approved RTK inhibitor originally approved for c-Abl-mediated chronic myeloid leukemia, gained FDA-approval for KIT-mediated GIST in 2002 and has validated the molecular-based approach of Kit inhibition for the treatment of GIST. (Giorgi and Verweij, *Mol. Cancer. Ther.* 2005 4(3): 495-501). Gain of function mutations of the Kit receptor are also associated with mast cell/myeloid leukemia and seminomas/dysgerminomas (Blume-Jensen *Nature* 2001 411(17): 355-365. KIT mutations have been also identified in certain melanomas and is recognized as a potential therapeutic target for melanoma (Curtain et al. *J Clin. Oncol.* 2006 24(26): 4340-4346).

There continues to be a need for the identification of small molecules that inhibit RTKs, particularly compounds useful for the treatment of CSF-1R- or KIT-mediated diseases.

BRIEF DESCRIPTION OF THE DRAWINGS

FIG. 1 depicts the mean microradiograph score from the rat MRMT-1 bone metastases model. A compound of Formula I was administered either once weekly or twice weekly for two weeks at 60 mg/kg or once weekly at 120 mg/kg for two weeks to rats inoculated with MRMT-1 rat mammary gland carcinoma cells. Both, once weekly dose and twice weekly dose, showed to be as protective against bone destruction as the positive control, zoledronate.

SUMMARY

Provided herein are compounds of formula (I) or pharmaceutically acceptable salts, solvates, hydrates or clathrates thereof. In certain embodiment, the compounds have activity as CSF-1R kinase modulators. The compounds are useful in medical treatments, pharmaceutical compositions and methods for modulating the activity of CSF-1R kinase, including wildtype and/or mutated forms of CSF-1R kinase. In certain embodiments, the compounds provided herein have activity as CSF-1R kinase modulators. In one embodiment, the compounds for use in the compositions and methods provided herein have formula (I).

In certain embodiments, provided herein are compounds of Formula I:

I

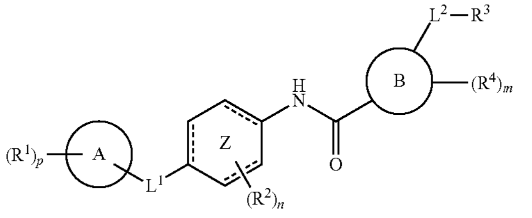

or pharmaceutically acceptable salts, solvates, hydrates or clathrates thereof, wherein:

A is azolyl;

B is 6-membered heteroaryl containing 1, 2 or 3 nitrogen atoms;

Z is phenyl, cyclohexenyl or cyclohexyl;

each $R^1$ is independently selected from hydrogen, halo, alkyl, alkenyl, alkynyl, alkoxy, hydroxyl, haloalkoxy, alkylthio, alkylsulfonyl, alkylsulfinyl, cycloalkyl, cycloalkylalkyl, cycloalkenyl, hydroxyalkyl, haloalkyl, alkylaminosulfonyl, alkylaminocarbonyl, aryl, arylalkyl, heterocyclyl, heterocyclylalkyl, heteroaryl, and heteroarylalkyl, where the alkyl, alkenyl, alkynyl, alkoxy, haloalkoxy, alkylthio, alkylsulfonyl, alkylsulfinyl, cycloalkyl, cycloalkylalkyl, cycloalkenyl, hydroxyalkyl, haloalkyl, alkylaminosulfonyl, alkylaminocarbonyl, aryl, heterocyclyl, and heteroaryl groups are optionally substituted with 1 to 5 groups selected from halo, hydroxy, alkoxy, alkyl, haloalkyl, cycloalkyl, cycloalkenyl, cyano, $—R^uN(R^y)(R^z)$ and $—R^uS(O)_tR^w$;

$L^1$ is

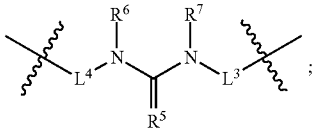

;

$R^5$ is O, S, N—CN, or N—$NO_2$;

$R^6$ and $R^7$ are each independently selected from hydrogen and optionally substituted alkyl; where the substituents, when present are each independently selected from alkyl, haloalkyl, amino, hydroxyl and alkoxy;

$L^3$ and $L^4$ are each independently a bond, alkylene, alkenylene, or alkynylene, each optionally substituted with one or more substituents selected from alkyl, haloalkyl, amino, hydroxyl and alkoxy;

each $R^2$ is independently selected from halo, alkyl, alkenyl, alkynyl, cycloalkyl, cycloalkenyl, haloalkyl, hydroxyalkyl, alkoxyalkyl, cycloalkylalkyl, cycloalkenylalkyl, cyano, amino, hydroxy, alkoxy, $—R^uN(R^y)(R^z)$, $—R^uS(O)_tR^w$, aryl, heterocyclyl, and heteroaryl;

each $R^4$ is independently selected from halo, alkyl, alkenyl, alkynyl, cycloalkyl, cycloalkenyl, haloalkyl, hydroxyalkyl, alkoxyalkyl, cycloalkylalkyl, cycloalkenylalkyl, cyano, amino, hydroxy, alkoxy, hydroxyalkoxyalkyl, $—R^uN(R^y)(R^z)$, $—R^uS(O)_tR^w$, aryl, heterocyclyl, and heteroaryl;

$L^2$ is direct bond, alkylene, alkenylene, alkynylene, $—R^8OR^9—$, $—R^8S(O)_tR^9—$ $—R^8N(R^{10})R^9—$, $—R^8C(O)R^9$, $—R^8C(O)N(R^{10})R^9—$, $—R^8S(O)_tN(R^{10})R^9—$, $—R^8N(R^{10})C(O)R^9—$ or $—R^8N(R^{10})S(O)_tR^9—$, where alkylene, alkenylene and alkynylene are optionally substituted with $—R^8OR^{10}$, $—R^8SR^{10}$, or $—R^8NR^{10}R^{10}$;

$R^8$ and $R^9$ are each independently direct bond, alkylene, alkenylene, alkynylene, $—R^uOR^u—$, $—R^uN(R^y)R^u—$ or $—R^uS(O)_tR^u—$;

each $R^{10}$ is independently hydrogen or alkyl;

$R^3$ is selected as follows:

i) $R^3$ is $—NR^{3a}R^{3b}$, or ii) $R^3$ is optionally substituted heterocyclyl or optionally substituted heteroaryl containing at least one nitrogen atom, and 0 to 1 additional heteroatom selected from O, N or S, wherein the heterocyclyl or heteroaryl ring is connected to $L^2$ on the carbon atom of the ring, and wherein the substituents, when present are selected from one or more, in one embodiment, 1-9, in one embodiment, 1-7, in another embodiment, 1-5, in another embodiment, one, two or three $Q^1$ groups;

$R^{3a}$ and $R^{3b}$ are each independently selected from (i) or (ii) below:

(i) $R^{3a}$ and $R^{3b}$ are each independently alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl; or (ii) $R^{3a}$ and $R^{3b}$, together with the nitrogen atom to which they are attached, form a heterocyclyl or heteroaryl, optionally substituted with one or more, in one embodiment, one, two or three $Q^1$ groups;

each $Q^1$ is independently selected from halo, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, $—R^uOR^x$, $—R^uOR^uN(R^y)(R^z)$, $—R^uN(R^y)(R^z)$, $—R^uSR^x$, $—R^uC(J)R^x$, $—R^uC(J)OR^x$, $—R^uC(J)N(R^y)(R^z)$, $—R^uC(J)SR^x$, $—R^uS(O)_tR^w$, $—R^uOC(J)R^x$, $—R^uOC(J)OR^x$, $—R^uOC(J)N(R^y)(R^z)$, $—R^uOC(J)SR^x$, $—R^uN(R^x)C(J)R^x$, $—R^uN(R^x)C(J)OR^x$, $—R^uN(R^x)C(J)N(R^y)(R^z)$, $—R^uN(R^x)C(J)SR^x$, or $—R^uN(R^x)S(O)_tR^w$; where the alkyl, haloalkyl, aminoalkyl, alkenyl, alkynyl, cycloalkyl, cycloalkenyl, aryl, heteroaryl, and heterocyclyl groups are optionally substituted with one or more $Q^2$ groups; each $Q^2$ is independently selected from halo, oxo, thioxo, alkyl, haloalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl, heterocyclylalkyl, $—R^uOR^x$, $—R^uOR^uN(R^y)(R^z)$, $—R^uN(R^y)(R^z)$, $—R^uSR^x$, $—R^uC(J)R^x$, $—R^uC(J)OR^x$, $—R^uC(J)N(R^y)(R^z)$, $—R^uC(J)SR^x$, $—R^uS(O)_tR^w$, $—R^uOC(J)R^x$, $—R^uOC(J)OR^x$, $—R^uOC(J)N(R^y)(R^z)$, $—R^uOC(J)SR^x$, $—R^uN(R^x)C(J)R^x$, $—R^uN(R^x)C(J)OR^x$, $—R^uN(R^x)C(J)N(R^y)(R^z)$, $—R^uN(R^x)C(J)SR^x$, or $—R^uN(R^x)S(O)_tR^w$;

each $R^u$ is independently alkylene or a direct bond;

$R^w$ is alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

each $R^x$ is independently hydrogen, alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl;

$R^y$ and $R^z$ are each independently selected from (i) or (ii) below:

(i) $R^y$ and $R^z$ are each independently hydrogen, alkyl, haloalkyl, hydroxyalkyl, alkoxyalkyl, alkenyl, alkynyl, cycloalkyl, cycloalkenyl, cycloalkylalkyl, cycloalkenylalkyl, heterocyclyl, heterocyclylalkyl, aryl, aralkyl, heteroaryl, or heteroaralkyl; or (ii) $R^y$ and $R^z$, together with the nitrogen atom to which they are attached, form a heterocyclyl or heteroaryl, optionally substituted with one or more, in one embodiment, one, two or three Q groups; each Q is independently selected from halo, oxo, thioxo, hydroxy, alkoxy, alkyl, haloalkyl, hydroxyalkyl, aminoalkyl, alkenyl, alkynyl, cycloalkyl, cycloalkenyl, cycloalkylalkyl, cycloalkenylalkyl, aryl, aralkyl, heteroaryl, heteroaralkyl, heterocyclyl and heterocyclylalkyl;

J is O, $NR^X$ or S;

each t is independently an integer from 0-2;

m and n are each independently an integer from 0-4; and p is an integer from 1-4, wherein the compound is selected such that i) when A is isoxazolyl, $R^1$ is tert-butyl, Z is phenyl, $L^1$ is —NH—C(O)—NH—, B is pyrimidinyl, m is 1, and, $R^4$ is oxo, then $L^2$ is not direct bond;

ii) when A is isoxazolyl, $R^1$ is tert-butyl, Z is phenyl, $L^1$ is —NH—C(O)—NH—, B is pyrimidinyl, m is 1, and $R^4$ is morpholinyl, then $L^2$ is not direct bond;

iii) when A is isoxazolyl, $R^1$ is tert-butyl, Z is phenyl, $L^1$ is —NH—C(O)—NH—, m is 0, and B is 3-pyridyl, then $R^{3a}$ and $R^{3b}$ are not both methyl; and iv) when A is isoxazolyl, $R^1$ is tert-butyl, Z is phenyl, $L^1$ is —NH—C(O)—NH—, B is 2-pyridyl, $L^2$ is —O—, $R^3$ is pyrimidinyl, and m is 0, then $Q^1$ is not methoxy.

In one embodiment, the compound provided herein is a compound of formula (I). In one embodiment, the compound provided herein is a pharmaceutically acceptable salt of the compound of formula (I). In one embodiment, the compound provided herein is a solvate of the compound of formula (I). In one embodiment, the compound provided herein is a hydrate of compound of formula (I). In one embodiment, the compound provided herein is a prodrug of the compound of formula (I). In one embodiment, the compound provided herein is a clathrate of the compound of formula (I).

Also provided are pharmaceutical compositions formulated for administration by an appropriate route and means containing effective concentrations of one or more of the compounds provided herein, or pharmaceutically acceptable salts, solvates, hydrates and prodrugs thereof, and optionally comprising at least one pharmaceutical carrier.

In one embodiment, the pharmaceutical compositions deliver amounts effective for the treatment, prevention, or amelioration of diseases or disorders that are modulated or otherwise affected by CSF-1R kinase, or one or more symptoms or causes thereof. Such diseases or disorders include without limitation, cancers, nonmalignant proliferation diseases, atherosclerosis, restenosis following vascular angioplasty, fibroproliferative disorders, inflammatory diseases or disorders related to immune dysfunction, infectious diseases, and/or diseases or disorders that can be treated, prevented or managed by modulating the activity, binding or sub-cellular distribution of kinases, wherein such methods comprise administering to a subject, e.g., a human, in need of such treatment, prevention or management a therapeutically and prophylactically effective amount of a compound provided herein. Such diseases or disorders are further described herein.

Also provided herein are combination therapies using one or more compounds or compositions provided herein, or pharmaceutically acceptable derivatives thereof, in combination with other pharmaceutically active agents for the treatment of the diseases and disorders described herein.

In one embodiment, such additional pharmaceutical agents include one or more chemotherapeutic agents, anti-proliferative agents, anti-inflammatory agents, immunomodulatory agents or immunosuppressive agents.

The compounds or compositions provided herein, or pharmaceutically acceptable derivatives thereof, may be administered simultaneously with, prior to, or after administration of one or more of the above agents. Pharmaceutical compositions containing a compound provided herein and one or more of the above agents are also provided.

In certain embodiments, provided herein are methods of treating, preventing or ameliorating a disease or disorder that is modulated or otherwise affected by CSF-1R kinase such as wild type and/or mutant CSF-1R kinase, or one or more symptoms or causes thereof.

In practicing the methods, effective amounts of the compounds or compositions containing therapeutically effective concentrations of the compounds, which are formulated for systemic delivery, including parenteral, oral, or intravenous delivery, or for local or topical application are administered to an individual exhibiting the symptoms of the disease or disorder to be treated. The amounts are effective to ameliorate or eliminate one or more symptoms of the disease or disorder.

Further provided is a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use of sale for human administration. The pack or kit can be labeled with information regarding mode of administration, sequence of drug administration (e.g., separately, sequentially or concurrently), or the like.

These and other aspects of the subject matter described herein will become evident upon reference to the following detailed description.

DETAILED DESCRIPTION

Provided herein are compounds of formula I that have activity as CSF-1R kinase modulators. Further provided are methods of treating, preventing or ameliorating diseases that are modulated by CSF-1R, and pharmaceutical compositions and dosage forms useful for such methods. The methods and compositions are described in detail in the sections below.

A. Definitions

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

"Alkyl" refers to a straight or branched hydrocarbon chain group consisting solely of carbon and hydrogen atoms, containing no unsaturation, having from one to ten, one to eight, one to six or one to four carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like.

The term "branched alkyl" refers to hydrocarbon chain containing at least one forked carbon in the chain, with the smallest branched alkyl being an isopropyl group. Examples of branched alkyl groups include but is not limited to $-CH(CH_3)_2$, $-C(CH_3)_3$, $-CH(CH_3)(CH_2CH_3)$, $-CH(CH_2CH_3)_2$, $-C(CH_3)(CH_2CH_3)_2$, $-C(CH_3)_2(CH_2CH_3)$, $-C(CH_2CH_3)_3$, $-C(CH_3)_2(CH(CH_3)_2)$ and $-C(CH_3)_2(C(CH_3)_3)$.

"Alkenyl" refers to a straight or branched hydrocarbon chain group consisting solely of carbon and hydrogen atoms, containing at least one double bond, having from two to ten carbon atoms, and which is attached to the rest of the molecule by a single bond or a double bond, e.g., ethenyl, prop-1-enyl, but-1-enyl, pent-1-enyl, penta-1,4-dienyl, and the like.

"Alkynyl" refers to a straight or branched hydrocarbon chain group consisting solely of carbon and hydrogen atoms, containing at least one triple bond, having from two to ten carbon atoms, and which is attached to the rest of the molecule by a single bond or a triple bond, e.g., ethynyl, prop-1-ynyl, but-1-ynyl, pent-1-ynyl, pent-3-ynyl and the like.

"Alkylene" and "alkylene chain" refer to a straight or branched divalent hydrocarbon chain consisting solely of carbon and hydrogen, containing no unsaturation and having from one to eight carbon atoms, e.g., methylene, ethylene, propylene, n-butylene and the like. The alkylene chain may be attached to the rest of the molecule through any two carbons within the chain.

"Alkenylene" or "alkenylene chain" refers to a straight or branched chain unsaturated divalent radical consisting solely of carbon and hydrogen atoms, having from two to eight carbon atoms, wherein the unsaturation is present only as double bonds and wherein the double bond can exist between any two carbon atoms in the chain, e.g., ethenylene, prop-1-enylene, but-2-enylene and the like. The alkenylene chain may be attached to the rest of the molecule through any two carbons within the chain.

"Alkynylene" or "alkynylene chain" refers to a straight or branched chain unsaturated divalent radical consisting solely of carbon and hydrogen atoms, having from two to eight carbon atoms, wherein the unsaturation is present only as triple bonds and wherein the triple bond can exist between any two carbon atoms in the chain, e.g., ethynylene, prop-1-ynylene, but-2-ynylene, pent-1-ynylene, pent-3-ynylene and the like. The alkynylene chain may be attached to the rest of the molecule through any two carbons within the chain.

"Alkoxy" refers to the group having the formula —OR wherein R is alkyl or haloalkyl. An "optionally substituted alkoxy" refers to the group having the formula —OR wherein R is an optionally substituted alkyl as defined herein.

"Amino" refers to a radical having the formula —NR'R" wherein R' and R" are each independently hydrogen, alkyl or haloalkyl. An "optionally substituted amino" refers to a radical having the formula NR'R" wherein one or both of R' and R" are optionally substituted alkyl as defined herein.

"Aryl" refers to a group of carbocylic ring system, including monocyclic, bicyclic, tricyclic, tetracyclic $C_6$-$C_{18}$ ring systems, wherein at least one of the rings is aromatic. The aryl may be fully aromatic, examples of which are phenyl, naphthyl, anthracenyl, acenaphthylenyl, azulenyl, fluorenyl, indenyl and pyrenyl. The aryl may also contain an aromatic ring in combination with a non-aromatic ring, examples of which are acenaphene, indene, and fluorene.

"Cycloalkyl" refers to a stable monovalent monocyclic or bicyclic hydrocarbon group consisting solely of carbon and hydrogen atoms, having from three to ten carbon atoms which is saturated, e.g., cyclopropyl, cyclobutyl, cyclopentyl, cyclohexyl, decalinyl, norbornane, norbornene, adamantyl, bicyclo[2.2.2]octane and the like.

"Cycloalkenyl" refers to a stable monovalent monocyclic or bicyclic hydrocarbon group consisting solely of carbon and hydrogen atoms, having from three to ten carbon atoms, which is partially unsaturated. Examples of cycloalkenyl include cyclopropene, cyclobutylene, cyclopentene and cyclohexene.

"Halo", "halogen" or "halide" refers to F, Cl, Br or I.

"Haloalkyl" refers to an alkyl group, in certain embodiments, $C_{1-6}$alkyl group in which one or more of the hydrogen atoms are replaced by halogen. Such groups include, but are not limited to, chloromethyl, trifluoromethyl 1-chloro-2-fluoroethyl, 2,2-difluoroethyl, 2-fluoropropyl, 2-fluoropropan-2-yl, 2,2,2-trifluoroethyl, 1,1-difluoroethyl, 1,3-difluoro-2-methylpropyl, 2,2-difluorocyclopropyl, (trifluoromethyl)cyclopropyl, 4,4-difluorocyclohexyl and 2,2,2-trifluoro-1,1-dimethyl-ethyl.

"Heterocyclyl" refers to a stable 3- to 15-membered non-aromatic ring radical which consists of carbon atoms and from one to five heteroatoms selected from a group consisting of nitrogen, oxygen and sulfur. In one embodiment, the heterocyclic ring system radical may be a monocyclic, bicyclic or tricyclic ring or tetracyclic ring system, which may include fused or bridged ring systems; and the nitrogen or sulfur atoms in the heterocyclic ring system radical may be optionally oxidized; the nitrogen atom may be optionally quaternized; and the heterocyclyl radical may be partially or fully saturated. The heterocyclic ring system may be attached to the main structure at any heteroatom or carbon atom which results in the creation of a stable compound. Exemplary heterocylic radicals include, morpholinyl, piperidinyl, piperazinyl, pyranyl, pyrrolidinyl, oxetanyl, azetidinyl, quinuclidinyl, octahydroquinolizinyl, decahydroquinolizinyl, azabicyclo[3.2.1]octanyl, azabicyclo[2.2.2]octanyl and others.

"Heteroaryl" refers to a heterocyclyl group as defined above which is aromatic. The heteroaryl group may be attached to the main structure at any heteroatom or carbon atom which results in the creation of a stable compound. Examples of such heteroaryl groups include, but are not limited to: furanyl, imidazolyl, oxazolyl, isoxazolyl, pyrimidinyl, pyridinyl, pyridazinyl, thiazolyl, thienyl and others.

"Heterocyclylalkyl" refers to a group of the formula $-R_aR_e$ wherein $R_a$ is an alkyl group as defined above and $R_e$ is a heterocyclyl group as defined herein, where the alkyl group $R_a$ may attach at either the carbon atom or the heteroatom of the heterocyclyl group $R_e$. The alkyl group and the heterocyclyl group may be optionally substituted as defined herein.

"$IC_{50}$" refers to an amount, concentration or dosage of a particular test compound that achieves a 50% inhibition of a maximal response, such as cell growth or proliferation measured via any the in vitro or cell based assay described herein.

"Oxo" refers to the group =O attached to a carbon atom.

Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates, fumarates and organic sulfonates.

As used herein and unless otherwise indicated, the term "hydrate" means a compound provided herein or a salt thereof, that further includes a stoichiometric or non-stoichiometeric amount of water bound by non-covalent intermolecular forces.

As used herein and unless otherwise indicated, the term "solvate" means a solvate formed from the association of one or more solvent molecules to a compound provided herein. The term "solvate" includes hydrates (e.g., mono-hydrate, dihydrate, trihydrate, tetrahydrate and the like).

As used herein, "substantially pure" means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

Unless stated otherwise specifically described in the specification, it is understood that the substitution can occur on any atom of the alkyl, alkenyl, alkynyl, cycloalkyl, heterocyclyl, aryl or heteroaryl group.

Unless specifically stated otherwise, where a compound may assume alternative tautomeric, regioisomeric and/or stereoisomeric forms, all alternative isomers are intended to be encompassed within the scope of the claimed subject matter. For example, where a compound is described as having one of two tautomeric forms, it is intended that the both tautomers be encompassed herein.

Thus, the compounds provided herein may be enantiomerically pure, or be stereoisomeric or diastereomeric mixtures.

It is to be understood that the compounds provided herein may contain chiral centers. Such chiral centers may be of either the (R) or (S) configuration, or may be a mixture thereof. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

Optically active (+) and (−), (R)- and (S)-, or (D)- and (L)-isomers may be prepared using chiral synthons or chiral reagents, or resolved using conventional techniques, such as chromatography on a chiral stationary phase.

As used herein, "isotopic composition" refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen", the position is understood to have hydrogen at its natural isotopic composition.

As used herein, "isotopically enriched" refers to an atom having an isotopic composition other than the natural isotopic composition of that atom. "Isotopically enriched" may also refer to a compound containing at least one atom having an isotopic composition other than the natural isotopic composition of that atom.

As used herein, "isotopic enrichment" refers to the percentage of incorporation of an amount of a specific isotope at a given atom in a molecule in the place of that atom's natural isotopic abundance. For example, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

Where the number of any given substituent is not specified (e.g., haloalkyl), there may be one or more substituents present. For example, "haloalkyl" may include one or more of the same or different halogens.

In the description herein, if there is any discrepancy between a chemical name and chemical structure, the structure controls.

"Anti-cancer agents" refers to anti-metabolites (e.g., 5-fluoro-uracil, methotrexate, fludarabine), antimicrotubule agents (e.g., vinca alkaloids such as vincristine, vinblastine; taxanes such as paclitaxel, docetaxel), alkylating agents (e.g., cyclophosphamide, melphalan, carmustine, nitrosoureas such as bischloroethylnitrosurea and hydroxyurea), platinum agents (e.g. cisplatin, carboplatin, oxaliplatin, JM-216 or satraplatin, CI-973), anthracyclines (e.g., doxrubicin, daunorubicin), antitumor antibiotics (e.g., mitomycin, idarubicin, adriamycin, daunomycin), topoisomerase inhibitors (e.g., etoposide, camptothecins), anti-angiogenesis agents (e.g. Sutent® and Bevacizumab) or any other cytotoxic agents, (estramustine phosphate, prednimustine), hormones or hormone agonists, antagonists, partial agonists or partial antagonists, kinase inhibitors, and radiation treatment.

"Anti-inflammatory agents" refers to matrix metalloproteinase inhibitors, inhibitors of pro-inflammatory cytokines (e.g., anti-TNF molecules, TNF soluble receptors, and IL1) non-steroidal anti-inflammatory drugs (NSAIDs) such as prostaglandin synthase inhibitors (e.g., choline magnesium salicylate, salicylsalicyclic acid), COX-1 or COX-2 inhibitors), or glucocorticoid receptor agonists such as corticosteroids, methylprednisone, prednisone, or cortisone.

As used herein, the abbreviations for any protective groups, amino acids and other compounds, are, unless indicated otherwise, in accord with their common usage, recognized abbreviations, or the IUPAC-IUB Commission on Biochemical Nomenclature (see, *Biochem.* 1972, 11:942-944).

B. Compounds

In certain embodiments, provided herein are compounds of Formula I or pharmaceutically acceptable salts, solvates, hydrates or clathrates thereof, wherein:

A is azolyl;

B is 6-membered heteroaryl containing 1 or 2 nitrogen atoms;

Z is phenyl, cyclohexenyl or cyclohexyl;

each $R^1$ is independently selected from hydrogen, halo, alkyl, alkenyl, alkynyl, alkoxy, hydroxyl, haloalkoxy, alkylthio, alkylsulfonyl, alkylsulfinyl, cycloalkyl, cycloalkylalkyl, cycloalkenyl, hydroxyalkyl, haloalkyl, alkylaminosulfonyl, alkylaminocarbonyl, aryl, arylalkyl, heterocyclyl, heterocyclylalkyl, heteroaryl, and heteroarylalkyl, where the alkyl, alkenyl, alkynyl, alkoxy, haloalkoxy, alkylthio, alkylsulfonyl, alkylsulfinyl, cycloalkyl, cycloalkylalkyl, cycloalkenyl, hydroxyalkyl, haloalkyl, alkylaminosulfonyl, alkylaminocarbonyl, aryl, heterocyclyl, and heteroaryl groups are optionally substituted with 1 to 5 groups selected from halo, alkyl, hydroxy, alkoxy, cycloalkyl, cycloalkenyl, cyano, $—R^uN(R^y)(R^z)$ and $—R^uS(O)_tR^w$;

$L^1$ is

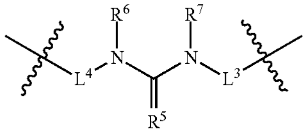

;

$R^5$ is O or S;

$R^6$ and $R^7$ are each independently selected from hydrogen and optionally substituted lower alkyl; where the substituents, when present are each independently selected from alkyl, haloalkyl, amino, hydroxyl and alkoxy;

$L^3$ and $L^4$ are each independently a bond, alkylene, alkenylene, or alkynylene, each optionally substituted with one or more substituents selected from alkyl, haloalkyl, amino, hydroxyl and alkoxy;

each $R^2$ is independently selected from alkyl, alkenyl, alkynyl, cycloalkyl, haloalkyl, hydroxyalkyl, alkoxyalkyl, cycloalkylalkyl, hydroxy, and alkoxy;

each $R^4$ is independently selected from alkyl, cycloalkyl, amino, hydroxy, and alkoxy;

$L^2$ is direct bond, alkylene, alkenylene, alkynylene, $—R^8OR^9—$, $—R^8SR^9—$, or $—R^8N(R^{10})R^9—$;

$R^8$ and $R^9$ are each independently direct bond, alkylene, alkenylene, or alkynylene;

$R^{10}$ is hydrogen or alkyl;

$R^3$ is selected as follows:

i) $R^3$ is $NR^{3a}R^{3b}$, or ii) $R^3$ is optionally substituted heterocyclyl or optionally substituted heteroaryl containing at least one nitrogen atom, and 0 to 1 additional heteroatom selected from O, N or S, wherein the heterocyclyl or heteroaryl ring is connected to $L^2$ on the carbon atom of the ring, and wherein the substituents, when present are selected from one or more, in one embodiment, 1-9, in one embodiment, 1-7, in another embodiment, 1-5, in another embodiment, one, two or three $Q^1$ groups;

$R^{3a}$ and $R^{3b}$ are each independently selected from (i) or (ii) below:

(i) $R^{3a}$ and $R^{3b}$ are each independently alkyl, haloalkyl, hydroxyalkyl, alkoxyalkyl, alkenyl, alkynyl, cycloalkyl, cycloalkylalkyl, heterocyclyl, heterocyclylalkyl, aryl, aralkyl, heteroaryl, or heteroaralkyl; or (ii) $R^{3a}$ and $R^{3b}$, together with the nitrogen atom to which they are attached, form a heterocyclyl or heteroaryl, optionally substituted with one or more, in one embodiment, one, two or three $Q^1$ groups;

each $R^u$ is independently alkylene or a direct bond;

$R^w$ is alkyl, alkenyl, alkynyl, cycloalkyl, cycloalkylalkyl, heterocyclyl, heterocyclylalkyl, aryl, aralkyl, heteroaryl, or heteroaralkyl;

each $R^x$ is independently hydrogen, alkyl, haloalkyl, alkenyl, alkynyl, cycloalkyl, cycloalkylalkyl, heterocyclyl, heterocyclylalkyl, aryl, aralkyl, heteroaryl, or heteroaralkyl;

$R^y$ and $R^z$ are each independently selected from (i) and (ii) below:

(i) $R^y$ and $R^z$ are each independently hydrogen, alkyl, alkenyl, alkynyl, cycloalkyl, or haloalkyl; or (ii) $R^y$ and $R^z$, together with the nitrogen atom to which they are attached, form a heterocyclyl or heteroaryl, optionally substituted with one or more, in one embodiment, one, two or three Q groups; each Q is independently selected from halo, oxo, thioxo, hydroxy, alkoxy, alkyl, haloalkyl, hydroxyalkyl, aminoalkyl, alkenyl, alkynyl, cycloalkyl, cycloalkylalkyl, aryl, aralkyl, heteroaryl, heteroaralkyl, heterocyclyl and heterocyclylalkyl;

each $Q^1$ is independently selected from halo, oxo, thioxo, alkyl, haloalkyl, aminoalkyl, alkenyl, alkynyl, cycloalkyl, cycloalkylalkyl, aryl, aralkyl, heteroaryl, heteroaralkyl, heterocyclyl, heterocyclylalkyl, $—R^uOR^x$, $—R^uOR^uN(R^y)(R^z)$, $—R^uN(R^y)(R^z)$, $—R^uC(J)R^x$, $—R^uC(J)OR^x$, $—R^uC(J)N(R^y)(R^z)$, $—R^uC(J)SR^x$, $—R^uS(O)_tR^w$, $—R^uOC(J)R^x$, $—R^uOC(J)OR^x$, $—R^uOC(J)N(R^y)(R^z)$, $—R^uOC(J)SR^x$, $—R^uN(R^x)C(J)R^x$, $—R^uN(R^x)C(J)OR^x$, $—R^uN(R^x)C(J)N(R^y)(R^z)$, $—R^uN(R^x)C(J)SR^x$, and $—R^uN(R^x)S(O)_tR^w$; where the alkyl, haloalkyl, aminoalkyl, alkenyl, alkynyl, cycloalkyl, aryl, heteroaryl, and heterocyclyl groups are optionally substituted with one, two or three $Q^2$ groups; each $Q^2$ is independently selected from is halo, oxo, thioxo, alkyl, haloalkyl, aminoalkyl, alkenyl, alkynyl, cycloalkyl, cycloalkylalkyl, aryl, aralkyl, heteroaryl, heteroaralkyl, heterocyclyl, heterocyclylalkyl, $—R^uOR^x$, $—R^uOR^uN(R^y)(R^z)$, $—R^uN(R^y)(R^z)$, $—R^uSR^x$, $—R^uC(J)R^x$, $—R^uC(J)OR^x$, $—R^uC(J)N(R^y)(R^z)$, $—R^uC(J)SR^x$, $—R^uS(O)_tR^w$, $—R^uOC(J)R^x$, $—R^uOC(J)OR^x$, $—R^uOC(J)N(R^y)(R^z)$, $—R^uOC(J)SR^x$, $—R^uN(R^x)C(J)R^x$, $—R^uN(R^x)C(J)OR^x$, $—R^uN(R^x)C(J)N(R^y)(R^z)$, $—R^uN(R^x)C(J)SR^x$, or $—R^uN(R^x)S(O)_tR^w$;

J is O, $NR^X$ or S;

each t is independently 0-2;

m and n are each independently 0-4; and p is 1-4.

In certain embodiments, the compounds provided herein are selected such that i) when A is isoxazolyl, $R^1$ is tert-butyl, Z is phenyl, $L^1$ is —NH—C(O)—NH—, m is 1, and B is pyrimidinyl, then $L^2$ is not direct bond; ii) when A is isoxazolyl, $R^1$ is tert-butyl, Z is phenyl, $L^1$ is —NH—C(O)—NH—, B is pyrimidinyl, m is 1, and $R^4$ is morpholinyl, then $R^3$ is not morpholinyl;

iii) when A is isoxazolyl, $R^1$ is tert-butyl, Z is phenyl, $L^1$ is —NH—C(O)—NH—, B is 3-pyridyl and m is 0, then $R^{3a}$ and $R^{3b}$ are not both alkyl, and iv) when A is isoxazolyl, $R^1$ is tert-butyl, Z is phenyl, $L^1$ is —NH—C(O)—NH—, B is 2-pyridinyl, $L^2$ is —O—, $R^3$ is pyrimidinyl, and m is 0, then $Q^1$ is not alkoxy.

In certain embodiments, the compound provided herein is selected such that when A is isoxazolyl, $R^1$ is tert-butyl, Z is phenyl, $L^1$ is —NH—C(O)—NH—, m is 1, and B is pyrimidinyl, then $R^4$ is not oxo.

In certain embodiments, the compound provided herein is selected such that when A is isoxazolyl, $R^1$ is tert-butyl, Z is phenyl, $L^1$ is —NH—C(O)—NH—, $R^4$ is oxo, B is pyrimidinyl, and $L^2$ is direct bond, then $R^3$ is not pyridyl.

In certain embodiments, the compound provided herein is selected such that when A is isoxazolyl, $R^1$ is tert-butyl, Z is phenyl, $L^1$ is —NH—C(O)—NH—, $R^4$ is oxo, B is pyrimidinyl, and $L^2$ is direct bond, then $R^3$ is not heteroaryl.

In certain embodiments, the compound provided herein is selected such that when A is isoxazolyl, $R^1$ is tert-butyl, Z is phenyl, $L^1$ is —NH—C(O)—NH—, m is 1, B is pyrimidinyl, and $L^2$ is direct bond, then $R^3$ is not heteroaryl.

In certain embodiments, the compound provided herein is selected such that when A is isoxazolyl, $R^1$ is tert-butyl, Z is phenyl, $L^1$ is —NH—C(O)—NH—, m is 1, and B is pyrimidinyl, then $R^3$ is not pyridyl.

In certain embodiments, the compound provided herein is selected such that when A is isoxazolyl, $R^1$ is tert-butyl, Z is phenyl, $L^1$ is —NH—C(O)—NH—, and B is pyrimidinyl, then $R^3$ is not heteroaryl.

In certain embodiments, the compound provided herein is selected such that when A is isoxazolyl, $R^1$ is tert-butyl, Z is phenyl, $L^1$ is —NH—C(O)—NH—, and B is pyrimidinyl, then $R^3$ is not pyridyl.

In certain embodiments, the compound provided herein is selected such that when A is isoxazolyl, $R^1$ is tert-butyl, Z is phenyl, $L^1$ is —NH—C(O)—NH— and B is pyrimidinyl, $L^2$ is direct bond, then $R^3$ is not morpholinyl.

In certain embodiments, the compound provided herein is selected such that when A is isoxazolyl, $R^1$ is tert-butyl, Z is phenyl, $L^1$ is —NH—C(O)—NH—, and $R^4$ is morpholinyl, $L^2$ is direct bond, then $R^3$ is not morpholinyl.

In certain embodiments, the compound provided herein is selected such that when A is isoxazolyl, $R^1$ is tert-butyl, Z is phenyl, $L^1$ is —NH—C(O)—NH—, m is 0, and B is 3-pyridyl, then $R^{3a}$ and $R^{3b}$ are not both alkyl.

In certain embodiments, the compound provided herein is selected such that when A is isoxazolyl, $R^1$ is tert-butyl, Z is phenyl, $L^1$ is —NH—C(O)—NH—, m is 0, and B is pyridyl, then $R^{3a}$ and $R^{3b}$ are not both methyl.

In certain embodiments, the compound provided herein is selected such that when A is isoxazolyl, $R^1$ is tert-butyl, Z is phenyl, $L^1$ is —NH—C(O)—NH—, m is 0, and B is pyridyl, then $R^{3a}$ and $R^{3b}$ are not both alkyl.

In certain embodiments, the compound provided herein is selected such that when A is isoxazolyl, $R^1$ is tert-butyl, Z is phenyl, $L^1$ is —NH—C(O)—NH—, and B is 3-pyridyl, then $R^3$ is not $NR^{3a}R^{3b}$.

In certain embodiments, the compound provided herein is selected such that when A is isoxazolyl, $R^1$ is tert-butyl, Z is phenyl, $L^1$ is —NH—C(O)—NH—, m is 0, B is 2-pyridyl, $L^2$ is —O—, and $R^3$ is pyrimidinyl, then $Q^1$ is not alkoxy.

In certain embodiments, the compound provided herein is selected such that when A is isoxazolyl, $R^1$ is tert-butyl, Z is phenyl, $L^1$ is —NH—C(O)—NH—, m is 0, B is 2-pyridyl and $L^2$ is —O—, then $R^3$ is not 4,6-dimethoxypyrimidinyl.

In certain embodiments, the compound provided herein is selected such that when A is isoxazolyl, $R^1$ is tert-butyl, Z is phenyl, $L^1$ is —NH—C(O)—NH—, m is 0, B is 2-pyridyl and $L^2$ is —O—, then $R^3$ is not pyrimidinyl.

In certain embodiments, provided herein are compounds of Formula I or pharmaceutically acceptable salts, solvates, hydrates or clathrates thereof, wherein:

A is azolyl;

B is 6-membered heteroaryl containing 1 or 2 nitrogen atoms;

Z is phenyl, cyclohexenyl or cyclohexyl;

each $R^1$ is independently selected from alkyl, halo and haloalkyl;

$L^1$ is

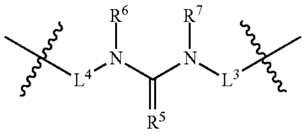

;

$R^5$ is O;

$R^6$ and $R^7$ are each independently selected from hydrogen and lower alkyl;

$L^3$ and $L^4$ are each independently a direct bond or alkylene;

each $R^2$ is independently selected from alkyl and alkoxy;

each $R^4$ is alkyl;

$L^2$ is direct bond, alkylene, alkenylene, alkynylene, $—R^8OR^9—$, $—R^8SR^9—$, or $—R^8N(R^{10})R^9—$; $R^8$ and $R^9$ are each independently direct bond or alkylene;

$R^{10}$ is hydrogen or alkyl;

$R^3$ is selected as follows:

i) $R^3$ is $NR^{3a}R^{3b}$, or ii) $R^3$ is optionally substituted heterocyclyl or optionally substituted heteroaryl containing at least one nitrogen atom, such that the heterocyclyl or heteroaryl ring is connected to $L^2$ on the carbon atom of the ring, and wherein the substituents, when present are selected from one or more, in one embodiment, 1-9, in another embodiment, 1-7, in another embodiment, 1-5 or in another embodiment, one, two or three $Q^1$ groups, each independently selected from oxo, alkyl, cycloalkyl, haloalkyl, heterocyclyl, $R^uC(J)OR^x$, $—R^uC(J)N(R^y)(R^z)$, and $—R^uS(O)_tR^w$; where the alkyl, cycloalkyl and heterocyclyl groups are optionally substituted with one, two or three $Q^2$ groups; each $Q^2$ is independently selected from is halo, oxo, thioxo, alkyl, haloalkyl, alkenyl, alkynyl, cycloalkyl, cycloalkylalkyl, aryl, aralkyl, heteroaryl, heteroaralkyl, heterocyclyl, heterocyclylalkyl, $—R^uOR^x$, $—R^uOR^uN(R^y)(R^z)$, $—R^uN(R^y)(R^z)$, $—R^uSR^x$, $—R^uC(J)R^x$, $—R^uC(J)OR^x$, $—R^uC(J)N(R^y)(R^z)$, $—R^uC(J)SR^x$, $—R^uS(O)_tR^w$, $—R^uOC(J)R^x$, $—R^uOC(J)OR^x$, $—R^uOC(J)N(R^y)(R^z)$, $—R^uOC(J)SR^x$, $—R^uN(R^x)C(J)R^x$, $—R^uN(R^x)C(J)OR^x$, $—R^uN(R^x)C(J)N(R^y)(R^z)$, $—R^uN(R^x)C(J)SR^x$, or $—R^uN(R^x)S(O)_tR^w$;

$R^{3a}$ and $R^{3b}$ are each independently selected from (i) or (ii) below:

(i) $R^{3a}$ and $R^{3b}$ are each independently alkyl, haloalkyl, hydroxyalkyl, alkoxyalkyl, alkenyl, alkynyl, cycloalkyl, cycloalkylalkyl, heterocyclyl, heterocyclylalkyl, aryl, aralkyl, heteroaryl, or heteroaralkyl; or (ii) $R^{3a}$ and $R^{3b}$, together with the nitrogen atom to which they are attached, form a heterocyclyl or heteroaryl, optionally substituted with one or more, in one embodiment, one, two or three $Q^1$ groups;

each $R^u$ is independently alkylene or a direct bond;

$R^w$ is alkyl;

each $R^x$ is alkyl;

$R^y$ and $R^z$ are each independently selected from (i) and (ii) below:

(i) $R^y$ and $R^z$ are each independently hydrogen, alkyl, alkenyl, alkynyl, cycloalkyl, or haloalkyl; and (ii) $R^y$ and $R^z$, together with the nitrogen atom to which they are attached, form a heterocyclyl or heteroaryl, where heterocyclyl and heteroaryl are each optionally substituted with an alkyl;

J is O;

each t is independently 0-2;

m and n are each independently 0, 1 or 2; and p is 1, 2 or 3.

In certain embodiments, A is optionally substituted azolyl, wherein substituents when present are selected from one, two or three $R^1$ groups each independently selected from hydrogen, halo, alkyl, alkenyl, alkynyl, alkoxy, hydroxyl, haloalkoxy, cycloalkyl, cycloalkylalkyl, hydroxyalkyl, haloalkyl, aryl, arylalkyl, heterocyclyl, heterocyclylalkyl, heteroaryl, and heteroarylalkyl, where the alkyl, alkenyl, alkynyl, alkoxy, haloalkoxy, cycloalkyl, cycloalkylalkyl, hydroxyalkyl, haloalkyl, aryl, heterocyclyl, and heteroaryl groups are optionally substituted with 1 to 5 groups selected from halo, hydroxy, alkoxy, cycloalkyl, cyano, and —$R^uN(R^y)(R^z)$, where $R^u$ is independently alkylene or a direct bond, $R^y$, and $R^z$ are each independently hydrogen or alkyl.

In certain embodiments, A is optionally substituted azolyl, wherein substituents when present are selected from one, two or three $R^1$ groups. In certain embodiments, A is optionally substituted isoxazolyl or optionally substituted pyrazolyl, wherein substituents when present are selected from one, two or three $R^1$ groups.

In certain embodiments, each $R^1$ is independently selected from hydrogen, halo, alkyl, alkenyl, alkynyl, alkoxy, hydroxyl, haloalkoxy, cycloalkyl, cycloalkylalkyl, hydroxyalkyl, haloalkyl, aryl, arylalkyl, heterocyclyl, heterocyclylalkyl, heteroaryl, and heteroarylalkyl, where the alkyl, alkenyl, alkynyl, alkoxy, haloalkoxy, cycloalkyl, cycloalkylalkyl, hydroxyalkyl, haloalkyl, aryl, heterocyclyl, and heteroaryl groups are optionally substituted with 1 to 5 groups selected from halo, hydroxy, alkoxy, cycloalkyl, cyano, and —$R^uN(R^y)(R^z)$, where $R^u$ is independently alkylene or a direct bond, and $R^y$, and $R^z$ are each independently hydrogen or alkyl.

In certain embodiments, each $R^1$ is independently selected from hydrogen, halo, alkyl, cycloalkyl, cycloalkylalkyl, hydroxyalkyl, and haloalkyl, where the alkyl, cycloalkyl, cycloalkylalkyl, hydroxyalkyl, and haloalkyl groups are optionally substituted with 1 to 5 groups selected from halo, hydroxy, alkoxy, cycloalkyl, cyano, and —$R^uN(R^y)(R^z)$, where $R^u$ is independently alkylene or a direct bond, and $R^y$, and $R^z$ are each independently hydrogen or alkyl.

In certain embodiments, A is selected from:

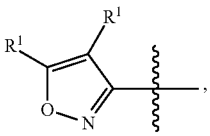,
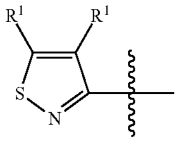,
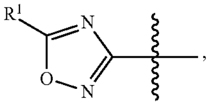,
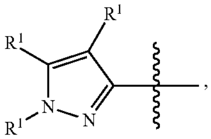,
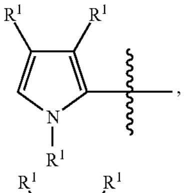,
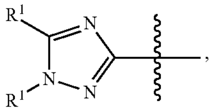,
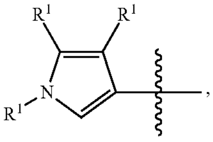,
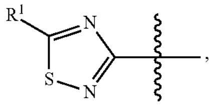, -continued

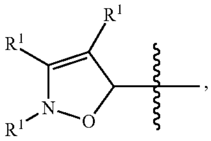,
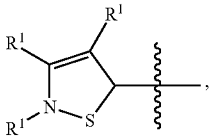,
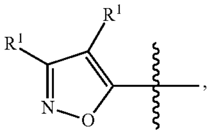,
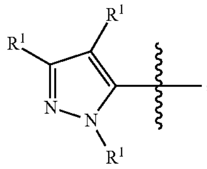,
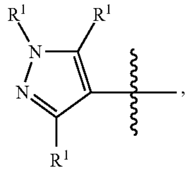,
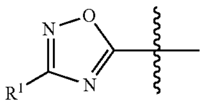,
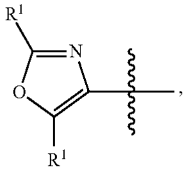,
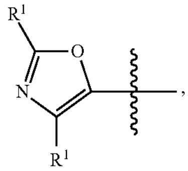,
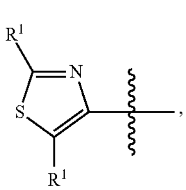,
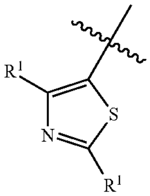,
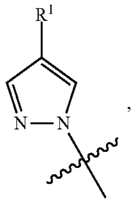,
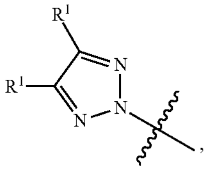,
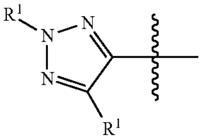,
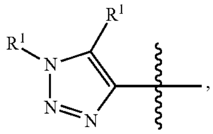,
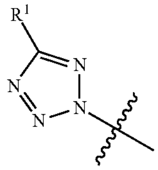 or
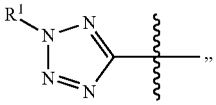, where each $R^1$ is independently selected from hydrogen, halo, haloalkyl, and alkyl, where the alkyl group is optionally substituted with, in one embodiment, 1 to 5, in another embodiment, 1 or 2 groups selected from halo, cyano, hydroxy, alkoxy, and cycloalkyl.

In one embodiment, A is

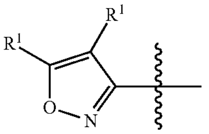,
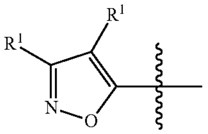,

-continued

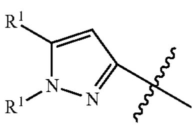,
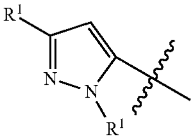
or
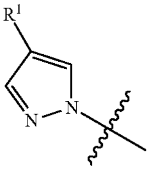, where $R^1$ is as described elsewhere herein. In one embodiment, each $R^1$ is independently hydrogen, alkyl, hydroxyalkyl, cycloalkyl, haloalkyl, cyanoalkyl, alkoxyalkyl, aryl or heteroaryl. In one embodiment, each $R^1$ is independently hydrogen, alkyl or haloalkyl. In one embodiment, each $R^1$ is t-butyl, $—CF_3$, $—CF(CH_3)_2$, $—C(CH_3)(CH_2F)_2$ or $—C(CH_3)_2CF_3$. In one embodiment, each $R^1$ is independently hydrogen, alkyl or haloalkyl. In one embodiment, each $R^1$ is independently t-butyl, $—CF_3$, $—CF(CH_3)_2$, $—C(CH_3)(CH_2F)_2$, $—C(CH_3)_2CF_3$ or

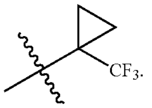 [SMILES: *C1(C(F)(F)F)CC1]

In one embodiment, A is

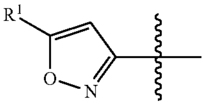
or
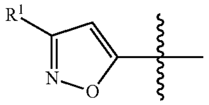, where $R^1$ is as described elsewhere herein. In one embodiment, $R^1$ is hydrogen, alkyl or haloalkyl. In one embodiment, $R^1$ is t-butyl, $—CF_3$, $—CF(CH_3)_2$, $—C(CH_3)(CH_2F)_2$ or $—C(CH_3)_2CF_3$. In one embodiment, $R^1$ is t-butyl, $—CF_3$, $—CF(CH_3)_2$, $—C(CH_3)(CH_2F)_2$, $—C(CH_3)_2CF_3$ or

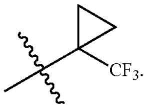 [SMILES: *C1(C(F)(F)F)CC1]

In one embodiment, A is

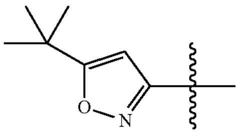
or
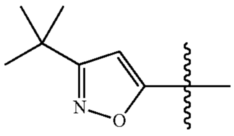.

In one embodiment, A is

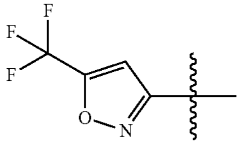
or
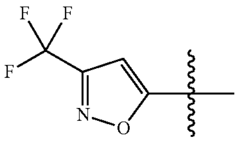.

In one embodiment, A is

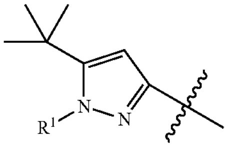,
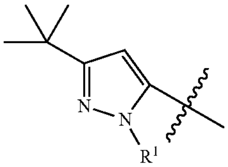,
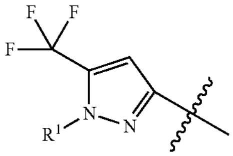
or
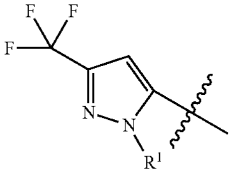,, where $R^1$ is hydrogen, alkyl, aryl or cycloalkyl. In one embodiment, where $R^1$ is hydrogen, or alkyl. In one embodiment, where $R^1$ is hydrogen, or methyl.

In certain embodiments, compounds provided herein have formula I, where B is

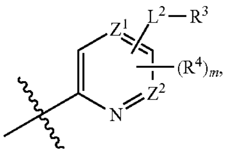

where m is 0 or 1; $Z^1$ and $Z^2$ are selected from (i), (ii) and (iii) as follows:

(i) $Z^1$ and $Z^2$ are both $CR^{4a}$, (ii) $Z^1$ is N, and $Z^2$ is $CR^{4a}$, and (iii) $Z^1$ is $CR^{4a}$, and $Z^2$ is N;

each $R^{4a}$ is independently hydrogen, $-L^2-R^3$ or $R^4$ provided there is only one $-L^2-R^3$ on the B ring, and $R^3$, $R^4$, and $L^2$ are as described elsewhere herein. In certain embodiments, m is 0. In certain embodiments, $L^2$ is direct bond, alkylene, or $R^8OR^9$, where $R^8$ is direct bond and $R^9$ is direct bond or alkylene. In certain embodiments, $L^2$ is direct bond, alkylene, or $—O—(CH_2)_{0-3}$. In certain embodiments, $L^2$ is direct bond, methylene, $—O—$, $—O—CH_2—$, $—O—CH_2—CH_2—$, or $—O—CH_2—CH_2—CH_2—$. In certain embodiments, $R^3$ is selected as follows:

i) $R^3$ is $NR^{3a}R^{3b}$, where $R^{3a}$ and $R^{ab}$ are alkyl; or ii) $R^3$ is optionally substituted heterocyclyl containing at least one nitrogen atom, such that the heterocyclyl ring is connected to $L^2$ on the carbon atom of the ring, and wherein the substituents, when present are selected from one or more, in one embodiment, 1-7, in another embodiment, 1-5, in another embodiment, one, two or three $Q^1$ groups, each independently selected from alkyl, haloalkyl, cycloalkyl, $—R^uC(J)OR^x$, $—R^uS(O)_tR^w$, $—R^uC(J)N(R^y)(R^z)$, and heterocyclyl, where each $R^u$ is independently alkylene or a direct bond, $R^w$ and $R^x$ are each alkyl; $R^y$ and $R^z$ are each hydrogen or alkyl; J is O; and t is 2. In one embodiment, each $Q^1$ group is independently selected from $—CH_3$, $—CH_2—CH_3$, $—CH_2CF_3$, $—CH—(CH_3)_2$, $—C(O)O(CH_3)_3$, $—(CH_2)_2S(O)_2CH_3$, $—CH_2C(O)N(CH_3)_2$, $—C(CH_3)_3$, cycloalkyl, and oxetanyl.

In certain embodiments, B is

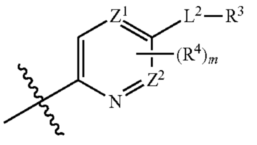

or

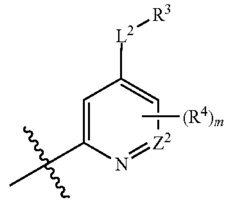

where m is 0 or 1; $Z^1$ and $Z^2$ are selected from (i), (ii) and (iii) as follows:

(i) $Z^1$ and $Z^2$ are both $CR^{4a}$;

(ii) $Z^1$ is N, and $Z^2$ is $CR^{4a}$; and (iii) $Z^1$ is $CR^{4a}$, and $Z^2$ is N;

each $R^{4a}$ is independently hydrogen or $R^4$, and $R^3$, $R^4$, and $L^2$ are as described elsewhere herein.

In certain embodiments, B is

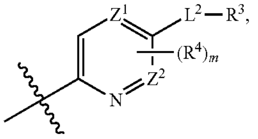

where m is 0 or 1; $Z^1$ and $Z^2$ are selected from (i), (ii) and (iii) as follows:

(i) $Z^1$ and $Z^2$ are both $CR^{4a}$;

(ii) $Z^1$ is N, and $Z^2$ is $CR^{4a}$; and (iii) $Z^1$ is $CR^{4a}$, and $Z^2$ is N;

each $R^{4a}$ is independently hydrogen or $R^4$; and $R^3$, $R^4$, and $L^2$ are as described elsewhere herein.

In certain embodiments, B is pyrimidinyl, pyridinyl, pyrazinyl or pyridazinyl. In certain embodiments, B is pyridinyl.

In certain embodiments, B is

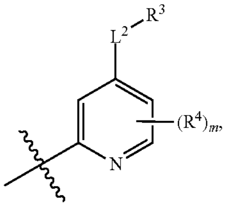

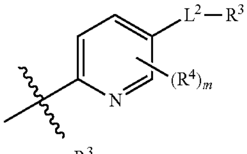

,

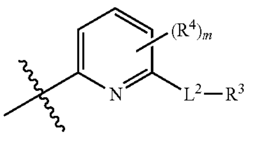

or

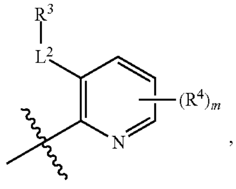

, where m is 0 or 1, $R^3$, $R^4$, and $L^2$ are as described elsewhere herein. In certain embodiments, m is 0. In certain embodiments, $L^2$ is direct bond, alkylene, or $—R^8OR^9$, where $R^8$ is direct bond and $R^9$ is direct bond or alkylene. In certain embodiments, $L^2$ is direct bond, alkylene or $—O—(CH_2)_{0-3}$. In certain embodiments, $L^2$ is direct bond, methylene, —O—, $—O—CH_2—$, $—O—CH_2—CH_2—$, or $O—CH_2—CH_2—CH_2—$. In certain embodiments, $R^3$ is selected as follows:

i) $R^3$ is $—NR^{3a}R^{3b}$, ii) $R^3$ is optionally substituted heterocyclyl containing at least one nitrogen atom, such that the heterocyclyl ring is connected to $L^2$ on the carbon atom of the ring, and wherein the substituents, when present are selected from one or more, in one embodiment, 1-7, in another embodiment, 1-5, in another embodiment, one, two or three $Q^1$ groups, where $R^{3a}$ and $R^{3b}$ are selected as follows:

i) $R^{3a}$ and $R^{3b}$ are alkyl; or ii) $R^{3a}$ and $R^{3b}$ together form optionally substituted heterocyclyl, wherein the substituents when present are selected from one, two or three $Q^1$ groups, each $Q^1$ is independently selected from alkyl, haloalkyl, cycloalkyl, $—R^uC(J)OR^x$, $—R^uS(O)_tR^w$, $—R^uC(J)N(R^y)(R^z)$, and heterocyclyl, where each $R^u$ is independently alkylene or a direct bond, $R^w$ and $R^x$ are each alkyl; $R^y$ and $R^z$ are each hydrogen or alkyl; J is O; and t is 2. In one embodiment, each $Q^1$ group is independently selected from $—CH_3$, $—CH_2—CH_3$, $—CH_2CF_3$, $—CH—(CH_3)_2$, $—(CH_2)_2S(O)_2CH_3$, $—CH_2C(O)N(CH_3)_2$, $—C(CH_3)_3$, cycloalkyl, and oxetanyl.

In certain embodiments, B is

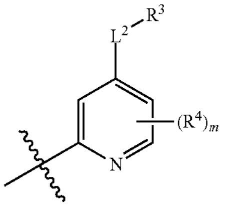

or

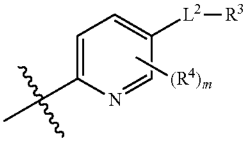

where m is 0 or 1, $R^3$, $R^4$, and $L^2$ are as described elsewhere herein. In certain embodiments, m is 0.

In certain embodiments, $L^2$ is direct bond, alkylene, or $—R^8OR^9$, where $R^8$ is direct bond and $R^9$ is direct bond or alkylene. In certain embodiments, $L^2$ is direct bond, alkylene, or $—O—(CH_2)_{0-3}$. In certain embodiments, $L^2$ is direct bond, methylene, —O—, $—O—CH_2—$, $—O—CH_2—CH_2—$, or $O—CH_2—CH_2—CH_2—$.

In certain embodiments, $L^2$ is direct bond, alkylene, alkenylene, alkynylene, $—R^8OR^9—$, $—R^8S(O)_tR^9—$ $—R^8N(R^{10})R^9—$, where $R^8$ and $R^9$ are each independently direct bond, alkylene, alkenylene, alkynylene, $—R^uOR^u—$, $—R^uN(R^y)R^u—$ or $—R^uS(O)_tR^u—$ and the other variables are as described elsewhere herein.

In certain embodiments, $R^3$ is selected as follows:

i) $R^3$ is $—NR^{3a}R^{3b}$, ii) $R^3$ is optionally substituted heterocyclyl containing at least one nitrogen atom, such that the heterocyclyl ring is connected to $L^2$ on the carbon atom of the ring, and wherein the substituents, when present are selected from one or more, in one embodiment, 1-7, in another embodiment, 1-5, in another embodiment, one, two or three $Q^1$ groups, where $R^{3a}$ and $R^{3b}$ are selected as follows:

i) $R^{3a}$ and $R^{3b}$ are alkyl or haloalkyl; or ii) $R^{3a}$ and $R^{3b}$ together form optionally substituted heterocyclyl, wherein the substituents when present are selected from one, two or three $Q^1$ groups, each $Q^1$ is independently selected from alkyl, haloalkyl, aminoalkyl, alkenyl, cycloalkyl, cycloalkylalkyl, $—R^uC(J)OR^x$, $—R^uS(O)_tR^w$, $—R^uC(J)N(R^y)(R^z)$, heterocyclyl and heterocyclylalkyl, where each $R^u$ is independently alkylene or a direct bond, $R^w$ and $R^x$ are each alkyl; $R^y$ and $R^z$ are each hydrogen or alkyl; J is O; and t is 2. In one embodiment, each $Q^1$ group is independently selected from —$CH_3$, —$CH_2$—$CH_3$, —$CH_2CF_3$, —CH—$(CH_3)_2$, —$(CH_2)_2S(O)_2CH_3$, —$CH_2C(O)N(CH_3)_2$, —$C(CH_3)_3$, cycloalkyl, and oxetanyl.

In certain embodiments, $R^3$ is selected as follows:

i) $R^3$ is —$NR^{3a}R^{3b}$, or ii) $R^3$ is optionally substituted heterocyclyl containing at least one nitrogen atom, such that the heterocyclyl ring is connected to $L^2$ on the carbon atom of the ring, and wherein the substituents, when present are selected from one or more, in one embodiment, 1-7, in another embodiment, 1-5, in another embodiment, one, two or three $Q^1$ groups, where $R^{3a}$ and $R^{3b}$ together form optionally substituted heterocyclyl, wherein the substituents when present are selected from one, two or three $Q^1$ groups, each $Q^1$ is independently selected from alkyl, haloalkyl, aminoalkyl, alkenyl, cycloalkyl, cycloalkylalkyl, —$R^uC(J)OR^x$, —$R^uS(O)_tR^w$, —$R^uC(J)N(R^y)(R^z)$, and heterocyclyl, where each $R^u$ is independently alkylene or a direct bond, $R^w$ and $R^x$ are each alkyl; $R^y$ and $R^z$ are each hydrogen or alkyl; J is O; and t is 2. In one embodiment, each $Q^1$ group is independently selected from $CH_3$, —$CH_2$—$CH_3$, —$CH_2CF_3$, —CH—$(CH_3)_2$, —$(CH_2)_2S(O)_2CH_3$, —$CH_2C(O)N(CH_3)_2$, —$C(CH_3)_3$, cycloalkyl, and oxetanyl.

In one embodiment, each $Q^1$ is independently selected from alkyl, haloalkyl, aminoalkyl, alkenyl, cycloalkyl, cycloalkylalkyl, —$R^uC(J)OR^x$, —$R^uS(O)_tR^w$—$R^uC(J)N(R^y)(R^z)$ and heterocyclyl where $R^u$ is alkylene and the other variables are as described elsewhere herein.

In certain embodiments, B is

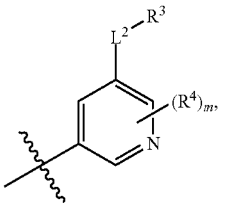

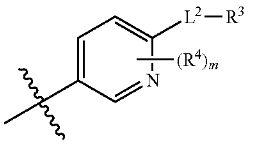
,

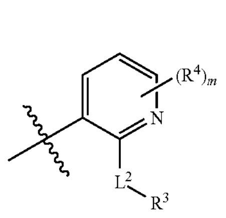
or
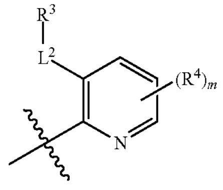
, where m is 0 or 1, $R^3$, $R^4$, and $L^2$ are as described elsewhere herein. In certain embodiments, m is 0. In certain embodiments, $L^2$ is direct bond, alkylene, or $R^8OR^9$, where $R^8$ is direct bond and $R^9$ is direct bond or alkylene. In certain embodiments, $L^2$ is direct bond, alkylene, —O—$(CH_2)_{0-3}$. In certain embodiments, $L^2$ is direct bond, methylene, —O—, —O—$CH_2$—, —O—$CH_2$—$CH_2$—, or —O—$CH_2$—$CH_2$—$CH_2$—. In certain embodiments, $R^3$ is selected as follows:

i) $R^3$ is —$NR^{3a}R^{3b}$, or ii) $R^3$ is optionally substituted heterocyclyl containing at least one nitrogen atom, such that the heterocyclyl ring is connected to $L^2$ on the carbon atom of the ring, and wherein the substituents, when present are selected from one or more, in one embodiment, 1-7, in another embodiment, 1-5, in another embodiment, one, two or three $Q^1$ groups, where $R^{3a}$ and $R^{3b}$ are selected as follows:

i) $R^{3a}$ and $R^{3b}$ are alkyl or haloalkyl; or ii) $R^{3a}$ and $R^{3b}$ together form optionally substituted heterocyclyl, wherein the substituents when present are selected from one, two or three $Q^1$ groups, each $Q^1$ is independently selected from alkyl, haloalkyl, cycloalkyl, —$R^uC(J)OR^x$, —$R^uS(O)_tR^w$, —$R^uC(J)N(R^y)(R^z)$, and heterocyclyl, where each $R^u$ is independently alkylene or a direct bond, $R^w$ and $R^x$ are each alkyl; $R^y$ and $R^z$ are each hydrogen or alkyl; J is O; and t is 2. In one embodiment, each $Q^1$ group is independently selected from $CH_3$, —$CH_2$—$CH_3$, —$CH_2CF_3$, —CH—$(CH_3)_2$, —$(CH_2)_2S(O)_2CH_3$, —$CH_2C(O)N(CH_3)_2$, —$C(CH_3)_3$, cycloalkyl, and oxetanyl.

In certain embodiments, B is

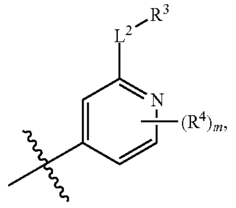

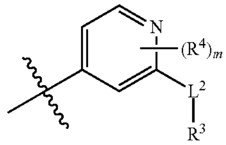
,

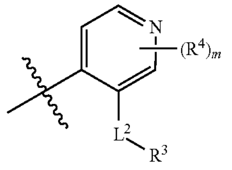
or
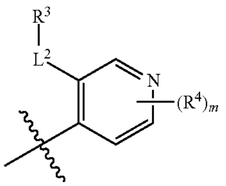

where m is 0 or 1, $R^3$, $R^4$, and $L^2$ are as described elsewhere herein. In certain embodiments, m is 0. In certain embodiments, $L^2$ is direct bond, alkylene, or —$R^8OR^9$, where $R^8$ is direct bond and $R^9$ is direct bond or alkylene. In certain embodiments, $L^2$ is direct bond, alkylene, —O—$(CH_2)_{0-3}$. In certain embodiments, $L^2$ is direct bond, methylene, —O—, —O—$CH_2$—, —O—$CH_2$—$CH_2$—, or —O—$CH_2$—$CH_2$—$CH_2$—. In certain embodiments, $R^3$ is selected as follows:

i) $R^3$ is —$NR^{3a}R^{3b}$, or ii) $R^3$ is optionally substituted heterocyclyl containing at least one nitrogen atom, such that the heterocyclyl ring is connected to $L^2$ on the carbon atom of the ring, and wherein the substituents, when present are selected from one or more, in one embodiment, 1-7, in another embodiment, 1-5, in another embodiment, one, two or three $Q^1$ groups, where $R^{3a}$ and $R^{3b}$ are selected as follows:

i) $R^{3a}$ and $R^{3b}$ are each alkyl or haloalkyl; or ii) $R^{3a}$ and $R^{3b}$ together form optionally substituted heterocyclyl, wherein the substituents when present are selected from one, two or three $Q^1$ groups, each $Q^1$ is independently selected from alkyl, haloalkyl, cycloalkyl, —$R^uC(J)OR^x$, —$R^uS(O)_tR^w$, —$R^uC(J)N(R^y)(R^z)$, and heterocyclyl, where each $R^u$ is independently alkylene or a direct bond, $R^w$ and $R^x$ are each alkyl; $R^y$ and $R^z$ are each hydrogen or alkyl; J is O; and t is 2. In one embodiment, each $Q^1$ group is independently selected from —$CH_3$, —$CH_2$—$CH_3$, —$CH_2CF_3$, —CH—$(CH_3)_2$, —$(CH_2)_2S(O)_2CH_3$, —$CH_2C(O)N(CH_3)_2$, —$C(CH_3)_3$, cycloalkyl, and oxetanyl.

In certain embodiments, B is

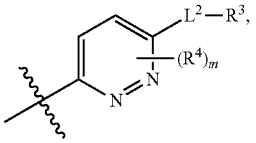

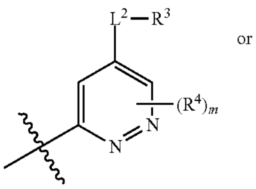

or

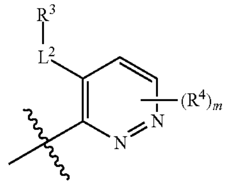

where m is 0 or 1, $R^3$, $R^4$, and $L^2$ are as described elsewhere herein. In certain embodiments, m is 0. In certain embodiments, $L^2$ is direct bond, alkylene, or $—R^8OR^9$, where $R^8$ is direct bond and $R^9$ is direct bond or alkylene. In certain embodiments, $L^2$ is direct bond, alkylene, $—O—(CH_2)_{0-3}$. In certain embodiments, $L^2$ is direct bond, methylene, —O—, $—O—CH_2—$, $—O—CH_2—CH_2—$, or $—O—CH_2—CH_2—CH_2—$. In certain embodiments, $R^3$ is selected as follows:

i) $R^3$ is $—NR^{3a}R^{3b}$, or ii) $R^3$ is optionally substituted heterocyclyl containing at least one nitrogen atom, such that the heterocyclyl ring is connected to $L^2$ on the carbon atom of the ring, and wherein the substituents, when present are selected from one or more, in one embodiment, 1-7, in another embodiment, 1-5, in another embodiment, one, two or three $Q^1$ groups, where $R^{3a}$ and $R^{3b}$ are selected as follows:

i) $R^{3a}$ and $R^{3b}$ are each alkyl or haloalkyl; or ii) $R^{3a}$ and $R^{3b}$ together form optionally substituted heterocyclyl, wherein the substituents when present are selected from one, two or three $Q^1$ groups, each $Q^1$ is independently selected from alkyl, haloalkyl, cycloalkyl, $—R^uC(J)OR^x$, $—R^uS(O)_tR^w$, $—R^uC(J)N(R^y)(R^z)$, and heterocyclyl, where each $R^u$ is independently alkylene or a direct bond, $R^w$ and $R^x$ are each alkyl; $R^y$ and $R^z$ are each hydrogen or alkyl; J is O; and t is 2. In one embodiment, each $Q^1$ group is independently selected from $CH_3$, $—CH_2—CH_3$, $—CH_2CF_3$, $—CH—(CH_3)_2$, $(CH_2)_2S(O)_2CH_3$, $—CH_2C(O)N(CH_3)_2$, $—C(CH_3)_3$, cycloalkyl, and oxetanyl.

In certain embodiments, B is

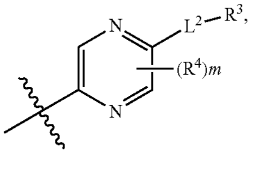

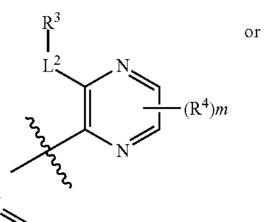

or

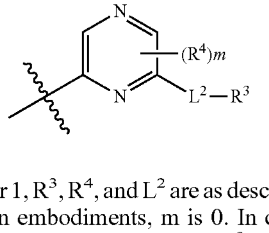

where m is 0 or 1, $R^3$, $R^4$, and $L^2$ are as described elsewhere herein. In certain embodiments, m is 0. In certain embodiments, $L^2$ is direct bond, alkylene, or $R^8OR^9$, where $R^8$ is direct bond and $R^9$ is direct bond or alkylene. In certain embodiments, $L^2$ is direct bond, alkylene, $—O—(CH_2)_{0-3}$. In certain embodiments, $L^2$ is direct bond, methylene, —O—, $—O—CH_2—$, $—O—CH_2—CH_2—$, or $—O—CH_2—CH_2—CH_2—$. In certain embodiments, $R^3$ is selected as follows:

i) $R^3$ is $—NR^{3a}R^{3b}$, or ii) $R^3$ is optionally substituted heterocyclyl containing at least one nitrogen atom, such that the heterocyclyl ring is connected to $L^2$ on the carbon atom of the ring, and wherein the substituents, when present are selected from one or more, in one embodiment, 1-7, in another embodiment, 1-5, in another embodiment, one, two or three $Q^1$ groups, where $R^{3a}$ and $R^{3b}$ are selected as follows:

i) $R^{3a}$ and $R^{3b}$ are each alkyl or haloalkyl; or ii) $R^{3a}$ and $R^{3b}$ together form optionally substituted heterocyclyl, wherein the substituents when present are selected from one, two or three $Q^1$ groups, each $Q^1$ is independently selected from alkyl, haloalkyl, cycloalkyl, $—R^uC(J)OR^x$, $—R^uS(O)_tR^w$, $—R^uC(J)N(R^y)(R^z)$, and heterocyclyl, where each $R^u$ is independently alkylene or a direct bond, $R^w$ and $R^x$ are each alkyl; $R^y$ and $R^z$ are each hydrogen or alkyl; J is O; and t is 2. In one embodiment, each $Q^1$ group is independently selected from $—CH_3$, $—CH_2—CH_3$, $—CH_2CF_3$, $—CH—(CH_3)_2$, $—(CH_2)_2S(O)_2CH_3$, $—CH_2C(O)N(CH_3)_2$, $—C(CH_3)_3$, cycloalkyl, and oxetanyl.

In certain embodiments, $L^2$ is direct bond, alkylene, $—R^8OR^9—$, or $—R^8N(R^{10})R^9—$;

$R^8$ and $R^9$ are each independently direct bond or alkylene;

$R^{10}$ is hydrogen or alkyl;

$R^3$ is selected as follows:

i) $R^3$ is $NR^{3a}R^{3b}$, or ii) $R^3$ is optionally substituted heterocyclyl or optionally substituted heteroaryl containing at least one nitrogen atom, such that the heterocyclyl or heteroaryl ring is connected to $L^2$ on the carbon atom of the ring, and wherein the substituents, when present are selected from one or more, in one embodiment, 1-7, in another embodiment, 1-5, in another embodiment, one, two or three $Q^1$ groups, where $R^{3a}$ and $R^{3b}$ are selected as follows:

i) $R^{3a}$ and $R^{3b}$ are each alkyl, alkenyl, alkynyl, cycloalkyl, or haloalkyl; or ii) $R^{3a}$ and $R^{3b}$ together form optionally substituted heterocyclyl, wherein the substituents when present are selected from one, two or three $Q^1$ groups, each $Q^1$ is independently selected from is halo, oxo, thioxo, alkyl, alkenyl, alkynyl, cycloalkyl, cycloalkylalkyl, aryl, aralkyl, heteroaryl, heteroaralkyl, heterocyclyl, heterocyclylalkyl, $—R^uOR^x$, $—R^uOR^uN(R^y)(R^z)$, $—R^uN(R^y)(R^z)$, $—R^uSR^x$, $—R^uC(J)R^x$, $—R^uC(J)OR^x$, $—R^uC(J)N(R^y)(R^z)$, $—R^uC(J)SR^x$, $—R^uS(O)_tR^w$, $—R^uOC(J)R^x$, $—R^uOC(J)OR^x$, $—R^uOC(J)N(R^y)(R^z)$, $—R^uOC(J)SR^x$, $—R^uN(R^x)C(J)R^x$, $—R^uN(R^x)C(J)OR^x$, $—R^uN(R^x)C(J)N(R^y)(R^z)$, $—R^uN(R^x)C(J)SR^x$, $—R^uN(R^x)S(O)_tR^w$, each $R^u$ is independently alkylene or a direct bond;

$R^w$ is alkyl, alkenyl, alkynyl, cycloalkyl, cycloalkylalkyl, heterocyclyl, heterocyclylalkyl, aryl, aralkyl, heteroaryl, or heteroaralkyl;

each $R^x$ is independently hydrogen, alkyl, haloalkyl, alkenyl, alkynyl, cycloalkyl, cycloalkylalkyl, heterocyclyl, heterocyclylalkyl, aryl, aralkyl, heteroaryl, or heteroaralkyl; and $R^y$ and $R^z$ are each independently selected from (i) or (ii) below:

(i) $R^y$ and $R^z$ are each independently hydrogen, alkyl, alkenyl, alkynyl, cycloalkyl, or haloalkyl; or (ii) $R^y$ and $R^z$, together with the nitrogen atom to which they are attached, form a heterocyclyl or heteroaryl, where heterocyclyl and heteroaryl are each optionally substituted with an alkyl.

In certain embodiments, $L^2$ is direct bond, alkylene, or —$R^8OR^9$—, where $R^8$ is direct bond and $R^9$ is direct bond or alkylene. In certain embodiments, $L^2$ is direct bond, alkylene, —O—$(CH_2)_{0-3}$—. In certain embodiments, $L^2$ is direct bond, methylene, —O—, —O—$CH_2$—, —O—$CH_2$—$CH_2$—, or —O—$CH_2$—$CH_2$—$CH_2$—.

In certain embodiments, $R^3$ is selected as follows:

i) $R^3$ is —$NR^{3a}R^{3b}$, or ii) $R^3$ is optionally substituted heterocyclyl or optionally substituted heteroaryl containing at least one nitrogen atom, such that the heterocyclyl or heteroaryl ring is connected to $L^2$ of the carbon atom of the ring, and wherein the substituents, when present are selected from one or more, in one embodiment, 1-7, in another embodiment, 1-5, in another embodiment, one, two or three $Q^1$ groups, where $R^{3a}$ and $R^{3b}$ are selected as follows:

i) $R^{3a}$ and $R^{3b}$ are each alkyl, alkenyl, alkynyl, cycloalkyl, or haloalkyl; or ii) $R^{3a}$ and $R^{3b}$ together form optionally substituted heterocyclyl, wherein the substituents when present are selected from one, two or three $Q^1$ groups, each $Q^1$ is independently selected from is halo, oxo, thioxo, alkyl, haloalkyl, alkenyl, alkynyl, cycloalkyl, cycloalkylalkyl, aryl, aralkyl, heteroaryl, heteroaralkyl, heterocyclyl, heterocyclylalkyl, —$R^uOR^x$, —$R^uOR^uN(R^y)(R^z)$, —$R^uN(R^y)(R^z)$, —$R^uSR^x$, —$R^uC(J)R^x$, —$R^uC(J)OR^x$, —$R^uC(J)N(R^y)(R^z)$, —$R^uC(J)SR^x$, —$R^uS(O)_tR^w$, —$R^uOC(J)R^x$, —$R^uOC(J)OR^x$, —$R^uOC(J)N(R^y)(R^z)$, —$R^uOC(J)SR^x$, —$R^uN(R^x)C(J)R^x$, —$R^uN(R^x)C(J)OR^x$, —$R^uN(R^x)C(J)N(R^y)(R^z)$, —$R^uN(R^x)C(J)SR^x$, —$R^uN(R^x)S(O)_tR^w$, each $R^u$ is independently alkylene or a direct bond;

$R^w$ is alkyl, alkenyl, alkynyl, cycloalkyl, cycloalkylalkyl, heterocyclyl, heterocyclylalkyl, aryl, aralkyl, heteroaryl, or heteroaralkyl;

each $R^x$ is independently hydrogen, alkyl, haloalkyl, alkenyl, alkynyl, cycloalkyl, cycloalkylalkyl, heterocyclyl, heterocyclylalkyl, aryl, aralkyl, heteroaryl, or heteroaralkyl; and $R^y$ and $R^z$ are each independently selected from (i) or (ii) below:

(i) $R^y$ and $R^z$ are each independently hydrogen, alkyl, alkenyl, alkynyl, cycloalkyl, or haloalkyl; or (ii) $R^y$ and $R^z$, together with the nitrogen atom to which they are attached, form a heterocyclyl or heteroaryl, where heterocyclyl and heteroaryl are each optionally substituted with an alkyl.

In certain embodiments, $R^3$ is selected as follows:

i) $R^3$ is —$NR^{3a}R^{3b}$ where $R^{3a}$ and $R^{3b}$ together form optionally substituted heterocyclyl, wherein the substituents when present are selected from one, two or three $Q^1$ groups, or ii) $R^3$ is optionally substituted heterocyclyl containing at least one nitrogen atom, such that the heterocyclyl ring is connected to $L^2$ of the carbon atom of the ring, and wherein the substituents, when present are selected from one or more, in one embodiment, 1-7, in another embodiment, 1-5, in another embodiment, one, two or three $Q^1$ groups, each $Q^1$ is independently selected from is halo, oxo, thioxo, alkyl, haloalkyl, alkenyl, alkynyl, cycloalkyl, cycloalkylalkyl, aryl, aralkyl, heteroaryl, heteroaralkyl, heterocyclyl, heterocyclylalkyl, —$R^uOR^x$, —$R^uOR^uN(R^y)(R^z)$, —$R^uN(R^y)(R^z)$, —$R^uSR^x$, —$R^uC(J)R^x$, —$R^uC(J)OR^x$, —$R^uC(J)N(R^y)(R^z)$, —$R^uC(J)SR^x$, —$R^uS(O)_tR^w$, —$R^uOC(J)R^x$, —$R^uOC(J)OR^x$, —$R^uOC(J)N(R^y)(R^z)$, —$R^uOC(J)SR^x$, —$R^uN(R^x)C(J)R^x$, —$R^uN(R^x)C(J)OR^x$, —$R^uN(R^x)C(J)N(R^y)(R^z)$, —$R^uN(R^x)C(J)SR^x$, —$R^uN(R^x)S(O)_tR^w$, each $R^u$ is independently alkylene or a direct bond;

$R^w$ is alkyl, alkenyl, alkynyl, cycloalkyl, cycloalkylalkyl, heterocyclyl, heterocyclylalkyl, aryl, aralkyl, heteroaryl, or heteroaralkyl;

each $R^x$ is independently hydrogen, alkyl, haloalkyl, alkenyl, alkynyl, cycloalkyl, cycloalkylalkyl, heterocyclyl, heterocyclylalkyl, aryl, aralkyl, heteroaryl, or heteroaralkyl; and $R^y$ and $R^z$ are each independently selected from (i) or (ii) below:

(i) $R^y$ and $R^z$ are each independently hydrogen, alkyl, alkenyl, alkynyl, cycloalkyl, or haloalkyl; or (ii) $R^y$ and $R^z$, together with the nitrogen atom to which they are attached, form a heterocyclyl or heteroaryl, where heterocyclyl and heteroaryl are each optionally substituted with an alkyl.

In certain embodiments, $R^3$ is selected as follows:

i) $R^3$ is —$NR^{3a}R^{3b}$, or ii) $R^3$ is optionally substituted heterocyclyl or optionally substituted heteroaryl containing at least one nitrogen atom, such that the heterocyclyl or heteroaryl ring is connected to $L^2$ on the carbon atom of the ring, and wherein the substituents, when present are selected from one or more, in one embodiment, 1-7, in another embodiment, 1-5, in another embodiment, one, two or three $Q^1$ groups, where $R^{3a}$ and $R^{3b}$ are selected as follows:

i) $R^{3a}$ and $R^{3b}$ are each alkyl or haloalkyl; or ii) $R^{3a}$ and $R^{3b}$ together form optionally substituted heterocyclyl, wherein the substituents when present are selected from one, two or three $Q^1$ groups, each $Q^1$ is independently selected from alkyl, haloalkyl, cycloalkyl, —$R^uC(J)ORx$, —$R^uS(O)_tR^w$, —$R^uC(J)N(R^y)(R^z)$, and heterocyclyl, where the alkyl and cycloalkyl groups are optionally substituted with one, two or three $Q^2$ groups; each $Q^2$ is independently selected from is halo, hydroxy, cycloalkyl and aryl;

each $R^u$ is independently alkylene or a direct bond, $R^w$ and $R^x$ are each alkyl; $R^y$ and $R^z$ are each hydrogen or alkyl; J is O; and t is 2.

In certain embodiments, $R^3$ is selected as follows:

i) $R^3$ is —$NR^{3a}R^{3b}$, or ii) $R^3$ is optionally substituted heterocyclyl containing at least one nitrogen atom, such that the heterocyclyl ring is connected to $L^2$ on the carbon atom of the ring, and wherein the substituents, when present are selected from one or more, in one embodiment, 1-7, in another embodiment, 1-5, in another embodiment, one, two or three $Q^1$ groups, where $R^{3a}$ and $R^{3b}$ are selected as follows:

i) $R^{3a}$ and $R^{3b}$ are each alkyl or haloalkyl; or ii) $R^{3a}$ and $R^{3b}$ together form optionally substituted heterocyclyl, wherein the substituents when present are selected from one, two or three $Q^1$ groups, each $Q^1$ is independently selected from $CH_3$, —$CH_2$—$CH_3$, —$CH_2CF_3$, —CH—$(CH_3)_2$, —$C(O)O(CH_3)_3$, —$(CH_2)_2S(O)_2CH_3$, —$CH_2C(O)N(CH_3)_2$, —$C(CH_3)_3$, cyclopropyl, and oxetanyl.

In certain embodiments, $R^3$ is optionally substituted piperidinyl, piperazinyl, azetidinyl, pyrrolidinyl, morpholinyl, quinuclidine, octahydroquinolizinyl, azabicyclo[3.2.1]octanyl, and wherein the substituents, when present are selected from one or more, in one embodiment, 1-7, in another embodiment, 1-5, in another embodiment, one, two or three $Q^1$ groups, each independently selected from $CH_3$, —$CH_2$—$CH_3$, —$CH_2CF_3$, —CH—$(CH_3)_2$, —$C(O)O(CH_3)_3$, —$(CH_2)_2S(O)_2CH_3$, —$CH_2C(C)N(CH_3)_2$, —$C(CH_3)_3$, cyclopropyl and oxetanyl.

In certain embodiments, $Q^1$ is selected from alkyl, haloalkyl, cycloalkyl, —$R^uC(J)OR^x$, —$R^uS(O)_tR^w$, —$R^uC(J)N(R^y)(R^z)$, and heterocyclyl, where the alkyl and cycloalkyl groups are optionally substituted with one, two or three $Q^2$ groups; each $Q^2$ is independently selected from is halo, hydroxy, cycloalkyl and aryl; each $R^u$ is independently alkylene or a direct bond, $R^w$ and $R^x$ are each alkyl; $R^y$ and $R^z$ are each hydrogen or alkyl; J is O; and t is 2.

In certain embodiments, $L^1$ is

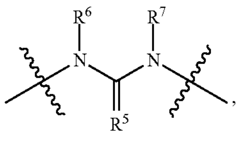

where $R^5$ is selected from O and S; and $R^6$ and $R^7$ are each independently selected from hydrogen and optionally substituted lower alkyl; where the substituents, when present are each independently selected from alkyl, haloalkyl, amino, hydroxyl and alkoxy.

In certain embodiments, $L^1$ is

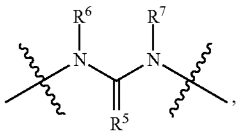

where $R^5$ is O; $R^6$ and $R^7$ are each hydrogen.

In certain embodiments, compounds provided herein are of Formula II

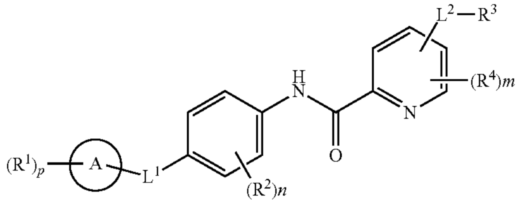

II or pharmaceutically acceptable salts, solvates, hydrates or clathrates thereof, wherein the variables are as described elsewhere herein.

In certain embodiments, compounds provided herein are of Formula II or pharmaceutically acceptable salts, solvates, hydrates or clathrates thereof, wherein:

A is azolyl;

each $R^1$ is independently selected from alkyl, halo and haloalkyl;

$L^1$ is

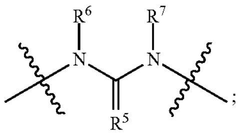

$R^5$ is O or S;

$R^6$ and $R^7$ are each independently selected from hydrogen and lower alkyl;

each $R^2$ is independently selected from alkyl and alkoxy;

each $R^4$ is alkyl;

$L^2$ is direct bond, alkylene, alkenylene, alkynylene, —$R^8OR^9$—, —$R^8SR^9$—, or —$R^8N(R^{10})R^9$—;

$R^8$ and $R^9$ are each independently direct bond or alkylene;

$R^9$ is hydrogen or alkyl;

$R^3$ is selected as follows:

i) $R^3$ is —$NR^{3a}R^{3b}$, or ii) $R^3$ is optionally substituted heterocyclyl or optionally substituted heteroaryl containing at least one nitrogen atom, such that the heterocyclyl or heteroaryl ring is connected to $L^2$ on the carbon atom of the ring, and wherein the substituents, when present are selected from one or more, in one embodiment, 1-9, in another embodiment, 1-7, in another embodiment, 1-5 or in another embodiment, one, two or three $Q^1$ groups, each independently selected from oxo, alkyl, cycloalkyl, haloalkyl, heterocyclyl, $R^uC(J)OR^x$, —$R^uC(J)N(R^y)(R^z)$, and —$R^uS(O)_tR^w$;

$R^{3a}$ and $R^{3b}$ are selected as follows:

i) $R^{3a}$ and $R^{3b}$ are each independently alkyl, alkenyl, alkynyl, cycloalkyl, or haloalkyl; or ii) $R^{3a}$ and $R^{3b}$ together form optionally substituted heterocyclyl, wherein the substituents when present are selected from one, two or three $Q^1$ groups, each $R^u$ is independently alkylene or a direct bond;

$R^w$ is alkyl;

each $R^x$ is alkyl;

$R^y$ and $R^z$ are each independently selected from (i) and (ii) below:

(i) $R^y$ and $R^z$ are each independently hydrogen, alkyl, alkenyl, alkynyl, cycloalkyl, or haloalkyl; and (ii) $R^y$ and $R^z$, together with the nitrogen atom to which they are attached, form a heterocyclyl or heteroaryl, where heterocyclyl and heteroaryl are each optionally substituted with an alkyl;

J is O;

t is 0-2;

m and n are each independently 0, 1 or 2; and p is 1, 2 or 3.

In certain embodiments, compounds provided herein are of Formula II or pharmaceutically acceptable salts, solvates, hydrates or clathrates thereof, wherein:

A is azolyl;

each $R^1$ is independently selected from alkyl and haloalkyl;

$L^1$ is

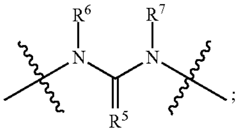

$R^5$ is O or S;

$R^6$ and $R^7$ are each independently selected from hydrogen and lower alkyl;

each $R^2$ is independently selected from alkyl and alkoxy;

each $R^4$ is alkyl;

$L^2$ is a direct bond, alkylene, —$R^8OR^9$—, —$R^8SR^9$—, or —$R^8N(R^{10})R^9$—;

$R^8$ and $R^9$ are each independently direct bond or alkylene;

$R^{10}$ is hydrogen or alkyl;

$R^3$ is selected as follows:

i) $R^3$ is —$NR^{3a}R^{3b}$, or ii) $R^3$ is optionally substituted heterocyclyl containing at least one nitrogen atom, such that the heterocyclyl or heteroaryl ring is connected to $L^2$ on the carbon atom of the ring, and wherein the substituents, when present are selected from one or more, in one embodiment, 1-9, in another embodiment, 1-7, in another embodiment, 1-5 or in another embodiment, one, two or three $Q^1$ groups, each independently selected from oxo, alkyl, cycloalkyl, haloalkyl, heterocyclyl, $R^uC(J)OR^x$, —$R^uC(J)N(R^y)(R^z)$, and —$R^uS(O)_tR^w$;

$R^{3a}$ and $R^{3b}$ are selected as follows:

i) $R^{3a}$ and $R^{3b}$ are each independently alkyl, alkenyl, alkynyl, cycloalkyl, or haloalkyl; or ii) $R^{3a}$ and $R^{3b}$ together form optionally substituted heterocyclyl, wherein the substituents when present are selected from one, two or three $Q^1$ groups, each $R^u$ is independently alkylene or a direct bond;

$R^w$ is alkyl;

each $R^x$ is alkyl;

$R^y$ and $R^z$ are each independently selected from (i) and (ii) below:

(i) $R^y$ and $R^z$ are each independently hydrogen, alkyl, alkenyl, alkynyl, cycloalkyl, or haloalkyl; and (ii) $R^y$ and $R^z$, together with the nitrogen atom to which they are attached, form a heterocyclyl or heteroaryl, where heterocyclyl and heteroaryl are each optionally substituted with an alkyl;

J is O;

t is 0-2;

m and n are each independently 0, 1 or 2; and p is 1, 2 or 3.

In certain embodiments, compounds provided herein are of Formula III

III

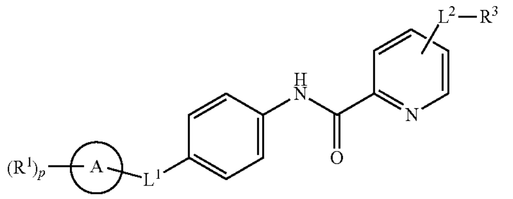

or pharmaceutically acceptable salts, solvates, hydrates or clathrates thereof, wherein the variables are as described elsewhere herein. In certain embodiments, compounds provided herein are of Formula III, wherein A is azolyl;

B is 6-membered heteroaryl containing 1 or 2 nitrogen atoms;

each $R^1$ is independently selected from alkyl, halo and haloalkyl;

$L^1$ is

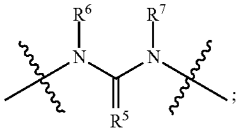

$R^5$ is O or S;

$R^6$ and $R^7$ are each independently selected from hydrogen and lower alkyl;

each $R^2$ is independently selected from alkyl and alkoxy;

each $R^4$ is alkyl;

$L^2$ is direct bond, alkylene, —$R^8OR^9$—, or —$R^8N(R^{10})R^9$—;

$R^8$ and $R^9$ are each independently direct bond or alkylene;

$R^{10}$ hydrogen or alkyl;

$R^3$ is selected as follows:

i) $R^3$ is —$NR^{3a}R^{3b}$, or ii) $R^3$ is optionally substituted heterocyclyl containing at least one nitrogen atom, such that the heterocyclyl ring is connected to $L^2$ on the carbon atom of the ring, and wherein the substituents, when present are selected from one or more, in one embodiment, 1-7, in another embodiment, 1-5, in another embodiment, one, two or three $Q^1$ groups, each independently selected from alkyl, haloalkyl, cycloalkyl, —$R^uC(J)OR^x$, —$R^uS(O)_tR^w$, —$R^uC(J)N(R^y)(R^z)$, and heterocyclyl, $R^{3a}$ and $R^{3b}$ are selected as follows:

i) $R^{3a}$ and $R^{3b}$ are each independently alkyl, alkenyl, alkynyl, cycloalkyl, or haloalkyl; or ii) $R^{3a}$ and $R^{3b}$ together form optionally substituted heterocyclyl, wherein the substituents when present are selected from one, two or three $Q^1$ groups, each $R^u$ is independently alkylene or a direct bond;

$R^w$ is alkyl;

each $R^x$ is alkyl;

$R^y$ and $R^z$ are each hydrogen or alkyl;

J is O; and

P is 0, 1 or 2;

t is 0-2.

In certain embodiments, compounds provided herein are of Formula III, wherein $R^1$ is tert-butyl; $R^3$ is optionally substituted piperidinyl, piperazinyl, azetidinyl, pyrrolidinyl, morpholinyl, quinuclidine, octahydroquinolizinyl, azabicyclo[3.2.1]octanyl, and wherein the substituents, when present are selected from one or more, in one embodiment, 1-7, in another embodiment, 1-5, in another embodiment, one, two or three $Q^1$ groups, each independently selected from —$CH_3$, —$CH_2$—$CH_3$, —$CH_2CF_3$, —CH—$(CH_3)_2$, —C(O)O$(CH_3)_3$, —$(CH_2)_2S(O)_2CH_3$, —$CH_2C(O)N(CH_3)_2$, —$C(CH_3)_3$, cyclopropyl and oxetanyl; and other variables are as described herein.

In certain embodiments, compounds provided herein are of Formula IVa or IVb:

IVa

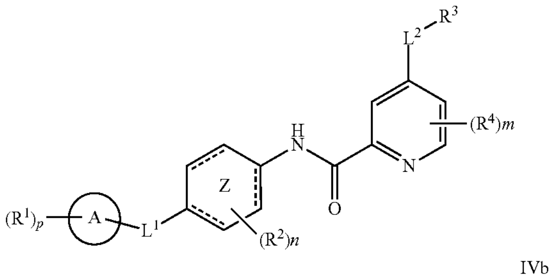

IVb

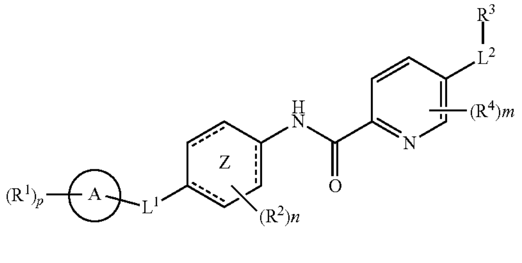

or pharmaceutically acceptable salts, solvates, hydrates or clathrates thereof, wherein the variables are as described elsewhere herein.

In certain embodiments, compounds provided herein are of Formula IVa or IVb, wherein Z is phenyl and all the variables are as described elsewhere herein. In certain embodiments, compounds provided herein are of Formula IVa or IVb, wherein $L^2$ is a direct bond, alkylene, alkenylene, alkynylene or —$R^8OR^9$—, wherein $R^8$ and $R^9$ are each independently a direct bond, alkylene or alkynylene, and all the other variables are as described elsewhere herein.

In certain embodiments, the compounds provided herein are of Formula IVc or IVd:

IVc

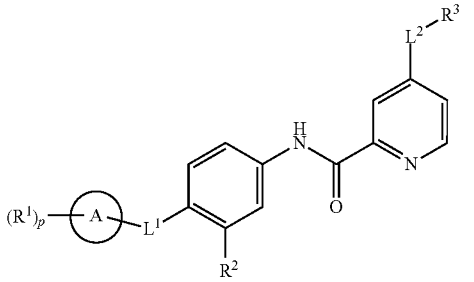

IVd

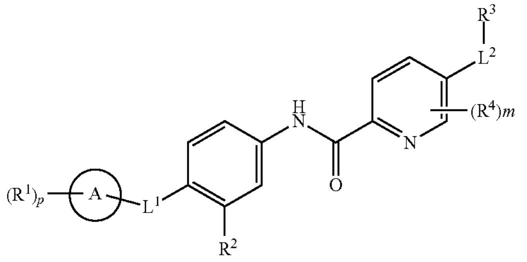

or pharmaceutically acceptable salts, solvates, hydrates or clathrates thereof, wherein the variables are as described elsewhere herein. In certain embodiments, provided herein are compounds of Formula IVc or IVd wherein $R^2$ is independently selected from alkyl, alkenyl, alkynyl, cycloalkyl, haloalkyl, hydroxyalkyl, alkoxyalkyl, cycloalkylalkyl, hydroxyl and alkoxy and the other variables are as described elsewhere herein. In certain embodiments, provided herein are compounds of Formula IVc or IVd wherein $R^2$ is alkyl, haloalkyl, halo or alkoxy, and the other variables are as described elsewhere herein. In certain embodiments, provided herein are compounds of Formula IVc or IVd wherein $R^2$ is alkyl or alkoxy and the other variables are as described elsewhere herein.

In certain embodiments, compounds provided herein are of Formula V

V

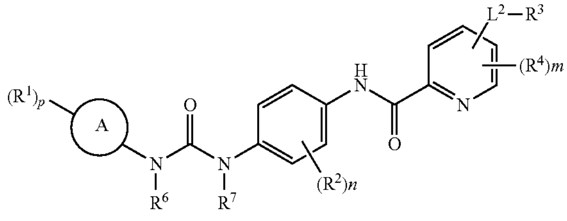

or pharmaceutically acceptable salts, solvates, hydrates or clathrates thereof, wherein the variables are as described elsewhere herein. In certain embodiments, compounds provided herein are of Formula V, wherein $R^1$ is tert-butyl; $R^3$ is optionally substituted piperidinyl, piperazinyl, azetidinyl, morpholinyl, pyrrolidinyl, quinuclidine, octahydroquinolizinyl, azabicyclo[3.2.1]octanyl, and wherein the substituents, when present are selected from one or more, in one embodiment, 1-7, in another embodiment, 1-5, in another embodiment, one, two or three $Q^1$ groups, each independently selected from —$CH_3$, —$CH_2$—$CH_3$, —$CH_2CF_3$, —CH—$(CH_3)_2$, —$C(O)O(CH_3)_3$, —$(CH_2)_2S(O)_2CH_3$, —$CH_2C(O)N(CH_3)_2$, —$C(CH_3)_3$, cyclopropyl and oxetanyl; and other variables are as described herein.

In certain embodiments, compounds provided herein are of Formula VI

VI

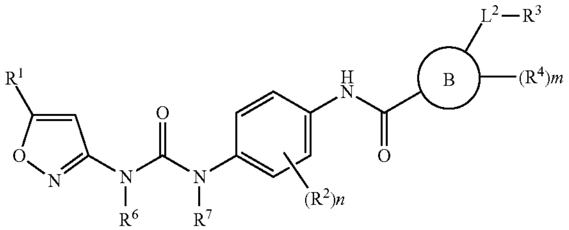

or pharmaceutically acceptable salts, solvates, hydrates or clathrates thereof, wherein the variables are as described elsewhere herein. In certain embodiments, compounds provided herein are of Formula VI, wherein $R^1$ is tert-butyl; B is

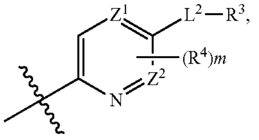

where m is 0 or 1; n is 0 or 1; $Z^1$ and $Z^2$ are selected from (i), (ii) and (iii) as follows:

((i) $Z^1$ and $Z^2$ are both $CR^{4a}$, (ii) $Z^1$ is N, and $Z^2$ is $CR^{4a}$, and (iii) $Z^1$ is $CR^{4a}$, and $Z^2$ is N;

each $CR^{4a}$ is independently hydrogen or $R^4$; $R^6$ and $R^7$ are each independently hydrogen or alkyl; $R^2$ is alkyl; and $R^3$ is optionally substituted piperidinyl, piperazinyl, azetidinyl, pyrrolidinyl, morpholinyl, quinuclidine, octahydroquinolizinyl, azabicyclo[3.2.1]octanyl, and wherein the substituents, when present are selected from one or more, in one embodiment, 1-7, in another embodiment, 1-5, in another embodiment, one, two or three $Q^1$ groups, each independently selected from —$CH_3$, —$CH_2$—$CH_3$, —$CH_2CF_3$, —CH—$(CH_3)_2$, —$C(O)O(CH_3)_3$, —$(CH_2)_2S(O)_2CH_3$, —$CH_2C(O)N(CH_3)_2$, —$C(CH_3)_3$, cyclopropyl and oxetanyl; and other variables are as described herein.

In certain embodiments, compounds provided herein are of Formula VII

VII

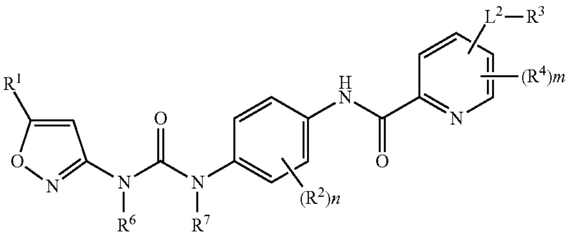

or pharmaceutically acceptable salts, solvates, hydrates or clathrates thereof, wherein the variables are as described elsewhere herein. In certain embodiments, compounds provided herein are of Formula VII, wherein B is 6-membered heteroaryl containing 1 or 2 nitrogen atoms;

$R^1$ is selected from alkyl, halo and haloalkyl;

$R^6$ and $R^7$ are each independently selected from hydrogen and lower alkyl;

each $R^2$ is independently selected from alkyl and alkoxy;

each $R^4$ is alkyl;

$L^2$ is direct bond, alkylene, —$R^8OR^9$— or —$R^8N(R^{10})R^9$—;

$R^8$ and $R^9$ are each independently direct bond or alkylene;

$R^{10}$ is hydrogen or alkyl;

$R^3$ is selected as follows:

i) $R^3$ is —$NR^{3a}R^{3b}$, or ii) $R^3$ is optionally substituted heterocyclyl containing at least one nitrogen atom, such that the heterocyclyl ring is connected to $L^2$ on the carbon atom of the ring, and wherein the substituents, when present are selected from one or more, in one embodiment, 1-7, in another embodiment, 1-5, in another embodiment, one, two or three $Q^1$ groups, each independently selected from alkyl, haloalkyl, cycloalkyl, —$R^uC(J)OR^x$, —$R^uS(O)_tR^w$, —$R^uC(J)N(R^y)(R^z)$, and heterocyclyl, $R^{3a}$ and $R^{3b}$ are selected as follows:

i) $R^{3a}$ and $R^{3b}$ are each independently alkyl, alkenyl, alkynyl, cycloalkyl, or haloalkyl; or ii) $R^{3a}$ and $R^{3b}$ together form optionally substituted heterocyclyl, wherein the substituents when present are selected from one, two or three $Q^1$ groups, each $R^u$ is independently alkylene or a direct bond;

$R^w$ is alkyl;

each $R^x$ is alkyl;

$R^y$ and $R^z$ are each hydrogen or alkyl;

J is O; and t is 0-2.

In certain embodiments, compounds provided herein are of Formula VII, wherein $R^1$ is tert-butyl; $R^3$ is optionally substituted piperidinyl, piperazinyl, azetidinyl, pyrrolidinyl, morpholinyl, quinuclidine, octahydroquinolizinyl, azabicyclo[3.2.1]octanyl, and wherein the substituents, when present are selected from one or more, in one embodiment, 1-7, in another embodiment, 1-5, in another embodiment, one, two or three $Q^1$ groups, each independently selected from —$CH_3$, —$CH_2$—$CH_3$, —$CH_2CF_3$, —CH—$(CH_3)_2$, —C(O)O$(CH_3)_3$, —$(CH_2)_2S(O)_2CH_3$, —$CH_2C(O)N(CH_3)_2$, —$C(CH_3)_3$, cyclopropyl and oxetanyl; and other variables are as described herein.

In certain embodiments, compounds provided herein are of Formula VIII

VIII

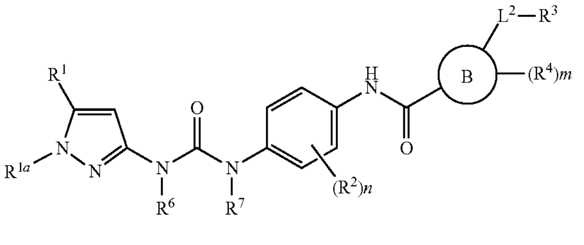

or pharmaceutically acceptable salts, solvates, hydrates or clathrates thereof, wherein B is 6-membered heteroaryl containing 1 or 2 nitrogen atoms;

$R^1$ is alkyl, halo or haloalkyl;

$R^{1a}$ is hydrogen or alkyl;

$R^6$ and $R^7$ are each independently selected from hydrogen and lower alkyl;

each $R^2$ is independently selected from alkyl and alkoxy;

each $R^4$ is alkyl;

$L^2$ is direct bond, alkylene, —$R^8OR^9$— or —$R^8N(R^{10})R^9$—;

$R^8$ and $R^9$ are each independently direct bond or alkylene;

$R^{10}$ is hydrogen or alkyl;

$R^3$ is selected as follows:

i) $R^3$ is —$NR^{3a}R^{3b}$, or ii) $R^3$ is optionally substituted heterocyclyl containing at least one nitrogen atom, such that the heterocyclyl ring is connected to $L^2$ on the carbon atom of the ring, and wherein the substituents, when present are selected from one or more, in one embodiment, 1-7, in another embodiment, 1-5, in another embodiment, one, two or three $Q^1$ groups, each independently selected from alkyl, haloalkyl, cycloalkyl, —$R^uC(J)OR^x$, —$R^uS(O)_tR^w$, —$R^uC(J)N(R^y)(R^z)$, and heterocyclyl, $R^{3a}$ and $R^{3b}$ are selected as follows:

i) $R^{3a}$ and $R^{3b}$ are each independently alkyl, alkenyl, alkynyl, cycloalkyl, or haloalkyl; or ii) $R^{3a}$ and $R^{3b}$ together form optionally substituted heterocyclyl, wherein the substituents when present are selected from one, two or three $Q^1$ groups, each $R^u$ is independently alkylene or a direct bond;

$R^w$ is alkyl;

each $R^x$ is alkyl;

$R^y$ and $R^z$ are each hydrogen or alkyl;

J is O; and t is 0-2.

In certain embodiments, compounds provided herein are of Formula VIII, wherein $R^1$ is tert-butyl; B is

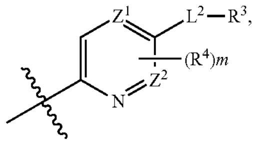

where m is 0 or 1; n is 0 or 1; $Z^1$ and $Z^2$ are selected from (i), (ii) and (iii) as follows:

(i) $Z^1$ and $Z^2$ are both $CR^{4a}$;

(ii) $Z^1$ is N, and $Z^2$ is $CR^{4a}$; and (iii) $Z^1$ is $CR^{4a}$, and $Z^2$ is N;

each $CR^{4a}$ is independently hydrogen or $R^4$; $R^6$ and $R^7$ are each independently hydrogen or alkyl; $R^2$ is alkyl; and $R^3$ is optionally substituted piperidinyl, piperazinyl, azetidinyl, pyrrolidinyl, morpholinyl, quinuclidine, octahydroquinolizinyl, azabicyclo[3.2.1]octanyl, and wherein the substituents, when present are selected from one or more, in one embodiment, 1-7, in another embodiment, 1-5, in another embodiment, one, two or three $Q^1$ groups, each independently selected from —$CH_3$, —$CH_2$—$CH_3$, —$CH_2CF_3$, —CH—$(CH_3)_2$, —$C(O)O(CH_3)_3$, —$(CH_2)_2S(O)_2CH_3$, —$CH_2C(O)N(CH_3)_2$, —$C(CH_3)_3$, cyclopropyl and oxetanyl; and other variables are as described herein.

In certain embodiments, compounds provided herein are of Formula IX

IX

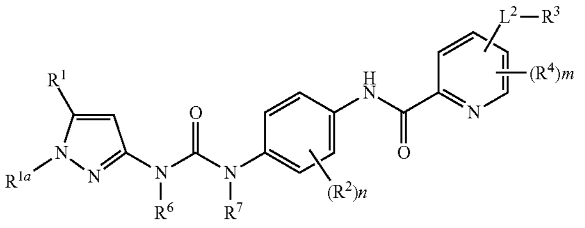

or pharmaceutically acceptable salts, solvates, hydrates or clathrates thereof, wherein the variables are as described elsewhere herein. In certain embodiments, compounds provided herein are of Formula IX, wherein $R^1$ is tert-butyl; $R^3$ is optionally substituted piperidinyl, piperazinyl, azetidinyl, morpholinyl, pyrrolidinyl, quinuclidine, octahydroquinolizinyl, azabicyclo[3.2.1]octanyl, and wherein the substituents, when present are selected from one or more, in one embodiment, 1-7, in another embodiment, 1-5, in another embodiment, one, two or three $Q^1$ groups, each independently selected from $—CH_3$, $—CH_2—CH_3$, $—CH_2CF_3$, $—CH—(CH_3)_2$, $—C(O)O(CH_3)_3$, $—(CH_2)_2S(O)_2CH_3$, $—CH_2C(O)N(CH_3)_2$, $—C(CH_3)_3$, cyclopropyl and oxetanyl; and other variables are as described herein.

In certain embodiments, compounds provided herein are of Formula X

X

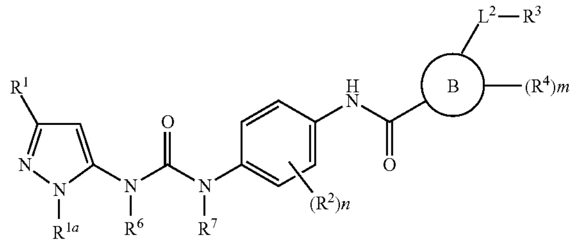

or pharmaceutically acceptable salts, solvates, hydrates or clathrates thereof, wherein the variables are as described elsewhere herein. In certain embodiments, compounds provided herein are of Formula X, wherein $R^1$ is tert-butyl; B is

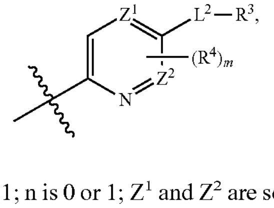

where m is 0 or 1; n is 0 or 1; $Z^1$ and $Z^2$ are selected from (i), (ii) and (iii) as follows:

(i) $Z^1$ and $Z^2$ are both $CR^{4a}$, (ii) $Z^1$ is N, and $Z^2$ is $CR^{4a}$, and (iii) $Z^1$ is $CR^{4a}$, and $Z^2$ is N;

each $CR^{4a}$ is independently hydrogen or $R^4$; $R^6$ and $R^7$ are each independently hydrogen or alkyl; $R^2$ is alkyl; and $R^3$ is optionally substituted piperidinyl, piperazinyl, azetidinyl, pyrrolidinyl, morpholinyl, quinuclidine, octahydroquinolizinyl, azabicyclo[3.2.1]octanyl, and wherein the substituents, when present are selected from one or more, in one embodiment, 1-7, in another embodiment, 1-5, in another embodiment, one, two or three $Q^1$ groups, each independently selected from $—CH_3$, $—CH_2—CH_3$, $—CH_2CF_3$, $—CH—(CH_3)_2$, $—C(O)O(CH_3)_3$, $—(CH_2)_2S(O)_2CH_3$, $—CH_2C(O)N(CH_3)_2$, $—C(CH_3)_3$, cyclopropyl and oxetanyl; and other variables are as described herein.

In certain embodiments, compounds are of Formula XI

XI

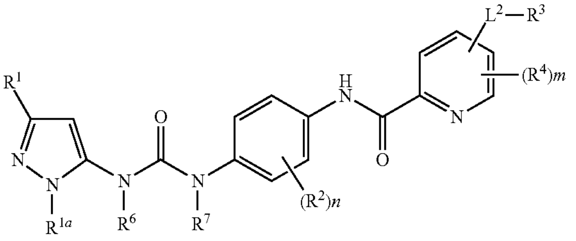

or pharmaceutically acceptable salts, solvates, hydrates or clathrates thereof, wherein the variables are as described elsewhere herein. In certain embodiments, compounds provided herein are of Formula XI, wherein $R^1$ is selected from alkyl, halo and haloalkyl;

$R^{1a}$ is hydrogen or alkyl;

$R^6$ and $R^7$ are each independently selected from hydrogen and lower alkyl;

each $R^2$ is independently selected from alkyl and alkoxy;

each $R^4$ is alkyl;

$L^2$ is direct bond, alkylene, $—R^8OR^9—$, or)$R^8N(R^{10})R^9—$;

$R^8$ and $R^9$ are each independently direct bond or alkylene;

$R^{10}$ is hydrogen or alkyl;

$R^3$ is selected as follows:

i) $R^3$ is $—NR^{3a}R^{3b}$, or ii) $R^3$ is optionally substituted heterocyclyl containing at least one nitrogen atom, such that the heterocyclyl ring is connected to $L^2$ on the carbon atom of the ring, and wherein the substituents, when present are selected from one or more, in one embodiment, 1-7, in another embodiment, 1-5, in another embodiment, one, two or three $Q^1$ groups, each independently selected from alkyl, haloalkyl, cycloalkyl, $—R^uC(J)OR^x$, $—R^uS(O)_tR^w$, $—R^uC(J)N(R^y)(R^z)$, and heterocyclyl, $R^{3a}$ and $R^{3b}$ are selected as follows:

i) $R^{3a}$ and $R^{3b}$ are each independently alkyl, alkenyl, alkynyl, cycloalkyl, or haloalkyl; or ii) $R^{3a}$ and $R^{3b}$ together form optionally substituted heterocyclyl, wherein the substituents when present are selected from one, two or three $Q^1$ groups, each $R^u$ is independently alkylene or a direct bond;

$R^w$ is alkyl;

each $R^x$ is alkyl;

$R^y$ and $R^z$ are each hydrogen or alkyl;

J is O; and t is 0-2.

In certain embodiments, compounds provided herein are of Formula XI, wherein $R^1$ is tert-butyl; $R^3$ is optionally substituted piperidinyl, piperazinyl, azetidinyl, pyrrolidinyl, morpholinyl, quinuclidine, octahydroquinolizinyl, azabicyclo[3.2.1]octanyl, and wherein the substituents, when present are selected from one or more, in one embodiment, 1-7, in another embodiment, 1-5, in another embodiment, one, two or three $Q^1$ groups, each independently selected from $—CH_3$, $-CH_2-CH_3$, $-CH_2CF_3$, $-CH-(CH_3)_2$, $-C(O)O(CH_3)_3$, $-(CH_2)_2S(O)_2CH_3$, $CH_2C(O)N(CH_3)_2$, $-C(CH_3)_3$, cyclopropyl and oxetanyl; and other variables are as described herein.

In certain embodiments, compounds provided herein are of Formula XII:

XII

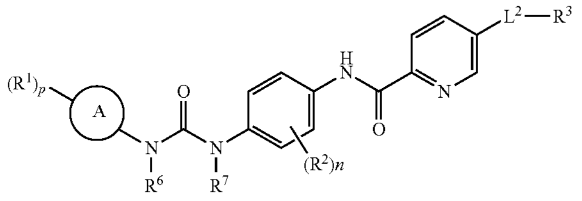

or pharmaceutically acceptable salts, solvates, hydrates or clathrates thereof, wherein the variables are as described elsewhere herein. In certain embodiments, the compounds provided herein are of Formula XII wherein $L^2$ is a direct bond, $-CH_2-$, $-O(CH_2)_{0-3}-$ and the other variables are as described elsewhere herein. In certain embodiments, n is 0.

In certain embodiments, compounds provided herein are of Formula XIIa:

XIIa

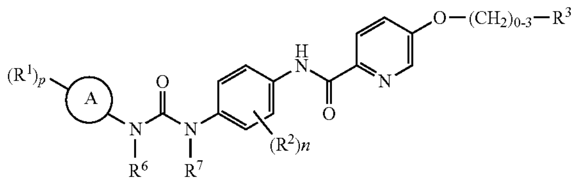

or pharmaceutically acceptable salts, solvates, hydrates or clathrates thereof, wherein the variables are as described elsewhere herein. In certain embodiments, compounds provided herein are of Formula XII or XIIa, wherein $R^1$ is tert-butyl; $R^3$ is optionally substituted piperidinyl, piperazinyl, azetidinyl, morpholinyl, pyrrolidinyl, quinuclidine, octahydroquinolizinyl, azabicyclo[3.2.1]octanyl, and wherein the substituents, when present are selected from one or more, in one embodiment, 1-7, in another embodiment, 1-5, in another embodiment, one, two or three $Q^1$ groups, each independently selected from $-CH_3$, $-CH_2-CH_3$, $-CH_2CF_3$, $-CH-(CH_3)_2$, $-C(O)O(CH_3)_3$, $-(CH_2)_2S(O)_2CH_3$, $-CH_2C(O)N(CH_3)_2$, $-C(CH_3)_3$, cyclopropyl and oxetanyl; and other variables are as described herein.

In certain embodiments, compounds provided herein are of Formula XIII

XIII

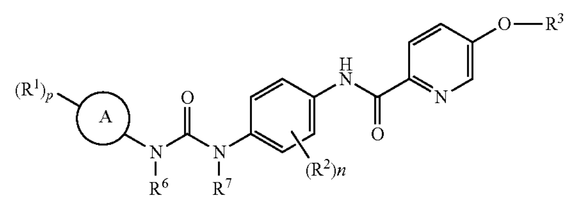

or pharmaceutically acceptable salts, solvates, hydrates or clathrates thereof, wherein the variables are as described elsewhere herein. In certain embodiments, compounds provided herein are of Formula XIII, wherein $R^1$ is tert-butyl; $R^3$ is optionally substituted piperidinyl, piperazinyl, azetidinyl, pyrrolidinyl, quinuclidine, octahydroquinolizinyl, azabicyclo[3.2.1]octanyl, and wherein the substituents, when present are selected from one or more, in one embodiment, 1-7, in another embodiment, 1-5, in another embodiment, one, two or three $Q^1$ groups, each independently selected from $-CH_3$, $-CH_2-CH_3$, $-CH_2CF_3$, $-CH-(CH_3)_2$, $-C(O)O(CH_3)_3$, $-(CH_2)_2S(O)_2CH_3$, $-CH_2C(O)N(CH_3)_2$, $-C(CH_3)_3$, cyclopropyl and oxetanyl; and other variables are as described herein.

In certain embodiments, compounds provided herein are of Formula XIVa or XIVb

XIVa

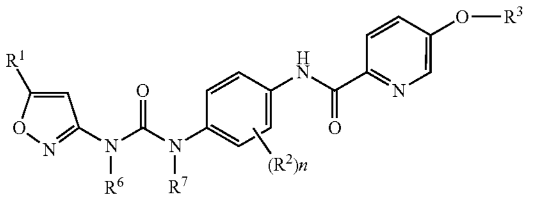

or

XIVb

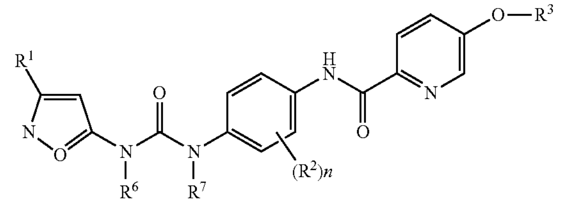

or pharmaceutically acceptable salts, solvates, hydrates or clathrates thereof, wherein the variables are as described elsewhere herein. In certain embodiments, compounds provided herein are of Formula XIVa or XIVb, wherein $R^1$ is tert-butyl; $R^3$ is optionally substituted piperidinyl, piperazinyl, azetidinyl, pyrrolidinyl, quinuclidine, octahydroquinolizinyl, azabicyclo[3.2.1]octanyl, and wherein the substituents, when present are selected from one or more, in one embodiment, 1-7, in another embodiment, 1-5, in another embodiment, one, two or three $Q^1$ groups, each independently selected from $-CH_3$, $-CH_2-CH_3$, $-CH_2CF_3$, $-CH-(CH_3)_2$, $-C(O)O(CH_3)_3$, $(CH_2)_2S(O)_2CH_3$, $-CH_2C(O)N(CH_3)_2$, $-C(CH_3)_3$, cyclopropyl and oxetanyl; and other variables are as described herein.

In certain embodiments, compounds provided herein are of Formula XV

XV

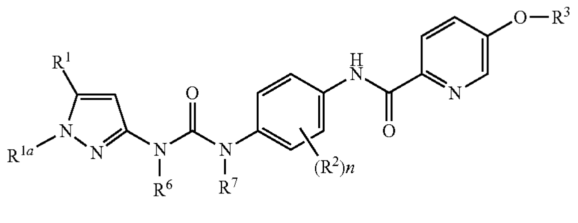

or pharmaceutically acceptable salts, solvates, hydrates or clathrates thereof, wherein the variables are as described elsewhere herein. In certain embodiments, compounds provided herein are of Formula XV, wherein $R^1$ is tert-butyl; $R^{1a}$ is hydrogen or alkyl, $R^3$ is optionally substituted piperidinyl, piperazinyl, azetidinyl, pyrrolidinyl, quinuclidine, octahydroquinolizinyl, azabicyclo[3.2.1]octanyl, and wherein the substituents, when present are selected from one or more, in one embodiment, 1-7, in another embodiment, 1-5, in another embodiment, one, two or three $Q^1$ groups, each independently selected from $—CH_3$, $—CH_2—CH_3$, $—CH_2CF_3$, $—CH—(CH_3)_2$, $—C(O)O(CH_3)_3$, $—(CH_2)_2S(O)_2CH_3$, $—CH_2C(O)N(CH_3)_2$, $—C(CH_3)_3$, cyclopropyl and oxetanyl; and other variables are as described herein.

In certain embodiments, compounds provided herein are of Formula XVI

XVI

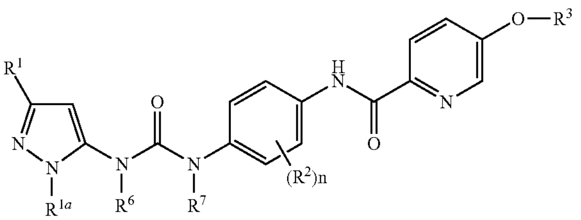

or pharmaceutically acceptable salts, solvates, hydrates or clathrates thereof, wherein the variables are as described elsewhere herein. In certain embodiments, compounds provided herein are of Formula XVI, wherein $R^1$ is tert-butyl; $R^{1a}$ is hydrogen or alkyl, $R^3$ is optionally substituted piperidinyl, piperazinyl, azetidinyl, pyrrolidinyl, quinuclidine, octahydroquinolizinyl, azabicyclo[3.2.1]octanyl, and wherein the substituents, when present are selected from one or more, in one embodiment, 1-7, in another embodiment, 1-5, in another embodiment, one, two or three $Q^1$ groups, each independently selected from $—CH_3$, $—CH_2—CH_3$, $—CH_2CF_3$, $—CH—(CH_3)_2$, $—C(O)O(CH_3)_3$, $—(CH_2)_2S(O)_2CH_3$, $—CH_2C(O)N(CH_3)_2$, $—C(CH_3)_3$, cyclopropyl and oxetanyl; and other variables are as described herein.

In certain embodiments, provided herein are compounds of Formula XVII:

XVII

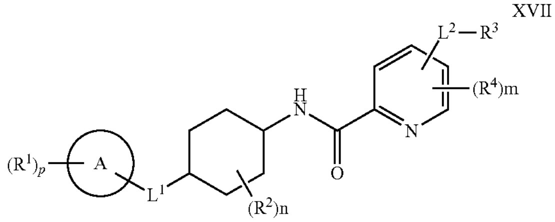

or pharmaceutically acceptable salts, solvates, hydrates or clathrates thereof, wherein the variables are as described elsewhere herein.

In certain embodiments, provided herein are compounds of Formula XVIII:

XVIII

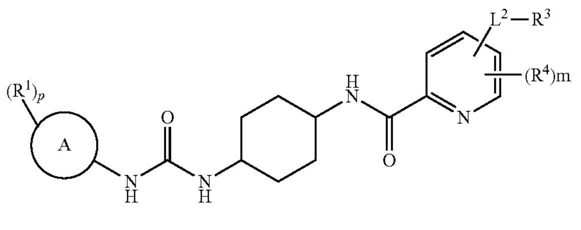

or pharmaceutically acceptable salts, solvates, hydrates or clathrates thereof, wherein the variables are as described elsewhere herein. In certain embodiments, provided herein are compounds of Formula XVIII or pharmaceutically acceptable salts, solvates, hydrates or clathrates thereof, wherein:

A is azolyl;

each $R^1$ is independently selected from halo, alkyl, alkenyl, alkynyl, alkoxy, hydroxyl, haloalkoxy, cycloalkyl, cycloalkylalkyl, hydroxyalkyl, haloalkyl, aryl, arylalkyl, heterocyclyl, heterocyclylalkyl, heteroaryl, and heteroarylalkyl, where the alkyl, alkenyl, alkynyl, alkoxy, haloalkoxy, cycloalkyl, cycloalkylalkyl, hydroxyalkyl, haloalkyl, aryl, heterocyclyl, and heteroaryl groups are optionally substituted with 1 to 5 groups selected from halo, hydroxy, alkoxy, cycloalkyl, cyano, and $—R^uN(R^y)(R^z)$;

each $R^4$ is independently selected from alkyl, cycloalkyl, amino, hydroxy, and alkoxy;

$L^2$ is direct bond, alkylene, alkenylene, alkynylene, $—R^8OR^9—$, $—R^8SR^9—$, or $—R^8N(R^{10})R^9—$;

$R^8$ and $R^9$ are each independently direct bond, alkylene, alkenylene, or alkynylene;

$R^{10}$ is hydrogen or alkyl;

$R^3$ is selected as follows:

i) $R^3$ is $—NR^{3a}R^{3b}$, or ii) $R^3$ is optionally substituted heterocyclyl or optionally substituted heteroaryl containing at least one nitrogen atom, such that the heterocyclyl or heteroaryl ring is connected to $L^2$ on the carbon atom of the ring, and wherein the substituents, when present are selected from one or more, in one embodiment, 1-9, in another embodiment, 1-7, in another embodiment, 1-5, in another embodiment, 1-3, or in another embodiment, one, two or three $Q^1$ groups;

$R^{3a}$ and $R^{3b}$ are selected as follows:

i) $R^{3a}$ and $R^{3b}$ are each independently alkyl, alkenyl, alkynyl, cycloalkyl, or haloalkyl; or ii) $R^{3a}$ and $R^{3b}$ together form optionally substituted heterocyclyl, wherein the substituents when present are selected from one, two or three $Q^1$ groups, each $R^u$ is independently alkylene or a direct bond;

$R^w$ is alkyl, alkenyl, alkynyl, cycloalkyl, cycloalkylalkyl, heterocyclyl, heterocyclylalkyl, aryl, aralkyl, heteroaryl, or heteroaralkyl;

each $R^x$ is independently hydrogen, alkyl, haloalkyl, alkenyl, alkynyl, cycloalkyl, cycloalkylalkyl, heterocyclyl, heterocyclylalkyl, aryl, aralkyl, heteroaryl, or heteroaralkyl;

$R^y$ and $R^z$ are each independently selected from (i) and (ii) below:

(i) $R^y$ and $R^z$ are each independently hydrogen, alkyl, alkenyl, alkynyl, cycloalkyl, or haloalkyl; or (ii) $R^y$ and $R^z$, together with the nitrogen atom to which they are attached, form a heterocyclyl or heteroaryl, optionally substituted with one, two or three Q groups selected from halo, oxo, thioxo, hydroxy, alkoxy, alkyl, haloalkyl, hydroxyalkyl, aminoalkyl, alkenyl, alkynyl, cycloalkyl, cycloalkylalkyl, aryl, aralkyl, heteroaryl, heteroaralkyl, heterocyclyl and heterocyclylalkyl;

each $Q^1$ is independently selected from halo, oxo, thioxo, alkyl, haloalkyl, alkenyl, alkynyl, cycloalkyl, cycloalkylalkyl, aryl, aralkyl, heteroaryl, heteroaralkyl, heterocyclyl, heterocyclylalkyl, $—R^uOR^x$, $—R^uOR^uN(R^y)(R^z)$, $—R^uN(R^y)(R^z)$, $—R^uC(J)R^x$, $—R^uC(J)OR^x$, $—R^uC(J)N(R^y)(R^z)$, $—R^uC(J)SR^x$, $—R^uS(O)_tR^w$, $—R^uOC(J)R^x$, $—R^uOC(J)OR^x$, $—R^uOC(J)N(R^y)(R^z)$, $—R^uOC(J)SR^x$, $—R^uN(R^x)C(J)R^x$, $—R^uN(R^x)C(J)OR^x$, $—R^uN(R^x)C(J)N(R^y)(R^z)$, $—R^uN(R^x)C(J)SR^x$, and $—R^uN(R^x)S(O)_tR^w$;

J is O, $NR^X$ or S;

t is 0-2;

m is 0-4; and p is 1-4.

In certain embodiments, provided herein are compounds of Formula XVIII:

XIX

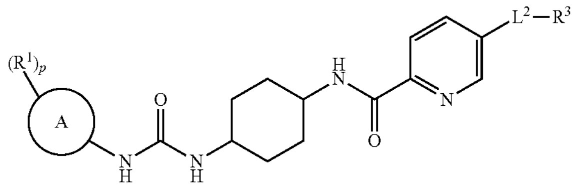

or pharmaceutically acceptable salts, solvates, hydrates or clathrates thereof, wherein the variables are as described elsewhere herein. In certain embodiments, provided herein are compounds of Formula XIX or pharmaceutically acceptable salts, solvates, hydrates or clathrates thereof, wherein:

A is azolyl;

each $R^1$ is independently selected from halo, alkyl, alkenyl, alkynyl, alkoxy, hydroxyl, haloalkoxy, cycloalkyl, cycloalkylalkyl, hydroxyalkyl, haloalkyl, aryl, arylalkyl, heterocyclyl, heterocyclylalkyl, heteroaryl, and heteroarylalkyl, where the alkyl, alkenyl, alkynyl, alkoxy, haloalkoxy, cycloalkyl, cycloalkylalkyl, hydroxyalkyl, haloalkyl, aryl, heterocyclyl, and heteroaryl groups are optionally substituted with 1 to 5 groups selected from halo, hydroxy, alkoxy, cycloalkyl, cyano, and —$R^uN(R^y)(R^z)$;

$L^2$ is direct bond, alkylene, alkenylene, alkynylene, —$R^8OR^9$—, —$R^8SR^9$—, or —$R^8N(R^{10})R^9$—;

$R^8$ and $R^9$ are each independently direct bond, alkylene, alkenylene, or alkynylene;

$R^{10}$ is hydrogen or alkyl;

$R^3$ is selected as follows:

i) $R^3$ is —$NR^{3a}R^{3b}$, or ii) $R^3$ is optionally substituted heterocyclyl or optionally substituted heteroaryl containing at least one nitrogen atom, such that the heterocyclyl or heteroaryl ring is connected to $L^2$ on the carbon atom of the ring, and wherein the substituents, when present are selected from one or more, in one embodiment, 1-9, in another embodiment, 1-7, in another embodiment, 1-5, in another embodiment, 1-3, or in another embodiment, one, two or three $Q^1$ groups;

$R^{3a}$ and $R^{3b}$ are selected as follows:

i) $R^{3a}$ and $R^{3b}$ are each independently alkyl, alkenyl, alkynyl, cycloalkyl, or haloalkyl; or ii) $R^{3a}$ and $R^{3b}$ together form optionally substituted heterocyclyl, wherein the substituents when present are selected from one, two or three $Q^1$ groups, each $R^u$ is independently alkylene or a direct bond;

$R^w$ is alkyl, alkenyl, alkynyl, cycloalkyl, cycloalkylalkyl, heterocyclyl, heterocyclylalkyl, aryl, aralkyl, heteroaryl, or heteroaralkyl;

each $R^x$ is independently hydrogen, alkyl, haloalkyl, alkenyl, alkynyl, cycloalkyl, cycloalkylalkyl, heterocyclyl, heterocyclylalkyl, aryl, aralkyl, heteroaryl, or heteroaralkyl;

$R^y$ and $R^z$ are each independently selected from (i) and (ii) below:

(i) $R^y$ and $R^z$ are each independently hydrogen, alkyl, alkenyl, alkynyl, cycloalkyl, or haloalkyl; or (ii) $R^y$ and $R^z$, together with the nitrogen atom to which they are attached, form a heterocyclyl or heteroaryl, optionally substituted with one, two or three Q groups selected from halo, oxo, thioxo, hydroxy, alkoxy, alkyl, haloalkyl, hydroxyalkyl, aminoalkyl, alkenyl, alkynyl, cycloalkyl, cycloalkylalkyl, aryl, aralkyl, heteroaryl, heteroaralkyl, heterocyclyl and heterocyclylalkyl;

each $Q^1$ is independently selected from halo, oxo, thioxo, alkyl, haloalkyl, alkenyl, alkynyl, cycloalkyl, cycloalkylalkyl, aryl, aralkyl, heteroaryl, heteroaralkyl, heterocyclyl, heterocyclylalkyl, —$R^uOR^x$, —$R^uOR^uN(R^y)(R^z)$, —$R^uN(R^y)(R^z)$, —$R^uC(J)R^x$, —$R^uC(J)OR^x$, —$R^uC(J)N(R^y)(R^z)$, —$R^uC(J)SR^x$, —$R^uS(O)_tR^w$, —$R^uOC(J)R^x$, —$R^uOC(J)OR^x$, —$R^uOC(J)N(R^y)(R^z)$, —$R^uOC(J)SR^x$, —$R^uN(R^x)C(J)R^x$, —$R^uN(R^x)C(J)OR^x$, —$R^uN(R^x)C(J)N(R^y)(R^z)$, —$R^uN(R^x)C(J)SR^x$, and —$R^uN(R^x)S(O)_tR^w$;

J is O, $NR^X$ or S;

t is 0-2;

p is 1-4.

In another embodiment, a compound provided herein is selected from

N-(4-(3-(5-tert-butylisoxazol-3-yl)ureido)phenyl)-4-(piperidin-4-yloxy)picolinamide hydrochloride, N-(4-(3-(5-tert-butylisoxazol-3-yl)ureido)phenyl)-4-(1-ethylpiperidin-4-yloxy)picolinamide, N-(4-(3-(5-tert-butylisoxazol-3-yl)ureido)phenyl)-4-(4-methylpiperazin-1-yl)picolinamide, N-(4-(3-(5-tert-butylisoxazol-3-yl)ureido)phenyl)-4-(1-methylpiperidin-4-yloxy)picolinamide, N-(4-(3-(5-tert-butylisoxazol-3-yl)ureido)phenyl)-4-(2-morpholinoethoxy)picolinamide, N-(4-(3-(5-tert-butylisoxazol-3-yl)ureido)phenyl)-5-(piperidin-4-yloxy)picolinamide hydrochloride, N-(4-(3-(5-tert-butylisoxazol-3-yl)ureido)phenyl)-5-(1-ethylpiperidin-4-yloxy)picolinamide, N-(4-(3-(5-tert-butylisoxazol-3-yl)ureido)phenyl)-4-((diethylamino)methyl)picolinamide, N-(4-(3-(5-tert-butylisoxazol-3-yl)ureido)phenyl)-5-(4-methylpiperazin-1-yl)picolinamide, N-(4-(3-(5-tert-butylisoxazol-3-yl)ureido)phenyl)-5-(piperidin-4-ylmethyl)picolinamide hydrochloride, N-(4-(3-(5-tert-butylisoxazol-3-yl)ureido)phenyl)-5-((1-ethylpiperidin-4-yl)methyl)picolinamide, N-(4-(3-(5-tert-butylisoxazol-3-yl)ureido)phenyl)-5-(morpholinomethyl)picolinamide, N-(4-(3-(5-tert-butylisoxazol-3-yl)ureido)phenyl)-5-(1-methylpiperidin-4-yl)picolinamide, N-(4-(3-(5-tert-butylisoxazol-3-yl)ureido)phenyl)-5-(1-ethylpiperidin-4-yl)picolinamide, N-(4-(3-(5-tert-butylisoxazol-3-yl)ureido)phenyl)-5-((4-methylpiperazin-1-yl)methyl)picolinamide, N-(4-(3-(5-(1,3-difluoro-2-methylpropan-2-yl)isoxazol-3-yl)ureido)phenyl)-5-(1-ethylpiperidin-4-yloxy)picolinamide, N-(4-(3-(5-(1,3-difluoro-2-methylpropan-2-yl)isoxazol-3-yl)ureido)phenyl)-5-(1-methylpiperidin-4-yloxy)picolinamide, N-(4-(3-(5-(1,3-difluoro-2-methylpropan-2-yl)isoxazol-3-yl)ureido)phenyl)-5-(1-(2,2,2-trifluoroethyl)piperidin-4-yloxy)picolinamide, N-(4-(3-(5-(1,3-difluoro-2-methylpropan-2-yl)isoxazol-3-yl)ureido)phenyl)-5-(1-isopropylpiperidin-4-yloxy)picolinamide, N-(4-(3-(5-tert-butylisoxazol-3-yl)ureido)phenyl)-5-(1-(2,2,2-trifluoroethyl)piperidin-4-yloxy)picolinamide, N-(4-(3-(5-tert-butylisoxazol-3-yl)ureido)phenyl)-5-(1-ethylazetidin-3-yloxy)picolinamide, N-(4-(3-(5-tert-butylisoxazol-3-yl)ureido)phenyl)-5-(1-isopropylazetidin-3-yloxy)picolinamide, N-(4-(3-(5-tert-butylisoxazol-3-yl)ureido)phenyl)-5-(1-(oxetan-3-yl)azetidin-3-yloxy)picolinamide, N-(4-(3-(5-tert-butylisoxazol-3-yl)ureido)phenyl)-5-(1-isopropylpyrrolidin-3-yloxy)picolinamide, N-(4-(3-(5-tert-butylisoxazol-3-yl)ureido)phenyl)-5-(1-ethylpyrrolidin-3-yloxy)picolinamide, 4-(6-(4-(3-(5-tert-butylisoxazol-3-yl)ureido)phenylcarbamoyl)pyridin-3-yloxy)-1-isopropylpiperidinium methanesulfonate, 3-(6-(4-(3-(5-tert-butylisoxazol-3-yl)ureido)phenylcarbamoyl)pyridin-3-yloxy)-1-(oxetan-3-yl)pyrrolidinium methanesulfonate, 1-ethyl-4-(6-(4-(3-(3-(2-fluoropropan-2-yl)isoxazol-5-yl)ureido)phenylcarbamoyl)pyridin-3-yloxy)piperidinium methanesulfonate, N-(4-(3-(5-(tert-butyl)isoxazol-3-yl)ureido)phenyl)-5-((1-methylpyrrolidin-3-yl)oxy)picolinamide, N-(4-(3-(5-(tert-butyl)isoxazol-3-yl)ureido)phenyl)-5-((1-isobutylpyrrolidin-3-yl)oxy)picolinamide, 3-(6-(4-(3-(5-tert-butylisoxazol-3-yl)-1-methylureido)phenylcarbamoyl)pyridin-3-yloxy)-1-isopropylpyrrolidinium methanesulfonate, 3-(6-(4-(3-(5-tert-butylisoxazol-3-yl)ureido)phenylcarbamoyl)pyridin-3-yloxy)-1-(2-(methylsulfonyl)ethyl)pyrrolidinium methanesulfonate, 3-(6-(4-(3-(5-tert-butylisoxazol-3-yl)ureido)phenylcarbamoyl)pyridin-3-yloxy)-1-(2-(dimethylamino)-2-oxoethyl)pyrrolidinium methanesulfonate, 4-(6-(4-(3-(5-tert-butylisoxazol-3-yl)ureido)phenylcarbamoyl)pyridin-3-yloxy)-1,2,2,6,6-pentamethylpiperidinium methanesulfonate, 4-(6-(4-(3-(5-tert-butylisoxazol-3-yl)ureido)phenylcarbamoyl)pyridin-3-yloxy)-1-cyclopropylpiperidinium methanesulfonate, 1-tert-butyl-4-(6-(4-(3-(5-tert-butylisoxazol-3-yl)ureido)phenylcarbamoyl)pyridin-3-yloxy)piperidinium methanesulfonate, 1-ethyl-4-(6-(4-(3-(5-(1,1,1-trifluoro-2-methylpropan-2-yl)isoxazol-3-yl)ureido)phenylcarbamoyl)pyridin-3-yloxy)piperidinium methanesulfonate, 1-isopropyl-4-(6-(4-(3-(5-(1,1,1-trifluoro-2-methylpropan-2-yl)isoxazol-3-yl)ureido)phenylcarbamoyl)pyridin-3-yloxy)piperidinium methanesulfonate, (3R)-3-(6-(4-(3-(5-tert-butylisoxazol-3-yl)ureido)phenylcarbamoyl)pyridin-3-yloxy)-1-isopropylpyrrolidinium methanesulfonate, 4-(6-(4-(3-(5-tert-butylisoxazol-3-yl)ureido)phenylcarbamoyl)pyridazin-3-yloxy)-1,2,2,6,6-pentamethylpiperidinium methanesulfonate, 4-(6-(4-(3-(5-tert-butylisoxazol-3-yl)ureido)-2-methylphenylcarbamoyl)pyridin-3-yloxy)-1,2,2,6,6-pentamethylpiperidinium methanesulfonate, 4-(6-(4-(3-(5-tert-butylisoxazol-3-yl)ureido)-3-methylphenylcarbamoyl)pyridin-3-yloxy)-1,2,2,6,6-pentamethylpiperidinium methanesulfonate, (3S)-3-(6-(4-(3-(5-tert-butylisoxazol-3-yl)ureido)phenylcarbamoyl)pyridin-3-yloxy)-1-isopropylpyrrolidinium methanesulfonate, (1R,5S)-3-(6-(4-(3-(5-tert-butylisoxazol-3-yl)ureido)phenylcarbamoyl)pyridin-3-yloxy)-8-methyl-8-azoniabicyclo[3.2.1]octane methanesulfonate, 4-(6-(4-(3-(5-tert-butylisoxazol-3-yl)ureido)-3-methoxyphenylcarbamoyl)pyridin-3-yloxy)-1,2,2,6,6-pentamethylpiperidinium methanesulfonate, 4-(5-(4-(3-(5-tert-butylisoxazol-3-yl)ureido)phenylcarbamoyl)pyrazin-2-yloxy)-1,2,2,6,6-pentamethylpiperidinium methanesulfonate, 5-((1,2,2,6,6-pentamethylpiperidin-4-yl)oxy)-N-(4-(3-(4-(trifluoromethyl)-1H-pyrazol-1-yl)ureido)phenyl)picolinamide, 4-(6-(4-(3-(3-(2-fluoropropan-2-yl)isoxazol-5-yl)ureido)phenylcarbamoyl)pyridin-3-yloxy)-1,2,2,6,6-pentamethylpiperidinium methanesulfonate, 4-(6-(4-(3-(5-(1,3-difluoro-2-methylpropan-2-yl)isoxazol-3-yl)ureido)phenylcarbamoyl)pyridin-3-yloxy)-1,2,2,6,6-pentamethylpiperidinium methanesulfonate, 1,2,2,6,6-pentamethyl-4-(6-(4-(3-(5-(1,1,1-trifluoro-2-methylpropan-2-yl)isoxazol-3-yl)ureido)phenylcarbamoyl)pyridin-3-yloxy)piperidinium methanesulfonate, N-(4-(3-(5-(tert-butyl)isoxazol-3-yl)ureido)phenyl)-5-((1-isopropyl-2,2,6,6-tetramethylpiperidin-4-yl)oxy)picolinamide, (5S)-5-((6-(4-(3-(5-tert-butylisoxazol-3-yl)ureido)phenylcarbamoyl)pyridin-3-yloxy)methyl)-1,2,2-trimethylpyrrolidinium methanesulfonate, 4-(6-(4-(3-(5-tert-butylisoxazol-3-yl)ureido)phenylcarbamoyl)pyridin-3-yloxy)-1-ethyl-2,2,6,6-tetramethylpiperidinium methanesulfonate, 4-(6-(4-(3-(3-tert-butylisoxazol-5-yl)ureido)phenylcarbamoyl)pyridin-3-yloxy)-1,2,2,6,6-pentamethylpiperidinium methanesulfonate, 4-(6-(4-(3-(3-tert-butylisoxazol-5-yl)ureido)phenylcarbamoyl)pyridin-3-yloxy)-1-isopropylpiperidinium methanesulfonate, (3R)-3-((6-(4-(3-(5-tert-butylisoxazol-3-yl)ureido)phenylcarbamoyl)pyridin-3-yloxy)methyl)-1-isopropylpyrrolidinium methanesulfonate, 4-(6-(4-(3-(3-tert-butylisoxazol-5-yl)ureido)phenylcarbamoyl)pyridin-3-yloxy)-1-ethyl-2,2,6,6-tetramethylpiperidinium methanesulfonate, 4-(6-(4-(3-(3-tert-butylisoxazol-5-yl)ureido)phenylcarbamoyl)pyridin-3-yloxy)-1-ethylpiperidinium methanesulfonate, (3R)-3-((6-(4-(3-(5-tert-butylisoxazol-3-yl)ureido)phenylcarbamoyl)pyridin-3-yloxy)methyl)-1-ethylpyrrolidinium methanesulfonate, 3-(6-(4-(3-(5-tert-butylisoxazol-3-yl)ureido)phenylcarbamoyl)pyridin-3-yl)-1,2,2,6,6-pentamethyl-4-oxopiperidinium methanesulfonate, 4-(6-(4-(3-(5-tert-butylisoxazol-3-yl)ureido)phenylcarbamoyl)pyridin-3-yloxy)-1,2,2,4,6,6-hexamethylpiperidinium methanesulfonate, 3-(6-(4-(3-(5-tert-butylisoxazol-3-yl)ureido)phenylcarbamoyl)pyridin-3-yloxy)-1-azoniabicyclo[2.2.2]octane methanesulfonate, (1S,9aS)-1-((6-(4-(3-(5-tert-butylisoxazol-3-yl)ureido)phenylcarbamoyl)pyridin-3-yloxy)methyl)decahydroquinolizinium methanesulfonate, N-(4-(3-(3-tert-butyl-1-methyl-1H-pyrazol-5-yl)ureido)phenyl)-5-(1,2,2,6,6-pentamethylpiperidin-4-yloxy)picolinamide, N-(4-(3-(1-methyl-5-(trifluoromethyl)-1H-pyrazol-3-yl)ureido)phenyl)-5-(1,2,2,6,6-pentamethylpiperidin-4-yloxy)picolinamide, 4-(6-(4-(3-(5-tert-butylisoxazol-3-yl)ureido)phenylcarbamoyl)pyridin-3-yloxy)-2,2,6,6-tetramethylpiperidinium methanesulfonate, N-(trans-4-(3-(5-(tert-butyl)isoxazol-3-yl)ureido)cyclohexyl)-5-(piperidin-4-yloxy)picolinamide hydrochloride, N-(trans-4-(3-(5-(tert-butyl)isoxazol-3-yl)ureido)cyclohexyl)-5-((1-ethylpiperidin-4-yl)oxy)picolinamide, N-(4-(3-(5-(tert-butyl)isoxazol-3-yl)ureido)phenyl)-6-(4-methylpiperazin-1-yl)picolinamide, N-(4-(3-(5-(tert-butyl)isoxazol-3-yl)ureido)phenyl)-6-(2-morpholinoethoxy)picolinamide, N-(4-(3-(5-(tert-butyl)isoxazol-3-yl)ureido)phenyl)-6-(piperidin-4-yloxy)picolinamide, N-(4-(3-(5-(tert-butyl)isoxazol-3-yl)ureido)phenyl)-6-((diethylamino)methyl)picolinamide, N-(4-(3-(5-(tert-butyl)isoxazol-3-yl)ureido)phenyl)-6-(morpholinomethyl)picolinamide, and 6-(aminomethyl)-N-(4-(3-(5-(tert-butyl)isoxazol-3-yl)ureido)phenyl)picolinamide hydrochloride.

Also provided herein are isotopically enriched analogs of the compounds provided herein. Isotopic enrichment (for example, deuteration) of pharmaceuticals to improve pharmacokinetics ("PK"), pharmacodynamics ("PD"), and toxicity profiles, has been demonstrated previously with some classes of drugs. See, for example, Lijinsky et. al., *Food Cosmet. Toxicol.,* 20: 393 (1982); Lijinsky et. al., *J. Nat. Cancer Inst.,* 69: 1127 (1982); Mangold et. al., *Mutation Res.* 308: 33 (1994); Gordon et. al., *Drug Metab. Dispos.,* 15: 589 (1987); Zello et. al., *Metabolism,* 43: 487 (1994); Gately et. al., *J. Nucl. Med.,* 27: 388 (1986); Wade D, *Chem. Biol. Interact.* 117: 191 (1999).

Isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrease the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a CH bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g, Foster et al., Adv. Drug Res., vol. 14, pp. 1-36 (1985); Kushner et al., Can. J. Physiol. Pharmacol., vol. 77, pp. 79-88 (1999)).

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects. Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, will provide a similar kinetic isotope effects.

In another embodiment, provided herein are methods of using the disclosed compounds and compositions, or pharmaceutically acceptable salts, solvates, or hydrates thereof, for the local or systemic treatment or prophylaxis of human and veterinary diseases, disorders and conditions modulated or otherwise affected mediated via CSF-1R kinase activity.

C. Formulation of Pharmaceutical Compositions

The pharmaceutical compositions provided herein contain therapeutically effective amounts of one or more of compounds provided herein that are useful in the prevention, treatment, or amelioration of CSF-1R kinase mediated diseases or one or more of the symptoms thereof.

The compositions contain one or more compounds provided herein. The compounds can be formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the compounds described above are formulated into pharmaceutical compositions using techniques and procedures well known in the art.

In the compositions, effective concentrations of one or more compounds or pharmaceutically acceptable salt, solvate, hydrate or prodrug is (are) mixed with a suitable pharmaceutical carrier or vehicle. The concentrations of the compounds in the compositions are effective for delivery of an amount, upon administration, that treats, prevents, or ameliorates one or more of the symptoms of CSF-1R kinase mediated diseases.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of CSF-1R kinase mediated diseases.

Typically a therapeutically effective dosage should produce a serum concentration of active ingredient of from about 1 ng/ml to about 50-100 μg/ml. The pharmaceutical compositions typically should provide a dosage of from about 10 mg to about 4000 mg of compound per kilogram of body weight per day. Pharmaceutical dosage unit forms are prepared to provide from about 10 mg to about 1000 mg and in certain embodiments, from about 10 mg to about 500 mg, from about 20 mg to about 250 mg or from about 25 mg to about 100 mg of the essential active ingredient or a combination of essential ingredients per dosage unit form. In certain embodiments, the pharmaceutical dosage unit forms are prepared to provide about 10 mg, 20 mg, 25 mg, 50 mg, 100 mg, 250 mg, 500 mg, 1000 mg or 2000 mg of the essential active ingredient.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. Compounds are included in an amount effective for ameliorating one or more symptoms of, or for treating or preventing CSF-1R kinase mediated diseases. The concentration of active compound in the composition will depend on absorption, inactivation, excretion rates of the active compound, the dosage schedule, amount administered, particular formulation as well as other factors known to those of skill in the art.

The compositions are intended to be administered by a suitable route, including, but not limited to, orally, parenterally, rectally, topically and locally. For oral administration, capsules and tablets can be formulated. The compositions are in liquid, semi-liquid or solid form and are formulated in a manner suitable for each route of administration.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. In one embodiment, the effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refer to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Sustained-release preparations can also be prepared. Suitable examples of sustained-release preparations include semipermeable matrices of solid hydrophobic polymers containing the compound provided herein, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated compound remain in the body for a long time, they may denature or aggregate as a result of exposure to moisture at 37° C., resulting in a loss of biological activity and possible changes in their structure. Rational strategies can be devised for stabilization depending on the mechanism of action involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions Dosage forms or compositions containing active ingredient in the range of 0.005% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain about 0.001%-100% active ingredient, in certain embodiments, about 0.1-85%, typically about 75-95%.

The active compounds or pharmaceutically acceptable derivatives may be prepared with carriers that protect the compound against rapid elimination from the body, such as time release formulations or coatings.

The compositions may include other active compounds to obtain desired combinations of properties. The compounds provided herein, or pharmaceutically acceptable derivatives thereof as described herein, may also be advantageously administered for therapeutic or prophylactic purposes together with another pharmacological agent known in the general art to be of value in treating one or more of the diseases or medical conditions referred to hereinabove, such as CSF-1R kinase mediated diseases. It is to be understood that such combination therapy constitutes a further aspect of the compositions and methods of treatment provided herein.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is encapsulated in a gelatin capsule. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

2. Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. In one embodiment, the composition is administered as an aqueous solution with hydroxypropyl-beta-cyclodextrin (HPBCD) as an excipient. In one embodiment, the aqueous solution contains about 1% to about 50% HPBCD. In one embodiment, the aqueous solution contains about 1%, 3%, 5%, 10% or about 20% HPBCD.

Implantation of a slow-release or sustained-release system, such that a constant level of dosage is maintained is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, such as more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose, hydroxypropyl-beta-cyclodextrin (HPBCD) or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10-1000 mg, 100-500 mg, 10-500 mg, 50-250 mg or 25-100 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, about 5-35 mg, or about 9-30 mg of lyophilized powder, is added per mL of sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation. These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns or less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

5. Compositions for other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

6. Sustained Release Compositions

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461, 6,419,961, 6,589,548, 6,613,358, 6,699,500 and 6,740,634, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In one embodiment, a pump may be used. In another embodiment, polymeric materials can be used. In yet another embodiment, a controlled release system can be placed in proximity of the therapeutic target, i.e., thus requiring only a fraction of the systemic dose. In some embodiments, a controlled release device is introduced into a subject in proximity of the site of inappropriate immune activation or a tumor. The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

7. Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

D. Evaluation of the Activity of the Compounds

Standard physiological, pharmacological and biochemical procedures are available for testing the compounds to identify those that possess biological activities that modulate the activity of CSF-1R kinase.

Such assays include, for example, biochemical assays such as binding assays, radioactivity incorporation assays, as well as a variety of cell based assays.

In certain embodiments, the compounds disclosed herein are tested in an M-NFS-60 cell proliferation assay to determine their cellular potency against CSF-1R. M-NFS-60s are mouse monocytic cells that depend on the binding of the ligand M-CSF to its receptor, CSF-1R, to proliferate Inhibition of CSF-1R kinase activity will cause reduced growth and/or cell death. This assay assesses the potency of compounds as CSF-1R inhibitors by measuring the reduction of Alamar Blue reagent by viable cells. An exemplary assay is described in the Examples section.

In certain embodiments, competition binding assays were performed as described in Fabian et al., *Nature Biotechnology* 2005, 23, 329-336.

In one embodiment, the compounds provided herein were found to have Kds of about or less than about 150 nM against FLT3 kinase. In one embodiment, the compounds provided herein have Kds of about 1 nM or less, 3 nM or less, 5 nM or less, 0.1-2 nM, 2-5 nM, 5-10 nM, 10-25 nM, 25-50 nM, or 50-150 nM, against FLT3 kinase. In one embodiment, the compounds provided herein have Kds of less than about 50, 25, 10, 5, 4, 3, 2, or 1 nM against FLT3 kinase. In another embodiment, the compounds provided herein have Kds of about or less than about 5 nM, 3 nM or 1 nM against FLT3 kinase.

In one embodiment, the compounds provided herein were found to have Kds of about or less than about 50 nM against KIT kinase. In one embodiment, the compounds provided herein have Kds of about 1 nM or less, 3 nM or less, 0.1-2 nM, 2-5 nM, 5-10 nM, or 10-25 M, against KIT kinase. In one embodiment, the compounds provided herein have Kds of less than about 10, 5, 4, 3, 2 or 1 nM against KIT kinase. In another embodiment, the compounds provided herein have Kds of about or less than about 5 nM, 3 nM or 1 nM against KIT kinase.

In one embodiment, the compounds provided herein were found to have Kds of about or less than about 100 nM or 50 nM against PDGFRB kinase. In one embodiment, the compounds provided herein have Kds of about 1 nM or less, 3 nM or less, 0.1-2 nM, 2-5 nM, 5-10 nM, or 10-25 M, against PDGFRB kinase.

In one embodiment, the compounds provided herein have Kds of less than about 10, 5, 4, 3, 2 or 1 nM against PDGFRB kinase. In another embodiment, the compounds provided herein have Kds of about or less than about 5 nM, 3 nM or 1 nM against PDGFRB kinase.

In one embodiment, the compounds provided herein were found to have Kds of about or less than about 100 nM or 50 nM against PDGFRA kinase. In one embodiment, the compounds provided herein have Kds of about 1 nM or less, 3 nM or less, 0.1-2 nM, 2-5 nM, 5-10 nM, or 10-25 M, against PDGFRA kinase.

In one embodiment, the compounds provided herein have Kds of less than about 10, 5, 4, 3, 2 or 1 nM against PDGFRA kinase. In another embodiment, the compounds provided herein have Kds of about or less than about 5 nM, 3 nM or 1 nM against PDGFRA kinase.

In one embodiment, the compounds provided herein were found to have Kds of about or less than about 1 μM against CSF-1R kinase. In one embodiment, the compounds provided herein were found to have Kds of less than about 1, 0.5, 0.1 or 0.01 μM against CSF-1R kinase. In one embodiment, the compounds provided herein were found to have Kds of less than about 300, 200, 100, 50, 10, 5, 4, 3, 2, or 1 nM against CSF-1R kinase. In another embodiment, the compounds provided herein were found to have Kds of about or less than about 5 nM, 3 nM or 1 nM against CSF-1R kinase.

E. Methods of Use of the Compounds and Compositions

Also provided herein are methods of using the disclosed compounds and compositions, or pharmaceutically acceptable salts, solvates, hydrates or prodrugs thereof, for the treatment, prevention, or amelioration of a disease or disorder that is mediated or otherwise affected via protein kinase activity or one or more symptoms of diseases or disorders that are mediated or otherwise affected via protein kinase activity (see, Krause and Van Etten, *N Engl J Med* (2005) 353(2):172-187, Blume-Jensen and Hunter, *Nature* (2001) 411(17): 355-365 and Plowman et al., DN&P, 7:334-339 (1994)).

In certain embodiments, provided herein are methods of treating the following diseases or disorders:

1) carcinomas include Kit-mediated and/or CSF-1R-mediated carcinomas, adenocarcinoma, squamous cell carcinoma, adenosquamous carcinoma, teratocarcinoma, head and neck cancer, brain cancer, intracranial carcinoma, glioblastoma including PDGFR-mediated glioblastoma, glioblastoma multiforme including PDGFR-mediated glioblastoma multiforme, neuroblastoma, cancer of the larynx, multiple endocrine neoplasias 2A and 2B (MENS 2A and MENS 2B) including RET-mediated MENS, thyroid cancer, including sporadic and familial medullary thyroid carcinoma, papillary thyroid carcinoma, parathyroid carcinoma including any RET-mediated thyroid carcinoma, follicular thyroid cancer, anaplastic thyroid cancer, bronchial carcinoid, oat cell carcinoma, lung cancer, small-cell lung cancer including flt-3 and/or Kit-mediated small cell lung cancer, stomach/gastric cancer, gastrointestinal cancer, gastrointestinal stromal tumors (GIST) including Kit-mediated GIST and PDGFRα-mediated GIST, colon cancer, colorectal cancer, pancreatic cancer, islet cell carcinoma, hepatic/liver cancer, metastases to the liver, bladder cancer, renal cell cancer including PDGFR-mediated renal cell cancer, cancers of the genitourinary tract, ovarian cancer including Kit-mediated and/or PDGFR-mediated and/or CSF-1R-mediated ovarian cancer, endometrial cancer including CSF-1R-mediated endometrial cancer, cervical cancer, breast cancer including Flt-3-mediated and/or PDGFR-mediated and/or CSF-1R-mediated breast cancer, prostate cancer including Kit-mediated prostate cancer, germ cell tumors including Kit-mediated germ cell tumors, seminomas including Kit-mediated seminomas, dysgerminomas, including Kit-mediated dysgerminomas, melanoma including PDGFR-mediated melanoma, metastases to the bone including CSF-1R-mediated bone metastases, metastatic tumors including VEGFR-mediated and/or CSF-1R metastatic tumors, stromal tumors, neuroendocrine tumors, tumor angiogenesis including VEGFR-mediated and/or CSF-1R-mediated tumor angiogenesis, mixed mesodermal tumors;

2) sarcomas including PDGFR-mediated sarcomas, osteosarcoma, osteogenic sarcoma, bone cancer, glioma including PDGFR-mediated and/or CSF-1R-mediated glioma, astrocytoma, vascular tumors including VEGFR-mediated vascular tumors, Kaposi's sarcoma, carcinosarcoma, hemangiosarcomas including VEGFR3-mediated hemangiosarcomas, lymphangiosarcoma including VEGFR3-mediated lymphangiosarcoma;

3) myeloma, leukemia, myeloproliferative diseases (MPD), acute myeloid leukemia (AML) including flt-3 mediated and/or KIT-mediated and/or CSF1R-mediated acute myeloid leukemia, chronic myeloid leukemias (CML) including Flt-3-mediated and/or PDGFR-mediated chronic myeloid leukemia, myelodysplastic leukemias including Flt-3-mediated myelodysplastic leukemia, acute megakaryoblastic leukemia CSF1R-mediated acute megakaryoblastic leukemia, myelodysplastic syndrome, including Flt-3 mediated and/or Kit-mediated myelodysplastic syndrome (MDS), idiopathic hypereosinophilic syndrome (HES) including PDGFR-mediated HES, chronic eosinophilic leukemia (CEL) including PDGFR-mediated CEL, chronic myelomonocytic leukemia (CMML), mast cell leukemia including Kit-mediated mast cell leukemia, or systemic mastocytosis including Kit-mediated systemic mastocytosis; and 4) lymphoma, Hodgkin's lymphoma, lymphoproliferative diseases, acute lymphoblastic leukemia (ALL), B-cell acute lymphoblastic leukemias, T-cell acute lymphoblastic leukemias, natural killer (NK) cell leukemia, B-cell lymphoma, T-cell lymphoma, and natural killer (NK) cell lymphoma, any of which may be Flt-3 mediated and/or PDGFR-mediated, Langerhans cell histiocytosis including CSF-1R-mediated and flt-3-mediated Langerhans cell histiocytosis, mast cell tumors and mastocytosis;

2) Nonmalignant proliferation diseases; atherosclerosis including CSF-1R mediated atherosclerosis or PDGFR-mediated atherosclerosis, restenosis following vascular angioplasty including PDGFR-mediated restenosis, and fibroproliferative disorders such as obliterative bronchiolitis and idiopathic myelofibrosis, both of which may be PDGFR-mediated, pulmonary fibrosis and obesity;

5) Inflammatory diseases or immune disorders including autoimmune diseases, which include, but is not limited to, tissue transplant rejection, graft-versus-host disease, wound healing, kidney disease, multiple sclerosis, thyroiditis, type 1 diabetes, sarcoidosis, allergic rhinitis, nephritis, Alzheimer's disease, inflammatory bowel disease including Crohn's disease and ulcerative colitis (UC), systemic lupus erythematosis (SLE), arthritis, osteoarthritis, rheumatoid arthritis, psoriatic arthritis, inflammatory arthritis, osteoporosis, asthma and chronic obstructive pulmonary disease (COPD), including any of the aforementioned diseases which are flt-3-mediated and/or CSF-1R-mediated and/or KIT-mediated;

6) Bone diseases including disorders relating to the mineralization, formation and resorption of the bone, including but not limited to osteoporosis, glucocorticoid-induced osteoporosis, periodontitis, bone loss due to cancer therapy, periprosthetic osteolysis, Paget's disease, hypercalcemia, osteomyelitis, and bone pain; and 7) Infectious diseases mediated either via viral or bacterial pathogens and sepsis, including KIT-mediated and/or CSF-1R-mediated sepsis.

Also provided are methods of modulating the activity, or subcellular distribution, of kinases in a cell, tissue or whole organism, using the compounds and compositions provided herein, or pharmaceutically acceptable derivatives thereof. In one embodiment, provided herein are methods of modulating the activity of Flt3 activity in a cell, tissue or whole organism using the compounds and compositions provided herein, or pharmaceutically acceptable derivatives thereof. In one embodiment, provided herein are methods of modulating the activity of CSF-1R activity in a cell, tissue or whole organism using the compounds and compositions provided herein, or pharmaceutically acceptable derivatives thereof. In one embodiment, provided herein are methods of modulating the activity of KIT activity in a cell, tissue or whole organism using the compounds and compositions provided herein, or pharmaceutically acceptable derivatives thereof.

In one embodiment, the methods provided herein are for treating tumor-associated osteolysis, osteoporosis including ovariectomy-induced bone loss, orthopedic implant failure, renal inflammation and glomerulonephritis, transplant rejection including renal and bone marrow allografts and skin xenograft, obesity, Alzheimer's Disease and Langerhans cell histiocytosis. In one embodiment, the methods provided herein are for treating chronic skin disorders including psoriasis.

In another embodiment, a method for treating periodontitis, Langerhans cell histiocytosis, osteoporosis, Paget's disease of bone (PDB), bone loss due to cancer therapy, periprosthetic osteolysis, glucocorticoid-induced osteoporosis, rheumatoid arthritis, psoriatic arthritis, osteoarthritis, and/or inflammatory arthritis is provided herein.

In one embodiment, the methods provided herein are for treating bone diseases including disorders relating to the mineralization, formation and resorption of the bone, including but not limited to osteoporosis, Paget's disease, hypercalcemia, osteolysis, osteomyelitis, and bone pain.

In one embodiment, the methods provided herein are for treating cancers, including, but not limited to head and neck cancer, (originating in lip, oral cavity, oropharynx, hypopharynx, larynx, nasopharynx, nasal cavity and paranasal sinuses or salivary glands); lung cancer, including small cell lung cancer, non-small cell lung cancer; gastrointestinal tract cancers, including esophageal cancer, gastric cancer, colorectal cancer, anal cancer, pancreatic cancer, liver cancer, gallbladder cancer, extrahepatic bile duct cancer, cancer of the ampulla of vater; breast cancer; gynecologic cancers, including, cancer of uterine cervix, cancer of the uterine body, vaginal cancer, vulvar cancer, ovarian cancer, gestational trophoblastic cancer neoplasia; testicular cancer; urinary tract cancers, including, renal cancer, urinary bladder cancer, prostate cancer, penile cancer, urethral cancer; neurologic tumors; endocrine neoplasms, including carcinoid and islet cell tumors, pheochromocytoma, adrenal cortical carcinoma, parathyroid carcinoma and metastases to endocrine glands. In another embodiment, the methods provided herein are for treating carcinoma, breast cancer, ovarian cancer, bone metastases, osteoporosis, Paget's disease, hypercalcemia, osteolysis, osteomyelitis, bone pain, inflammatory bowel disease (IBD), Crohn's disease, ulcerative colitis (UC), systemic lupus erythematosis (SLE), arthritis, osteoarthritis, rheumatoid arthritis, osteoporosis, asthma, chronic obstructive pulmonary disease (COPD), psoriasis and multiple sclerosis. In another embodiment, provided herein are methods for treating inflammatory diseases of the eye including conjunctivitis, uveitis, iritis, scleritis, blepheritis, meibomitis and optical neuritis. In yet another embodiment, provided herein are methods for treating glaucoma, diabetic retinopathy and macular degeneration.

Further examples of cancers are basal cell carcinoma; squamous cell carcinoma; chondrosarcoma (a cancer arising in cartilage cells); mesenchymal-chondrosarcoma; soft tissue sarcomas, including, malignant tumours that may arise in any of the mesodermal tissues (muscles, tendons, vessels that carry blood or lymph, joints and fat); soft tissue sarcomas include; alveolar soft-part sarcoma, angiosarcoma, fibrosarcoma, leiomyosarcoma, liposarcoma, malignant fibrous histiocytoma, hemangiopericytoma, mesenchymoma, schwannoma, peripheral neuroectodermal tumours, rhabdomyosarcoma, synovial sarcoma; gestational trophoblastic tumour (malignancy in which the tissues formed in the uterus following conception become cancerous); Hodgkin's lymphoma and laryngeal cancer.

In one embodiment, the cancer is a leukemia. In one embodiment, the leukemia is chronic lymphocytic leukemia, chronic myelocytic leukemia, acute lymphoblastic leukemia, acute myeloid leukemia, and acute myeloblastic leukemia.

In another embodiment, the leukemia is acute leukemia. In one embodiment, the acute leukemia is acute myeloid leukemia (AML). In one embodiment, acute myeloid leukemia is undifferentiated AML (M0), myeloblastic leukemia (M1), myeloblastic leukemia (M2), promyelocytic leukemia (M3 or M3 variant [M3V]), myelomonocytic leukemia (M4 or M4 variant with eosinophilia [M4E]), monocytic leukemia (M5), erythroleukemia (M6), or megakaryoblastic leukemia (M7). In another embodiment, the acute myeloid leukemia is undifferentiated AML (M0). In yet another embodiment, the acute myeloid leukemia is myeloblastic leukemia (M1). In yet another embodiment, the acute myeloid leukemia is myeloblastic leukemia (M2). In yet another embodiment, the acute myeloid leukemia is promyelocytic leukemia (M3 or M3 variant [M3V]). In yet another embodiment, the acute myeloid leukemia is myelomonocytic leukemia (M4 or M4 variant with eosinophilia [M4E]). In yet another embodiment, the acute myeloid leukemia is monocytic leukemia (M5). In yet another embodiment, the acute myeloid leukemia is erythroleukemia (M6). In yet another embodiment, the acute myeloid leukemia is megakaryoblastic leukemia (M7). In yet another embodiment, the acute myeloid leukemia is promyelocytic leukemia In another embodiment, the acute leukemia is acute lymphocytic leukemia (ALL). In one embodiment, the acute lymphocytic leukemia is leukemia that originates in the blast cells of the bone marrow (B-cells), thymus (T-cells), or lymph nodes. The acute lymphocytic leukemia is categorized according to the French-American-British (FAB) Morphological Classification Scheme as L1—Mature-appearing lymphoblasts (T-cells or pre-B-cells), L2—Immature and pleomorphic (variously shaped) lymphoblasts (T-cells or pre-B-cells), and L3—Lymphoblasts (B-cells; Burkitt's cells). In another embodiment, the acute lymphocytic leukemia originates in the blast cells of the bone marrow (B-cells). In yet another embodiment, the acute lymphocytic leukemia originates in the thymus (T-cells). In yet another embodiment, the acute lymphocytic leukemia originates in the lymph nodes. In yet another embodiment, the acute lymphocytic leukemia is L1 type characterized by mature-appearing lymphoblasts (T-cells or pre-B-cells). In yet another embodiment, the acute lymphocytic leukemia is L2 type characterized by immature and pleomorphic (variously shaped) lymphoblasts (T-cells or pre-B-cells). In yet another embodiment, the acute lymphocytic leukemia is L3 type characterized by lymphoblasts (B-cells; Burkitt's cells).

In yet another embodiment, the leukemia is T-cell leukemia. In one embodiment, the T-cell leukemia is peripheral T-cell leukemia, T-cell lymphoblastic leukemia, cutaneous T-cell leukemia, and adult T-cell leukemia. In another embodiment, the T-cell leukemia is peripheral T-cell leukemia. In yet another embodiment, the T-cell leukemia is T-cell lymphoblastic leukemia. In yet another embodiment, the T-cell leukemia is cutaneous T-cell leukemia. In still another embodiment, the T-cell leukemia is adult T-cell leukemia.

In yet another embodiment, the leukemia is Philadelphia positive. In one embodiment, the Philadelphia positive leukemia is Philadelphia positive AML, including, but not limited to, undifferentiated AML (M0), myeloblastic leukemia (M1), myeloblastic leukemia (M2), promyelocytic leukemia (M3 or M3 variant [M3V]), myelomonocytic leukemia (M4 or M4 variant with eosinophilia [M4E]), monocytic leukemia (M5), erythroleukemia (M6), or megakaryoblastic leukemia (M7). In another embodiment, the Philadelphia positive leukemia is Philadelphia positive ALL.

In still another embodiment, the leukemia is drug resistant. In still another embodiment, the gastrointestinal stromal tumor (GIST) is drug resistant. In still another embodiment, the melanoma is drug resistant. In one embodiment, the subject has developed drug resistance to the anticancer therapy.

The cancers to be treated herein may be primary or metastatic. In one embodiment, the cancer is a solid or blood born metastatic tumor. In another embodiment, the cancer is metastatic cancer of bone.

Also provided are methods of modulating the activity, or subcellular distribution, of CSF-1R kinase in a cell, tissue or whole organism, using the compounds and compositions provided herein, or a pharmaceutically acceptable salt, solvate or hydrate thereof thereof.

The active ingredient(s) in one embodiment are administered in an amount sufficient to deliver to a patient a therapeutically effective amount of the active compound in order to e.g., treat the diseases described herein, without causing serious toxic effects in a treated subject.

A typical dose of the compound may be in the range of from about 1 to about 50 mg/kg, from about 1 to about 20 mg/kg, from about 0.1 to about 10 mg/kg, from about 0.5 mg/kg to about 10 mg/kg, of body weight per day, more generally from about 0.1 to about 100 mg/kg body weight of the recipient per day. Alternatively, a typical dose of the compound may be in the range of from about 50 mg to about 500 mg. Lower dosages may be used, for example, doses of about 0.5-100 mg, 0.5-10 mg, or 0.5-5 mg per kilogram body weight per day. Even lower doses may be useful, and thus ranges can include from about 0.1-0.5 mg/kg body weight of the recipient per day. The effective dosage range of the pharmaceutically acceptable derivatives is calculated based on the weight of the parent compound to be delivered. If the derivative compound itself exhibits activity, then the effective dosage can be estimated as above using the weight of the derivative, or by other means known to those of skill in the art.

The compounds are conveniently administered in units of any suitable dosage form, including but not limited to one containing from about 1 to 2000 mg, from about 10 to 1000 mg, or from about 25 to 700 mg of active ingredient per unit dosage form. In one embodiment, the unit dose is selected from 12, 18, 25, 27, 40, 50, 60, 90, 100, 135, 200, 250, 300, 400, 450, 500, 600, 675, 700, 800, 900 and 1000 mgs. For example, an oral dosage of from about 25 to 1000 mg is usually convenient, including in one or multiple dosage forms of 10, 12, 18, 25, 27, 40, 50, 60, 90, 100, 135, 200, 250, 300, 400, 450, 500, 600, 675, 700, 800, 900 or 1000 mgs. In certain embodiments, lower dosages may be used, for example, from about 10-100 or 1-50 mgs. Also contemplated are doses of 0.1-50 mg, 0.1-20 mg, or 0.1-10 mg. Furthermore, lower doses may be utilized in the case of administration by a non-oral route, as for example, by injection or inhalation.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the compositions provided herein.

In certain embodiments, the compound or composition provided herein can be administered as a single once-a-day dose (QD) or as divided doses throughout a day. In particular embodiments, the compound or composition is administered four times per day (QID). In particular embodiments, the compound or composition is administered three times per day (TID). In particular embodiments, the compound or composition is administered two times per day (BID). In particular embodiments, the compound or composition is administered once per day (QD).

The administration can also be continuous (i.e., daily for consecutive days or every day) or intermittent. The term "intermittent" or "intermittently" as used herein is intended to mean stopping and starting at either regular or irregular intervals. For example, intermittent administration of the compound of Formula I may be administration for one to six days per week or administration on alternate days.

In one embodiment, the compound or composition provided herein is administered intermittently. In yet another embodiment, the compound or composition provided herein is administered intermittently once weekly, twice weekly or three times weekly. In yet another embodiment, the compound or composition provided herein is administered once weekly. In yet another embodiment, the compound or composition provided herein is administered twice weekly. In yet another embodiment, the compound or composition provided herein is administered three times weekly. In one embodiment, the compound or composition provided herein is administered QD intermittently once weekly, twice weekly or three times weekly. In yet another embodiment, the compound or composition provided herein is administered QD once weekly. In another embodiment, the compound or composition provided herein is administered QD twice weekly. In another embodiment, the compound or composition provided herein is administered QD three times weekly.

In one embodiment, the active ingredient is administered to achieve peak plasma concentrations of the active compound of from about 0.02 to 20 μM, from about 0.2 to about 5 μM or from about 0.5 to 10 μM. For example, this can be achieved by intravenous injection of a 0.1 to 5% solution of active ingredient, optionally in saline, or administered as a bolus of active ingredient. It is to be understood that for any particular subject, specific dosage regimens should be adjusted over time to meet individual needs, and will vary depending upon absorption, inactivation and excretion rates of the drug. The concentrations set forth here are exemplary only and are not intended to limit the scope or practice of the claimed composition. The active ingredient may be administered all at once, or may be divided into a number of smaller doses to be administered at varying intervals of time.

The subject matter has been described in an illustrative manner, and it is to be understood that the terminology used is intended to be in the nature of description rather than of limitation. Thus, it will be appreciated by those of skill in the art that conditions such as choice of solvent, temperature of reaction, volumes, reaction time may vary while still producing the desired compounds. In addition, one of skill in the art will also appreciate that many of the reagents provided in the examples may be substituted with other suitable reagents. See, e.g., Smith & March, *Advanced Organic Chemistry,* $5^{th}$ ed. (2001).

F. Combination Therapy

Furthermore, it will be understood by those skilled in the art that the compounds, isomers, and pharmaceutically acceptable salts provided herein, including pharmaceutical compositions and formulations containing these compounds, can be used in a wide variety of combination therapies to treat the conditions and diseases described above. Thus, also contemplated herein is the use of compounds, and pharmaceutically acceptable salts provided herein in combination with other active pharmaceutical agents for the treatment of the disease/conditions described herein.

In one embodiment, such additional pharmaceutical agents include without limitation anti-cancer agents (including chemotherapeutic agents and anti-proliferative agents), anti-inflammatory agents, immunomodulatory agents or immunosuppressive agents.

In certain embodiments, the anti-cancer agents include anti-metabolites (e.g., 5-fluoro-uracil, cytarabine, clofarabine, methotrexate, fludarabine and others), antimicrotubule agents (e.g., vinca alkaloids such as vincristine, vinblastine; taxanes such as paclitaxel and docetaxel), alkylating agents (e.g., cyclophosphamide, melphalan, carmustine, nitrosoureas such as bischloroethylnitrosurea and hydroxyurea), platinum agents (e.g. cisplatin, carboplatin, oxaliplatin, satraplatin and CI-973), anthracyclines (e.g., doxrubicin and daunorubicin), antitumor antibiotics (e.g., mitomycin, idarubicin, adriamycin and daunomycin), topoisomerase inhibitors (e.g., etoposide and camptothecins), anti-angiogenesis agents (e.g. Sutent®, sorafenib and Bevacizumab) or any other cytotoxic agents, (e.g. estramustine phosphate, prednimustine), hormones or hormone agonists, antagonists, partial agonists or partial antagonists, kinase inhibitors (such as imatinib), and radiation treatment.

In certain embodiments, the anti-inflammatory agents include matrix metalloproteinase inhibitors, inhibitors of pro-inflammatory cytokines (e.g., anti-TNF molecules, TNF soluble receptors, and IL1) non-steroidal anti-inflammatory drugs (NSAIDs) such as prostaglandin synthase inhibitors (e.g., choline magnesium salicylate and salicylsalicyclic acid), COX-1 or COX-2 inhibitors, glucocorticoid receptor agonists (e.g., corticosteroids, methylprednisone, prednisone, and cortisone) or antifolates such as methotrexate.

The compound or composition provided herein, or pharmaceutically acceptable salt of the compound, may be administered simultaneously with, prior to, or after administration of one or more of the above agents.

Pharmaceutical compositions containing a compound provided herein or pharmaceutically acceptable salt thereof, and one or more of the above agents are also provided.

Also provided, in one embodiment, is a combination therapy that treats or prevents the onset of the symptoms, or associated complications of cancer and related diseases and disorders, said therapy comprising the administration to a subject in need thereof, one of the compounds or compositions disclosed herein, or pharmaceutically acceptable salts thereof, with one or more anti-cancer agents. Also provided, in another embodiment, is a combination therapy that treats or prevents the onset of the symptom of osteoporosis and related diseases and disorders, said therapy comprising the administration to a subject in need thereof, one of the compounds or compositions disclosed herein, or pharmaceutically acceptable salts thereof, with one or more anti-inflammatory or immunomodulatory agents. Also provided, in yet another embodiment, is a combination therapy that treats or prevents the onset of the symptom of rheumatoid arthritis and related diseases and disorders, said therapy comprising the administration to a subject in need thereof, one of the compounds or compositions disclosed herein, or pharmaceutically acceptable salts thereof, with one or more anti-inflammatory or immunomodulatory agents.

G. Preparation of Compounds

Starting materials in the synthesis examples provided herein are either available from commercial sources or via literature procedures (e.g., March *Advanced Organic Chemistry Reactions, Mechanisms, and Structure*, (1992) 4th Ed.; Wiley Interscience, New York). All commercially available compounds were used without further purification unless otherwise indicated. 300 MHz Proton ($^1H$) nuclear magnetic resonance (NMR) spectra were recorded on a Bruker Avance 300 NMR spectrometer. Significant peaks are tabulated and typically include: number of protons, and multiplicity (s, singlet; d, double; t, triplet; q, quartet; m, multiplet; br s, broad singlet). Chemical shifts are reported as parts per million (δ) relative to tetramethylsilane. Low resolution mass spectra (MS) were obtained as electrospray ionization (ESI) mass spectra, which were recorded on a Shimadzu HPLC/MS instrument using reverse-phase conditions (acetonitrile/water, 0.05% acetic acid). Preparative reverse phase HPLC was typically performed using a Varian HPLC system equipped with a Phenomenex phenylhexyl, a Phenomenex Luna C18, or a Varian Pursuit diphenyl reverse phase column; typical elution conditions utilized a gradient containing an increasing composition of organic cosolvent (0.05% $HOAc/CH_3CN$ or 0.05% HOAc/MeOH) to aqueous cosolvent (0.05% aq HOAc). Silica gel chromatography was either performed manually, typically following the published procedure for flash chromatography (Still et al. (1978) *J. Org. Chem.* 43:2923), or on an automated system (for example, Biotage SP instrument) using pre-packed silica gel columns.

It is understood that in the following description, combinations of substituents and/or variables of the depicted formulae are permissible only if such contributions result in stable compounds under standard conditions.

It will also be appreciated by those skilled in the art that in the process described below, the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R (where R is alkyl, aryl or aralkyl), p-methoxybenzyl, trityl and the like. Suitable protecting groups for carboxylic acid include alkyl, aryl or aralkyl esters.

Protecting groups may be added or removed in accordance with standard techniques, which are well-known to those skilled in the art and as described herein. The use of protecting groups is described in detail in Green, T. W. and P. G. M. Wutz, *Protective Groups in Organic Synthesis* (1991), 2nd Ed., Wiley-Interscience.

One of ordinary skill in the art could easily ascertain which choices for each substituent are possible for the reaction conditions of each Scheme. Moreover, the substituents are selected from components as indicated in the specification heretofore, and may be attached to starting materials, intermediates, and/or final products according to schemes known to those of ordinary skill in the art.

Also it will be apparent that the compounds provided herein could exist as one or more isomers, that is, E/Z isomers, enantiomers and/or diastereomers.

Compounds of formula (I) may be generally prepared as depicted in the following schemes, unless otherwise noted, the various substituents are as defined elsewhere herein.

Standard abbreviations and acronyms as defined in *J. Org. Chem.* 2007 72(1): 23A-24A are used herein. Other abbreviations and acronyms used herein are as follows:

| | |
|---|---|
| AcOH | acetic acid |
| DIEA | diisopropylethylamine |
| DCM | dichloromethane |
| DMA | N,N-dimethylacetamide |
| EDCI | N-(3-Dimethylaminopropyl)-N'-ethylcarbodiimide hydrochloride |
| EtOAc | ethyl acetate |
| EtOH | ethanol |
| HATU | O-(7-azabenzotriazol-1yl)-N,N,N',N'-tetramethyluronium hexafluorophosphate |
| HOAc | acetic acid |
| MeOH | methanol |
| NaOAc | sodium acetate |
| NaOtBu | sodium tert-butoxide |
| $Pd_2(dba)_3$ | Tris(dibenzylideneacetone)dipalladium |
| t-BuOK | postassium tert-butoxide |
| TEA | triethylamine |
| TBTU | 2-(1H-benzotriazole-1-yl)-1,1,3,3-tetramethyluronium tetrafluoroborate |

Scheme 1: General synthesis of azolyl ureas.

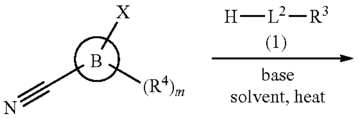

2

(X = leaving group)

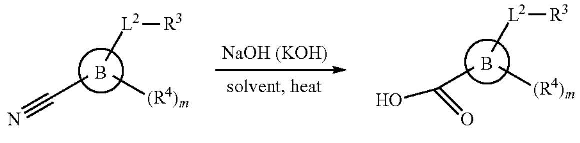

3

4

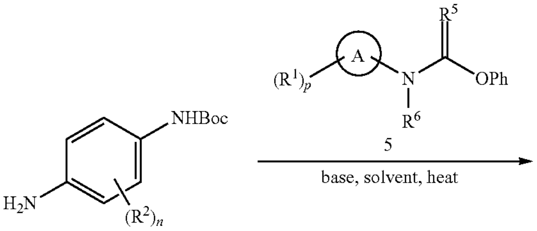

6

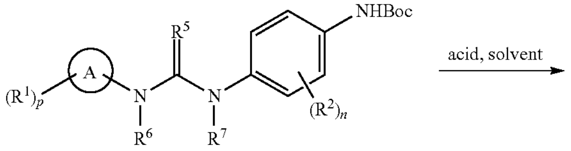

7

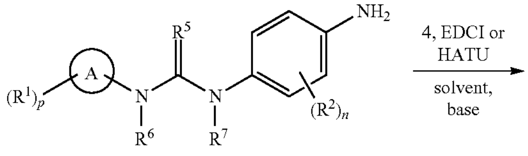

8

-continued

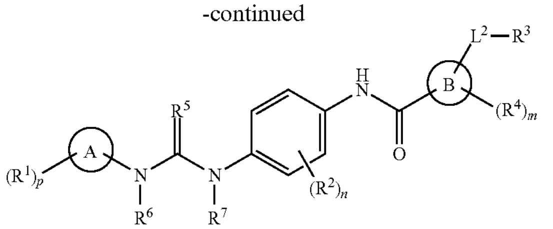

9

In an illustrative method, urea compounds of formula (I) may be routinely prepared according to the synthetic routes outlined in Scheme 1. The commercially available nucleophiles 1 (H-$L^2$-$R^3$, in which $L^2$ may represent —$OR^9$, —$SR^9$, or —$N(R^{10})R^9$) and cyano-substituted heteroaryl compound 2 with a leaving group, such as, but not limited to, chloride or fluoride, are condensed under nucleophilic substitution conditions to give compounds 3. The reaction is promoted by bases such as, but not limited to, NaH or t-BuOK in solvents such as, but not limited to, DMF and THF. The reaction can be promoted using heating in a conventional oil bath or in a microwave reactor. The cyano group of compounds 3 is hydrolyzed under basic conditions, such as, but not limited to, aqueous NaOH in EtOH to give the carboxylic acids 4. The reaction is promoted using heating in a conventional oil bath. The diaryl ureas 7 can be prepared by the reaction of the phenylenediamine derivatives 6 with activated arylcarbamic acid derivatives 5 in solvents such as THF or DMF, promoted with bases such as DIEA or DMAP and by heating as necessary at elevated temperatures. The tert-butyloxy carbonyl group of 7 is cleaved under acidic conditions, such as, but not limited to, TFA in DCM or 4N HCl in 1,4-dioxane, to give the anilines 8. The anilines 8 can couple with acids 4 using appropriate coupling reagents, such as, but not limited to, EDCI or HATU, promoted by bases such as DIEA, TEA, or DMAP to give the amide derivates 9.

In an illustrative method, urea amide compounds of formula (I) may also be routinely prepared according to the synthetic route outlined in Scheme 2. In cases when $R^3$ (either acylic or cyclic) contains a protected amino group, such as, but not limited to, the tert-butyloxy carbonyl group, the protecting group within the amide derivatives 10 can be deprotected to give amines 11, using various conditions, such as, but not limited to, TFA in DCM or 4N HCl in 1,4-dioxane. Amines 11 can undergo reductive amination with various aldehydes and ketones, using reducing agents, such as, but not limited to $NaCNBH_3$, $Na(OAc)_3BH$, or $NaBH_4$. The reaction can be conducted in a pH~4 NaOAc/AcOH buffer in MeOH, or promoted by addition of AcOH in dichloroethane. The reaction can be run at ambient temperature for reaction with aldehydes to give amines 12a, or be promoted using heating in a conventional oil bath for reaction with ketones to give amines 12b. The amines 11 can also undergo Michael addition with electron-withdrawing group (EWG)-activated vinyl derivatives to give amines 12c. The reaction may be promoted with the addition of bases, such as, but not limited to, DIEA, at elevated temperature if necessary. The amines 11 can also be alkylated with appropriate electrophiles, such as, but not limited to, alkyl halides or alkyl triflate, to give amines 12d. The reaction may be promoted with the addition of bases, such as, but not limited to, DIEA or TEA, at elevated temperature if necessary.

Scheme 2: General synthesis of azolyl ureas.

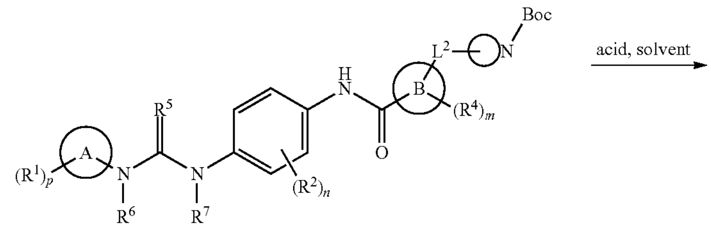

10

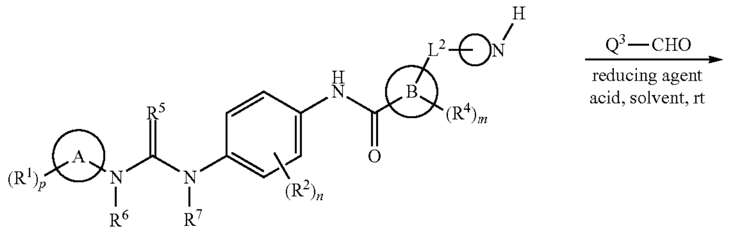

11

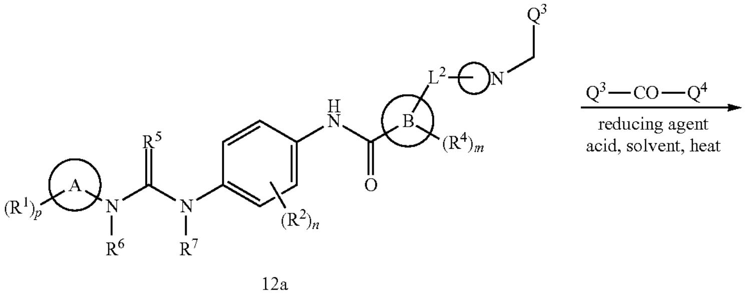

12a

-continued

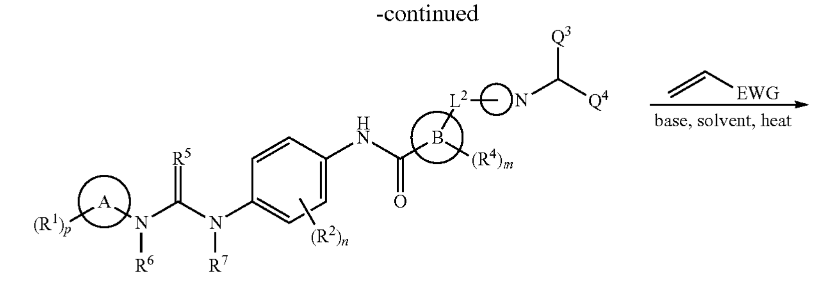

12b

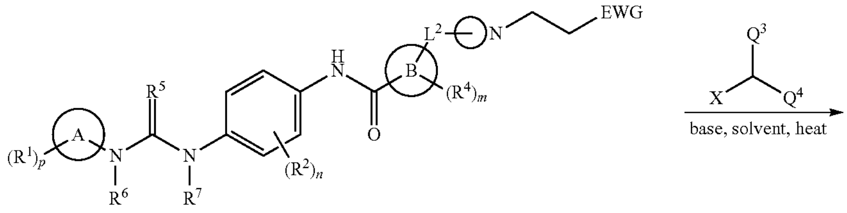

12c

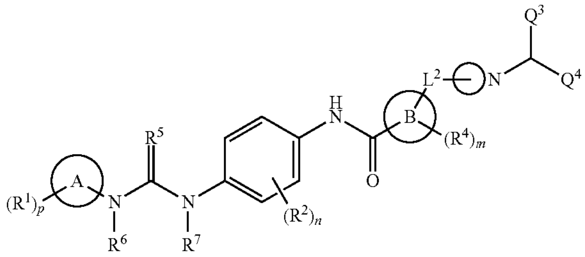

12d

X = Cl, Br, I, OTf
$Q^3$, and $Q^4$ each independently
alkyl, aryl, heteroaryl, heterocyclyl, cycloalkyl;
EWG is electron withdrawing group In an illustrative method, urea amide compounds of formula (I) may also be routinely prepared according to the synthetic route outlined in Scheme 3. In cases when $R^3$ contains a primary alcohol (13a) or secondary alcohol (13b), such as, but not limited to, the hydroxymethyl group, the hydroxyl group within the amide derivatives 13 can be oxidized to give aldehydes 14a or ketones 14b, using oxidizing agents, such as, but not limited to, Dess-Martin periodinane. Aldehydes 14a or ketones 14b can undergo reductive amination with various amines, using reducing agents, such as, but not limited to $NaCNBH_3$, $Na(OAc)_3BH$, or $NaBH_4$. The reaction can be done in a pH~4 NaOAc/AcOH buffer in MeOH, or promoted by addition of AcOH in dichloroethane. The reaction can be run at ambient temperature for aldehydes to give amines 15a, or be promoted using heating in a conventional oil bath for ketones to give amines 15b.

Scheme 3: General synthesis of azolyl ureas.

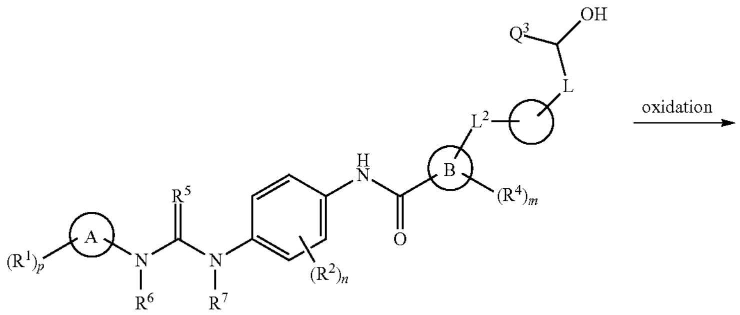

L = alkylene, cycloalkylene
13a (($Q^3$ = H)
13b ($Q^3$ = alkyl, aryl, cycloalkyl, heterocyclyl, heteroaryl, etc)

-continued

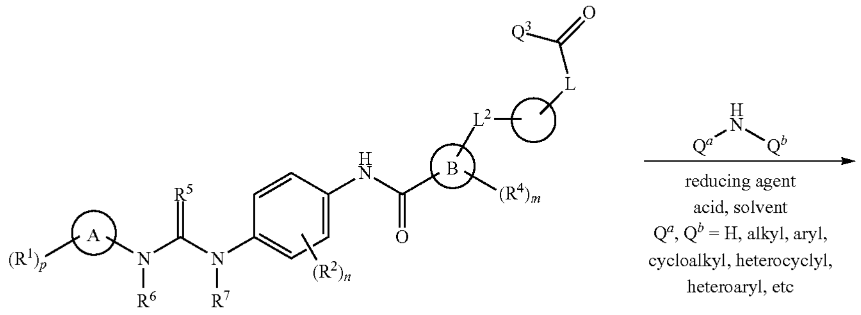

14a ($Q^3$ = H)
14b ($Q^3$ = alkyl, aryl, cycloalkyl, heterocyclyl, heteroaryl, etc)

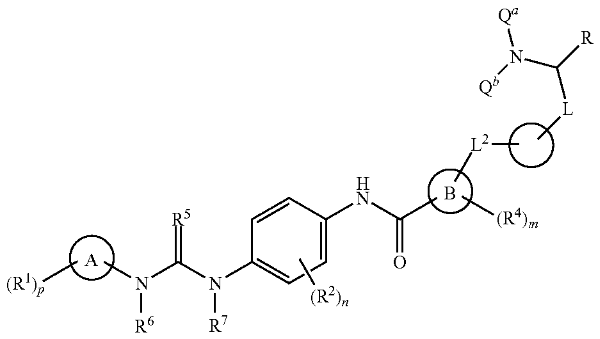

15a (R = H)
15b (R = R')

In an illustrative method, urea amide compounds of formula (I) may also be routinely prepared according to the synthetic route outlined in Scheme 4. The amide derivatives 16 containing a heteroaryl moiety B substituted with a reactive halogen atom, such as, but not limited to, bromide or iodide, can undergo a variety of transition metal-mediated catalyzed reactions with various organometallic reagents or nucleophiles. For example, the halogen-containing amide derivatives 16 can undergo Negishi coupling with organozinc reagents to give compounds 17a, in which $L^2$ is such as, but not limited to, an alkylene or a direct bond. Such coupling reactions are catalyzed using transition metal catalysts, such as, but not limited to, $Cl_2Ni(Ph_2PCH_2CH_2PPh_2)$.

In another example, the halogen-containing amide derivatives 16 can also undergo Suzuki coupling with reagents, such as, but not limited to, boronic acids, boronate esters, or trifluoroborates, to give compounds 17b, in which $L^2$ maybe, but is not limited to, a direct bond, an alkylene, an alkenylene. Such coupling reactions are catalyzed using transition metal catalysts, such as, but not limited to, $Pd(Ph_3P)_4$, and are promoted by bases, such as, but not limited to, $Na_2CO_3$, and using heating in a conventional oil bath or in a microwave reactor. The addition of ligands, such as, but not limited to, Xphos, may be necessary to facilitate the transformations.

In yet another example, the halogen-containing amide derivatives 16 can also undergo Buchwald-Hartwig coupling with various nucleophiles, such as, but not limited to, amines, mercaptans, alcohols, and carbon nucleophiles, to give compounds 17c, in which $L^2$ is $—NR^{12}R^{12a}$, $—SR^{12}$, $—OR^{12}$, or an alkylene. Such coupling reactions are catalyzed using transition metal catalysts, such as, but not limited to, $Pd_2(dba)_3$, and are promoted by the addition of ligands, such as, but not limited to, Xantphos, by the addition of bases, such as, but not limited to NaOt-Bu or $K_3PO_4$, and using heating in a conventional oil bath heating or in a microwave reactor, in solvents, such as, but not limited to toluene or 1,4-dioxane.

In yet another example, the halogen-containing amide derivatives 16 can also undergo Sonogashira coupling with various alkynylenes, to give compounds 17d, in which $L^2$ is an alkynylene. Such coupling reactions are catalyzed using transition metal catalysts, such as, but not limited to, $PdCl_2(PPh_3)_2$ and copper (I) iodide, by the addition of bases, such as, but not limited to DIEA, and using heating in a conventional oil bath heating or in a microwave reactor.

Scheme 4: General synthesis of azolyl ureas.

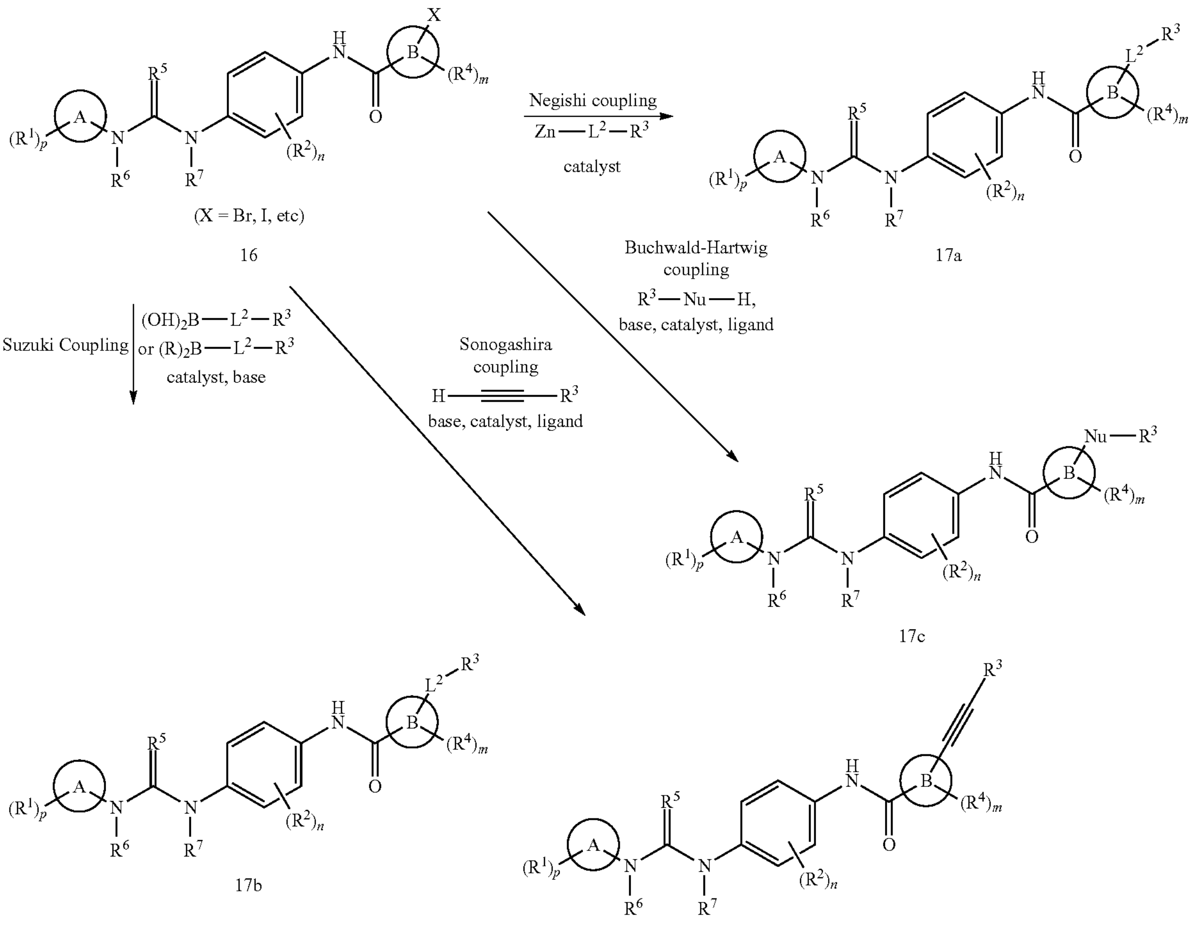

16, 17a, 17c, 17b, 17d

In an illustrative method, urea amide compounds of formula (I) may also be routinely prepared according to the synthetic route outlined in Scheme 5. The transition-metal mediated couplings as detailed for Scheme 4, such as, but not limited to, Negishi coupling, Suzuki coupling, Buchwald-Hartwig coupling, and Sonogashira coupling, can be performed with bromo/iodo-containing heteroaryl carboxylates 18, to give compounds 19. The carboxylate of 19 can be hydrolyzed under basic conditions, such as, but not limited to, aqueous NaOH in EtOH to give the carboxylic acids 4. The carboxylic acids 4 can then be converted to mixed anhydrides by reacting with an alkyl chloroformate, such as, but not limited to, ethyl chloroformate, with the addition of bases, such as, but not limited to, TEA. The mixed anhydride can then be condensed with the anilines 8 to give the amide derivatives 9. The condensation may be promoted using heating in a conventional oil bath.

Scheme 5: General synthesis of azolyl ureas.

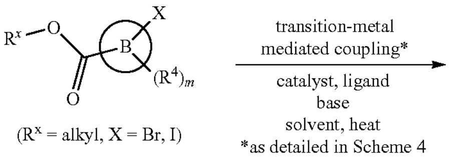

($R^x$ = alkyl, X = Br, I)

18

-continued

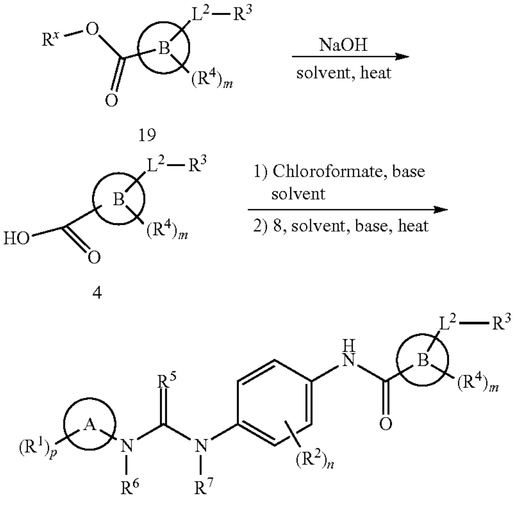

19, 4, 9

In an illustrative method, urea amide compounds of formula (I) may also be routinely prepared according to the synthetic route outlined in Scheme 6. The commercially available 4-nitroanilines 20 can react with activated arylcarbamic acid derivatives, such as 5, in solvents such as THF or DMF, promoted with bases such as DIEA or DMAP and by heating as necessary at elevated temperatures, to give the ureas 21. The nitro group of 21 can be reduced to anilines 8, using reducing agents, such as, but not limited to, zinc/AcOH or SnCl in EtOH. The reaction can be promoted using heating in a conventional oil bath. The anilines 8 can then couple with acids 4 using appropriate coupling reagents, as detailed for Scheme 1, to give the amide derivates 9.

Scheme 6: General synthesis of azolyl ureas.

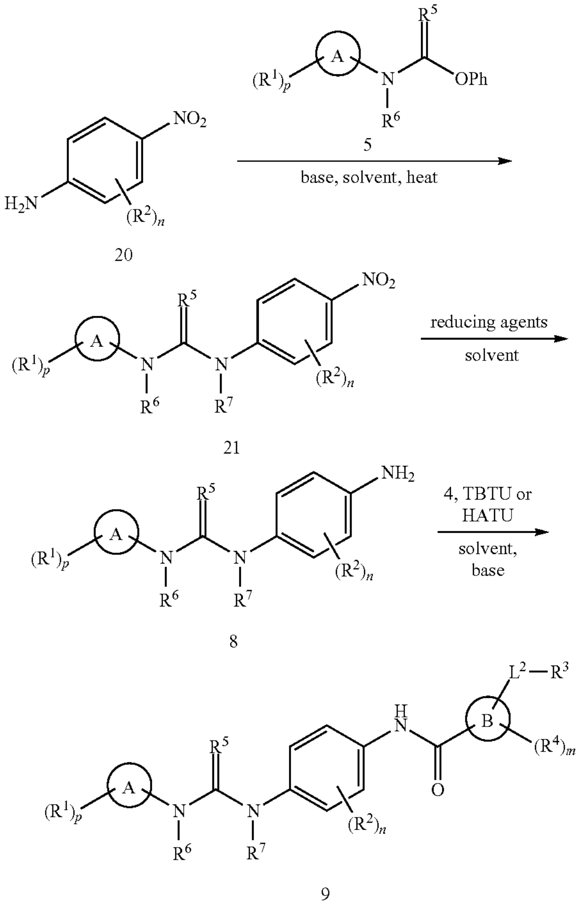

In an illustrative method, urea amide compounds of formula (I) may also be routinely prepared according to the synthetic route outlined in Scheme 7. The commercially available 1-isocyanato-4-nitrobenzenes 22 can react with amino azole derivatives 23, in solvents such as THF, and by heating as necessary at elevated temperatures, to give the ureas 21, which can then be converted to the amide derivatives 9, as detailed in Schemes 6 and 1.

Scheme 7: General synthesis of azolyl ureas.

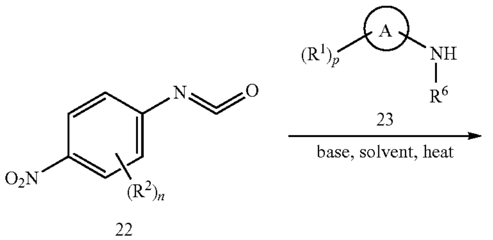

-continued

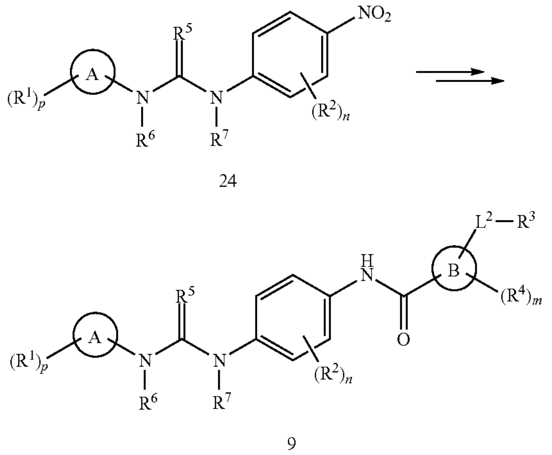

In an illustrative method, urea amide compounds of formula (I) may also be routinely prepared according to the synthetic route outlined in Scheme 8. The commercially available phenyleneamine derivatives 6 can couple with the carboxylic acids 4 using appropriate coupling reagents, such as, but not limited to, EDCI or HATU, promoted by bases such as DIEA, TEA, or DMAP to give the amide derivates 25. The tert-butyloxy carbonyl group of 25 is cleaved to give the anilines 26 under acidic conditions, such as, but not limited to, TFA in DCM or 4N HCl in 1,4-dioxane. The diaryl azolyl ureas 9 can be prepared by the reaction of the phenylenediamine derivatives 26 with activated arylcarbamic acid derivatives, such as 5, in solvents such as THF or DMF, promoted with bases such as DIEA or DMAP and by heating as necessary at elevated temperatures.

Scheme 8: General synthesis of azolyl ureas.

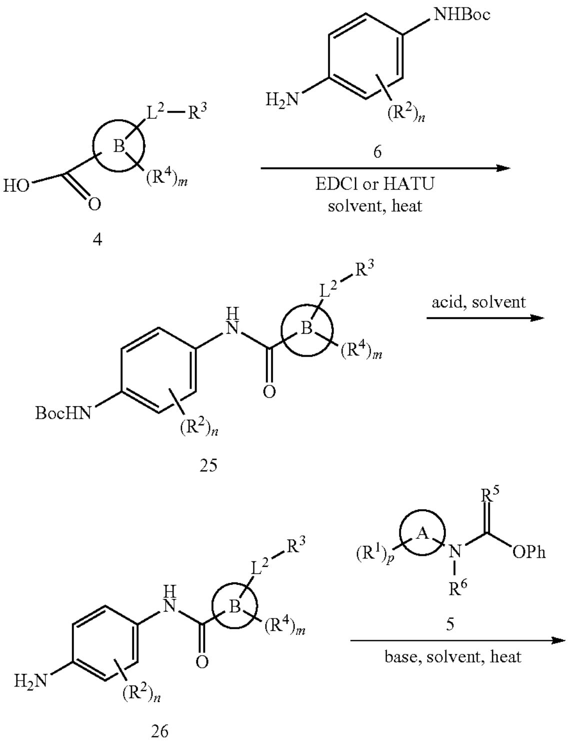

-continued

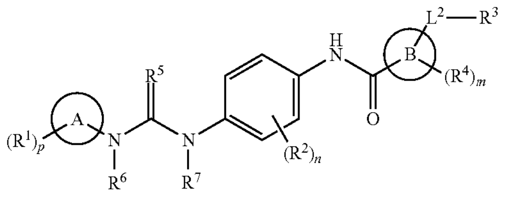

9

Heteroaryl carboxylic acid derivatives 30 may also be prepared in an illustrative method as outlined in Scheme 9. Any carboxylic acid-containing heteroaryls and heterocycles (27) can be reduced to the corresponding alcohols 28 using a reducing agent, such as, but not limited to, diborane in THF, at elevated temperature if necessary. The alcohols 28 are condensed under nucleophilic substitution conditions with compounds 2 to give compounds 29. The reaction is promoted by bases such as, but not limited to, NaH or t-BuOK in solvents such as, but not limited to, DMF and THF, at elevated temperature. The cyano group of compounds 29 is hydrolyzed under basic conditions, such as, but not limited to, aqueous NaOH in EtOH to give the carboxylic acids 30.

Scheme 9: General synthesis of carboxylic acids.

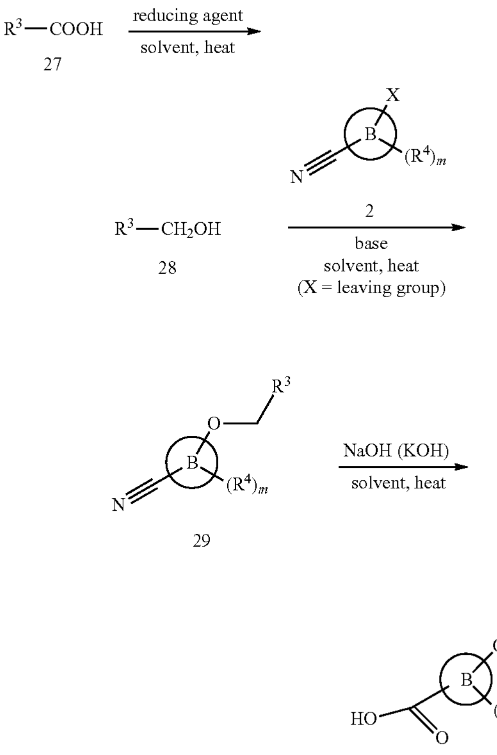

27, 28, 29, 30

Heteroaryl carboxylic acid derivatives 33 may also be prepared in an illustrative method as outlined in Scheme 10. Any ketone-containing heterocycles (31) can react with a Grignard reagent (e.g. R—Mg—Cl) to give the corresponding alcohols 32. The alcohols 32 can then be converted to compounds 33 as described in Scheme 9.

Scheme 10: General synthesis of carboxylic acids.

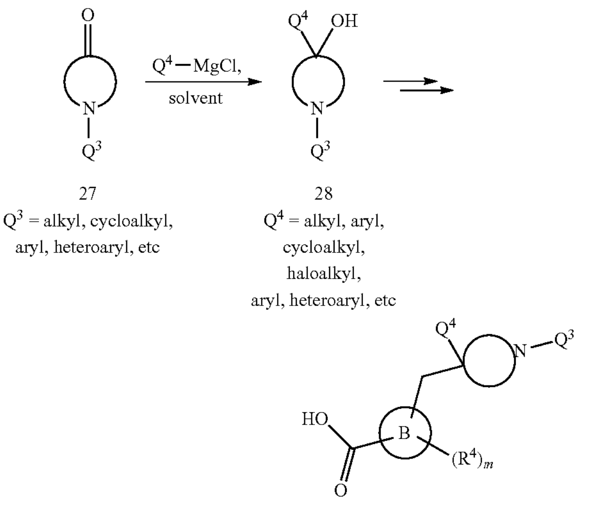

29

Heteroaryl carboxylic acid derivatives 36 may also be prepared in an illustrative method as outlined in Scheme 11. The α-proton of a ketone-containing heterocycles 34 can be deprotonated with bases, such as, but not limited to, NaH or LDA. The enolate formed can then undergo nucleophilic substitution with halo-substituted heteroaryl ring B (2) to give compounds 35. The reaction can be promoted using heating in a conventional oil bath. The cyano group of compounds 35 is hydrolyzed to give the carboxylic acids 36 under basic conditions, such as, but not limited to, aqueous NaOH in EtOH. The reaction is promoted using heating in a conventional oil bath.

Scheme 11: General synthesis of carboxylic acids.

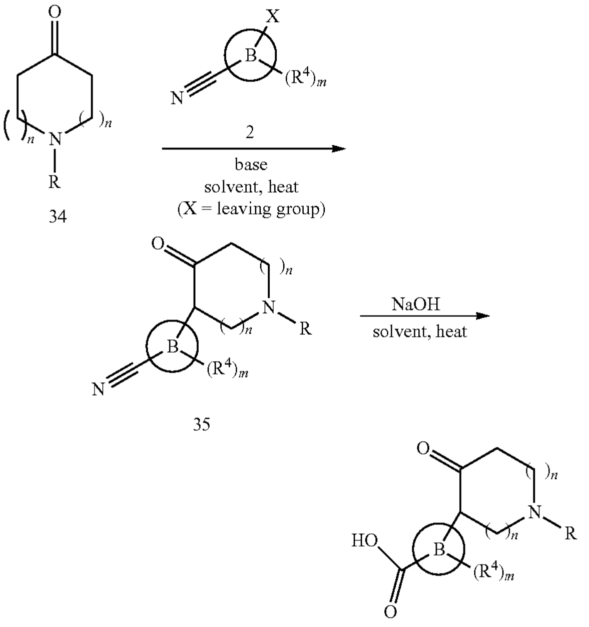

36

$n = 0, 1, 2$

Azole amine derivatives $(R^1)_p$-A-$NH_2$, wherein the heteroaryl ring A is a 5-membered isoxazole ring, may be prepared by condensation of appropriate fragments and precursors by methods well known in the art and described in texts such as Gilchrist, T. L., *Heterocyclic Chemistry* (1992), 2nd Ed., Longman Scientific & Technical and John Wiley & Sons. Scheme 12 shows one example where $(R^1)$p-A-$NH_2$ is 5-substituted-3-aminoisoxazole, whereby an appropriate 3-oxonitrile (39) is treated with hydroxylamine under appropriate conditions of pH and temperature which are described, for example, in Takase et al. *Heterocycles* 1991 32(6), 1153-1158, to afford the desired azole amine product (40). This method is particularly applicable for cases in which the atom of $R^1$ directly attached to the aromatic ring is highly substituted, for example, is an α,α-dialkyl substituent (See Takase et al. *Heterocycles* 1991 32(6), 1153-1158). The requisite 3-oxonitriles (39) can be prepared by reaction of an $R^1$-containing carboxylic ester (37) with an akali metal salt of acetonitrile (38) (See, for example, U.S. Pat. No. 4,728,743).

Scheme 12: General synthesis of 3-aminoisoxazole derivatives.

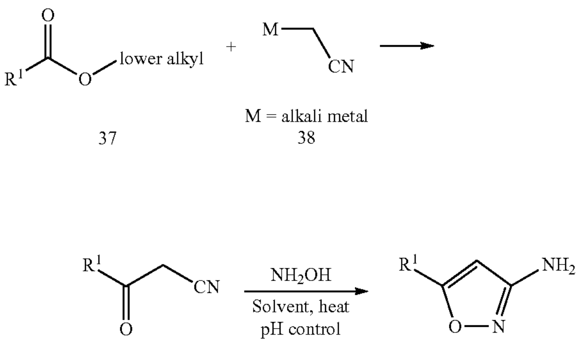

37 38 39 40

Scheme 13 shows an example for the synthesis of azole amine derivatives $(R^1)_p$-A-$NH_2$, wherein the heteroaryl ring A is 3-substituted-5-aminoisoxazole, whereby an appropriate 3-oxonitrile 39, prepared as described in Scheme 12, is treated with hydroxylamine under appropriate conditions of pH and temperature, as described again in Takase et al. *Heterocycles* 1991 32(6), 1153-1158, to afford the desired aryl amine product (41). This method is particularly applicable for cases in which the atom of $R^1$ directly attached to the aromatic ring is not highly substituted, for example, is not an α,α-dialkyl substituent (See Eddington et al. *Eur. J. Med. Chem.* 2002 37, 635-648), or when $R^1$ contains one or more highly electron-withdrawing groups, for example fluorine, or under special conditions of pH and solvent, such as an ethanol and water mixture as described in EP 0220947.

Scheme 13: General synthesis of 5-aminoisoxazole derivatives.

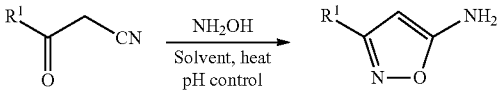

39 41

Azole amine derivatives $(R^1)_p$-A-$NH_2$, wherein the $NH_2$ group is directly attached to a nitrogen atom of the azole ring, may be prepared by amination of the corresponding azoles using methods well known in the art. Scheme 14 shows one example where $(R^1)$p-A is 4-substituted-pyrazole 42, whereby the amination can be realized by treating with a base, such as, but not limited to, NaH, and using amination reagents, such as, but not limited to, hydroxylamine-O-sulfonic acid or chloroamine. The reaction can be run in solvents such as, but not limited to, DMF and THF. The reaction can be promoted using heating in a conventional oil bath. Azole amine derivatives 43 can then be converted to the corresponding activated arylcarbamic acid derivatives 44 by reacting with phenyl chloroformate in the presence of a base, such as, but not limited to, $K_2CO_3$, in a solvent, such as, but not limited to, THF.

Scheme 14: General synthesis of 1-aminopyrazole derivatives and arylcarbamic acid derivatives.

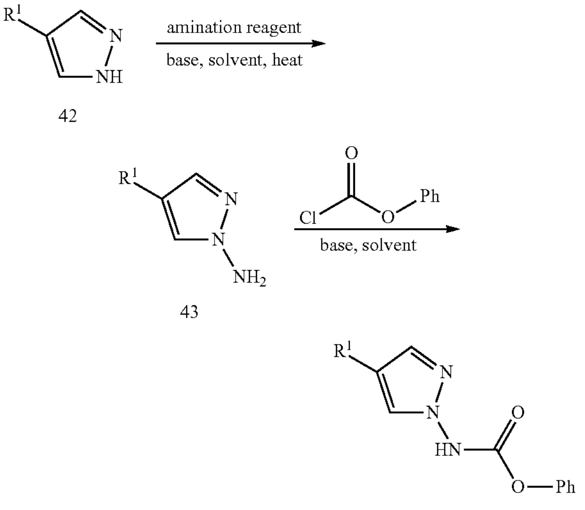

42 43 44

In an illustrative method, cyclohexane urea compounds of formula (I) may also be routinely prepared according to the synthetic routes outlined in Scheme 15. The cyclohexane ureas 46 can be prepared by the reaction of the cyclohexanediamine derivatives 45 with activated arylcarbamic acid derivatives 5 in solvents such as THF or DMF, promoted with bases such as DIEA or DMAP and by heating as necessary at elevated temperatures. The tert-butyloxy carbonyl group of 46 is cleaved under acidic conditions, such as, but not limited to, TFA in DCM or 4N HCl in 1,4-dioxane, to give the cyclohexaneamines 47. The amines 47 can couple with acids 4 using appropriate coupling reagents, such as, but not limited to, EDCI or HATU, promoted by bases such as DIEA, TEA, or DMAP to give the amide derivative 48.

Scheme 15: General synthesis of cyclohexane urea amides.

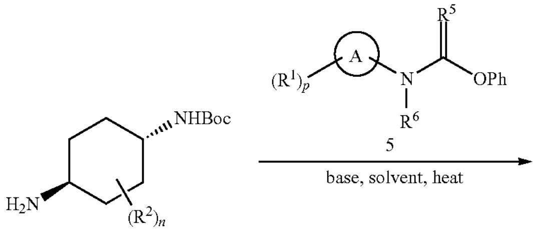

5 45

-continued

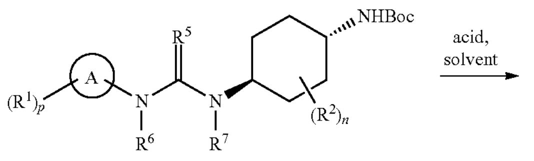

46

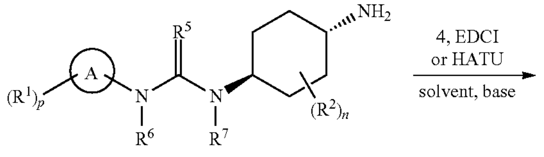

47

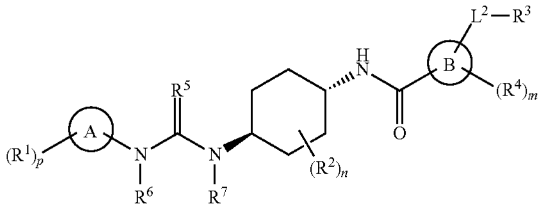

48

In an illustrative method, cyclohexane urea amide compounds of formula (I) may also be routinely prepared according to the synthetic route outlined in Scheme 16. In cases when $R^3$ (either acylic or cyclic) contains a protected amino group, such as, but not limited to, the tert-butyloxy carbonyl group, the protecting group within the amide derivatives 49 can be deprotected to give amines 50, using various conditions, such as, but not limited to, TFA in DCM or 4N HCl in 1,4-dioxane. Amines 50 can undergo reductive amination with various aldehydes and ketones, using reducing agents, such as, but not limited to $NaCNBH_3$, $Na(OAc)_3BH$, or $NaBH_4$. The reaction can be conducted in a pH~4 NaOAc/AcOH buffer in MeOH, or promoted by addition of AcOH in dichloroethane. The reaction can be run at ambient temperature for reaction with aldehydes to give amines 51a, or be promoted using heating in a conventional oil bath for reaction with ketones to give amines 51b.

Scheme 16: General synthesis of cyclohexane urea amides.

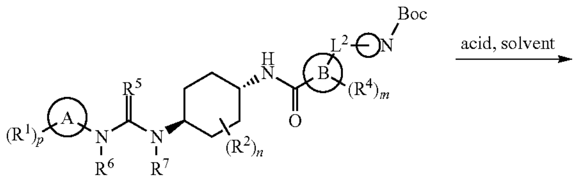

49

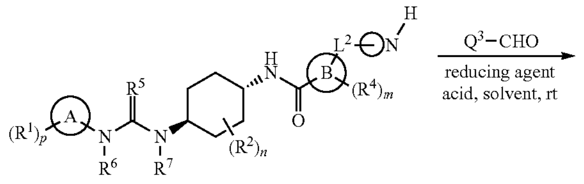

50

-continued

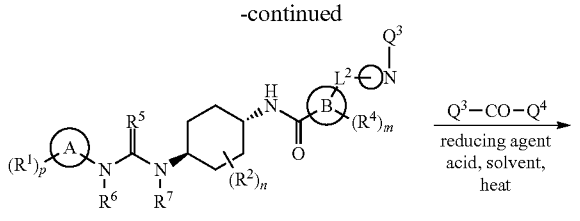

51a

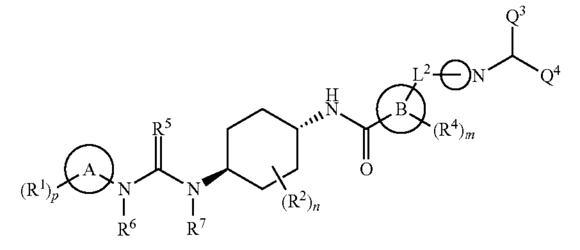

51b

The subject matter has been described in an illustrative manner, and it is to be understood that the terminology used is intended to be in the nature of description rather than of limitation. Thus, it will be appreciated by those of skill in the art that conditions such as choice of solvent, temperature of reaction, volumes, reaction time may vary while still producing the desired compounds. In addition, one of skill in the art will also appreciate that many of the reagents provided in the following examples may be substituted with other suitable reagents. See, e.g., Smith & March, *Advanced Organic Chemistry*, $5^{th}$ ed. (2001). Such changes and modifications, including without limitation those relating to the chemical structures, substituents, derivatives, intermediates, syntheses, formulations and/or methods of use provided herein, may be made without departing from the spirit and scope thereof. U.S. patents and publications referenced herein are incorporated by reference.

EXAMPLES

Example 1

Preparation of N-(4-(3-(5-tert-butylisoxazol-3-yl)ureido)phenyl)-4-(piperidin-4-yloxy)picolinamide hydrochloride

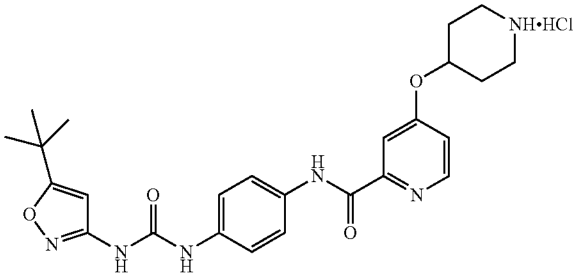

Step 1: NaH (60% in mineral oil, 303 mg, 7.6 mmol) in 15 mL of DMF was stirred at rt in a round-bottom flask. tert-Butyl 4-hydroxypiperidine-1-carboxylate (1.42 g, 7.0 mmol) was added in portions and the resulting mixture was stirred at rt for 30 min. 4-Chlorocyanopicoline (750 mg, 5.4 mmol) in 5 mL of DMF was added dropwise. After stirring at rt for 1 h, LC-MS indicated that the reaction was complete. The reaction mixture was then partitioned between EtOAc (30 mL)

and water (25 mL). The organic layer was washed with brine (10 mL), dried over $MgSO_4$, filtered, and concentrated under reduced pressure to give an oil which was purified by silica gel flash chromatography, eluting with 0-20% EtOAc in hexanes, to give tert-butyl 4-(2-cyanopyridin-4-yloxy)piperidine-1-carboxylate (1.2 g, 71%) as a light yellow oil. LC-MS (ESI) m/z 304 $(M+H)^+$.

Step 2: tert-Butyl 4-(2-cyanopyridin-4-yloxy)piperidine-1-carboxylate from Step 1 (1.2 g, 4.0 mmol) was stirred in 25 mL of EtOH. Aq. NaOH (3N, 4.0 mL) was added. The resulting mixture was refluxed for over night. LC-MS indicated that the hydrolysis was complete. The reaction mixture was then cooled to rt, most of the volatile solvent was evaporated under reduced pressure. The residue was acidified with 3N aq. HCl to pH~5, and extracted with DCM (2×20 mL). The combined organic layers were dried over $Na_2SO_4$, filtered, and concentrated under reduced pressure to give 4-(1-(tert-butoxycarbonyl)piperidin-4-yloxy)picolinic acid (1.0 g, 78%) as a white solid. LC-MS (ESI) m/z 323 $(M+H)^+$.

Step 3: 4-(1-(tert-Butoxycarbonyl)piperidin-4-yloxy)picolinic acid from Step 2 (188 mg, 0.58 mmol) was stirred in 3 mL of DMF. TBTU (244 mg, 0.76 mmol) was added, followed by TEA (82 μL, 0.058 mmol). After 10 min, 1-(4-aminophenyl)-3-(5-tert-butylisoxazol-3-yl)urea (Ref: Milanov, Zdravko V. et al. WO2005/48948 A2, 2005 Jun. 2) (160 mg, 0.58 mmol) was added, followed by TEA (82 μL, 0.058 mmol). The resulting mixture was stirred at rt for 3 h. LC-MS indicated that the reaction was complete. Water (20 mL) was then added, the precipitates were collected by filtration and washed with cold water, dried in vacuum oven to give tert-butyl 4-(2-(4-(3-(5-tert-butylisoxazol-3-yl)ureido)phenylcarbamoyl)pyridin-4-yloxy)piperidine-1-carboxylate (280 mg, 83%) as an off-white solid. LC-MS (ESI) m/z 579 $(M+H)^+$.

Step 4: tert-Butyl 4-(2-(4-(3-(5-tert-butylisoxazol-3-yl)ureido)phenylcarbamoyl)pyridin-4-yloxy)piperidine-1-carboxylate from Step 3 (280 mg, 0.48 mmol) was stirred in 4N HCl/1,4-Dioxane (10 mL) for 2 h at rt. LC-MS indicated that the reaction was complete. The reaction mixture was diluted with $CH_3CN$ (20 mL) and evaporated under reduced pressure. The residue was taken up in $CH_3CN/Et_2O$ (1:5, v/v), sonicated at rt for 15 min, and filtered to give N-(4-(3-(5-tert-butylisoxazol-3-yl)ureido)phenyl)-4-(piperidin-4-yloxy)picolinamide hydrochloride as a yellow solid (190 mg, 77% yield). LC-MS (ESI) m/z 479 $(M+H)^+$; $^1H$ NMR (300 MHz, DMSO-$d_6$) δ 10.78 (s, 1H), 9.69 (s, 1H), 9.36 (br. s., 1H), 9.07 (br. s., 1H), 8.60 (d, J=5.84 Hz, 1H), 7.97 (br. s., 1H), 7.83 (d, J=8.85 Hz, 2H), 7.46 (d, J=9.04 Hz, 2H), 7.39 (dd, J=2.17, 5.75 Hz, 1H), 6.51 (s, 1H), 5.07 (br. s., 1H), 4.50 (br. s., 1H), 3.25 (br. s., 2H), 3.13 (d, J=3.58 Hz, 2H), 2.20 (d, J=14.32 Hz, 2H), 1.93 (d, J=9.04 Hz, 2H), 1.30 (s, 9H).

Example 2

Preparation of N-(4-(3-(5-tert-butylisoxazol-3-yl)ureido)phenyl)-4-(1-ethylpiperidin-4-yloxy)picolinamide

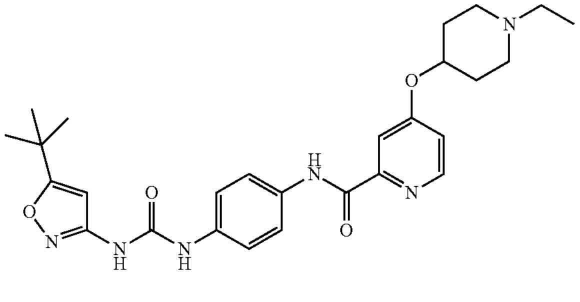 [SMILES: CCN1CCC(Oc2ccnc(C(=O)Nc3ccc(NC(=O)Nc4cc(C(C)(C)C)on4)cc3)c2)CC1]

To a stirred solution of N-(4-(3-(5-tert-butylisoxazol-3-yl)ureido)phenyl)-4-(piperidin-4-yloxy)picolinamide hydrochloride from Example 1 (100 mg, 0.19 mmol) in 2 mL of pH~4 MeOH/NaOAc buffer (21 grams of $NaOAc.3H_2O$ and 48 mL of AcOH, diluted to 1.0 L with methanol) was added acetaldehyde (0.2 mL, excess) and $NaCNBH_3$ (25 mg, excess). The resulting mixture was stirred at rt for 3 h. LC-MS indicated that the reaction was complete. The crude product was purified by reverse phase HPLC to afford N-(4-(3-(5-tert-butylisoxazol-3-yl)ureido)phenyl)-4-(1-ethylpiperidin-4-yloxy)picolinamide as a white powder (52 mg, 53% yield). LC-MS (ESI) m/z 507 $(M+H)^+$; $^1H$ NMR (300 MHz, DMSO-$d_6$) δ 10.55 (s, 1H), 9.49 (s, 1H), 8.79 (s, 1H), 8.54 (d, J=5.65 Hz, 1H), 7.83 (d, J=9.04 Hz, 2H), 7.67 (br. s., 1H), 7.43 (d, J=8.85 Hz, 2H), 7.26 (dd, J=2.45, 5.65 Hz, 1H), 6.50 (s, 1H), 4.82 (br. s., 1H), 2.75-3.14 (m, 3H), 2.07 (br. s., 2H), 1.75 (br. s., 2H), 1.30 (s, 9H), 1.13 (br. s., 3H).

Example 3

Preparation of N-(4-(3-(5-tert-butylisoxazol-3-yl)ureido)phenyl)-4-(4-methylpiperazin-1-yl)picolinamide

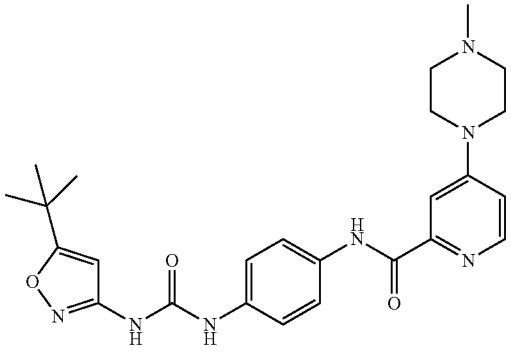 [SMILES: CN1CCN(c2ccnc(C(=O)Nc3ccc(NC(=O)Nc4cc(C(C)(C)C)on4)cc3)c2)CC1]

N-(4-(3-(5-tert-Butylisoxazol-3-yl)ureido)phenyl)-4-(4-methylpiperazin-1-yl)picolinamide (35 mg, 27% yield) was prepared using a procedure analogous to that described in Step 3 of Example 1, substituting 4-(4-methylpiperazin-1-yl)picolinic acid for 4-(1-(tert-butoxycarbonyl)piperidin-4-yloxy)picolinic acid used in Example 1. LC-MS (ESI) m/z 478 $(M+H)^+$; $^1H$ NMR (300 MHz, DMSO-$d_6$) δ 10.47 (s, 1H), 9.48 (s, 1H), 8.79 (s, 1H), 8.28 (d, J=6.03 Hz, 1H), 7.81 (d, J=9.04 Hz, 2H), 7.55 (d, J=2.64 Hz, 1H), 7.42 (d, J=9.04 Hz, 2H), 7.05 (dd, J=2.73, 5.93 Hz, 1H), 6.50 (s, 1H), 3.39-3.47 (m, 4H), 2.37-2.48 (m, 4H), 2.24 (s, 3H), 1.30 (s, 9H).

Example 4

Preparation of N-(4-(3-(5-tert-butylisoxazol-3-yl)ureido)phenyl)-4-(1-methylpiperidin-4-yloxy)picolinamide

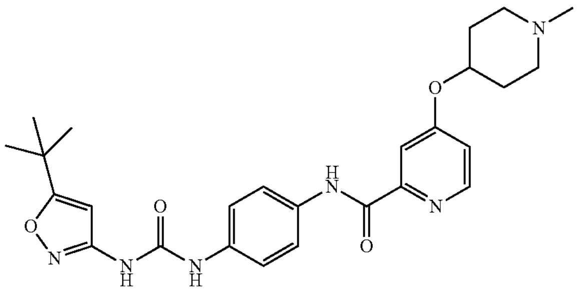 [SMILES: CN1CCC(Oc2ccnc(C(=O)Nc3ccc(NC(=O)Nc4cc(C(C)(C)C)on4)cc3)c2)CC1]

N-(4-(3-(5-tert-butylisoxazol-3-yl)ureido)phenyl)-4-(1-methylpiperidin-4-yloxy)picolinamide was prepared as a white powder (42 mg, 55% yield) using a procedure analogous to that described in Example 2, substituting formalin for acetaldehyde used in Example 2. LC-MS (ESI) m/z 493 $(M+H)^+$; $^1H$ NMR (300 MHz, DMSO-$d_6$) δ 10.54 (s, 1H), 9.49 (s, 1H), 8.80 (s, 1H), 8.52 (d, J=5.84 Hz, 1H), 7.82 (d, J=9.04 Hz, 2H), 7.64 (d, J=2.45 Hz, 1H), 7.43 (d, J=9.04 Hz, 2H), 7.25 (dd, J=2.54, 5.75 Hz, 1H), 6.50 (s, 1H), 4.74 (br. s., 1H), 3.61 (br. s., 1H), 3.14 (br. s., 2H), 2.78 (br. s., 2H), 2.35 (br. s., 3H), 2.01 (br. s., 2H), 1.76 (br. s, 2H), 1.30 (s, 9H).

Example 5

Preparation of N-(4-(3-(5-tert-butylisoxazol-3-yl) ureido)phenyl)-4-(2-morpholinoethoxy)picolinamide

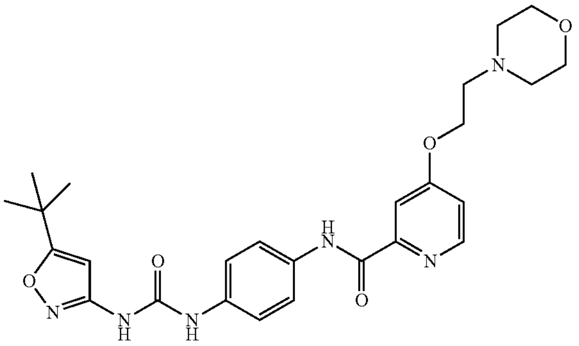 [SMILES: CC(C)(C)c1cc(NC(=O)Nc2ccc(NC(=O)c3cc(OCCN4CCOCC4)ccn3)cc2)no1]

N-(4-(3-(5-tert-Butylisoxazol-3-yl)ureido)phenyl)-4-(2-morpholinoethoxy)picolinamide was prepared as a white powder (90 mg) using procedures analogous to those described in Steps 1-3 of Example 1, substituting 2-morpholinoethanol for tert-butyl 4-hydroxypiperidine-1-carboxylate used in the Step 1 of Example 1. LC-MS (ESI) m/z 493 $(M+H)^+$; $^1H$ NMR (300 MHz, DMSO-$d_6$) δ 10.55 (s, 1H), 9.50 (s, 1H), 8.81 (s, 1H), 8.53 (d, J=5.65 Hz, 1H), 7.83 (d, J=8.85 Hz, 2H), 7.65 (d, J=2.45 Hz, 1H), 7.43 (d, J=9.04 Hz, 2H), 7.24 (dd, J=2.64, 5.65 Hz, 1H), 6.50 (s, 1H), 4.30 (t, J=5.56 Hz, 2H), 3.50-3.65 (m, 4H), 2.74 (t, J=5.56 Hz, 2H), 2.43-2.48 (m, 4H), 1.30 (s, 9H).

Example 6

Preparation of N-(4-(3-(5-tert-butylisoxazol-3-yl) ureido)phenyl)-5-(piperidin-4-yloxy)picolinamide hydrochloride Step 1: 5-(1-(tert-Butoxycarbonyl)piperidin-4-yloxy)picolinic acid (1.50 g, 76% over two steps) was prepared using procedures analogous to those described in the Steps 1-2 of Example 1, substituting 5-fluoropicolinonitrile for 4-chlorocyanopicoline used in Example 1. LC-MS (ESI) m/z 323 $(M+H)^+$.

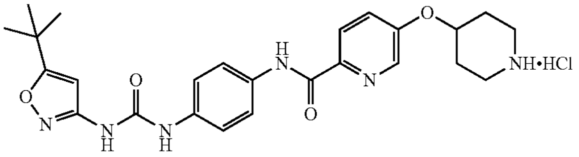

Step 2: N-(4-(3-(5-tert-Butylisoxazol-3-yl)ureido)phenyl)-5-(piperidin-4-yloxy)picolinamide hydrochloride was prepared as a yellow solid (170 mg, 85%) using procedures analogous to those described in Steps 3-4 of Example 1, substituting 5-(1-(tert-butoxycarbonyl)piperidin-4-yloxy)picolinic acid from Step 1 of this example for 4-(1-(tert-butoxycarbonyl)piperidin-4-yloxy)picolinic acid used in Step 3 of Example 1. LC-MS (ESI) m/z 479 $(M+H)^+$; $^1H$ NMR (300 MHz, DMSO-$d_6$) δ 10.40 (s, 1H), 9.62 (s, 1H), 9.16 (br. s., 1H), 8.98 (br. s., 2H), 8.42 (d, J=2.83 Hz, 1H), 8.12 (d, J=8.85 Hz, 1H), 7.80 (d, J=9.04 Hz, 2H), 7.72 (dd, J=2.83, 8.85 Hz, 1H), 7.43 (d, J=9.04 Hz, 2H), 6.51 (s, 1H), 4.80-4.96 (m, 1H), 3.26 (br. s., 2H), 3.11 (br. s., 2H), 2.17 (br. s, 2H), 1.81-2.00 (m, 2H), 1.30 (s, 9H).

Example 7

Preparation of N-(4-(3-(5-tert-butylisoxazol-3-yl) ureido)phenyl)-5-(1-ethylpiperidin-4-yloxy)picolinamide

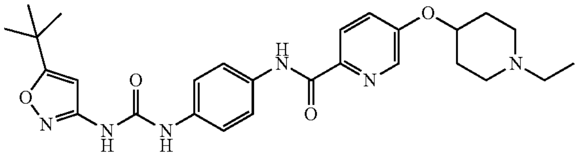 [SMILES: CCN1CCC(Oc2ccc(C(=O)Nc3ccc(NC(=O)Nc4cc(C(C)(C)C)on4)cc3)nc2)CC1]

N-(4-(3-(5-tert-Butylisoxazol-3-yl)ureido)phenyl)-5-(1-ethylpiperidin-4-yloxy)picolinamide was prepared as a white powder (60 mg, 68% yield) using a procedure analogous to that described in Example 2, substituting N-(4-(3-(5-tert-butylisoxazol-3-yl)ureido)phenyl)-5-(piperidin-4-yloxy)picolinamide hydrochloride from Example 6 for N-(4-(3-(5-tert-butylisoxazol-3-yl)ureido)phenyl)-4-(piperidin-4-yloxy)picolinamide hydrochloride from Step 4 of Example 1. LC-MS (ESI) m/z 507 $(M+H)^+$; $^1H$ NMR (300 MHz, DMSO-$d_6$) δ 10.39 (s, 1H), 9.52 (s, 1H), 8.87 (s, 1H), 8.38 (d, J=2.83 Hz, 1H), 8.10 (d, J=8.67 Hz, 1H), 7.81 (d, J=9.04 Hz, 2H), 7.68 (dd, J=2.83, 8.85 Hz, 1H), 7.43 (d, J=9.04 Hz, 2H), 6.50 (s, 1H), 4.65-4.78 (m, 1H), 2.88-3.04 (m, 2H), 2.58-2.75 (m, 3H), 2.37 (s, 3H), 1.99-2.15 (m, 2H), 1.91 (s, 2H), 1.73-1.86 (m, 2H), 1.30 (s, 9H), 1.10 (t, J=7.25 Hz, 3H).

Example 8

Preparation of 4-(aminomethyl)-N-(4-(3-(5-tert-butylisoxazol-3-yl)ureido)phenyl)picolinamide hydrochloride

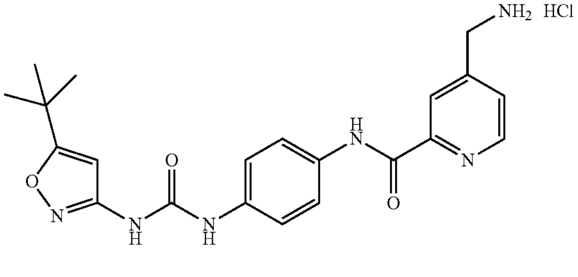 [SMILES: Cl ; CC(C)(C)c1cc(NC(=O)Nc2ccc(NC(=O)c3cc(CN)ccn3)cc2)no1]

4-(Aminomethyl)-N-(4-(3-(5-tert-butylisoxazol-3-yl)ureido)phenyl)picolinamide hydrochloride (160 mg, 91% yield over two steps) was prepared using procedures analogous to those described in Steps 3-4 of Example 1, substituting 4-((tert-butoxycarbonylamino)methyl)picolinic acid for 4-(1-(tert-butoxycarbonyl)piperidin-4-yloxy)picolinic acid used in Example 1. LC-MS (ESI) m/z 409 $(M+H)^+$; $^1H$ NMR (300 MHz, DMSO-$d_6$) δ 10.63 (s, 1H), 9.63 (br. s., 1H), 9.14-9.30 (m, 1H), 8.78 (d, J=5.09 Hz, 1H), 8.52-8.63 (m, 1H), 8.30 (s, 1H), 7.84 (d, J=9.04 Hz, 2H), 7.71-7.78 (m, 1H), 7.45 (d, J=9.04 Hz, 2H), 6.51 (s, 1H), 4.16-4.29 (m, 2H), 1.30 (s, 9H).

Example 9

Preparation of N-(4-(3-(5-tert-butylisoxazol-3-yl)ureido)phenyl)-4-((diethylamino)methyl)picolinamide

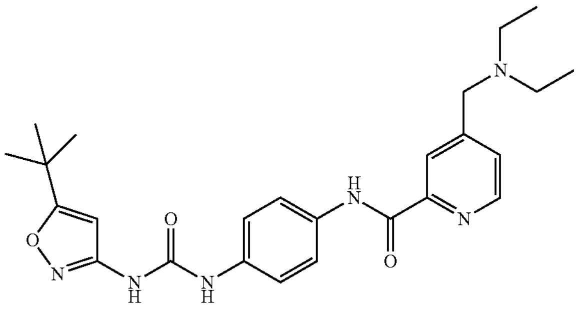 [SMILES: CCN(CC)Cc1ccnc(C(=O)Nc2ccc(NC(=O)Nc3cc(C(C)(C)C)on3)cc2)c1]

N-(4-(3-(5-tert-Butylisoxazol-3-yl)ureido)phenyl)-4-((diethylamino)methyl)picolinamide (90 mg, 96% yield) was prepared using a procedure analogous to that described in Example 2, substituting 4-(aminomethyl)-N-(4-(3-(5-tert-butylisoxazol-3-yl)ureido)phenyl)picolinamide hydrochloride from Example 8 for N-(4-(3-(5-tert-butylisoxazol-3-yl)ureido)phenyl)-4-(piperidin-4-yloxy)picolinamide hydrochloride used in Example 2. LC-MS (ESI) m/z 465 $(M+H)^+$; $^1$H NMR (300 MHz, DMSO-$d_6$) δ 10.57 (s, 1H), 9.48 (s, 1H), 8.79 (s, 1H), 8.64 (d, J=5.09 Hz, 1H), 8.12 (d, J=0.57 Hz, 1H), 7.83 (d, J=9.04 Hz, 2H), 7.56-7.63 (m, 1H), 7.38-7.49 (m, 2H), 6.50 (s, 1H), 3.68 (s, 2H), 2.55-2.44 (overlapping q, 4H), 1.30 (s, 9H), 1.00 (t, J=7.06 Hz, 6H).

Example 10

Preparation of N-(4-(3-(5-tert-butylisoxazol-3-yl)ureido)phenyl)-5-(4-methylpiperazin-1-yl)picolinamide

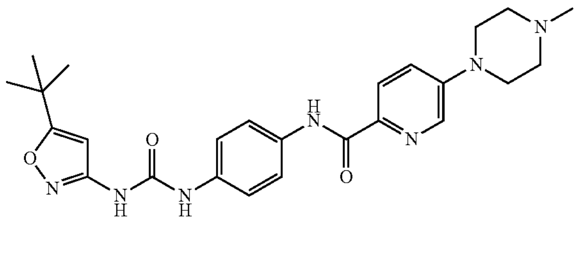 [SMILES: CN1CCN(c2ccc(C(=O)Nc3ccc(NC(=O)Nc4cc(C(C)(C)C)on4)cc3)nc2)CC1]

Step 1: 5-(4-Methylpiperazin-1-yl)picolinic acid was prepared as a light yellow solid using procedures analogous to those described in Step 1-2 of Example 1, substituting N-methylpiperazine for tert-butyl 4-hydroxypiperidine-1-carboxylate, and 5-fluoro-2-cyanopyridine for 4-chlorocyanopicoline used in Step 1 of Example 1. LC-MS (ESI) m/z 221 $(M+H)^+$.

Step 2: To a stirred solution of 5-(4-methylpiperazin-1-yl)picolinic acid (185 mg, 0.46 mmol) in 5 mL of DCM was added DIEA (82 μL, 0.46 mmol) and ethyl chloroformate (45 μL, 0.46 mmol). The resulting mixture was stirred at rt for 15 min, sonicated for 10 min. 1-(4-Aminophenyl)-3-(5-tert-butylisoxazol-3-yl)urea (128 mg, 0.46 mmol) was added. The resulting mixture was refluxed for 30 min. LC-MS indicated the reaction mostly done. Solvent was then removed under reduced pressure and residue was purified on reverse phase HPLC to give N-(4-(3-(5-tert-butylisoxazol-3-yl)ureido)phenyl)-5-(4-methylpiperazin-1-yl)picolinamide (65 mg, 29%) as a white foamy solid. LC-MS (ESI) m/z 478 $(M+H)^+$. $^1$H NMR (300 MHz, DMSO-$d_6$) δ 10.26 (s, 1H), 9.48 (s, 1H), 8.79 (s, 1H), 8.36 (d, J=2.45 Hz, 1H), 7.96 (d, J=8.85 Hz, 1H), 7.80 (d, J=8.85 Hz, 2H), 7.47 (dd, J=2.64, 8.85 Hz, 1H), 7.41 (d, J=9.04 Hz, 2H), 6.50 (s, 1H), 3.35 (br. s., 8H), 2.26 (s, 3H), 1.30 (s, 9H).

Example 11

Preparation of N-(4-(3-(5-tert-butylisoxazol-3-yl)ureido)phenyl)-5-(piperidin-4-ylmethyl)picolinamide hydrochloride

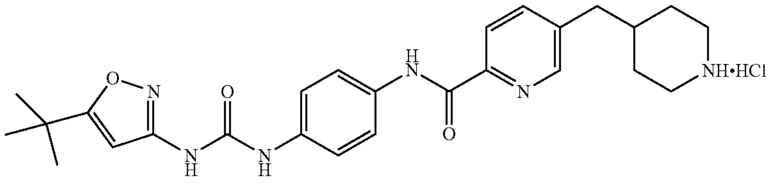

Step 1: Rieke Zinc (slightly excess by estimation) was stirred in 10 mL of THF under argon. tert-Butyl 4-(bromomethyl)piperidine-1-carboxylate (1.0 g, 3.6 mmol) in 5 mL of THF was added. The resulting mixture was stirred at rt for 3 h. The solution was then allowed to settle and the supernatant was transferred via a syringe to a stirred 5 mL of DMA solution. Methyl 5-bromopicolinate (0.78 g, 3.6 mmol) and $Cl_2Ni(Ph_2PCH_2CH_2PPh_2)$ were added sequentially, and the resulting mixture was stirred at rt for 60 h. LC-MS indicated a partial conversion. The reaction mixture was quenched with 15 mL of sat. $NH_4Cl$, and extracted with 50 mL of EtOAc. The organic layer was washed with brine (20 mL), dried over $MgSO_4$, filtered, and concentrated under reduced pressure to give an oil which was purified by silica gel flash chromatography, eluting with 10-80% EtOAc in hexanes, to give methyl 5-((1-(tert-butoxycarbonyl)piperidin-4-yl)methyl)picolinate as a white solid (200 mg, 17%).

Step 2: Methyl 5-((1-(tert-butoxycarbonyl)piperidin-4-yl)methyl)picolinate (200 mg, 0.60 mmol) was stirred at rt in THF/MeOH (1:1, v/v). 3N NaOH (0.2 mL, 0.60 mmol) was added and the resulting mixture was stirred at rt for 5 h. TLC indicated the reaction was complete. Most of the volatile solvent was evaporated under reduced pressure. The residue was acidified with 3N aq. HCl to pH~5, and extracted with DCM (2×20 mL). The combined organic layers were dried over $Na_2SO_4$, filtered, and concentrated under reduced pressure to give 5-((1-(tert-butoxycarbonyl)piperidin-4-yl)methyl)picolinic acid as a white semi-solid (200 mg, quantitative).

Step 3: N-(4-(3-(5-tert-butylisoxazol-3-yl)ureido)phenyl)-5-(piperidin-4-ylmethyl)picolinamide hydrochloride (100 mg) was prepared as a yellow solid using procedures analogous to those described in Steps 3-4 of Example 1, substituting 5-((1-(tert-butoxycarbonyl)piperidin-4-yl)methyl)picolinic acid from Step 2 of this Example for 4-(1-(tert-butoxycarbonyl)piperidin-4-yloxy)picolinic acid used in Step 3 of Example 1. LC-MS (ESI) m/z 477 $(M+H)^+$; $^1H$ NMR (300 MHz, DMSO-$d_6$) δ 10.54 (s, 1H), 9.67 (s, 1H), 9.30 (s, 1H), 8.91 (br. s., 1H), 8.68 (d, J=9.61 Hz, 1H), 8.58 (d, J=1.32 Hz, 1H), 8.11 (d, J=8.10 Hz, 1H), 7.91 (dd, J=2.07, 8.10 Hz, 1H), 7.82 (d, J=9.04 Hz, 2H), 7.44 (d, J=9.04 Hz, 2H), 6.51 (s, 1H), 3.23 (d, J=12.06 Hz, 2H), 2.73-2.88 (m, 2H), 2.70 (d, J=6.78 Hz, 2H), 1.88 (br. s., 1H), 1.71 (d, J=12.81 Hz, 2H), 1.33-1.49 (m, 2H), 1.30 (s, 9H).

Example 12

Preparation of N-(4-(3-(5-tert-butylisoxazol-3-yl)ureido)phenyl)-5-((1-ethylpiperidin-4-yl)methyl)picolinamide

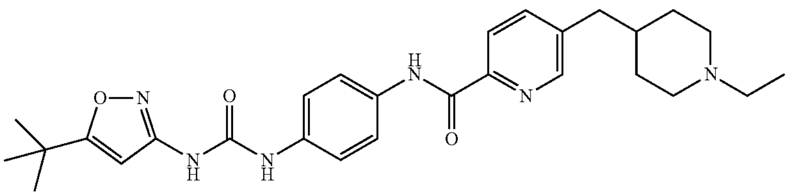 [SMILES: CCN1CCC(Cc2ccc(C(=O)Nc3ccc(NC(=O)Nc4cc(C(C)(C)C)on4)cc3)nc2)CC1]

N-(4-(3-(5-tert-Butylisoxazol-3-yl)ureido)phenyl)-5-((1-ethylpiperidin-4-yl)methyl)picolinamide was prepared as a white powder (45 mg, 83% yield) using a procedure analogous to that described in Example 2, substituting N-(4-(3-(5-tert-butylisoxazol-3-yl)ureido)phenyl)-5-(piperidin-4-ylmethyl)picolinamide hydrochloride from Example 11 for N-(4-(3-(5-tert-butylisoxazol-3-yl)ureido)phenyl)-4-(piperidin-4-yloxy)picolinamide hydrochloride used in Example 2. LC-MS (ESI) m/z 505 $(M+H)^+$; $^1H$ NMR (300 MHz, DMSO-$d_6$) δ 10.53 (s, 1H), 9.49 (s, 1H), 8.80 (s, 1H), 8.56 (s, 1H), 8.09 (d, J=8.10 Hz, 1H), 7.88 (dd, J=2.07, 8.10 Hz, 1H), 7.82 (d, J=8.85 Hz, 2H), 7.43 (d, J=9.04 Hz, 2H), 6.50 (s, 1H), 3.01-3.28 (m, 3H), 2.70 (d, J=6.59 Hz, 4H), 1.70 (d, J=12.43 Hz, 3H), 1.30 (s, 9H), 1.18-1.42 (m, 3H), 1.11 (t, J=8.70 Hz, 3H).

Example 13

Preparation of N-(4-(3-(5-tert-butylisoxazol-3-yl)ureido)phenyl)-5-(morpholinomethyl)picolinamide

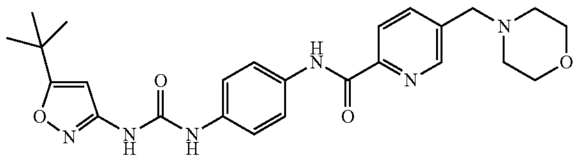 [SMILES: CC(C)(C)c1cc(NC(=O)Nc2ccc(NC(=O)c3ccc(CN4CCOCC4)cn3)cc2)no1]

Step 1: 5-Bromo-N-(4-(3-(5-tert-butylisoxazol-3-yl)ureido)phenyl)picolinamide (250 mg, 86%) was prepared as a white powder using a procedure analogous to that described in Step 3 of Example 1, substituting 5-bromopicolinic acid for 4-(1-(tert-butoxycarbonyl)piperidin-4-yloxy)picolinic acid used in Example 1. LC-MS (ESI) m/z 458, 460 $(M+H)^+$.

Step 2: To a 5 mL of microwave vial was charged with $Pd(OAc)_2$ (4 mg, 0.019 mmol), $Cs_2CO_3$ (370 mg, 1.14 mmol), potassium 1-trifluoroboratomethylmorpholine (86 mg, 0.42 mmol), and X-phos (18 mg, 0.038 mmol). The vial was then flushed with argon while 5-bromo-N-(4-(3-(5-tert-butylisoxazol-3-yl)ureido)phenyl)picolinamide (150 mg, 0.38 mmol) from Step 1 of this Example and 3 mL of THF/$H_2O$ (10:1, v/v) were added. The vial was then capped and heated in a microwave reactor at 140° C. for 10 min. LC-MS indicated that the reaction was complete. The reaction mixture was then partitioned between EtOAc (25 mL) and water (10 mL). The organic layer was washed with brine (10 mL), dried over $MgSO_4$, filtered, and concentrated under reduced pressure to give an oil which was purified by preparative HPLC to give N-(4-(3-(5-tert-butylisoxazol-3-yl)ureido)phenyl)-5-(morpholinomethyl)picolinamide (70 mg, 38% yield) as a white powder. LC-MS (ESI) m/z 479 $(M+H)^+$; $^1H$ NMR (300 MHz, DMSO-$d_6$) δ 10.56 (s, 1H), 9.57 (s, 1H), 8.89 (s, 1H), 8.65 (d, J=1.51 Hz, 1H), 8.12 (d, J=7.91 Hz, 1H), 7.98 (dd, J=1.98, 8.01 Hz, 1H), 7.83 (d, J=9.04 Hz, 2H), 7.43 (d, J=8.85 Hz, 2H), 6.50 (s, 1H), 3.52-3.67 (m, 6H), 2.31-2.44 (m, 4H), 1.30 (s, 9H).

Example 14

Preparation of N-(4-(3-(5-tert-butylisoxazol-3-yl)ureido)phenyl)-5-(1-methylpiperidin-4-yl)picolinamide

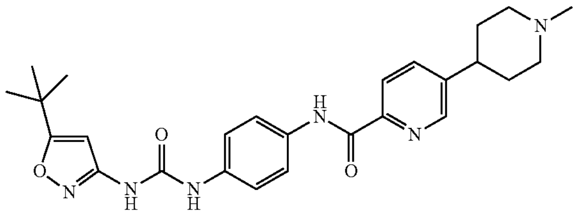 [SMILES: CN1CCC(c2ccc(C(=O)Nc3ccc(NC(=O)Nc4cc(C(C)(C)C)on4)cc3)nc2)CC1]

Step 1: To a microwave vial was charged with methyl 5-bromopicolinate (250 mg, 1.22 mmol), tert-butyl 4-(4,4,5,5-tetramethyl-1,3-dioxolan-2-yl)-5,6-dihydropyridine-1(2H)-carboxylate (393 mg, 1.34 mmol), $K_2CO_3$ (400 mg, 3.03 mmol), and 3 mL of DMF. The vial was then flushed with argon while $PdCl_2(dppf)_2$ (42 mg, 0.060 mmol) was added. The resulting mixture was then capped and heated at 140° C. for 10 min in a microwave reactor. LC-MS indicated that the reaction was complete. The reaction mixture was then partitioned between EtOAc (25 mL) and water (10 mL). The organic layer was washed with brine (10 mL), dried over $MgSO_4$, filtered, and concentrated under reduced pressure to give an oil which was purified by silica gel column chromatography, eluting with 0-60% EtOAc in hexanes, to give methyl 5-(1-(tert-butoxycarbonyl)-1,2,3,6-tetrahydropyridin-4-yl)picolinate (250 mg, 68%). LC-MS (ESI) m/z 319 $(M+H)^+$.

Step 2: 5-(1-(tert-Butoxycarbonyl)-1,2,3,6-tetrahydropyridin-4-yl)picolinate from Step 1 (250 mg, 0.79 mmol) was taken up in MeOH/EtOAC (3:1, v/v) and 10% Pd/C (50 mg) was added. The resulting mixture was hydrogenation with a hydrogen balloon at rt for over night. Hydrogenation continued for another 3 h at 55° C. LC-MS indicated that the reaction was complete. The reaction mixture was filtered over a celite plug and washed with MeOH. The filtrate was evaporated under reduced pressure and dried in vacuum oven to give methyl 5-(1-(tert-butoxycarbonyl)piperidin-4-yl)picolinate (250 mg, 100%). LC-MS (ESI) m/z 321 $(M+H)^+$.

Step 3: N-(4-(3-(5-tert-Butylisoxazol-3-yl)ureido)phenyl)-5-(piperidin-4-yl)picolinamide hydrochloride (250 mg) was prepared as a white solid using procedures analogous to those described in Steps 2-3 of Example 11, substituting methyl 5-(1-(tert-butoxycarbonyl)piperidin-4-yl)picolinate from Step 2 of this example for methyl 5-((1-(tert-butoxycarbonyl)piperidin-4-yl)methyl)picolinate from Step 1 of Example 11. LC-MS (ESI) m/z 463 $(M+H)^+$.

Step 4: N-(4-(3-(5-tert-Butylisoxazol-3-yl)ureido)phenyl)-5-(1-methylpiperidin-4-yl)picolinamide (55 mg, 89%) was prepared as a white solid using a procedure analogous to that described in Example 2, substituting N-(4-(3-(5-tert-butylisoxazol-3-yl)ureido)phenyl)-5-(piperidin-4-yl)picolinamide hydrochloride from Step 3 of this example for N-(4-(3-(5-tert-butylisoxazol-3-yl)ureido)phenyl)-4-(piperidin-4-yloxy)picolinamide hydrochloride, and formalin for acetaldehyde used in Example 2. LC-MS (ESI) m/z 477 $(M+H)^+$; $^1H$ NMR (300 MHz, DMSO-$d_6$) δ 10.52 (s, 1H), 9.54 (s, 1H), 8.85 (br. s., 1H), 8.63 (d, J=1.70 Hz, 1H), 8.07 (d, J=8.10 Hz, 1H), 7.94 (dd, J=1.88, 8.10 Hz, 1H), 7.83 (d, J=8.85 Hz, 2H), 7.43 (d, J=8.85 Hz, 2H), 6.50 (s, 1H), 2.89 (d, J=11.49 Hz, 2H), 2.58-2.75 (m, 1H), 2.21 (s, 3H), 1.92-2.06 (m, 2H), 1.63-1.85 (m, 4H), 1.30 (s, 9H).

Example 15

Preparation of N-(4-(3-(5-tert-butylisoxazol-3-yl)ureido)phenyl)-5-(1-ethylpiperidin-4-yl)picolinamide

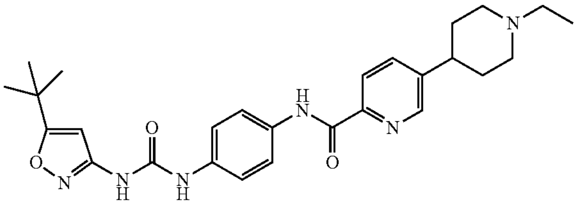 [SMILES: CCN1CCC(c2ccc(C(=O)Nc3ccc(NC(=O)Nc4cc(C(C)(C)C)on4)cc3)nc2)CC1]

N-(4-(3-(5-tert-Butylisoxazol-3-yl)ureido)phenyl)-5-(1-ethylpiperidin-4-yl)picolinamide (65 mg, 83%) was prepared as a white solid using a procedure analogous to that described in Example 2, substituting N-(4-(3-(5-tert-butylisoxazol-3-yl)ureido)phenyl)-5-(piperidin-4-yl)picolinamide hydrochloride from Step 3 of Example 14 for N-(4-(3-(5-tert-butylisoxazol-3-yl)ureido)phenyl)-4-(piperidin-4-yloxy)picolinamide hydrochloride used in Example 2. LC-MS (ESI) m/z 491 $(M+H)^+$.

Example 16

Preparation of N-(4-(3-(5-tert-butylisoxazol-3-yl)ureido)phenyl)-5-((4-methylpiperazin-1-yl)methyl)picolinamide

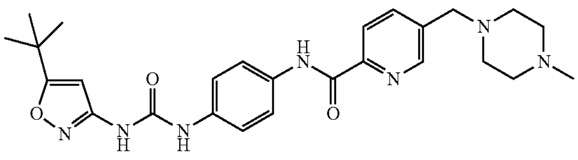 [SMILES: CN1CCN(Cc2ccc(C(=O)Nc3ccc(NC(=O)Nc4cc(C(C)(C)C)on4)cc3)nc2)CC1]

N-(4-(3-(5-tert-butylisoxazol-3-yl)ureido)phenyl)-5-((4-methylpiperazin-1-yl)methyl)picolinamide (65 mg, 38%) was prepared as a white powder using a procedure analogous to that described in Example 13, substituting potassium 1-methyl-4-trifluoroboratomethylpiperazine for potassium 1-trifluoroboratomethylmorpholine used in Example 13. LC-MS (ESI) m/z 479 $(M+H)^+$; $^1H$ NMR (300 MHz, DMSO-$d_6$) δ 10.55 (s, 1H), 9.48 (s, 1H), 8.79 (s, 1H), 8.62 (s, 1H), 8.00-8.16 (m, 1H), 7.95 (d, J=7.91 Hz, 1H), 7.83 (d, J=8.85 Hz, 2H), 7.43 (d, J=8.85 Hz, 2H), 6.50 (s, 1H), 3.62 (s, 2H), 2.40 (br. s., 8H), 2.18 (s, 3H), 1.30 (s, 9H).

Example 17

Preparation of N-(4-(3-(5-(1,3-difluoro-2-methylpropan-2-yl)isoxazol-3-yl)ureido)phenyl)-5-(1-ethylpiperidin-4-yloxy)picolinamide

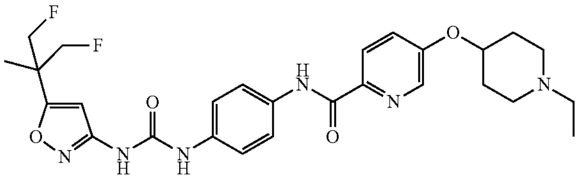 [SMILES: CCN1CCC(Oc2ccc(C(=O)Nc3ccc(NC(=O)Nc4cc(C(C)(CF)CF)on4)cc3)nc2)CC1]

Step 1: Phenyl 5-(1,3-difluoro-2-methylpropan-2-yl)isoxazol-3-ylcarbamate was synthesized using procedures analogous to those described in Steps 1-3 of Example 29, substituting methyl 3-fluoro-2-(fluoromethyl)-2-methylpropanoate for methyl 2-fluoro-2-methylpropanoate used in Example 29.

Step 2: To a stirred solution of tert-butyl 4-aminophenylcarbamate (176 mg, 0.85 mmol) in 5 mL of THF was added phenyl 5-(1,3-difluoro-2-methylpropan-2-yl)isoxazol-3-ylcarbamate (250 mg, 0.85 mmol), DIEA (147 mL, 0.85 mmol), and DMAP (5.2 mg, 0.043 mmol). The resulting mixture was heated at 65° C. for 90 min. LC-MS indicated that the reaction was complete. The organic solvent was removed under reduced pressure and the residue was purified with silica gel column chromatography, eluting with 0-50% EtOAc in hexanes, to give tert-butyl 4-(3-(5-(1,3-difluoro-2-methylpropan-2-yl)isoxazol-3-yl)ureido)phenylcarbamate (350 mg, 95%). LC-MS (ESI) m/z 411 $(M+H)^+$.

Step 3: 1-(4-Aminophenyl)-3-(5-(1,3-difluoro-2-methylpropan-2-yl)isoxazol-3-yl)urea hydrochloride (320 mg, 100%) was prepared as a white powder using a procedure analogous to that described in Step 4 of Example 1, substituting tert-butyl 4-(3-(5-(1,3-difluoro-2-methylpropan-2-yl)isoxazol-3-yl)ureido)phenylcarbamate from Step 1 of this example for tert-butyl 4-(2-(4-(3-(5-tert-butylisoxazol-3-yl)ureido)phenylcarbamoyl)pyridin-4-yloxy)piperidine-1-carboxylate from Step 3 of Example 1. LC-MS (ESI) m/z 311 $(M+H)^+$.

Step 4: N-(4-(3-(5-(1,3-Difluoro-2-methylpropan-2-yl)isoxazol-3-yl)ureido)phenyl)-5-(piperidin-4-yloxy)picolinamide hydrochloride (270 mg, 94% over two steps) was prepared as a white powder using procedures analogous to those described in Steps 3-4 of Example 1, substituting 1-(4-aminophenyl)-3-(5-(1,3-difluoro-2-methylpropan-2-yl)isoxazol-3-yl)urea hydrochloride from Step 2 of this example for 1-(4-aminophenyl)-3-(5-tert-butylisoxazol-3-yl)urea, and 5-(1-(tert-butoxycarbonyl)piperidin-4-yloxy)picolinic acid from Step 1 of Example 6 for 4-(1-(tert-butoxycarbonyl)piperidin-4-yloxy)picolinic acid from the Step 2 of Example 1 used in Example 1. LC-MS (ESI) m/z 515 $(M+H)^+$.

Step 5: N-(4-(3-(5-(1,3-Difluoro-2-methylpropan-2-yl)isoxazol-3-yl)ureido)phenyl)-5-(1-ethylpiperidin-4-yloxy)picolinamide (65 mg, 94%) was prepared as a white powder using a procedure analogous to that described in Example 2, substituting N-(4-(3-(5-(1,3-difluoro-2-methylpropan-2-yl)isoxazol-3-yl)ureido)phenyl)-5-(piperidin-4-yloxy)picolinamide hydrochloride from Step 3 of this example for N-(4-(3-(5-tert-butylisoxazol-3-yl)ureido)phenyl)-4-(piperidin-4-yloxy)picolinamide hydrochloride used in Example 2. LC-MS (ESI) m/z 543 $(M+H)^+$; $^1$H NMR (300 MHz, DMSO-$d_6$) δ 10.40 (s, 1H), 9.60 (s, 1H), 8.79 (s, 1H), 8.38 (s, 1H), 8.10 (d, J=8.85 Hz, 1H), 7.81 (d, J=9.04 Hz, 2H), 7.63-7.72 (m, 1H), 7.42 (d, J=9.04 Hz, 2H), 6.79 (s, 1H), 4.73 (s, 2H), 4.58 (s, 2H), 2.73 (br. s., 1H), 2.27 (br. s., 3H), 1.97-2.17 (m, 2H), 1.91 (s, 2H), 1.75 (s, 2H), 1.34 (s, 3H), 0.90-1.20 (m, 4H).

Example 18

Preparation of N-(4-(3-(5-(1,3-difluoro-2-methylpropan-2-yl)isoxazol-3-yl)ureido)phenyl)-5-(1-methylpiperidin-4-yloxy)picolinamide

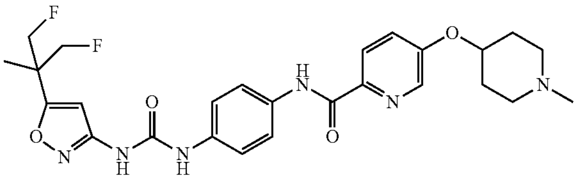 [SMILES: CN1CCC(Oc2ccc(C(=O)Nc3ccc(NC(=O)Nc4cc(C(C)(CF)CF)on4)cc3)nc2)CC1]

N-(4-(3-(5-(1,3-difluoro-2-methylpropan-2-yl)isoxazol-3-yl)ureido)phenyl)-5-(1-methylpiperidin-4-yloxy)picolinamide (60 mg, 89%) was prepared as a white powder using a procedure analogous to that described in Example 2, substituting N-(4-(3-(5-(1,3-difluoro-2-methylpropan-2-yl)isoxazol-3-yl)ureido)phenyl)-5-(piperidin-4-yloxy)picolinamide hydrochloride from Step 4 of Example 17 for N-(4-(3-(5-tert-butylisoxazol-3-yl)ureido)phenyl)-4-(piperidin-4-yloxy)picolinamide hydrochloride, and formalin for acetaldehyde used in Example 2. LC-MS (ESI) m/z 529 $(M+H)^+$; $^1$H NMR (300 MHz, DMSO-$d_6$) δ 10.39 (s, 1H), 9.60 (s, 1H), 8.81 (br. s., 1H), 8.37 (d, J=2.83 Hz, 1H), 8.10 (d, J=8.85 Hz, 1H), 7.81 (d, J=9.04 Hz, 2H), 7.67 (dd, J=2.83, 8.85 Hz, 1H), 7.42 (d, J=8.85 Hz, 2H), 6.79 (s, 1H), 4.73 (s, 2H), 4.63-4.71 (m, 1H), 4.57 (s, 2H), 2.84 (br. s., 1H), 2.50 (overlapping s, 3H), 2.38 (br. s., 3H), 2.02 (br. s., 2H), 1.67-1.85 (m, 2H), 1.26-1.39 (m, 3H).

Example 19

Preparation of N-(4-(3-(5-(1,3-difluoro-2-methylpropan-2-yl)isoxazol-3-yl)ureido)phenyl)-5-(1-(2,2,2-trifluoroethyl)piperidin-4-yloxy)picolinamide

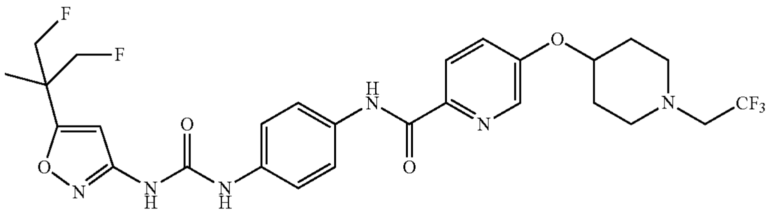 [SMILES: CC(CF)(CF)c1cc(NC(=O)Nc2ccc(NC(=O)c3ccc(OC4CCN(CC(F)(F)F)CC4)cn3)cc2)no1]

To a stirred solution of N-(4-(3-(5-(1,3-difluoro-2-methylpropan-2-yl)isoxazol-3-yl)ureido)phenyl)-5-(piperidin-4-yloxy)picolinamide hydrochloride (50 mg, 0.091 mmol) from Step 4 of Example 17 in 3 mL of $CH_3CN$ was added DIEA (32 mL, 0.18 mmol) and 2,2,2-trifluoroethyl trifluoromethanesulfonate (21 mg, 0.18 mmol). The resulting mixture was then stirred at rt for 1 h, heated at 85° C. for 1 h. $CH_3CN$ was then evaporated under reduced pressure and the residue was taken up in 2 mL of DMF. To the reaction mixture was then added DIEA (32 μL, 0.18 mmol) and 2,2,2-trifluoroethyl trifluoromethanesulfonate (21 mg, 0.18 mmol), and heated at 85° C. for 2 h. LC-MS indicated that the reaction was complete. Purification by reverse phase HPLC yielded N-(4-(3-(5-(1,3-difluoro-2-methylpropan-2-yl)isoxazol-3-yl)ureido)phenyl)-5-(1-(2,2,2-trifluoroethyl)piperidin-4-yloxy)picolinamide (40 mg, 74%) as a white solid. LC-MS (ESI) m/z 597 $(M+H)^+$; $^1$H NMR (300 MHz, DMSO-$d_6$) δ 10.40 (s, 1H), 9.59 (s, 1H), 8.77 (s, 1H), 8.36 (d, J=2.83 Hz, 1H), 8.08 (d, J=8.85 Hz, 1H), 7.81 (d, J=8.85 Hz, 2H), 7.67 (dd, J=2.83, 8.85 Hz, 1H), 7.42 (d, J=8.85 Hz, 2H), 6.79 (s, 1H), 4.73 (s, 2H), 4.65 (td, J=3.93, 8.15 Hz, 1H), 4.57 (s, 2H), 3.23 (q, J=10.24 Hz, 2H), 2.80-2.96 (m, 2H), 2.62 (t, J=9.42 Hz, 2H), 1.97 (br. s., 2H), 1.60-1.76 (m, 2H), 1.34 (s, 3H).

Example 20

Preparation of N-(4-(3-(5-(1,3-difluoro-2-methylpropan-2-yl)isoxazol-3-yl)ureido)phenyl)-5-(1-isopropylpiperidin-4-yloxy)picolinamide

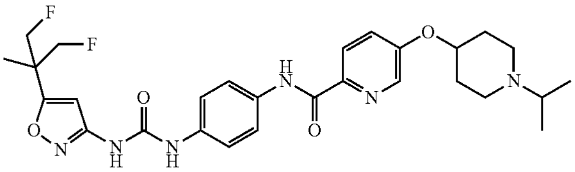 [SMILES: CC(C)N1CCC(Oc2ccc(C(=O)Nc3ccc(NC(=O)Nc4cc(C(C)(CF)CF)on4)cc3)nc2)CC1]

To a stirred solution of N-(4-(3-(5-(1,3-difluoro-2-methylpropan-2-yl)isoxazol-3-yl)ureido)phenyl)-5-(piperidin-4-yloxy)picolinamide hydrochloride (50 mg, 0.091 mmol) from Step 4 of Example 17 (65 mg, 0.12 mmol) in 2 mL of pH~4 MeOH/NaOAc buffer was added acetone (0.3 mL, excess) and $NaCNBH_3$ (25 mg, excess). The resulting mixture was reflux at 80° C. for 3 h. LC-MS indicated that the reaction was 50% complete. The reaction was cooled to rt and the crude product was purified by reverse phase HPLC to give N-(4-(3-(5-(1,3-difluoro-2-methylpropan-2-yl)isoxazol-3-yl)ureido)phenyl)-5-(1-isopropylpiperidin-4-yloxy)picolinamide as a white solid (20 mg, 31% yield). LC-MS (ESI) m/z 557 $(M+H)^+$; $^1H$ NMR (300 MHz, DMSO-$d_6$) δ 10.38 (s, 1H), 9.83 (br. s., 1H), 9.03 (br. s., 1H), 8.35 (d, J=2.83 Hz, 1H), 8.08 (d, J=8.67 Hz, 1H), 7.81 (d, J=9.04 Hz, 2H), 7.65 (dd, J=2.73, 8.76 Hz, 1H), 7.43 (d, J=9.04 Hz, 2H), 6.79 (s, 1H), 4.73 (s, 2H), 4.57 (s, 3H), 2.73 (d, J=6.40 Hz, 3H), 2.23-2.45 (m, 2H), 1.99 (br. s., 2H), 1.53-1.73 (m, 2H), 1.34 (s, 3H), 0.98 (d, J=6.59 Hz, 6H).

Example 21

Preparation of N-(4-(3-(5-tert-butylisoxazol-3-yl)ureido)phenyl)-5-(1-(2,2,2-trifluoroethyl)piperidin-4-yloxy)picolinamide

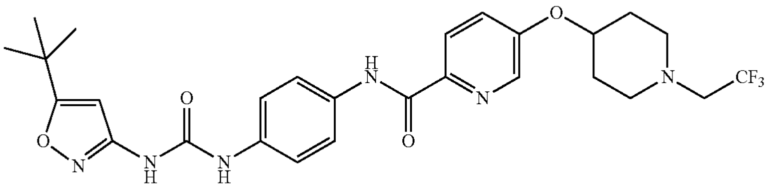 [SMILES: CC(C)(C)c1cc(NC(=O)Nc2ccc(NC(=O)c3ccc(OC4CCN(CC(F)(F)F)CC4)cn3)cc2)no1]

N-(4-(3-(5-tert-Butylisoxazol-3-yl)ureido)phenyl)-5-(1-(2,2,2-trifluoroethyl)piperidin-4-yloxy)picolinamide (40 mg, 46%) was prepared as a white powder using a procedure analogous to that described in Example 19, substituting N-(4-(3-(5-tert-butylisoxazol-3-yl)ureido)phenyl)-5-(piperidin-4-yloxy)picolinamide hydrochloride from Step 2 of Example 6 for N-(4-(3-(5-(1,3-difluoro-2-methylpropan-2-yl)isoxazol-3-yl)ureido)phenyl)-5-(piperidin-4-yloxy)picolinamide hydrochloride used in Example 19. LC-MS (ESI) m/z 557 $(M+H)^+$; $^1H$ NMR (300 MHz, DMSO-$d_6$) δ 10.39 (s, 1H), 9.48 (s, 1H), 8.77 (s, 1H), 8.36 (d, J=2.64 Hz, 1H), 8.09 (d, J=8.67 Hz, 1H), 7.81 (d, J=8.85 Hz, 2H), 7.67 (dd, J=2.83, 8.85 Hz, 1H), 7.41 (d, J=9.04 Hz, 2H), 6.50 (s, 1H), 4.64 (td, J=4.00, 8.19 Hz, 1H), 3.22 (q, J=10.30 Hz, 2H), 2.79-2.96 (m, 2H), 2.61 (t, J=8.95 Hz, 2H), 1.99 (d, J=10.55 Hz, 2H), 1.59-1.78 (m, 2H), 1.30 (s, 9H).

Example 22

Preparation of N-(4-(3-(5-tert-butylisoxazol-3-yl)ureido)phenyl)-5-(1-ethylazetidin-3-yloxy)picolinamide

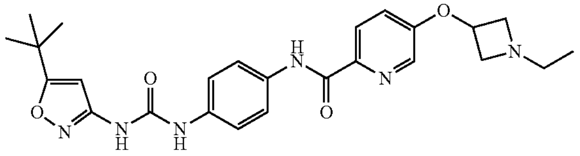 [SMILES: CCN1CC(Oc2ccc(C(=O)Nc3ccc(NC(=O)Nc4cc(C(C)(C)C)on4)cc3)nc2)C1]

Step 1: 5-(1-(tert-Butoxycarbonyl)azetidin-3-yloxy)picolinic acid (1.3 g) prepared using procedures analogous to those described in Steps 1-2 of Example 1, substituting 5-fluoropicolinonitrile for 4-chlorocyanopicoline, and tert-butyl 3-hydroxyazetidine-1-carboxylate for tert-butyl 4-hydroxypiperidine-1-carboxylate used in Example 1. LC-MS (ESI) m/z 295 $(M+H)^+$.

Step 2: 5-(Azetidin-3-yloxy)-N-(4-(3-(5-tert-butylisoxazol-3-yl)ureido)phenyl)picolinamide hydrochloride (350 mg) was prepared as an off-white solid using procedures analogous to those described in Steps 3-4 of Example 1, substituting 5-(1-(tert-butoxycarbonyl)azetidin-3-yloxy)picolinic acid from Step 1 of this example for 4-(1-(tert-butoxycarbonyl)piperidin-4-yloxy)picolinic acid used in Step 3 of Example 1. LC-MS (ESI) m/z 451 $(M+H)^+$.

Step 3: N-(4-(3-(5-tert-Butylisoxazol-3-yl)ureido)phenyl)-5-(1-ethylazetidin-3-yloxy)picolinamide (13 mg, 34%) was prepared as an off-white powder using a procedure analogous to that described in Example 2, substituting 5-(azetidin-3-yloxy)-N-(4-(3-(5-tert-butylisoxazol-3-yl)ureido)phenyl)picolinamide hydrochloride from Step 2 of this example for N-(4-(3-(5-tert-butylisoxazol-3-yl)ureido)phenyl)-4-(piperidin-4-yloxy)picolinamide hydrochloride used in Example 2. LC-MS (ESI) m/z 479 $(M+H)^+$; $^1H$ NMR (300 MHz, DMSO-$d_6$) δ 10.41 (s, 1H), 9.51 (s, 1H), 8.81 (s, 1H), 8.32 (br. s., 1H), 8.08 (d, J=8.29 Hz, 1H), 7.81 (d, J=8.29 Hz, 2H), 7.49 (d, J=8.85 Hz, 1H), 7.42 (d, J=7.54 Hz, 2H), 6.50 (s, 1H), 4.99 (t, J=4.71 Hz, 1H), 3.61-3.82 (m, 2H), 2.99 (t, J=5.93 Hz, 2H), 2.46 (br. s., 2H), 1.30 (s, 9H), 0.90 (t, J=6.97 Hz, 3H).

Example 23

Preparation of N-(4-(3-(5-tert-butylisoxazol-3-yl)ureido)phenyl)-5-(1-isopropylazetidin-3-yloxy)picolinamide

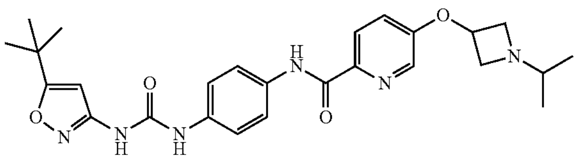 [SMILES: CC(C)N1CC(Oc2ccc(C(=O)Nc3ccc(NC(=O)Nc4cc(C(C)(C)C)on4)cc3)nc2)C1]

N-(4-(3-(5-tert-Butylisoxazol-3-yl)ureido)phenyl)-5-(1-isopropylazetidin-3-yloxy)picolinamide (25 mg, 19%) was prepared as an off-white powder using a procedure analogous to that described in Example 20, substituting 5-(azetidin-3-yloxy)-N-(4-(3-(5-tert-butylisoxazol-3-yl)ureido)phenyl)picolinamide hydrochloride from Step 2 of this example for N-(4-(3-(5-(1,3-difluoro-2-methylpropan-2-yl)isoxazol-3-yl)ureido)phenyl)-5-(piperidin-4-yloxy)picolinamide hydrochloride used in Example 20. LC-MS (ESI) m/z 493 $(M+H)^+$; $^1H$ NMR (300 MHz, DMSO-$d_6$) δ 10.40 (s, 1H), 9.48 (s, 1H), 8.78 (s, 1H), 8.31 (s, 1H), 8.08 (dd, J=1.32, 8.67 Hz, 1H), 7.81 (d, J=7.35 Hz, 2H), 7.50 (dd, J=2.64, 8.67 Hz, 1H), 7.41 (d, J=7.16 Hz, 2H), 6.50 (d, J=1.88 Hz, 1H), 4.94 (t, J=5.46 Hz, 1H), 3.73 (t, J=6.40 Hz, 2H), 3.00 (t, J=6.03 Hz, 2H), 2.29-2.41 (m, 1H), 1.29 (d, J=1.88 Hz, 9H), 0.77-0.95 (m, 6H).

Example 24

Preparation of N-(4-(3-(5-tert-butylisoxazol-3-yl)ureido)phenyl)-5-(1-(oxetan-3-yl)azetidin-3-yloxy)picolinamide

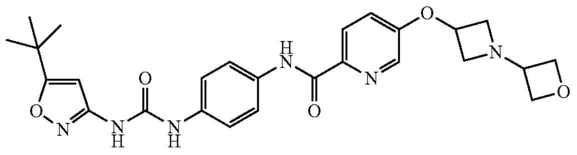 [SMILES: CC(C)(C)c1cc(NC(=O)Nc2ccc(NC(=O)c3ccc(OC4CN(C5COC5)C4)cn3)cc2)no1]

N-(4-(3-(5-tert-Butylisoxazol-3-yl)ureido)phenyl)-5-(1-(oxetan-3-yl)azetidin-3-yloxy)picolinamide (18 mg, 18%) was prepared as a white powder using a procedure analogous to that described in Example 20, substituting 5-(azetidin-3-yloxy)-N-(4-(3-(5-tert-butylisoxazol-3-yl)ureido)phenyl)picolinamide hydrochloride from Step 2 of Example 22 for N-(4-(3-(5-(1,3-difluoro-2-methylpropan-2-yl)isoxazol-3-yl)ureido)phenyl)-5-(piperidin-4-yloxy)picolinamide hydrochloride, and oxetan-3-one for acetone used in Example 20. LC-MS (ESI) m/z 493 $(M+H)^+$. $^1$H NMR (300 MHz, DMSO-$d_6$) δ 10.41 (s, 1H), 9.48 (s, 1H), 8.79 (s, 1H), 8.32 (br. s., 1H), 8.09 (d, J=8.67 Hz, 1H), 7.81 (d, J=8.48 Hz, 2H), 7.50 (d, J=8.48 Hz, 1H), 7.42 (d, J=8.67 Hz, 2H), 6.50 (s, 1H), 4.94-5.14 (m, 1H), 4.46-4.64 (m, 2H), 4.37 (t, J=5.65 Hz, 2H), 3.65-3.87 (m, 3H), 3.09-3.25 (m, 2H), 1.29 (s, 9H).

Example 25

Preparation of N-(4-(3-(5-tert-butylisoxazol-3-yl)ureido)phenyl)-5-(1-isopropylpyrrolidin-3-yloxy)picolinamide

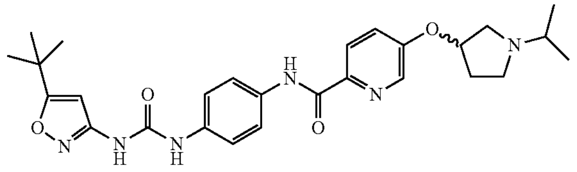 [SMILES: CC(C)N1CCC(Oc2ccc(C(=O)Nc3ccc(NC(=O)Nc4cc(C(C)(C)C)on4)cc3)nc2)C1]

Step 1: 5-(1-(tert-Butoxycarbonyl)pyrrolidin-3-yloxy)picolinic acid (738 mg, 30% over two steps) prepared using procedures analogous to those described in Steps 1-2 of Example 1, substituting 5-fluoropicolinonitrile for 4-chlorocyanopicoline, and tert-butyl 3-hydroxypyrrolidine-1-carboxylate for tert-butyl 4-hydroxypiperidine-1-carboxylate used in Example 1. LC-MS (ESI) m/z 309 $(M+H)^+$.

Step 2: N-(4-(3-(5-tert-Butylisoxazol-3-yl)ureido)phenyl)-5-(pyrrolidin-3-yloxy)picolinamide hydrochloride (903 mg, 48% over two steps) was prepared as a yellow solid using procedures analogous to those described in Steps 3-4 of Example 1, substituting 5-(1-(tert-butoxycarbonyl)pyrrolidin-3-yloxy)picolinic acid from Step 1 of this example for 4-(1-(tert-butoxycarbonyl)piperidin-4-yloxy)picolinic acid used in Example 1. LC-MS (ESI) m/z 465 $(M+H)^+$.

Step 3: N-(4-(3-(5-tert-Butylisoxazol-3-yl)ureido)phenyl)-5-(1-isopropylpyrrolidin-3-yloxy)picolinamide (30 mg, 27%) was prepared using a procedure analogous to that described Example 20, substituting N-(4-(3-(5-tert-butylisoxazol-3-yl)ureido)phenyl)-5-(pyrrolidin-3-yloxy)picolinamide hydrochloride from Step 2 of this example for N-(4-(3-(5-(1,3-difluoro-2-methylpropan-2-yl)isoxazol-3-yl)ureido)phenyl)-5-(piperidin-4-yloxy)picolinamide hydrochloride used in Example 20. LC-MS (ESI) m/z 507 $(M+H)^+$; $^1$H NMR (300 MHz, DMSO-$d_6$) δ 10.39 (s, 1H), 9.58 (br. s., 1H), 8.89 (br. s., 1H), 8.33 (br. s., 1H), 8.08 (d, J=8.48 Hz, 1H), 7.81 (d, J=8.48 Hz, 2H), 7.56 (d, J=8.67 Hz, 1H), 7.42 (d, J=8.29 Hz, 2H), 6.50 (s, 1H), 5.05 (br. s., 1H), 2.84-2.95 (m, 1H), 2.69-2.84 (m, 2H), 2.21-2.47 (m, 3H), 1.69-1.87 (m, 1H), 1.30 (s, 9H), 1.03 (d, J=5.65 Hz, 6H).

Example 26

Preparation of N-(4-(3-(5-tert-butylisoxazol-3-yl)ureido)phenyl)-5-(1-ethylpyrrolidin-3-yloxy)picolinamide

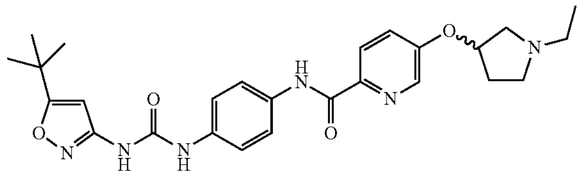 [SMILES: CCN1CCC(Oc2ccc(C(=O)Nc3ccc(NC(=O)Nc4cc(C(C)(C)C)on4)cc3)nc2)C1]

N-(4-(3-(5-tert-butylisoxazol-3-yl)ureido)phenyl)-5-(1-ethylpyrrolidin-3-yloxy)picolinamide (13 mg, 12%) was prepared as an off-white powder using a procedure analogous to that described in Example 2, substituting N-(4-(3-(5-tert-butylisoxazol-3-yl)ureido)phenyl)-5-(pyrrolidin-3-yloxy)picolinamide hydrochloride from Step 2 of Example 25 for N-(4-(3-(5-tert-butylisoxazol-3-yl)ureido)phenyl)-4-(piperidin-4-yloxy)picolinamide hydrochloride used in Example 2. LC-MS (ESI) m/z 493 $(M+H)^+$; $^1$H NMR (300 MHz, DMSO-$d_6$) δ 10.39 (s, 1H), 9.52 (s, 1H), 8.83 (s, 1H), 8.33 (s, 1H), 8.09 (d, J=8.48 Hz, 1H), 7.81 (d, J=8.10 Hz, 2H), 7.56 (d, J=8.85 Hz, 1H), 7.42 (d, J=7.91 Hz, 2H), 6.50 (s, 1H), 5.06 (br. s., 1H), 2.67-2.87 (m, 3H), 2.40-2.48 (m, 2H), 2.37 (d, J=6.59 Hz, 2H), 1.80 (t, J=11.02 Hz, 1H), 1.30 (s, 9H), 1.04 (t, J=7.06 Hz, 3H).

Example 27

Preparation of 4-(6-(4-(3-(5-tert-butylisoxazol-3-yl)ureido)phenylcarbamoyl)pyridin-3-yloxy)-1-isopropylpiperidinium methanesulfonate

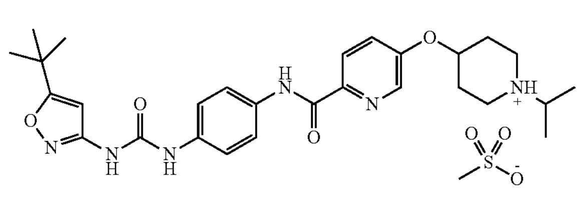

Step 1: N-(4-(3-(5-tert-Butylisoxazol-3-yl)ureido)phenyl)-5-(1-isopropylpiperidin-4-yloxy)picolinamide (50 mg, 50%) was prepared as an off-white powder using a procedure analogous to that described in Example 20, substituting N-(4-(3-(5-tert-butylisoxazol-3-yl)ureido)phenyl)-5-(piperidin-4-yloxy)picolinamide hydrochloride from Step 2 of Example 6 for N-(4-(3-(5-(1,3-difluoro-2-methylpropan-2-yl)isoxazol-3-yl)ureido)phenyl)-5-(piperidin-4-yloxy)picolinamide hydrochloride used in Example 20. LC-MS (ESI) m/z 521 $(M+H)^+$.

Step 2: 4-(6-(4-(3-(5-tert-Butylisoxazol-3-yl)ureido)phenylcarbamoyl)pyridin-3-yloxy)-1-isopropylpiperidinium methanesulfonate (50 mg, 0.096 mmol) from Step 1 of this example was stirred in 3 mL of anhydrous EtOH, and methanesulfonic acid (6.2 μL, 0.096 mmol) was added. The resulting mixture was heated at 60° C. for 1 h. The organic solvent was removed under reduced pressure and the residue was dissolved in 15 mL of water. The solution was frozen in an acetone/dry ice bath and lyophilized to give N-(4-(3-(5-tert-butylisoxazol-3-yl)ureido)phenyl)-5-(1-isopropylpiperidin-4-yloxy)picolinamide methanesulfonate as a light yellow powder (56 mg, 95%). LC-MS (ESI) m/z 521 $(M+H)^+$; $^1H$ NMR (300 MHz, DMSO-$d_6$) δ 10.39 (s, 1H), 9.57-9.80 (m, 1H), 9.50 (br. s., 1H), 8.83 (br. s., 1H), 8.39 (br. s., 1H), 8.11 (d, J=7.72 Hz, 1H), 7.81 (d, J=7.72 Hz, 2H), 7.69 (d, J=8.29 Hz, 1H), 7.42 (d, J=8.29 Hz, 2H), 6.50 (s, 1H), 4.74 (br. s., 1H), 3.02 (br. s., 4H), 2.31 (s, 3H), 2.12 (br. s., 2H), 1.79 (br. s., 2H), 1.30 (s, 9H), 1.12 (d, J=7.72 Hz, 6H).

Example 28

Preparation of 3-(6-(4-(3-(5-tert-butylisoxazol-3-yl)ureido)phenylcarbamoyl)pyridin-3-yloxy)-1-(oxetan-3-yl)pyrrolidinium methanesulfonate

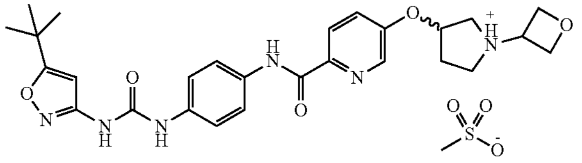

Step 1: N-(4-(3-(5-tert-Butylisoxazol-3-yl)ureido)phenyl)-5-(1-(oxetan-3-yl)pyrrolidin-3-yloxy)picolinamide (77 mg, 73%) was prepared as a white powder using a procedure analogous to that described in Example 20, substituting N-(4-(3-(5-tert-butylisoxazol-3-yl)ureido)phenyl)-5-(pyrrolidin-3-yloxy)picolinamide hydrochloride from Step 2 of Example 25 for N-(4-(3-(5-(1,3-difluoro-2-methylpropan-2-yl)isoxazol-3-yl)ureido)phenyl)-5-(piperidin-4-yloxy)picolinamide hydrochloride, and oxetan-3-one for acetone used in Example 20. LC-MS (ESI) m/z 521 $(M+H)^+$.

Step 2: 3-(6-(4-(3-(5-tert-Butylisoxazol-3-yl)ureido)phenylcarbamoyl)pyridin-3-yloxy)-1-(oxetan-3-yl)pyrrolidinium methanesulfonate (90 mg, 73%) was prepared as a yellow powder using a procedure analogous to that described in Step 2 of Example 27, substituting N-(4-(3-(5-tert-Butylisoxazol-3-yl)ureido)phenyl)-5-(1-(oxetan-3-yl)pyrrolidin-3-yloxy)picolinamide from Step 1 of this example for N-(4-(3-(5-tert-butylisoxazol-3-yl)ureido)phenyl)-5-(1-isopropylpiperidin-4-yloxy)picolinamide used in Example 27. LC-MS (ESI) m/z 521 $(M+H)^+$; $^1H$ NMR (300 MHz, DMSO-$d_6$) δ 11.24 (br. s., 1H), 10.41 (s, 1H), 9.49 (s, 1H), 8.80 (s, 1H), 8.40 (br. s., 1H), 8.15 (d, J=8.29 Hz, 1H), 7.81 (d, J=7.91 Hz, 2H), 7.68 (d, J=7.91 Hz, 1H), 7.43 (d, J=8.48 Hz, 2H), 6.49 (s, 1H), 5.42 (br. s., 1H), 4.78 (d, J=6.59 Hz, 2H), 4.68 (br. s., 3H), 3.68-4.21 (m, 2H), 3.23 (br. s., 2H), 2.57-2.77 (m, 1H), 2.31 (s, 3H), 2.07-2.25 (m, 1H), 1.30 (s, 9H).

Example 29

Preparation of 1-ethyl-4-(6-(4-(3-(3-(2-fluoropropan-2-yl)isoxazol-5-yl)ureido)phenylcarbamoyl)pyridin-3-yloxy)piperidinium methanesulfonate

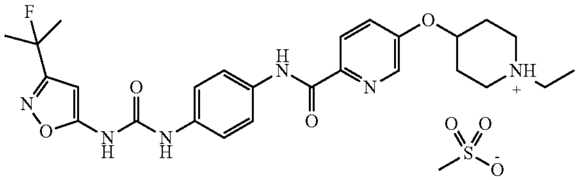

Step 1: To a stirred suspension of 60% NaH/mineral oil (12.48 g, 0.31 mol) in dry THF at 75° C. was added dropwise methyl 2-fluoro-2-methylpropanoate (24 g, 0.2 mol) in dry acetonitrile (16 mL, 0.31 mol) over the course of 45 min. The resulting pale yellow suspension was heated at 70° C. overnight, whereupon analysis by TLC indicated a single new product. After cooling to rt, the mixture was poured into water, acidified to pH~2 with 2N HCl, and extracted with diethyl ether (1 L). The organic layer was dried over $Na_2SO_4$ and concentrated under reduced pressure. The residue was purified by silica gel chromatography eluting with 0-30% EtOAc in petroleum ether to afford 4-fluoro-4-methyl-3-oxo-pentanenitrile as a colorless oil (18 g, 72% yield). LC-MS (ESI) m/z 128 $(M-H)^+$.

Step 2: To a stirred solution of 4-fluoro-4-methyl-3-oxo-pentanenitrile from Step 1 (12.9 g, 0.1 mol) and sodium hydroxide (8.20 g, 0.11 mol) in 1:1 water/EtOH (184 mL) was added hydroxylamine sulfate (17.23 g, 0.11 mol). The mixture was adjusted to pH 7.5 with 1N NaOH, then heated at 80° C. for 15 h. After cooling to rt, the mixture was concentrated to dryness under reduced pressure. The resulting solid was partitioned between water and dichloromethane, and the separated organic layer was washed with brine, dried over $MgSO_4$, and concentrated under reduced pressure. The residue was purified by silica gel chromatography eluting with 0-10% EtOAc in petroleum ether to afford 3-(2-fluoropropan-2-yl)isoxazol-5-amine as a yellow solid (5 g, 35%). LC-MS (ESI) m/z 145 $(M+H)^+$.

Step 3: To a mixture of 3-(2-fluoropropan-2-yl)isoxazol-5-amine (4.32 g, 0.03 mol) and $K_2CO_3$ (8.28 g, 0.06 mol) in THF (100 mL) at 0° C. was added dropwise a solution of phenyl carbonochloridate (6 mL, 0.045 mol) in THF (50 mL). The mixture was stirred at 0° C. for 1 h, then at 40° C. for 20 h. Analysis by LC-MS and TLC indicated that the starting material was almost completely consumed and a new product had formed. The mixture was poured into water (150 mL) and the resulting mixture was extracted with EtOAc (100 mL). The organic layer was dried over $Na_2SO_4$ and concentrated under reduced pressure. The residue was purified by silica gel chromatography eluting with 0-4% EtOAc in petroleum ether to afford phenyl 3-(2-fluoropropan-2-yl)isoxazol-5-ylcarbamate as a white solid (6 g, 76%).

Step 4: 5-(1-Ethylpiperidin-4-yloxy)-N-(4-(3-(3-(2-fluoropropan-2-yl)isoxazol-5-yl)ureido)phenyl)picolinamide (81 mg, 76%) was prepared as a white powder according to the procedure described in Steps 2-5 of Example 17, substituting phenyl 3-(2-fluoropropan-2-yl)isoxazol-5-ylcarbamate from Step 3 of this example for 5-(1,3-difluoro-2-methylpropan-2-yl)isoxazol-3-ylcarbamate used in Step 2 of Example 17. LC-MS (ESI) m/z 511 $(M+H)^+$.

Step 5: 1-Ethyl-4-(6-(4-(3-(3-(2-fluoropropan-2-yl)isoxazol-5-yl)ureido)phenylcarbamoyl)pyridin-3-yloxy)piperidinium methanesulfonate (102 mg, 94%) was prepared as a yellow powder using a procedure analogous to that described in Example 27, substituting 5-(1-ethylpiperidin-4-yloxy)-N-(4-(3-(3-(2-fluoropropan-2-yl)isoxazol-5-yl)ureido)phenyl)picolinamide from Step 4 of this example for N-(4-(3-(5-tert-butylisoxazol-3-yl)ureido)phenyl)-5-(1-isopropylpiperidin-4-yloxy)picolinamide used in Example 27. LC-MS (ESI) m/z 511 $(M+H)^+$; $^1H$ NMR (300 MHz, DMSO-$d_6$) δ 10.43 (br. s., 1H), 10.33 (br. s., 1H), 9.23 (br. s., 1H), 8.91 (br. s., 1H), 8.42 (d, J=8.67 Hz, 1H), 8.14 (d, J=8.29 Hz, 1H), 7.82 (d, J=8.29 Hz, 2H), 7.65-7.78 (m, 1H), 7.44 (d, J=7.91 Hz, 2H), 6.15 (s, 1H), 4.67-5.07 (m, 1H), 3.35-3.95 (m, 4H), 2.97-3.29 (m, 3H), 2.31 (s, 3H), 1.96-2.21 (m, 2H), 1.77-1.95 (m, 1H), 1.72 (s, 3H), 1.64 (s, 3H), 1.25 (t, J=7.16 Hz, 3H).

Example 30

Preparation of N-(4-(3-(5-(tert-butyl)isoxazol-3-yl)ureido)phenyl)-5-((1-methylpyrrolidin-3-yl)oxy)picolinamide

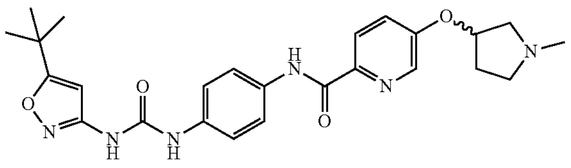 [SMILES: CN1CCC(Oc2ccc(C(=O)Nc3ccc(NC(=O)Nc4cc(C(C)(C)C)on4)cc3)nc2)C1]

The title compound may be prepared using a procedure analogous to that described in Example 2, substituting N-(4-(3-(5-tert-butylisoxazol-3-yl)ureido)phenyl)-5-(pyrrolidin-3-yloxy)picolinamide hydrochloride from Step 2 of Example 25 for N-(4-(3-(5-tert-butylisoxazol-3-yl)ureido)phenyl)-4-(piperidin-4-yloxy)picolinamide hydrochloride, and formalin for acetaldehyde used in Example 2.

Example 31

Preparation of N-(4-(3-(5-(tert-butyl)isoxazol-3-yl)ureido)phenyl)-5-((1-isobutylpyrrolidin-3-yl)oxy)picolinamide

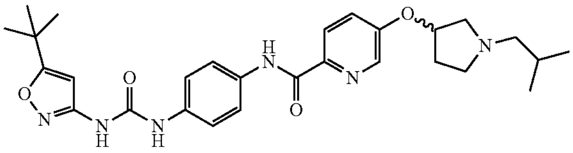 [SMILES: CC(C)CN1CCC(Oc2ccc(C(=O)Nc3ccc(NC(=O)Nc4cc(C(C)(C)C)on4)cc3)nc2)C1]

The title compound may be prepared using a procedure analogous to that described in Example 2, substituting N-(4-(3-(5-tert-butylisoxazol-3-yl)ureido)phenyl)-5-(pyrrolidin-3-yloxy)picolinamide hydrochloride from Step 2 of Example 25 for N-(4-(3-(5-tert-butylisoxazol-3-yl)ureido)phenyl)-4-(piperidin-4-yloxy)picolinamide hydrochloride, and isobutyraldehyde for acetaldehyde used in Example 2.

Example 32

Preparation of 3-(6-(4-(3-(5-tert-butylisoxazol-3-yl)-1-methylureido)phenylcarbamoyl)pyridin-3-yloxy)-1-isopropylpyrrolidinium methanesulfonate

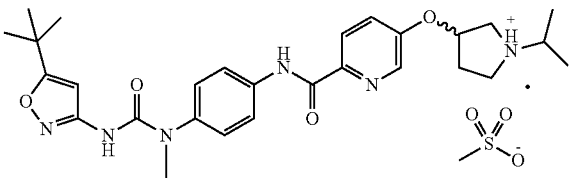

Step 1: tert-Butyl 3-(6-(4-(3-(5-tert-butylisoxazol-3-yl)-1-methylureido)phenylcarbamoyl)pyridin-3-yloxy)pyrrolidine-1-carboxylate ( ) was prepared using procedures analogous to those described in Steps 1-3 of Example 42, substituting 5-(1-(tert-butoxycarbonyl)pyrrolidin-3-yloxy)picolinic acid from Step 1 of Example 25 for 5-(1,2,2,6,6-pentamethylpiperidin-4-yloxy)picolinic acid, and N-methyl-4-nitroaniline for 3-methyl-4-nitroaniline used in Example 42. LC-MS (ESI) m/z 579 $(M+H)^+$.

Step 2: N-(4-(3-(5-tert-Butylisoxazol-3-yl)-1-methylureido)phenyl)-5-(pyrrolidin-3-yloxy)picolinamide hydrochloride was prepared using a procedure analogous to that described in Step 4 of Example 1, substituting tert-butyl 3-(6-(4-(3-(5-tert-butylisoxazol-3-yl)-1-methylureido)phenylcarbamoyl)pyridin-3-yloxy)pyrrolidine-1-carboxylate for tert-butyl 4-(2-(4-(3-(5-tert-butylisoxazol-3-yl)ureido)phenylcarbamoyl)pyridin-4-yloxy)piperidine-1-carboxylate used in Example 1. LC-MS (ESI) m/z 479 $(M+H)^+$.

Step 3: N-(4-(3-(5-tert-Butylisoxazol-3-yl)-1-methylureido)phenyl)-5-(1-isopropylpyrrolidin-3-yloxy)picolinamide (45 mg, 68%) was prepared using a procedure analogous to that described in Example 20, substituting N-(4-(3-(5-tert-butylisoxazol-3-yl)-1-methylureido)phenyl)-5-(pyrrolidin-3-yloxy)picolinamide hydrochloride from the Step 2 of this example for N-(4-(3-(5-(1,3-difluoro-2-methylpropan-2-yl)isoxazol-3-yl)ureido)phenyl)-5-(piperidin-4-yloxy)picolinamide hydrochloride used in Example 20. LC-MS (ESI) m/z 521 $(M+H)^+$.

Step 4: 3-(6-(4-(3-(5-tert-Butylisoxazol-3-yl)-1-methylureido)phenylcarbamoyl)pyridin-3-yloxy)-1-isopropylpyrrolidinium methanesulfonate (50 mg, 95%) was prepared using a procedure analogous to that described in Example 27, substituting N-(4-(3-(5-tert-butylisoxazol-3-yl)-1-methylureido)phenyl)-5-(1-isopropylpyrrolidin-3-yloxy)picolinamide from Step 2 of this example for N-(4-(3-(5-tert-butylisoxazol-3-yl)ureido)phenyl)-5-(1-isopropylpiperidin-4-yloxy)picolinamide used in Step 2 of Example 27. LC-MS (ESI) m/z 521 $(M+H)^+$; $^1H$ NMR (300 MHz, DMSO-$d_6$) δ 10.60 (s, 1H), 10.11 (br. s., 1H), 9.09 (s, 1H), 8.41 (br. s., 1H), 8.17 (d, J=8.48 Hz, 1H), 7.93 (d, J=7.72 Hz, 2H), 7.69 (d, J=8.67 Hz, 1H), 7.29 (d, J=7.91 Hz, 2H), 6.49 (s, 1H), 5.40 (br. s., 1H), 3.91-4.21 (m, 1H), 3.62-3.88 (m, 2H), 3.51 (d, J=15.45 Hz, 2H), 3.25 (s, 3H), 2.62 (br. s., 1H), 2.31 (s, 3H), 2.16 (br. s., 1H), 1.28 (s, 15H).

Example 33

Preparation of 3-(6-(4-(3-(5-tert-butylisoxazol-3-yl)ureido)phenylcarbamoyl)pyridin-3-yloxy)-1-(2-(methylsulfonyl)ethyl)pyrrolidinium methanesulfonate

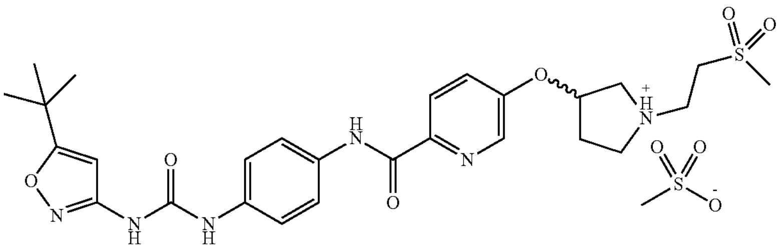

Step 1: N-(4-(3-(5-tert-Butylisoxazol-3-yl)ureido)phenyl)-5-(pyrrolidin-3-yloxy)picolinamide hydrochloride (150 mg, 0.30 mmol) was suspended in 3 mL of THF at rt. Methylsulfonylethene (29 μL, 0.33 mmol) and TEA (126 μL, 0.90 mmol) were added sequentially. The resulting mixture was heated at 60° C. for 1 h, then heated at 52° C. for 60 h. LC-MS indicated the reaction was complete. The organic solvent was evaporated under reduced pressure and the residue was purified by reverse phase HPLC to give N-(4-(3-(5-tert-butylisoxazol-3-yl)ureido)phenyl)-5-(1-(2-(methylsulfonyl)ethyl)pyrrolidin-3-yloxy)picolinamide (136 mg, 79%). LC-MS (ESI) m/z 571 $(M+H)^+$.

Step 2: 3-(6-(4-(3-(5-tert-Butylisoxazol-3-yl)ureido)phenylcarbamoyl)pyridin-3-yloxy)-1-(2-(methylsulfonyl)ethyl)pyrrolidinium methanesulfonate (150 mg, 95%) was prepared using a procedure analogous to that described in Example 27, substituting N-(4-(3-(5-tert-butylisoxazol-3-yl)ureido)phenyl)-5-(1-(2-(methylsulfonyl)ethyl)pyrrolidin-3-yloxy)picolinamide from Step 1 of this example for N-(4-(3-(5-tert-butylisoxazol-3-yl)ureido)phenyl)-5-(1-isopropylpiperidin-4-yloxy)picolinamide used in Step 2 of Example 27. LC-MS (ESI) m/z 571 $(M+H)^+$; $^1H$ NMR (300 MHz, DMSO-$d_6$) δ 10.41 (s, 1H), 9.51 (s, 1H), 8.83 (s, 1H), 8.39 (br. s., 1H), 8.14 (d, J=8.67 Hz, 1H), 7.81 (d, J=8.29 Hz, 2H), 7.67 (d, J=8.29 Hz, 1H), 7.43 (d, J=8.48 Hz, 2H), 6.50 (s, 1H), 5.39 (br. s., 1H), 3.66 (br. s., 7H), 3.12 (s, 3H), 2.70 (d, J=16.39 Hz, 1H), 2.42-2.29 (overlapping m, 1H), 2.35 (s, 3H), 2.15 (d, J=10.17 Hz, 1H), 1.30 (s, 9H).

Example 34

Preparation of 3-(6-(4-(3-(5-tert-butylisoxazol-3-yl)ureido)phenylcarbamoyl)pyridin-3-yloxy)-1-(2-(dimethylamino)-2-oxoethyl)pyrrolidinium methanesulfonate

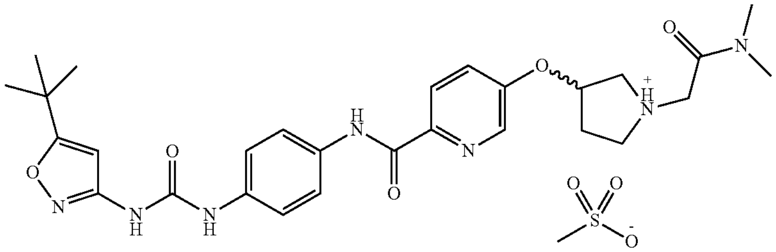

Step 1: To a stirred suspension of N-(4-(3-(5-tert-butylisoxazol-3-yl)ureido)phenyl)-5-(pyrrolidin-3-yloxy)picolinamide hydrochloride (150 mg, 0.30 mmol) in $CH_3CN$ (3 mL) was added TEA (126 μL, 0.90 mmol), KI (10 mg, 0.060 mmol), and 2-chloro-N,N-dimethylacetamide (21 μL, 0.30 mmol). The resulting mixture was heated at 85° C. for 1 h. LC-MS indicated that the reaction was complete. The reaction mixture was evaporated under reduced pressure and the residue was purified by reverse phase HPLC to give N-(4-(3-(5-tert-butylisoxazol-3-yl)ureido)phenyl)-5-(1-(2-(dimethylamino)-2-oxoethyl)pyrrolidin-3-yloxy)picolinamide (110 mg, 67%). LC-MS (ESI) m/z 550 $(M+H)^+$.

Step 2: 3-(6-(4-(3-(5-tert-Butylisoxazol-3-yl)ureido)phenylcarbamoyl)pyridin-3-yloxy)-1-(2-(dimethylamino)-2-oxoethyl)pyrrolidinium methanesulfonate (120 mg, 95%) was prepared using a procedure analogous to that described in Example 27, substituting N-(4-(3-(5-tert-butylisoxazol-3-yl)ureido)phenyl)-5-(1-(2-(dimethylamino)-2-oxoethyl)pyrrolidin-3-yloxy)picolinamide from Step 1 of this example for N-(4-(3-(5-tert-butylisoxazol-3-yl)ureido)phenyl)-5-(1-isopropylpiperidin-4-yloxy)picolinamide used in Step 2 of Example 27. LC-MS (ESI) m/z 550 $(M+H)^+$; $^1H$ NMR (300 MHz, DMSO-$d_6$) δ 10.41 (br. s., 2H), 9.56 (br. s., 1H), 8.99 (br. s., 1H), 8.39 (br. s., 1H), 8.13 (d, J=8.85 Hz, 1H), 7.81 (d, J=8.29 Hz, 2H), 7.66 (d, J=7.35 Hz, 1H), 7.43 (d, J=8.85 Hz, 2H), 6.50 (s, 1H), 5.33 (br. s., 1H), 4.28 (br. s., 2H), 3.70 (br. s., 1H), 3.46 (br. s., 2H), 3.33 (br. s., 2H), 2.93 (br. s., 3H), 2.89 (br. s., 3H), 2.32 (s, 3H), 2.19 (br. s., 1H), 1.30 (br. s., 9H).

Example 35

Preparation of 4-(6-(4-(3-(5-tert-butylisoxazol-3-yl)ureido)phenylcarbamoyl)pyridin-3-yloxy)-1,2,2,6,6-pentamethylpiperidinium methanesulfonate

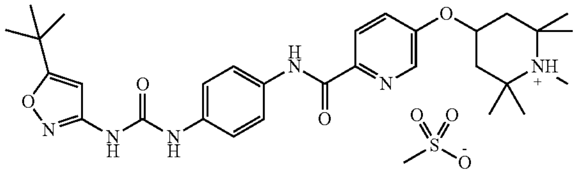

Step 1: 5-(1,2,2,6,6-Pentamethylpiperidin-4-yloxy)picolinic acid was prepared using procedures analogous to those described in Steps 1-2 of Example 1, substituting 1,2,2,6,6-pentamethylpiperidin-4-ol for tert-butyl 4-hydroxypiperidine-1-carboxylate, and 5-fluoropicolinonitrile for 4-chlorocyanopicoline used in Example 1. LC-MS (ESI) m/z 293 $(M+H)^+$.

Step 2: N-(4-(3-(5-tert-Butylisoxazol-3-yl)ureido)phenyl)-5-(1,2,2,6,6-pentamethylpiperidin-4-yloxy)picolinamide (102 mg, 72%) was prepared using a procedure analogous to that described in Step 3 of Example 1, substituting 5-(1,2,2,6,6-pentamethylpiperidin-4-yloxy)picolinic acid from Step 1 of this example for 4-(1-(tert-butoxycarbonyl)piperidin-4-yloxy)picolinic acid used in Step 3 of Example 1. LC-MS (ESI) m/z 549 $(M+H)^+$.

Step 3: 4-(6-(4-(3-(5-tert-butylisoxazol-3-yl)ureido)phenylcarbamoyl)pyridin-3-yloxy)-1,2,2,6,6-pentamethylpiperidinium methanesulfonate (120 mg, 100%) was prepared using a procedure analogous to that described in Example 27, substituting N-(4-(3-(5-tert-butylisoxazol-3-yl)ureido)phenyl)-5-(1,2,2,6,6-pentamethylpiperidin-4-yloxy)picolinamide from Step 2 of this example for N-(4-(3-(5-tert-butylisoxazol-3-yl)ureido)phenyl)-5-(1-isopropylpiperidin-4-yloxy)picolinamide used in Step 2 of Example 27. LC-MS (ESI) m/z 549 $(M+H)^+$; $^1H$ NMR (300 MHz, DMSO-$d_6$) δ 10.39 (s, 1H), 9.51 (s, 1H), 8.86 (s, 1H), 8.79 (d, J=4.52 Hz, 1H), 8.41 (d, J=2.64 Hz, 1H), 8.13 (d, J=8.67 Hz, 1H), 7.81 (d, J=9.04 Hz, 2H), 7.73 (dd, J=2.83, 8.85 Hz, 1H), 7.44 (d, J=9.04 Hz, 2H), 6.50 (s, 1H), 5.03-5.25 (m, 1H), 2.77 (d, J=4.90 Hz, 3H), 2.38 (s, 3H), 2.26-2.45 (m, 2H), 1.86 (t, J=12.34 Hz, 2H), 1.47 (d, J=7.91 Hz, 12H), 1.30 (s, 9H).

Example 36

Preparation of 4-(6-(4-(3-(5-tert-butylisoxazol-3-yl) ureido)phenylcarbamoyl)pyridin-3-yloxy)-1-cyclopropylpiperidinium methanesulfonate

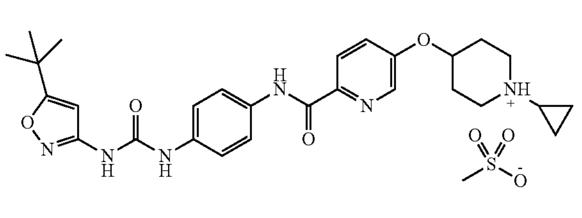

Step 1: N-(4-(3-(5-tert-Butylisoxazol-3-yl)ureido)phenyl)-5-(1-cyclopropylpiperidin-4-yloxy)picolinamide (82 mg, 61%) was prepared using procedures analogous to those described in Steps 1-3 of Example 1, substituting 1-cyclopropylpiperidin-4-ol (Reference: Brown, D. S.; Nash, I. A. WO2005/42502 A1) for tert-butyl 4-hydroxypiperidine-1-carboxylate, and 5-fluoropicolinonitrile for 4-chlorocyanopicoline used in Example 1. LC-MS (ESI) m/z 519 $(M+H)^+$.

Step 2: 4-(6-(4-(3-(5-tert-Butylisoxazol-3-yl)ureido)phenylcarbamoyl)pyridin-3-yloxy)-1-cyclopropylpiperidinium methanesulfonate (90 mg, 95%) was prepared using a procedure analogous to that described in Example 27, substituting N-(4-(3-(5-tert-butylisoxazol-3-yl)ureido)phenyl)-5-(1-cyclopropylpiperidin-4-yloxy)picolinamide from Step 1 of this example for N-(4-(3-(5-tert-butylisoxazol-3-yl)ureido)phenyl)-5-(1-isopropylpiperidin-4-yloxy)picolinamide used in Step 2 of Example 27. LC-MS (ESI) m/z 519 $(M+H)^+$; $^1$H NMR (300 MHz, DMSO-$d_6$) δ 10.41 (d, J=4.33 Hz, 1H), 9.51 (s, 1H), 8.96 (br. s., 1H), 8.83 (br. s., 1H), 8.44 (d, J=13.37 Hz, 1H), 8.13 (br. s., 1H), 7.81 (d, J=8.10 Hz, 2H), 7.73 (t, J=7.54 Hz, 1H), 7.43 (d, J=8.10 Hz, 2H), 6.50 (s, 1H), 4.91-5.45 (m, 3H), 4.81 (br. s., 1H), 3.63 (d, J=11.30 Hz, 1H), 3.34 (d, J=10.74 Hz, 1H), 2.81-3.12 (m, 1H), 2.37 (s, 3H), 1.94-2.23 (m, 2H), 1.82 (d, J=11.87 Hz, 1H), 1.30 (s, 9H), 0.98 (br. s., 2H), 0.85 (d, J=6.03 Hz, 2H).

Example 37

Preparation of 1-tert-butyl-4-(6-(4-(3-(5-tert-butylisoxazol-3-yl)ureido)phenylcarbamoyl)pyridin-3-yloxy)piperidinium methanesulfonate

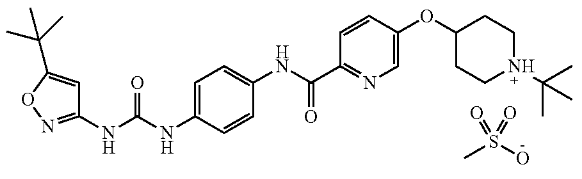

Step 1: N-(4-(3-(5-tert-Butylisoxazol-3-yl)ureido)phenyl)-5-(1-tert-butylpiperidin-4-yloxy)picolinamide (98 mg, 67%) was prepared using procedures analogous to those described in Steps 1-3 of Example 1, substituting 1-tert-butylpiperidin-4-ol (Reference: Amato, J. S.; Chung, J. Y. L.; Cvetovich, R. J.; Gong, X.; McLaughlin, M.; Reamer, R. A. *J. Org. Chem.* 2005, 70, 1930-1933) for tert-butyl 4-hydroxypiperidine-1-carboxylate, and 5-fluoropicolinonitrile for 4-chlorocyanopicoline used in Example 1. LC-MS (ESI) m/z 535 $(M+H)^+$.

Step 2: 1-tert-Butyl-4-(6-(4-(3-(5-tert-butylisoxazol-3-yl) ureido)phenylcarbamoyl)pyridin-3-yloxy)piperidinium methanesulfonate (110 mg, 95%) was prepared using a procedure analogous to that described in Example 27, substituting N-(4-(3-(5-tert-butylisoxazol-3-yl)ureido)phenyl)-5-(1-tert-butylpiperidin-4-yloxy)picolinamide from Step 1 of this example for N-(4-(3-(5-tert-butylisoxazol-3-yl)ureido)phenyl)-5-(1-isopropylpiperidin-4-yloxy)picolinamide used in Step 2 of Example 27. LC-MS (ESI) m/z 535 $(M+H)^+$; $^1$H NMR (300 MHz, DMSO-$d_6$) δ 10.40 (br. s., 1H), 9.50 (br. s., 1H), 8.93 (br. s., 1H), 8.82 (br. s., 1H), 8.44 (d, J=16.20 Hz, 1H), 8.13 (d, J=8.85 Hz, 1H), 7.81 (d, J=8.48 Hz, 2H), 7.72 (d, J=8.48 Hz, 1H), 7.43 (d, J=8.48 Hz, 2H), 6.50 (s, 1H), 4.64-5.08 (m, 1H), 3.26-3.72 (m, 2H), 3.12 (br. s., 2H), 2.35 (br. s., 4H), 2.17 (br. s., 2H), 1.89 (d, J=11.49 Hz, 1H), 1.37 (br. s., 9H), 1.30 (br. s., 9H).

Example 38

Preparation of 1-ethyl-4-(6-(4-(3-(5-(1,1,1-trifluoro-2-methylpropan-2-yl)isoxazol-3-yl)ureido)phenylcarbamoyl)pyridin-3-yloxy)piperidinium methanesulfonate

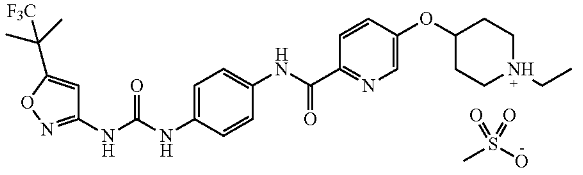

Step 1: Phenyl 5-(1,1,1-trifluoro-2-methylpropan-2-yl) isoxazol-3-ylcarbamate was synthesized using procedures analogous to those described in Steps 1-3 of Example 29, substituting methyl 3,3,3-trifluoro-2,2-dimethylpropanoate for methyl 2-fluoro-2-methylpropanoate used in Example 29.

Step 2: 5-(Piperidin-4-yloxy)-N-(4-(3-(5-(1,1,1-trifluoro-2-methylpropan-2-yl)isoxazol-3-yl)ureido)phenyl)picolinamide hydrochloride was prepared using procedures analogous to those described in Steps 2-4 of Example 17, substituting phenyl 5-(1,1,1-trifluoro-2-methylpropan-2-yl) isoxazol-3-ylcarbamate from Step 1 of this example for 5-(1,3-difluoro-2-methylpropan-2-yl)isoxazol-3-ylcarbamate used in Example 17. LC-MS (ESI) m/z 533 $(M+H)^+$.

Step 3: 5-(1-Ethylpiperidin-4-yloxy)-N-(4-(3-(5-(1,1,1-trifluoro-2-methylpropan-2-yl)isoxazol-3-yl)ureido)phenyl) picolinamide (79 mg, 68%) was prepared using a procedure analogous to that described in Example 2, substituting 5-(piperidin-4-yloxy)-N-(4-(3-(5-(1,1,1-trifluoro-2-methylpropan-2-yl)isoxazol-3-yl)ureido)phenyl)picolinamide hydrochloride from Step 2 of this example for N-(4-(3-(5-tert-butylisoxazol-3-yl)ureido)phenyl)-4-(piperidin-4-yloxy) picolinamide hydrochloride used in Example 2. LC-MS (ESI) m/z 561 $(M+H)^+$.

Step 4: 1-Ethyl-4-(6-(4-(3-(5-(1,1,1-trifluoro-2-methylpropan-2-yl)isoxazol-3-yl)ureido)phenylcarbamoyl)pyridin-3-yloxy)piperidinium methanesulfonate (90 mg, 95%) was prepared using a procedure analogous to that described in Example 27, substituting 5-(1-ethylpiperidin-4-yloxy)-N-(4-(3-(5-(1,1,1-trifluoro-2-methylpropan-2-yl)isoxazol-3-yl) ureido)phenyl)picolinamide from Step 3 of this example for N-(4-(3-(5-tert-butylisoxazol-3-yl)ureido)phenyl)-5-(1-isopropylpiperidin-4-yloxy)picolinamide used in Step 2 of Example 27. LC-MS (ESI) m/z 561 $(M+H)^+$; $^1H$ NMR (300 MHz, DMSO-$d_6$) δ 10.41 (br. s., 1H), 9.68 (s, 1H), 9.20 (br. s., 1H), 8.84 (br. s., 1H), 8.42 (d, J=9.42 Hz, 1H), 8.13 (d, J=8.48 Hz, 1H), 7.82 (d, J=8.48 Hz, 2H), 7.63-7.76 (m, 1H), 7.43 (d, J=7.91 Hz, 2H), 6.89 (s, 1H), 4.69-5.07 (m, 1H), 3.60 (d, J=10.93 Hz, 1H), 2.98-3.27 (m, 4H), 2.32 (s, 4H), 1.96-2.22 (m, 2H), 1.83 (d, J=11.49 Hz, 1H), 1.56 (s, 6H), 1.25 (t, J=6.69 Hz, 3H).

Example 39

Preparation of 1-isopropyl-4-(6-(4-(3-(5-(1,1,1-trifluoro-2-methylpropan-2-yl)isoxazol-3-yl)ureido)phenylcarbamoyl)pyridin-3-yloxy)piperidinium methanesulfonate

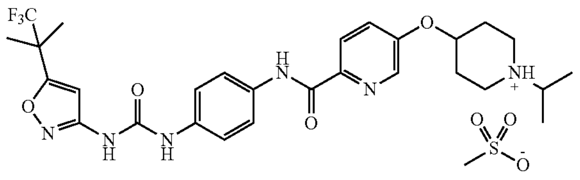

Step 1: 5-(1-Isopropylpiperidin-4-yloxy)-N-(4-(3-(5-(1,1,1-trifluoro-2-methylpropan-2-yl)isoxazol-3-yl)ureido)phenyl)picolinamide (89 mg, 80%) was prepared using a procedure analogous to that described in Example 20, substituting 5-(piperidin-4-yloxy)-N-(4-(3-(5-(1,1,1-trifluoro-2-methylpropan-2-yl)isoxazol-3-yl)ureido)phenyl)picolinamide hydrochloride from Step 2 of Example 38 for N-(4-(3-(5-(1,3-difluoro-2-methylpropan-2-yl)isoxazol-3-yl)ureido)phenyl)-5-(piperidin-4-yloxy)picolinamide hydrochloride used in Example 20. LC-MS (ESI) m/z 575 $(M+H)^+$.

Step 2: 1-Isopropyl-4-(6-(4-(3-(5-(1,1,1-trifluoro-2-methylpropan-2-yl)isoxazol-3-yl)ureido)phenylcarbamoyl)pyridin-3-yloxy)piperidinium methanesulfonate (90 mg, 95%) was prepared using a procedure analogous to that described in Example 27, substituting 5-(1-ethylpiperidin-4-yloxy)-N-(4-(3-(5-(1,1,1-trifluoro-2-methylpropan-2-yl)isoxazol-3-yl)ureido)phenyl)picolinamide from Step 1 of this example for N-(4-(3-(5-tert-butylisoxazol-3-yl)ureido)phenyl)-5-(1-isopropylpiperidin-4-yloxy)picolinamide used in Step 2 of Example 27. (ESI) m/z 575 $(M+H)^+$; $^1H$ NMR (300 MHz, DMSO-$d_6$) δ 10.41 (br. s., 1H), 9.69 (s, 1H), 9.14 (br. s., 1H), 8.86 (br. s., 1H), 8.43 (d, J=14.88 Hz, 1H), 8.13 (d, J=8.67 Hz, 1H), 7.82 (d, J=8.67 Hz, 2H), 7.71 (d, J=8.67 Hz, 1H), 7.44 (d, J=8.67 Hz, 2H), 6.90 (s, 1H), 4.70-5.07 (m, 1H), 3.49 (d, J=11.68 Hz, 2H), 3.16 (d, J=10.55 Hz, 2H), 2.35 (d, J=0.75 Hz, 4H), 2.15 (br. s., 2H), 1.70-1.97 (m, 1H), 1.56 (s, 6H), 1.12-1.39 (m, 6H).

Example 40

Preparation of (3R)-3-(6-(4-(3-(5-tert-butylisoxazol-3-yl)ureido)phenylcarbamoyl)pyridin-3-yloxy)-1-isopropylpyrrolidinium methanesulfonate

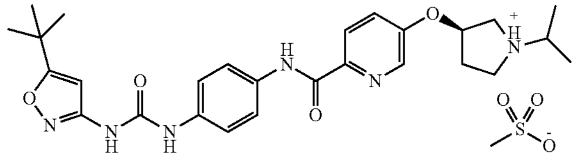

Step 1: (R)-N-(4-(3-(5-tert-Butylisoxazol-3-yl)ureido)phenyl)-5-(pyrrolidin-3-yloxy)picolinamide hydrochloride was prepared using procedures analogous to those described in Steps 1-4 of Example 1, substituting (R)-tert-butyl 3-hydroxypyrrolidine-1-carboxylate for tert-butyl 4-hydroxypiperidine-1-carboxylate, and 5-fluoropicolinonitrile for 4-chlorocyanopicoline used in Example 1. LC-MS (ESI) m/z 465 $(M+H)^+$.

Step 2: (R)-N-(4-(3-(5-tert-Butylisoxazol-3-yl)ureido)phenyl)-5-(1-isopropylpyrrolidin-3-yloxy)picolinamide (95 mg, 94%) was prepared using a procedure analogous to that described in Example 20, substituting (R)-N-(4-(3-(5-tert-butylisoxazol-3-yl)ureido)phenyl)-5-(pyrrolidin-3-yloxy)picolinamide hydrochloride from Step 1 of this example for N-(4-(3-(5-(1,3-difluoro-2-methylpropan-2-yl)isoxazol-3-yl)ureido)phenyl)-5-(piperidin-4-yloxy)picolinamide hydrochloride used in Example 20. LC-MS (ESI) m/z 507 $(M+H)^+$.

Step 3: (3R)-3-(6-(4-(3-(5-tert-Butylisoxazol-3-yl)ureido)phenylcarbamoyl)pyridin-3-yloxy)-1-isopropylpyrrolidinium methanesulfonate (96 mg, 93%) was prepared using a procedure analogous to that described in Example 27, substituting (R)-N-(4-(3-(5-tert-butylisoxazol-3-yl)ureido)phenyl)-5-(1-isopropylpyrrolidin-3-yloxy)picolinamide from Step 2 of this example for N-(4-(3-(5-tert-butylisoxazol-3-yl)ureido)phenyl)-5-(1-isopropylpiperidin-4-yloxy)picolinamide used in Step 2 of Example 27. LC-MS (ESI) m/z 507 $(M+H)^+$; $^1H$ NMR (300 MHz, DMSO-$d_6$) δ 10.41 (br. s., 1H), 9.81-10.08 (m, 1H), 9.49 (s, 1H), 8.80 (s, 1H), 8.39 (s, 1H), 8.15 (d, J=8.85 Hz, 1H), 7.81 (d, J=8.29 Hz, 2H), 7.67 (d, J=8.10 Hz, 1H), 7.43 (d, J=7.72 Hz, 2H), 6.49 (s, 1H), 5.40 (br. s., 1H), 3.62-3.88 (m, 2H), 3.19-3.33 (m, 1H), 2.73 (br. s., 2H), 2.30 (s, 4H), 2.16 (s, 1H), 1.30 (s, 15H).

Example 41

Preparation of 4-(6-(4-(3-(5-tert-butylisoxazol-3-yl)ureido)phenylcarbamoyl)pyridazin-3-yloxy)-1,2,2,6,6-pentamethylpiperidinium methanesulfonate

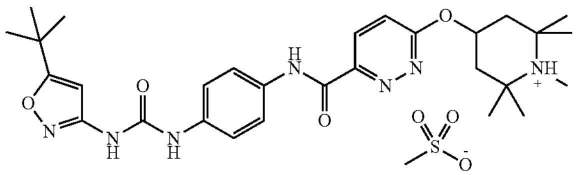

Step 1: N-(4-(3-(5-tert-Butylisoxazol-3-yl)ureido)phenyl)-6-(1,2,2,6,6-pentamethylpiperidin-4-yloxy)pyridazine-3-carboxamide (45 mg) was prepared using procedures analogous to those described in Steps 1-3 of Example 1, substituting 1,2,2,6,6-pentamethylpiperidin-4-ol for tert-butyl 4-hydroxypiperidine-1-carboxylate, and 6-chloropyridazine-3-carbonitrile for 4-chlorocyanopicoline used in Example 1. LC-MS (ESI) m/z 550 $(M+H)^+$.

Step 2: 4-(6-(4-(3-(5-tert-Butylisoxazol-3-yl)ureido)phenylcarbamoyl)pyridazin-3-yloxy)-1,2,2,6,6-pentamethylpiperidinium methanesulfonate (55 mg, 100%) was prepared using a procedure analogous to that described in Example 27, substituting N-(4-(3-(5-tert-butylisoxazol-3-yl)ureido)phenyl)-6-(1,2,2,6,6-pentamethylpiperidin-4-yloxy)pyridazine-3-carboxamide from Step 1 of this example for N-(4-(3-(5-tert-butylisoxazol-3-yl)ureido)phenyl)-5-(1-isopropylpiperidin-4-yloxy)picolinamide used in Step 2 of Example 27. LC-MS (ESI) m/z 550 $(M+H)^+$. $^1H$ NMR (300 MHz, DMSO-$d_6$) δ 10.88 (s, 1H), 9.50 (s, 1H), 8.83 (br. s., 2H), 8.24 (d, J=9.04 Hz, 1H), 7.84 (d, J=8.29 Hz, 2H), 7.45 (d, J=8.85 Hz, 3H), 6.50 (s, 1H), 5.75 (br. s., 1H), 2.80 (d, J=3.96 Hz, 3H), 2.56 (br. s., 1H), 2.32 (s, 4H), 1.95 (t, J=12.53 Hz, 2H), 1.48 (s, 12H), 1.30 (s, 9H).

Example 42

Preparation of 4-(6-(4-(3-(5-tert-butylisoxazol-3-yl)ureido)-2-methylphenylcarbamoyl)pyridin-3-yloxy)-1,2,2,6,6-pentamethylpiperidinium methanesulfonate

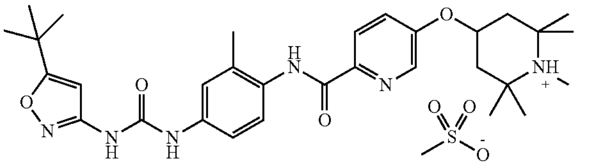

Step 1: To a stirred solution of 3-methyl-4-nitroaniline (566 mg, 3.7 mmol) in THF (10 mL) was added phenyl 5-tert-butylisoxazol-3-ylcarbamate (1.0 g, 3.7 mmol), DIEA (972 mL, 5.6 mmol), and DMAP (50 mg, 0.41 mmol). The resulting mixture was refluxed for 60 h. The reaction mixture was then cooled to rt, partitioned between EtOAc (50 mL) and 3N HCl (15 mL). The organic layer was washed with sat. $NaHCO_3$ (15 mL), brine (20 mL), dried over $MgSO_4$, filtered, and concentrated under reduced pressure to afford crude 1-(5-tert-butylisoxazol-3-yl)-3-(3-methyl-4-nitrophenyl)urea (2.0 g, 6.1 mmol). LC-MS (ESI) m/z 319 $(M+H)^+$.

Step 2: To a stirred solution of crude 1-(5-tert-butylisoxazol-3-yl)-3-(3-methyl-4-nitrophenyl)urea (2.0 g, 6.1 mmol) from Step 1 of this example in DCM (10 mL) was added AcOH (1.8 mL, 31.2 mmol), followed by zinc (1.99 g, 31.2 mmol) in small portions. The resulting mixture was stirred at rt for 1 h. LC-MS indicated that the reaction was complete. The reaction mixture was carefully quenched with sat. $NaHCO_3$ (50 mL) at rt, and the resulting biphasic mixture was extracted with EtOAc (50 mL). The organic layer was washed with brine (20 mL), dried over $MgSO_4$, filtered, and concentrated under reduced pressure. The residue was purified by silica gel flash chromatography, eluting with 0-65% EtOAc in hexanes, to give 1-(4-amino-3-methylphenyl)-3-(5-tert-butylisoxazol-3-yl)urea (560 mg, 61% over two steps). LC-MS (ESI) m/z 289 $(M+H)^+$.

Step 3: N-(4-(3-(5-tert-Butylisoxazol-3-yl)ureido)phenyl)-5-(1,2,2,6,6-pentamethylpiperidin-4-yloxy)picolinamide (50 mg, 34%) was prepared using a procedure analogous to that described in Step 3 of Example 1, substituting 5-(1,2,2,6,6-pentamethylpiperidin-4-yloxy)picolinic acid from Step 1 of Example 35 for 4-(1-(tert-butoxycarbonyl)piperidin-4-yloxy)picolinic acid, and 1-(4-amino-3-methylphenyl)-3-(5-tert-butylisoxazol-3-yl)urea from Step 2 of this example for 1-(4-aminophenyl)-3-(5-tert-butylisoxazol-3-yl)urea used in Example 1. LC-MS (ESI) m/z 563 $(M+H)^+$.

Step 4: 4-(6-(4-(3-(5-tert-Butylisoxazol-3-yl)ureido)-2-methylphenylcarbamoyl)pyridin-3-yloxy)-1,2,2,6,6-pentamethylpiperidinium methanesulfonate (60 mg, 100%) was prepared using a procedure analogous to that described in Example 27, substituting N-(4-(3-(5-tert-butylisoxazol-3-yl)ureido)phenyl)-5-(1,2,2,6,6-pentamethylpiperidin-4-yloxy)picolinamide from Step 3 of this example for N-(4-(3-(5-tert-butylisoxazol-3-yl)ureido)phenyl)-5-(1-isopropylpiperidin-4-yloxy)picolinamide used in Step 2 of Example 27. LC-MS (ESI) m/z 563 $(M+H)^+$; $^1H$ NMR (300 MHz, DMSO-$d_6$) δ 9.98 (s, 1H), 9.51 (s, 1H), 8.79 (br. s., 1H), 8.45 (br. s., 1H), 8.12 (d, J=9.04 Hz, 1H), 7.70 (t, J=8.57 Hz, 2H), 7.39 (br. s., 1H), 7.29 (d, J=8.85 Hz, 1H), 6.50 (s, 1H), 5.18 (br. s., 1H), 2.77 (d, J=3.39 Hz, 3H), 2.40 (d, J=13.94 Hz, 2H), 2.30 (s, 4H), 2.26 (s, 3H), 1.83 (t, J=12.34 Hz, 2H), 1.47 (d, J=9.42 Hz, 12H), 1.30 (s, 9H).

Example 43

Preparation of 4-(6-(4-(3-(5-tert-butylisoxazol-3-yl)ureido)-3-methylphenylcarbamoyl)pyridin-3-yloxy)-1,2,2,6,6-pentamethylpiperidinium methanesulfonate

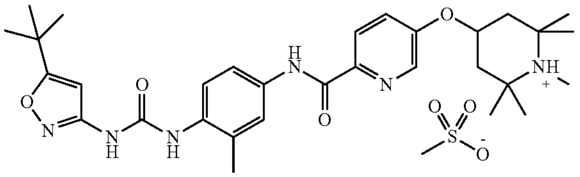

4-(6-(4-(3-(5-tert-Butylisoxazol-3-yl)ureido)-3-methylphenylcarbamoyl)pyridin-3-yloxy)-1,2,2,6,6-pentamethylpiperidinium methanesulfonate (75 mg) was prepared using procedures analogous to those described in Steps 1-4 of Example 42, substituting 2-methyl-4-nitroaniline for 3-methyl-4-nitroaniline used in Step 1 of Example 42. LC-MS (ESI) m/z 563 $(M+H)^+$; $^1H$ NMR (300 MHz, DMSO-$d_6$) δ 10.34 (s, 1H), 9.81 (s, 1H), 8.79 (br. s., 1H), 8.41 (br. s., 1H), 8.26 (s, 1H), 8.13 (d, J=8.48 Hz, 1H), 7.75 (br. s., 2H), 7.68 (br. s., 1H), 6.45 (s, 1H), 5.17 (br. s., 1H), 2.77 (d, J=3.77 Hz, 3H), 2.36 (s, 5H), 2.24 (s, 3H), 1.85 (t, J=12.34 Hz, 2H), 1.47 (d, J=8.67 Hz, 12H), 1.30 (s, 9H).

Example 44

Preparation of (3S)-3-(6-(4-(3-(5-tert-butylisoxazol-3-yl)ureido)phenylcarbamoyl)pyridin-3-yloxy)-1-isopropylpyrrolidinium methanesulfonate

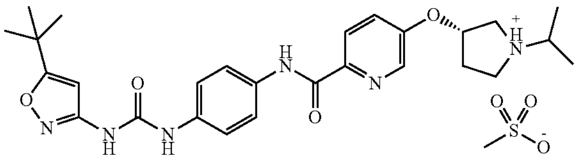

Step 1: (S)-N-(4-(3-(5-tert-Butylisoxazol-3-yl)ureido)phenyl)-5-(pyrrolidin-3-yloxy)picolinamide hydrochloride (500 mg) was prepared using procedures analogous to those described in Steps 1-4 of Example 1, substituting (S)-tert-butyl 3-hydroxypyrrolidine-1-carboxylate for tert-butyl 4-hydroxypiperidine-1-carboxylate, and 5-fluoropicolinonitrile for 4-chlorocyanopicoline used in Example 1. LC-MS (ESI) m/z 465 $(M+H)^+$.

Step 2: (S)-N-(4-(3-(5-tert-Butylisoxazol-3-yl)ureido)phenyl)-5-(1-isopropylpyrrolidin-3-yloxy)picolinamide (50 mg, 94%) was prepared using a procedure analogous to that described in Example 20, substituting (S)-N-(4-(3-(5-tert-butylisoxazol-3-yl)ureido)phenyl)-5-(pyrrolidin-3-yloxy)picolinamide hydrochloride from Step 1 of this example for N-(4-(3-(5-(1,3-difluoro-2-methylpropan-2-yl)isoxazol-3-yl)ureido)phenyl)-5-(piperidin-4-yloxy)picolinamide hydrochloride used in Example 20. LC-MS (ESI) m/z 507 $(M+H)^+$.

Step 3: (3S)-3-(6-(4-(3-(5-tert-Butylisoxazol-3-yl)ureido)phenylcarbamoyl)pyridin-3-yloxy)-1-isopropylpyrrolidinium methanesulfonate (60 mg, 95%) was prepared using a procedure analogous to that described in Example 27, substituting (S)-N-(4-(3-(5-tert-butylisoxazol-3-yl)ureido)phenyl)-5-(1-isopropylpyrrolidin-3-yloxy)picolinamide from Step 2 of this example for N-(4-(3-(5-tert-butylisoxazol-3-yl)ureido)phenyl)-5-(1-isopropylpiperidin-4-yloxy)picolinamide used in Step 2 of Example 27. LC-MS (ESI) m/z 507 $(M+H)^+$; $^1H$ NMR (300 MHz, DMSO-$d_6$) δ 10.41 (br. s., 1H), 10.03 (br. s., 1H), 9.50 (s, 1H), 8.82 (s, 1H), 8.39 (br. s., 1H), 8.15 (d, J=8.85 Hz, 1H), 7.81 (d, J=8.10 Hz, 2H), 7.68 (d, J=8.85 Hz, 1H), 7.43 (d, J=8.10 Hz, 2H), 6.50 (s, 1H), 5.28-5.46 (m, 1H), 3.78 (d, J=11.49 Hz, 1H), 3.47 (d, J=7.72 Hz, 1H), 3.30 (br. s., 1H), 2.63 (d, J=6.03 Hz, 1H), 2.33 (s, 4H), 2.06-2.22 (m, 1H), 1.30 (s, 15H).

Example 45

Preparation of (1R,5S)-3-(6-(4-(3-(5-tert-butylisoxazol-3-yl)ureido)phenylcarbamoyl)pyridin-3-yloxy)-8-methyl-8-azoniabicyclo[3.2.1]octane methanesulfonate

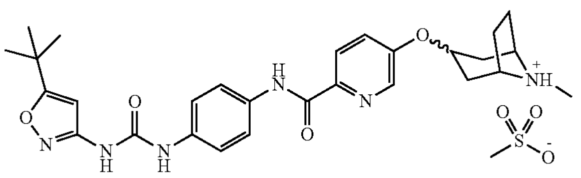

Step 1: N-(4-(3-(5-tert-Butylisoxazol-3-yl)ureido)phenyl)-5-((1R,5S)-8-methyl-8-azabicyclo[3.2.1]octan-3-yloxy)picolinamide (140 mg) was prepared using procedures analogous to those described in Steps 1-3 of Example 1, substituting (1R,5S)-8-methyl-8-azabicyclo[3.2.1]octan-3-ol for tert-butyl 4-hydroxypiperidine-1-carboxylate, and 5-fluoropicolinonitrile for 4-chlorocyanopicoline used in Example 1. LC-MS (ESI) m/z 519 $(M+H)^+$.

Step 2: (1R,5S)-3-(6-(4-(3-(5-tert-Butylisoxazol-3-yl)ureido)phenylcarbamoyl)pyridin-3-yloxy)-8-methyl-8-azoniabicyclo[3.2.1]octane methanesulfonate (160 mg, 100%) was prepared using a procedure analogous to that described in Example 27, substituting N-(4-(3-(5-tert-butylisoxazol-3-yl)ureido)phenyl)-5-((1R,5S)-8-methyl-8-azabicyclo[3.2.1]octan-3-yloxy)picolinamide from Step 1 of this example for N-(4-(3-(5-tert-butylisoxazol-3-yl)ureido)phenyl)-5-(1-isopropylpiperidin-4-yloxy)picolinamide used in Step 2 of Example 27. LC-MS (ESI) m/z 519 $(M+H)^+$; $^1H$ NMR (300 MHz, DMSO-$d_6$) δ 10.40 (s, 1H), 9.50 (s, 2H), 8.82 (s, 1H), 8.40 (br. s., 1H), 8.12 (d, J=8.67 Hz, 1H), 7.81 (d, J=8.10 Hz, 2H), 7.66 (d, J=8.85 Hz, 1H), 7.43 (d, J=8.10 Hz, 2H), 6.50 (s, 1H), 4.93 (br. s., 1H), 3.90 (br. s., 2H), 2.72 (d, J=3.96 Hz, 3H), 2.30-2.46 (m, 5H), 2.06-2.29 (m, 6H), 1.30 (s, 9H).

Example 46

Preparation of 4-(6-(4-(3-(5-tert-butylisoxazol-3-yl)ureido)-3-methoxyphenylcarbamoyl)pyridin-3-yloxy)-1,2,2,6,6-pentamethylpiperidinium methanesulfonate

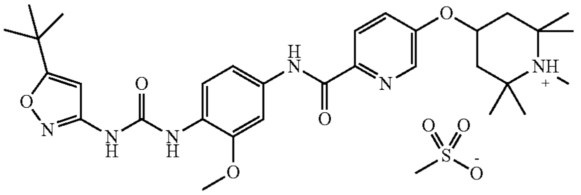

Step 1: A stirred mixture of 1-isocyanato-2-methoxy-4-nitrobenzene (500 mg, 2.6 mmol) and 5-tert-butylisoxazol-3-amine (361 mg, 2.6 mmol) in THF (30 mL) was heated at 65° C. for 3 h. LC-MS indicated that the reaction was complete. The reaction mixture was cooled to rt and evaporated under reduced pressure. The residue, 1-(5-tert-butylisoxazol-3-yl)-3-(2-methoxy-4-nitrophenyl)urea (850 mg, 98%), was used directly for the next step. LC-MS (ESI) m/z 335 $(M+H)^+$.

Step 2: 1-(4-Amino-2-methoxyphenyl)-3-(5-tert-butylisoxazol-3-yl)urea was prepared using a procedure analogous to that described in Step 2 of Example 42, substituting 1-(5-tert-butylisoxazol-3-yl)-3-(2-methoxy-4-nitrophenyl)urea for 1-(5-tert-butylisoxazol-3-yl)-3-(3-methyl-4-nitrophenyl)urea used in Example 42. LC-MS (ESI) m/z 305 $(M+H)^+$.

Step 3: N-(4-(3-(5-tert-Butylisoxazol-3-yl)ureido)-3-methoxyphenyl)-5-(1,2,2,6,6-pentamethylpiperidin-4-yloxy)picolinamide (50 mg, 38%) was prepared using a procedure analogous to that described in Step 3 of Example 1, substituting 5-(1,2,2,6,6-pentamethylpiperidin-4-yloxy)picolinic acid from Step 2 of this example for 4-(1-(tert-butoxycarbonyl)piperidin-4-yloxy)picolinic acid used in Example 1. LC-MS (ESI) m/z 579 $(M+H)^+$.

Step 4: 4-(6-(4-(3-(5-tert-Butylisoxazol-3-yl)ureido)-3-methoxyphenylcarbamoyl)pyridin-3-yloxy)-1,2,2,6,6-pentamethylpiperidinium methanesulfonate (60 mg, 100%) was prepared using a procedure analogous to that described in Example 27, substituting N-(4-(3-(5-tert-butylisoxazol-3-yl)ureido)-3-methoxyphenyl)-5-(1,2,2,6,6-pentamethylpiperidin-4-yloxy)picolinamide from Step 3 of this example for N-(4-(3-(5-tert-butylisoxazol-3-yl)ureido)phenyl)-5-(1-isopropylpiperidin-4-yloxy)picolinamide used in Step 2 of Example 27. LC-MS (ESI) m/z 579 $(M+H)^+$; $^1H$ NMR (300 MHz, DMSO-$d_6$) δ 10.40 (s, 1H), 9.98 (s, 1H), 8.78 (br. s., 1H), 8.61 (br. s., 1H), 8.41 (br. s., 1H), 8.14 (d, J=8.67 Hz, 1H), 8.02 (d, J=8.67 Hz, 1H), 7.66-7.81 (m, 2H), 7.49 (d, J=8.48 Hz, 1H), 6.46 (s, 1H), 5.17 (br. s., 1H), 3.88 (s, 3H), 2.77 (d, J=4.33 Hz, 3H), 2.28-2.46 (m, 5H), 1.86 (t, J=12.43 Hz, 2H), 1.49 (s, 6H), 1.46 (s, 6H), 1.30 (s, 9H).

Example 47

Preparation of 4-(5-(4-(3-(5-tert-butylisoxazol-3-yl)ureido)phenylcarbamoyl)pyrazin-2-yloxy)-1,2,2,6,6-pentamethylpiperidinium methanesulfonate

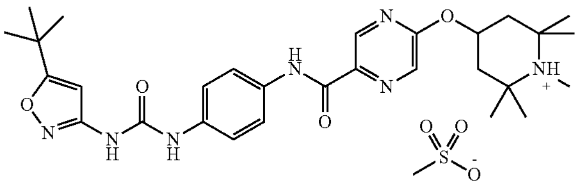

Step 1: N-(4-(3-(5-tert-butylisoxazol-3-yl)ureido)phenyl)-5-(1,2,2,6,6-pentamethylpiperidin-4-yloxy)pyrazine-2-carboxamide (12 mg) was prepared using procedures analogous to those described in Steps 1-3 of Example 1, substituting 1,2,2,6,6-pentamethylpiperidin-4-ol for tert-butyl 4-hydroxypiperidine-1-carboxylate, and 5-chloropyrazine-2-carbonitrile for 4-chlorocyanopicoline used in Example 1. LC-MS (ESI) m/z 550 $(M+H)^+$.

Step 2: 4-(5-(4-(3-(5-tert-Butylisoxazol-3-yl)ureido)phenylcarbamoyl)pyrazin-2-yloxy)-1,2,2,6,6-pentamethylpiperidinium methanesulfonate (15 mg, 100%) was prepared using a procedure analogous to that described in Example 27, substituting N-(4-(3-(5-tert-butylisoxazol-3-yl)ureido)phenyl)-5-(1,2,2,6,6-pentamethylpiperidin-4-yloxy)pyrazine-2-carboxamide from Step 1 of this example for N-(4-(3-(5-tert-butylisoxazol-3-yl)ureido)phenyl)-5-(1-isopropylpiperidin-4-yloxy)picolinamide used in Step 2 of Example 27. LC-MS (ESI) m/z 550 $(M+H)^+$; $^1$H NMR (300 MHz, DMSO-$d_6$) δ 10.42 (s, 1H), 9.49 (br. s., 1H), 8.84 (d, J=10.93 Hz, 2H), 8.34 (br. s., 1H), 7.81 (d, J=8.29 Hz, 2H), 7.42 (d, J=8.29 Hz, 2H), 6.50 (s, 1H), 5.43 (br. s., 1H), 2.22 (br. s., 3H), 2.04 (br. s., 2H), 1.53 (br. s., 2H), 1.30 (s, 12H), 1.13 (d, J=10.93 Hz, 12H).

Example 48

Preparation of 5-((1,2,2,6,6-pentamethylpiperidin-4-yl)oxy)-N-(4-(3-(4-(trifluoromethyl)-1H-pyrazol-1-yl)ureido)phenyl)picolinamide The title compound may be prepared using a procedure analogous to that described in Step 3 of Example 29, substituting 4-(trifluoromethyl)-1H-pyrazol-1-amine (Ref: Piotrowski, D. W. et al. US2003/0236287, 2003) for 3-(2-fluoropropan-2-yl)isoxazol-5-amine used in Example 29.

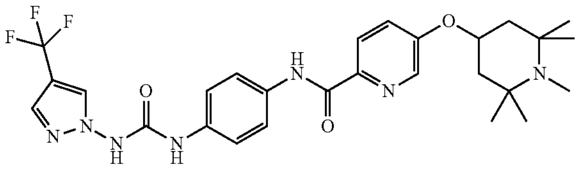 [SMILES: CN1C(C)(C)CC(Oc2ccc(C(=O)Nc3ccc(NC(=O)Nn4cc(C(F)(F)F)cn4)cc3)nc2)CC1(C)C]

The title compound may be prepared using a procedure analogous to that described in Step 2 of Example 17, substituting N-(4-aminophenyl)-5-(1,2,2,6,6-pentamethylpiperidin-4-yloxy)picolinamide dihydrochloride from Step 2 of Example 49 for tert-butyl 4-aminophenylcarbamate, and phenyl (4-(trifluoromethyl)-1H-pyrazol-1-yl)carbamate from Step 1 of this example for phenyl 5-(1,3-difluoro-2-methylpropan-2-yl)isoxazol-3-ylcarbamate used in Step 2 of Example 17.

Example 49

Preparation of 4-(6-(4-(3-(3-(2-fluoropropan-2-yl)isoxazol-5-yl)ureido)phenylcarbamoyl)pyridin-3-yloxy)-1,2,2,6,6-pentamethylpiperidinium methanesulfonate

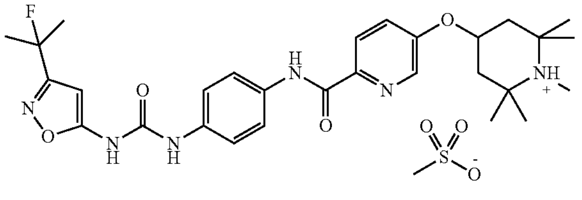

Step 1: To a stirred solution of 5-(1,2,2,6,6-pentamethylpiperidin-4-yloxy)picolinic acid (250 mg, 0.86 mmol) in DCM/THF (6 mL, 2:1, v/v) at rt was added TEA (144 μL, 1.03 mmol) and ethyl chloroformate (82 μL, 0.86 mmol). The resulting mixture was stirred at rt for 20 min before tert-butyl 4-aminophenylcarbamate (178 mg, 0.86 mmol) was added. The resulting mixture was heated at 50° C. for 1 h. LC-MS indicated the reaction was complete. Solvents were then removed under reduced pressure and the residue was partitioned between EtOAc (30 mL) and brine (20 mL). The organic layer was dried over $MgSO_4$, filtered, and concentrated under reduced pressure to give crude tert-butyl 4-(5-(1,2,2,6,6-pentamethylpiperidin-4-yloxy)picolinamido)phenylcarbamate (500 mg) as an off-white foam. LC-MS (ESI) m/z 483 $(M+H)^+$.

Step 2: N-(4-Aminophenyl)-5-(1,2,2,6,6-pentamethylpiperidin-4-yloxy)picolinamide dihydrochloride (350 mg) was prepared using a procedure analogous to that described in Step 4 of Example 1, substituting tert-butyl 4-(5-(1,2,2,6,6-pentamethylpiperidin-4-yloxy)picolinamido)phenylcarbamate from Step 1 of this Example for tert-butyl 4-(2-(4-(3-(5-tert-butylisoxazol-3-yl)ureido)phenylcarbamoyl)pyridin-4-yloxy)piperidine-1-carboxylate used in Example 1. LC-MS (ESI) m/z 383 $(M+H)^+$.

Step 3: N-(4-(3-(3-(2-Fluoropropan-2-yl)isoxazol-5-yl)ureido)phenyl)-5-(1,2,2,6,6-pentamethylpiperidin-4-yloxy)picolinamide (40 mg) was prepared using a procedure analogous to that described in Step 2 of Example 17, substituting N-(4-aminophenyl)-5-(1,2,2,6,6-pentamethylpiperidin-4-yloxy)picolinamide dihydrochloride from Step 2 of this example for tert-butyl 4-aminophenylcarbamate, and phenyl 3-(2-fluoropropan-2-yl)isoxazol-5-ylcarbamate from Step 3 of Example 29 for phenyl 5-(1,3-difluoro-2-methylpropan-2-yl)isoxazol-3-ylcarbamate used in Step 2 of Example 17. LC-MS (ESI) m/z 553 $(M+H)^+$.

Step 4: 4-(6-(4-(3-(3-(2-fluoropropan-2-yl)isoxazol-5-yl)ureido)phenylcarbamoyl)pyridin-3-yloxy)-1,2,2,6,6-pentamethylpiperidinium methanesulfonate (45 mg, 100%) was prepared using a procedure analogous to that described in Example 27, substituting N-(4-(3-(3-(2-fluoropropan-2-yl)isoxazol-5-yl)ureido)phenyl)-5-(1,2,2,6,6-pentamethylpiperidin-4-yloxy)picolinamide from Step 3 of this Example for N-(4-(3-(5-tert-butylisoxazol-3-yl)ureido)phenyl)-5-(1-isopropylpiperidin-4-yloxy)picolinamide used in Step 2 of Example 27. LC-MS (ESI) m/z 553 $(M+H)^+$; $^1$H NMR (300 MHz, DMSO-$d_6$) δ 10.42 (br. s., 1H), 10.36 (br. s., 1H), 8.96 (br. s., 1H), 8.77 (br. s., 1H), 8.42 (br. s., 1H), 8.13 (d, J=8.29 Hz, 1H), 7.83 (d, J=8.10 Hz, 2H), 7.73 (d, J=8.85 Hz, 1H), 7.45 (d, J=8.48 Hz, 2H), 6.15 (s, 1H), 5.17 (br. s., 1H), 2.77 (br. s., 3H), 2.19-2.45 (m, 5H), 1.84 (t, J=11.96 Hz, 2H), 1.72 (s, 3H), 1.64 (s, 3H), 1.47 (d, J=9.04 Hz, 12H).

Example 50

Preparation of 4-(6-(4-(3-(5-(1,3-difluoro-2-methylpropan-2-yl)isoxazol-3-yl)ureido)phenylcarbamoyl)pyridin-3-yloxy)-1,2,2,6,6-pentamethylpiperidinium methanesulfonate

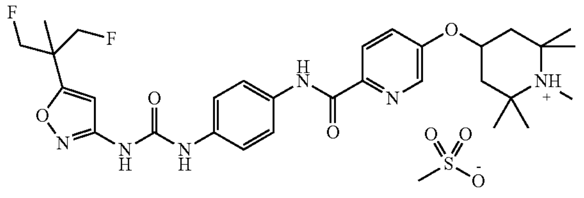

Step 1: N-(4-(3-(5-(1,3-Difluoro-2-methylpropan-2-yl)isoxazol-3-yl)ureido)phenyl)-5-(1,2,2,6,6-pentamethylpiperidin-4-yloxy)picolinamide (70 mg, 55%) was prepared using a procedure analogous to that described in Step 2 of Example 17, substituting N-(4-aminophenyl)-5-(1,2,2,6,6-pentamethylpiperidin-4-yloxy)picolinamide dihydrochloride from Step 2 of Example 49 for tert-butyl 4-aminophenylcarbamate used in Step 2 of Example 17. LC-MS (ESI) m/z 585 $(M+H)^+$.

Step 2: 4-(6-(4-(3-(5-(1,3-Difluoro-2-methylpropan-2-yl)isoxazol-3-yl)ureido)phenylcarbamoyl)pyridin-3-yloxy)-1,2,2,6,6-pentamethylpiperidinium methanesulfonate (75 mg, 100%) was prepared using a procedure analogous to that described in Example 27, substituting N-(4-(3-(5-(1,3-difluoro-2-methylpropan-2-yl)isoxazol-3-yl)ureido)phenyl)-5-(1,2,2,6,6-pentamethylpiperidin-4-yloxy)picolinamide from Step 1 of this example for N-(4-(3-(5-tert-butylisoxazol-3-yl)ureido)phenyl)-5-(1-isopropylpiperidin-4-yloxy)picolinamide used in Step 2 of Example 27. LC-MS (ESI) m/z 585 $(M+H)^+$; $^1$H NMR (300 MHz, DMSO-$d_6$) δ 10.41 (s, 1H), 9.62 (s, 1H), 8.83 (s, 1H), 8.41 (br. s., 1H), 8.13 (d, J=8.67 Hz, 1H), 7.82 (d, J=8.29 Hz, 2H), 7.73 (d, J=8.85 Hz, 1H), 7.43 (d, J=8.10 Hz, 2H), 6.79 (s, 1H), 5.17 (br. s., 1H), 4.73 (s, 2H), 4.58 (s, 2H), 3.39-3.51 (m, 1H), 2.77 (d, J=3.96 Hz, 3H), 2.22-2.46 (m, 5H), 1.83 (t, J=12.24 Hz, 2H), 1.39-1.59 (m, 12H), 1.34 (s, 3H).

Example 51

Preparation of 1,2,2,6,6-pentamethyl-4-(6-(4-(3-(5-(1,1,1-trifluoro-2-methylpropan-2-yl)isoxazol-3-yl)ureido)phenylcarbamoyl)pyridin-3-yloxy)piperidinium methanesulfonate

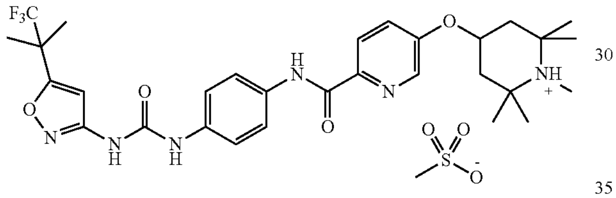

Step 1: 5-(1,2,2,6,6-Pentamethylpiperidin-4-yloxy)-N-(4-(3-(5-(1,1,1-trifluoro-2-methylpropan-2-yl)isoxazol-3-yl)ureido)phenyl)picolinamide (35 mg, 51%) was prepared using a procedure analogous to that described in Step 2 of Example 17, substituting N-(4-aminophenyl)-5-(1,2,2,6,6-pentamethylpiperidin-4-yloxy)picolinamide dihydrochloride from Step 2 of Example 49 for tert-butyl 4-aminophenylcarbamate, and phenyl 5-(1,1,1-trifluoro-2-methylpropan-2-yl)isoxazol-3-ylcarbamate from Step 1 of Example 38 for phenyl 5-(1,3-difluoro-2-methylpropan-2-yl)isoxazol-3-ylcarbamate used in Step 2 of Example 17. LC-MS (ESI) m/z 603 $(M+H)^+$.

Step 2: 1,2,2,6,6-Pentamethyl-4-(6-(4-(3-(5-(1,1,1-trifluoro-2-methylpropan-2-yl)isoxazol-3-yl)ureido)phenylcarbamoyl)pyridin-3-yloxy)piperidinium methanesulfonate (40 mg, 100%) was prepared using a procedure analogous to that described in Example 27, substituting 5-(1,2,2,6,6-pentamethylpiperidin-4-yloxy)-N-(4-(3-(5-(1,1,1-trifluoro-2-methylpropan-2-yl)isoxazol-3-yl)ureido)phenyl)picolinamide from Step 1 of this example for N-(4-(3-(5-tert-butylisoxazol-3-yl)ureido)phenyl)-5-(1-isopropylpiperidin-4-yloxy)picolinamide used in Step 2 of Example 27. LC-MS (ESI) m/z 603 $(M+H)^+$; $^1$H NMR (300 MHz, DMSO-$d_6$) δ 10.41 (s, 1H), 9.68 (s, 1H), 8.85 (s, 1H), 8.75 (br. s., 1H), 8.41 (br. s., 1H), 8.13 (d, J=8.67 Hz, 1H), 7.82 (d, J=8.48 Hz, 2H), 7.73 (d, J=8.85 Hz, 1H), 7.44 (d, J=8.29 Hz, 2H), 6.89 (s, 1H), 5.17 (br. s., 1H), 2.77 (d, J=3.58 Hz, 3H), 2.24-2.45 (m, 2H), 2.34 (s, 3H), 1.83 (t, J=12.34 Hz, 2H), 1.56 (s, 6H), 1.47 (d, J=9.80 Hz, 12H).

Example 52

Preparation of N-(4-(3-(5-(tert-butyl)isoxazol-3-yl)ureido)phenyl)-5-((1-isopropyl-2,2,6,6-tetramethylpiperidin-4-yl)oxy)picolinamide

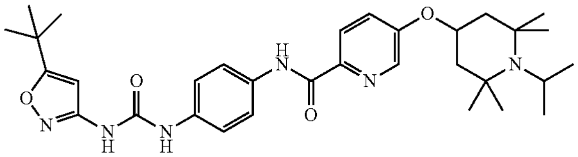 [SMILES: CC(C)N1C(C)(C)CC(Oc2ccc(C(=O)Nc3ccc(NC(=O)Nc4cc(C(C)(C)C)on4)cc3)nc2)CC1(C)C]

The title compound may be prepared using procedures analogous to those described in the Steps 1-2 of Example 54, substituting 1-isopropyl-2,2,6,6-tetramethylpiperidin-4-ol (Ref: Randell, D. R. et al. U.S. Pat. No. 4,014,887 A1, 1977) for 1-ethyl-2,2,6,6-tetramethylpiperidin-4-ol used in Example 54.

Example 53

Preparation of (5S)-5-((6-(4-(3-(5-tert-butylisoxazol-3-yl)ureido)phenylcarbamoyl)pyridin-3-yloxy)methyl)-1,2,2-trimethylpyrrolidinium methanesulfonate

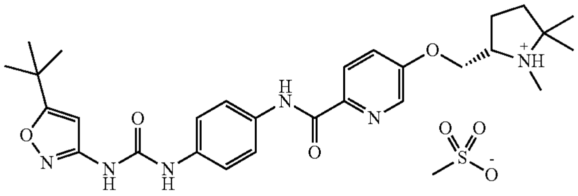

Step 1: Lithium aluminum hydride (312 mg, 8.2 mmol) was stirred in THF (35 mL) at 0° C. (S)-1-(tert-butoxycarbonyl)-5,5-dimethylpyrrolidine-2-carboxylic acid (500 mg, 2.1 mmol) in THF (5 mL) was added dropwise over 15 min. The resulting mixture was stirred at rt for 1 h, and heated at 55° C. for 1 h. Another batch of lithium aluminum hydride (140 mg, 3.7 mmol) was added and the resulting mixture was heated at 60° C. for 2 h. LC-MS indicated partial conversion to the product. The reaction mixture was cooled to 0° C. and quenched with 0.5 mL of $H_2O$, 0.5 mL of 10% NaOH, and 1.5 mL of $H_2O$ sequentially. The resulting mixture was stirred at rt for 30 min before it was filtered through a celite plug. The filtrate was evaporated under reduced pressure to give crude (S)-(1,5,5-trimethylpyrrolidin-2-yl)methanol (380 mg) as a clear oil. LC-MS (ESI) m/z 144 $(M+H)^+$.

Step 2: (S)-N-(4-(3-(5-tert-Butylisoxazol-3-yl)ureido)phenyl)-5-((1,5,5-trimethylpyrrolidin-2-yl)methoxy)picolinamide (96 mg) was prepared using procedures analogous to those described in Step 1-3 of Example 1, substituting (S)-(1,5,5-trimethylpyrrolidin-2-yl)methanol from Step 1 of this example for tert-butyl 4-hydroxypiperidine-1-carboxylate, and 5-fluoropicolinonitrile for 4-chlorocyanopicoline used in Example 1. LC-MS (ESI) m/z 521 $(M+H)^+$.

Step 3: (5S)-5-((6-(4-(3-(5-tert-butylisoxazol-3-yl)ureido)phenylcarbamoyl)pyridin-3-yloxy)methyl)-1,2,2-trimethylpyrrolidinium methanesulfonate (98 mg, 100%) was prepared using a procedure analogous to that described in Example 27, substituting (S)-N-(4-(3-(5-tert-butylisoxazol-3-yl)ureido)phenyl)-5-((1,5,5-trimethylpyrrolidin-2-yl)methoxy)picolinamide from Step 2 of this example for N-(4-(3-(5-tert-butylisoxazol-3-yl)ureido)phenyl)-5-(1-isopropylpiperidin-4-yloxy)picolinamide used in Step 2 of Example 27. LC-MS (ESI) m/z 521 $(M+H)^+$; $^1H$ NMR (300 MHz, DMSO-$d_6$) δ 10.43 (s, 1H), 9.50 (s, 1H), 9.21 (br. s., 1H), 8.82 (s, 1H), 8.48 (br. s., 1H), 8.17 (d, J=8.67 Hz, 1H), 7.82 (d, J=8.48 Hz, 2H), 7.70 (d, J=9.04 Hz, 1H), 7.43 (d, J=8.10 Hz, 2H), 6.49 (s, 1H), 4.41-4.61 (m, 2H), 2.87 (d, J=4.33 Hz, 3H), 2.38-2.22 (m, 2H), 2.32 (s, 3H), 1.97-2.13 (m, 1H), 1.72-1.96 (m, 2H), 1.44 (s, 3H), 1.16-1.37 (m, 12H).

Example 54

Preparation of 4-(6-(4-(3-(5-tert-butylisoxazol-3-yl)ureido)phenylcarbamoyl)pyridin-3-yloxy)-1-ethyl-2,2,6,6-tetramethylpiperidinium methanesulfonate

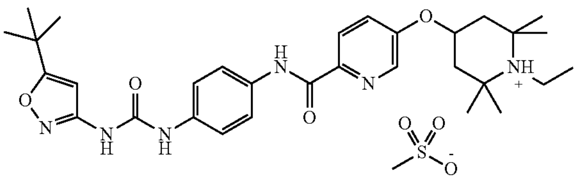

Step 1: 5-(1-Ethyl-2,2,6,6-tetramethylpiperidin-4-yloxy)picolinic acid was prepared using procedures analogous to those described in Step 1-2 of Example 1, substituting 1-ethyl-2,2,6,6-tetramethylpiperidin-4-ol (Reference: Gan, H.; Whitten, D. G.; *J. Amer. Chem. Soc.* 115, 1993, 8031-8037) for tert-butyl 4-hydroxypiperidine-1-carboxylate, and 5-fluoropicolinonitrile for 4-chlorocyanopicoline used in Example 1. LC-MS (ESI) m/z 293 $(M+H)^+$.

Step 2: N-(4-(3-(5-tert-Butylisoxazol-3-yl)ureido)phenyl)-5-(1-ethyl-2,2,6,6-tetramethylpiperidin-4-yloxy)picolinamide (188 mg, 51%) was prepared using a procedure analogous to that described in Step 3 of Example 1, substituting 5-(1-ethyl-2,2,6,6-tetramethylpiperidin-4-yloxy)picolinic acid from Step 1 of this example for 4-(1-(tert-butoxycarbonyl)piperidin-4-yloxy)picolinic acid used in Step 3 of Example 1. LC-MS (ESI) m/z 563 $(M+H)^+$.

Step 3: 4-(6-(4-(3-(5-tert-Butylisoxazol-3-yl)ureido)phenylcarbamoyl)pyridin-3-yloxy)-1-ethyl-2,2,6,6-tetramethylpiperidinium methanesulfonate (220 mg, 100%) was prepared using a procedure analogous to that described in Example 27, substituting N-(4-(3-(5-tert-butylisoxazol-3-yl)ureido)phenyl)-5-(1-ethyl-2,2,6,6-tetramethylpiperidin-4-yloxy)picolinamide from Step 2 of this example for N-(4-(3-(5-tert-butylisoxazol-3-yl)ureido)phenyl)-5-(1-isopropylpiperidin-4-yloxy)picolinamide used in Step 2 of Example 27. LC-MS (ESI) m/z 563 $(M+H)^+$; $^1H$ NMR (300 MHz, DMSO-$d_6$) δ 10.40 (s, 1H), 9.51 (s, 1H), 8.83 (s, 1H), 8.41 (d, J=2.83 Hz, 1H), 8.13 (d, J=8.85 Hz, 1H), 7.99 (br. s., 1H), 7.81 (d, J=9.04 Hz, 2H), 7.72 (dd, J=2.83, 8.85 Hz, 1H), 7.43 (d, J=8.85 Hz, 2H), 6.50 (s, 1H), 5.04-5.27 (m, 1H), 3.32 (br. s., 2H), 2.39-2.24 (m, 2H), 2.32 (s, 3H), 1.96 (t, J=12.34 Hz, 2H), 1.48 (d, J=10.74 Hz, 12H), 1.34 (t, 3H), 1.30 (s, 9H).

Example 55

Preparation of 4-(6-(4-(3-(3-tert-butylisoxazol-5-yl)ureido)phenylcarbamoyl)pyridin-3-yloxy)-1,2,2,6,6-pentamethylpiperidinium methanesulfonate

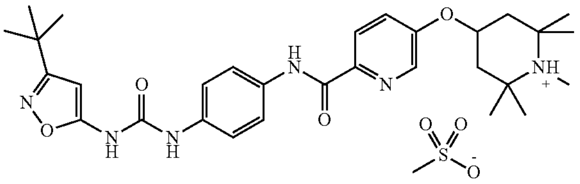

Step 1: Phenyl 3-tert-butylisoxazol-5-ylcarbamate was synthesized using a procedure analogous to that described in Step 3 of Example 29, substituting 3-tert-butylisoxazol-5-amine for 3-(2-fluoropropan-2-yl)isoxazol-5-amine used in Example 29.

Step 2: N-(4-(3-(3-tert-Butylisoxazol-5-yl)ureido)phenyl)-5-(1,2,2,6,6-pentamethylpiperidin-4-yloxy)picolinamide (62 mg, 66%) was prepared using a procedure analogous to that described in Step 2 of Example 17, substituting N-(4-aminophenyl)-5-(1,2,2,6,6-pentamethylpiperidin-4-yloxy)picolinamide dihydrochloride from Step 2 of Example 49 for tert-butyl 4-aminophenylcarbamate, and phenyl 3-tert-butylisoxazol-5-ylcarbamate from Step 1 of this example for phenyl 5-(1,3-difluoro-2-methylpropan-2-yl)isoxazol-3-ylcarbamate used in Step 1 of Example 49. LC-MS (ESI) m/z 549 $(M+H)^+$.

Step 2: 4-(6-(4-(3-(3-tert-Butylisoxazol-5-yl)ureido)phenylcarbamoyl)pyridin-3-yloxy)-1,2,2,6,6-pentamethylpiperidinium methanesulfonate (65 mg, 100%) was prepared using a procedure analogous to that described in Example 27, substituting N-(4-(3-(3-tert-butylisoxazol-5-yl)ureido)phenyl)-5-(1,2,2,6,6-pentamethylpiperidin-4-yloxy)picolinamide from Step 2 of this example for N-(4-(3-(5-tert-butylisoxazol-3-yl)ureido)phenyl)-5-(1-isopropylpiperidin-4-yloxy)picolinamide used in Step 2 of Example 27. LC-MS (ESI) m/z 549 $(M+H)^+$; $^1H$ NMR (300 MHz, DMSO-$d_6$) δ 10.42 (s, 1H), 10.13 (s, 1H), 8.88 (s, 1H), 8.78 (br. s., 1H), 8.41 (br. s., 1H), 8.13 (d, J=8.67 Hz, 1H), 7.82 (d, J=8.67 Hz, 2H), 7.73 (d, J=6.22 Hz, 1H), 7.44 (d, J=8.67 Hz, 1H), 7.09 (d, J=8.48 Hz, 1H), 6.05 (s, 1H), 5.17 (br. s., 1H), 2.77 (d, J=4.33 Hz, 3H), 2.45-2.18 (m, 2H), 2.34 (s, 3H), 1.84 (t, J=11.96 Hz, 2H), 1.47 (d, J=9.04 Hz, 12H), 1.26 (s, 9H).

Example 56

Preparation of 4-(6-(4-(3-(3-tert-butylisoxazol-5-yl)ureido)phenylcarbamoyl)pyridin-3-yloxy)-1-isopropylpiperidinium methanesulfonate

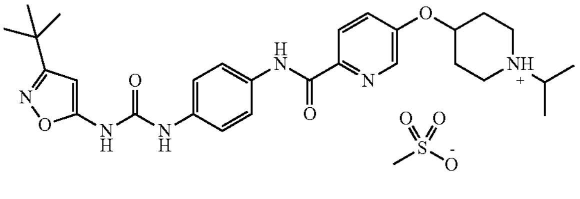

Step 1: 1-(4-Aminophenyl)-3-(3-tert-butylisoxazol-5-yl)urea hydrochloride (550 mg) was prepared using procedures analogous to those described in Steps 2-3 of Example 17, substituting phenyl 3-tert-butylisoxazol-5-ylcarbamate from Step 1 of Example 55 for phenyl 5-(1,3-difluoro-2-methylpropan-2-yl)isoxazol-3-ylcarbamate used in Step 2 of Example 17. LC-MS (ESI) m/z 275 $(M+H)^+$.

Step 2: N-(4-(3-(3-tert-Butylisoxazol-5-yl)ureido)phenyl)-5-(piperidin-4-yloxy)picolinamide hydrochloride was prepared as a yellow solid (500 mg) using procedures analogous to those described in Steps 3-4 of Example 1, substituting 541-(tert-butoxycarbonyl)piperidin-4-yloxy)picolinic acid from Example 6 for 4-(1-(tert-butoxycarbonyl)piperidin-4-yloxy)picolinic acid, and 1-(4-aminophenyl)-3-(3-tert-butylisoxazol-5-yl)urea hydrochloride from Step 1 of this example for 1-(4-aminophenyl)-3-(5-tert-butylisoxazol-3-yl)urea used in Example 1. LC-MS (ESI) m/z 479 $(M+H)^+$.

Step 3: N-(4-(3-(3-tert-Butylisoxazol-5-yl)ureido)phenyl)-5-(1-isopropylpiperidin-4-yloxy)picolinamide (63 mg, 52%) was prepared using a procedure analogous to that described in Example 20, substituting N-(4-(3-(3-tert-butylisoxazol-5-yl)ureido)phenyl)-5-(piperidin-4-yloxy)picolinamide hydrochloride from Step 2 of this example for N-(4-(3-(5-(1,3-difluoro-2-methylpropan-2-yl)isoxazol-3-yl)ureido)phenyl)-5-(piperidin-4-yloxy)picolinamide hydrochloride used in Example 20. LC-MS (ESI) m/z 521 $(M+H)^+$.

Step 4: 4-(6-(4-(3-(3-tert-Butylisoxazol-5-yl)ureido)phenylcarbamoyl)pyridin-3-yloxy)-1-isopropylpiperidinium methanesulfonate (68 mg, 100%) was prepared using a procedure analogous to that described in Example 27, substituting N-(4-(3-(3-tert-butylisoxazol-5-yl)ureido)phenyl)-5-(1-isopropylpiperidin-4-yloxy)picolinamide from Step 3 of this example for N-(4-(3-(5-tert-butylisoxazol-3-yl)ureido)phenyl)-5-(1-isopropylpiperidin-4-yloxy)picolinamide used in Step 2 of Example 27. LC-MS (ESI) m/z 521 $(M+H)^+$; $^1H$ NMR (300 MHz, DMSO-$d_6$) δ 10.41 (br. s., 1H), 10.13 (s, 1H), 9.12 (br. s., 1H), 8.88 (s, 1H), 8.43 (d, J=14.88 Hz, 1H), 8.13 (d, J=8.48 Hz, 1H), 7.82 (d, J=8.29 Hz, 2H), 7.71 (d, J=8.85 Hz, 1H), 7.44 (d, J=8.10 Hz, 2H), 6.05 (s, 1H), 4.72-5.07 (m, 1H), 3.35 (d, J=10.36 Hz, 1H), 3.03-3.26 (m, 2H), 2.42-2.29 (m, 2H), 2.35 (s, 3H), 2.16 (br. s., 2H), 1.73-1.98 (m, 1H), 1.11-1.38 (m, 15H).

Example 57

Preparation of (3R)-3-((6-(4-(3-(5-tert-butylisoxazol-3-yl)ureido)phenylcarbamoyl)pyridin-3-yloxy)methyl)-1-isopropylpyrrolidinium methanesulfonate

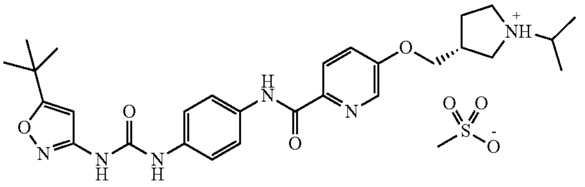

Step 1: To a stirred solution of (R)-1-(tert-butoxycarbonyl)pyrrolidine-3-carboxylic acid (1.21 g, 5.6 mmol) in THF (30 mL) at 0° C. was added borane THF (1.0 M, 17 mL, 16.9 mmol) dropwise. The resulting mixture was warmed to rt over 30 min and then heated at 45° C. for 1 h, then at 55° C. for 90 min. The reaction mixture was then cooled to 0° C. and quenched carefully with 3N HCl (30 mL). The resulting mixture was stirred at rt for 20 min before it was extracted with $Et_2O$ (50 mL). The organic layer was washed with sat. $NaHCO_3$ (20 mL) brine (20 mL), dried over $NaSO_4$, filtered, and concentrated under reduced pressure to give (R)-tert-butyl 3-(hydroxymethyl)pyrrolidine-1-carboxylate (1.1 g, 91%) as a colorless oil.

Step 2: (R)-N-(4-(3-(5-tert-Butylisoxazol-3-yl)ureido)phenyl)-5-(pyrrolidin-3-ylmethoxy)picolinamide hydrochloride was prepared as a light yellow solid (400 mg) using procedures analogous to those described in Steps 1-4 of Example 1, substituting (R)-tert-butyl 3-(hydroxymethyl)pyrrolidine-1-carboxylate from Step 1 of this example for tert-butyl 4-hydroxypiperidine-1-carboxylate, and 5-fluoropicolinonitrile for 4-chlorocyanopicoline used in Example 1. LC-MS (ESI) m/z 479 $(M+H)^+$.

Step 3: (R)-N-(4-(3-(5-tert-Butylisoxazol-3-yl)ureido)phenyl)-5-((1-isopropylpyrrolidin-3-yl)methoxy)picolinamide (26 mg, 20%) was prepared using a procedure analogous to that described in Example 20, substituting (R)-N-(4-(3-(5-tert-butylisoxazol-3-yl)ureido)phenyl)-5-(pyrrolidin-3-ylmethoxy)picolinamide hydrochloride from Step 2 of this example for N-(4-(3-(5-(1,3-difluoro-2-methylpropan-2-yl)isoxazol-3-yl)ureido)phenyl)-5-(piperidin-4-yloxy)picolinamide hydrochloride used in Example 20. LC-MS (ESI) m/z 521 $(M+H)^+$.

Step 4: (3R)-3-((6-(4-(3-(5-tert-Butylisoxazol-3-yl)ureido)phenylcarbamoyl)pyridin-3-yloxy)methyl)-1-isopropylpyrrolidinium methanesulfonate (25 mg, 90%) was prepared using a procedure analogous to that described in Example 27, substituting (R)-N-(4-(3-(5-tert-butylisoxazol-3-yl)ureido)phenyl)-5-((1-isopropylpyrrolidin-3-yl)methoxy)picolinamide from Step 2 of this example for N-(4-(3-(5-tert-butylisoxazol-3-yl)ureido)phenyl)-5-(1-isopropylpiperidin-4-yloxy)picolinamide used in Step 2 of Example 27. LC-MS (ESI) m/z 521 $(M+H)^+$; $^1H$ NMR (300 MHz, DMSO-$d_6$) δ 10.40 (s, 1H), 9.50 (s, 1H), 8.83 (s, 1H), 8.40 (d, J=2.45 Hz, 1H), 8.14 (d, J=8.67 Hz, 1H), 7.81 (d, J=7.54 Hz, 2H), 7.63 (d, J=8.67 Hz, 1H), 7.34-7.49 (m, 2H), 6.49 (d, J=1.70 Hz, 1H), 4.08-4.31 (m, 2H), 3.67-3.80 (m, 1H), 3.58 (br. s., 1H), 3.30-3.50 (m, 2H), 3.07-3.27 (m, 1H), 2.69-3.06 (m, 2H), 2.35 (d, J=2.07 Hz, 5H), 2.03-2.31 (m, 1H), 1.64-2.00 (m, 1H), 1.16-1.39 (m, 12H).

Example 58

Preparation of 4-(6-(4-(3-(3-tert-butylisoxazol-5-yl)ureido)phenylcarbamoyl)pyridin-3-yloxy)-1-ethyl-2,2,6,6-tetramethylpiperidinium methanesulfonate

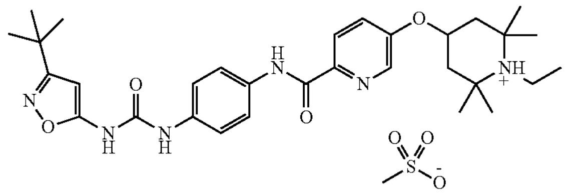

Step 1: N-(4-(3-(3-tert-Butylisoxazol-5-yl)ureido)phenyl)-5-(1-ethyl-2,2,6,6-tetramethylpiperidin-4-yloxy)picolinamide (161 mg, 88%) was prepared using a procedure analogous to that described in Step 3 of Example 1, substituting 5-(1-ethyl-2,2,6,6-tetramethylpiperidin-4-yloxy)picolinic acid from Step 1 of Example 54 for 4-(1-(tert-butoxycarbonyl)piperidin-4-yloxy)picolinic acid, and 1-(4-aminophenyl)-3-(3-tert-butylisoxazol-5-yl)urea hydrochloride from Step 1 of Example 56 for 1-(4-aminophenyl)-3-(5-tert-butylisoxazol-3-yl)urea used in Step 3 of Example 1. LC-MS (ESI) m/z 563 $(M+H)^+$.

Step 2: 4-(6-(4-(3-(3-tert-Butylisoxazol-5-yl)ureido)phenylcarbamoyl)pyridin-3-yloxy)-1-ethyl-2,2,6,6-tetramethylpiperidinium methanesulfonate (180 mg, 100%) was prepared using a procedure analogous to that described in Example 27, substituting N-(4-(3-(3-tert-butylisoxazol-5-yl)ureido)phenyl)-5-(1-ethyl-2,2,6,6-tetramethylpiperidin-4-yloxy)picolinamide from Step 1 of this example for N-(4-(3-(5-tert-butylisoxazol-3-yl)ureido)phenyl)-5-(1-isopropylpiperidin-4-yloxy)picolinamide used in Step 2 of Example 27. LC-MS (ESI) m/z 563 $(M+H)^+$; $^1H$ NMR (300 MHz, DMSO-$d_6$) δ 10.41 (s, 1H), 10.14 (s, 1H), 8.89 (s, 1H), 8.41 (d, J=2.83 Hz, 1H), 8.13 (d, J=8.67 Hz, 1H), 7.86 (s, 1H), 7.82 (d, J=8.85 Hz, 2H), 7.72 (dd, J=2.64, 8.85 Hz, 1H), 7.45 (d, J=8.85 Hz, 2H), 6.05 (s, 1H), 5.15 (d, J=10.17 Hz, 1H), 2.69 (s, 2H), 2.34 (s, 3H), 2.30 (br. s., 2H), 1.96 (t, J=12.43 Hz, 2H), 1.40-1.62 (m, 12H), 1.34 (t, J=7.06 Hz, 3H), 1.26 (s, 9H).

Example 59

Preparation of 4-(6-(4-(3-(3-tert-butylisoxazol-5-yl)ureido)phenylcarbamoyl)pyridin-3-yloxy)-1-ethylpiperidinium methanesulfonate

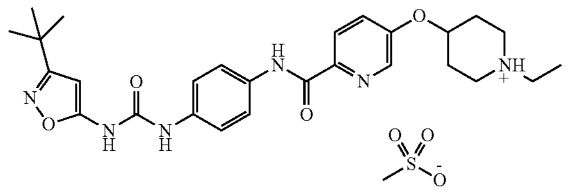

Step 1: N-(4-(3-(3-tert-Butylisoxazol-5-yl)ureido)phenyl)-5-(1-ethylpiperidin-4-yloxy)picolinamide (100 mg, 98%) was prepared using a procedure analogous to that described in Example 2, substituting N-(4-(3-(3-tert-butylisoxazol-5-yl)ureido)phenyl)-5-(piperidin-4-yloxy)picolinamide hydrochloride from Step 2 of Example 56 for N-(4-(3-(5-tert-butylisoxazol-3-yl)ureido)phenyl)-4-(piperidin-4-yloxy)picolinamide hydrochloride used in Example 2. LC-MS (ESI) m/z 507 $(M+H)^+$.

Step 2: 4-(6-(4-(3-(3-tert-Butylisoxazol-5-yl)ureido)phenylcarbamoyl)pyridin-3-yloxy)-1-ethylpiperidinium methanesulfonate (95 mg, 80%) was prepared using a procedure analogous to that described in Example 27, substituting N-(4-(3-(3-tert-butylisoxazol-5-yl)ureido)phenyl)-5-(1-ethylpiperidin-4-yloxy)picolinamide from Step 1 of this example for N-(4-(3-(5-tert-butylisoxazol-3-yl)ureido)phenyl)-5-(1-isopropylpiperidin-4-yloxy)picolinamide used in Step 2 of Example 27. LC-MS (ESI) m/z 507 $(M+H)^+$; $^1H$ NMR (300 MHz, DMSO-$d_6$) δ 10.42 (br. s., 1H), 10.16 (br. s., 1H), 9.22 (br. s., 1H), 8.92 (br. s., 1H), 8.43 (d, J=9.80 Hz, 1H), 8.13 (d, J=8.29 Hz, 1H), 7.82 (d, J=8.48 Hz, 2H), 7.72 (t, J=8.29 Hz, 1H), 7.45 (d, J=8.10 Hz, 2H), 6.05 (s, 1H), 4.69-5.07 (m, 1H), 3.60 (d, J=11.68 Hz, 1H), 3.42 (d, J=11.11 Hz, 1H), 2.96-3.28 (m, 3H), 2.43-2.27 (m, 2H), 2.38 (s, 3H), 1.96-2.23 (m, 2H), 1.70-1.95 (m, 1H), 1.13-1.37 (m, 12H).

Example 60

Preparation of (3R)-3-((6-(4-(3-(5-tert-butylisoxazol-3-yl)ureido)phenylcarbamoyl)pyridin-3-yloxy)methyl)-1-ethylpyrrolidinium methanesulfonate

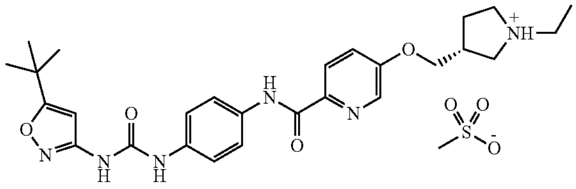

Step 1: (R)-N-(4-(3-(5-tert-Butylisoxazol-3-yl)ureido)phenyl)-5-((1-ethylpyrrolidin-3-yl)methoxy)picolinamide (80 mg, 68%) was prepared using a procedure analogous to that described in Example 2, substituting N-(4-(3-(3-tert-butylisoxazol-5-yl)ureido)phenyl)-5-(piperidin-4-yloxy)picolinamide hydrochloride from Step 2 of Example 57 for N-(4-(3-(5-tert-butylisoxazol-3-yl)ureido)phenyl)-4-(piperidin-4-yloxy)picolinamide hydrochloride used in Example 2. LC-MS (ESI) m/z 507 $(M+H)^+$.

Step 2: (3R)-3-((6-(4-(3-(5-tert-Butylisoxazol-3-yl)ureido)phenylcarbamoyl)pyridin-3-yloxy)methyl)-1-ethylpyrrolidinium methanesulfonate (80 mg, 82%) was prepared using a procedure analogous to that described in Example 27, substituting (R)-N-(4-(3-(5-tert-butylisoxazol-3-yl)ureido)phenyl)-5-((1-ethylpyrrolidin-3-yl)methoxy)picolinamide from Step 1 of this example for N-(4-(3-(5-tert-butylisoxazol-3-yl)ureido)phenyl)-5-(1-isopropylpiperidin-4-yloxy)picolinamide used in Step 2 of Example 27. LC-MS (ESI) m/z 507 $(M+H)^+$; $^1H$ NMR (300 MHz, DMSO-$d_6$) δ 10.41 (s, 1H), 9.51 (s, 1H), 8.85 (s, 1H), 8.40 (br. s., 1H), 8.14 (d, J=8.48 Hz, 1H), 7.81 (d, J=8.29 Hz, 2H), 7.64 (d, J=8.67 Hz, 1H), 7.43 (d, J=8.29 Hz, 2H), 6.50 (s, 1H), 4.06-4.30 (m, 2H), 3.44-3.89 (m, 2H), 2.70-3.38 (m, 4H), 2.36 (s, 5H), 1.64-2.20 (m, 1H), 1.30 (s, 12H).

Example 61

Preparation of 3-(6-(4-(3-(5-tert-butylisoxazol-3-yl)ureido)phenylcarbamoyl)pyridin-3-yl)-1,2,2,6,6-pentamethyl-4-oxopiperidinium methanesulfonate

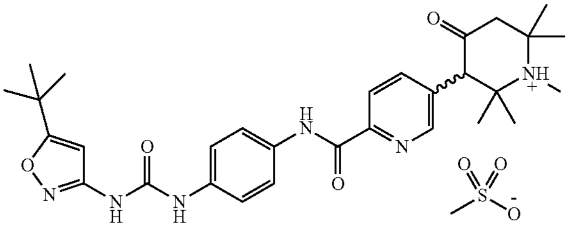

Step 1: 5-(1,2,2,6,6-Pentamethyl-4-oxopiperidin-3-yl)picolinic acid (140 mg, 87%) was prepared using a procedure analogous to that described in Step 2 of Example 1, substituting 5-(1,2,2,6,6-pentamethyl-4-oxopiperidin-3-yl)picolinitrile from Step 2 of Example 62 for tert-butyl 4-(2-cyanopyridin-4-yloxy)piperidine-1-carboxylate used in Step 2 of Example 1. LC-MS (ESI) m/z 291 $(M+H)^+$.

Step 2: N-(4-(3-(5-tert-Butylisoxazol-3-yl)ureido)phenyl)-5-(1,2,2,6,6-pentamethyl-4-oxopiperidin-3-yl)picolinamide (250 mg, 78%) was prepared using a procedure analogous to that described in Step 3 of Example 1, substituting 5-(1,2,2,6,6-pentamethyl-4-oxopiperidin-3-yl)picolinic acid from Step 1 of this example for 4-(1-(tert-butoxycarbonyl)piperidin-4-yloxy)picolinic acid used in Step 3 of Example 1. LC-MS (ESI) m/z 547 $(M+H)^+$.

Step 3: 3-(6-(4-(3-(5-tert-Butylisoxazol-3-yl)ureido)phenylcarbamoyl)pyridin-3-O-1,2,2,6,6-pentamethyl-4-oxopiperidinium methanesulfonate (260 mg, 100%) was prepared using a procedure analogous to that described in Example 27, substituting N-(4-(3-(5-tert-butylisoxazol-3-yl)ureido)phenyl)-5-(1,2,2,6,6-pentamethyl-4-oxopiperidin-3-yl)picolinamide from Step 2 of this example for N-(4-(3-(5-tert-butylisoxazol-3-yl)ureido)phenyl)-5-(1-isopropylpiperidin-4-yloxy)picolinamide used in Step 2 of Example 27. LC-MS (ESI) m/z 547 $(M+H)^+$; $^1H$ NMR (300 MHz, DMSO-$d_6$) δ 10.51 (s, 1H), 9.51 (s, 1H), 8.84 (s, 1H), 8.50 (br. s., 1H), 8.20 (d, J=8.67 Hz, 1H), 7.65-7.87 (m, 3H), 7.44 (d, J=8.67 Hz, 2H), 6.50 (s, 1H), 5.31 (s, 1H), 2.70-2.95 (m, 4H), 2.38-2.48 (m, 2H), 2.35 (s, 3H), 1.51 (s, 2H), 1.46 (d, J=6.59 Hz, 6H), 1.39 (s, 3H), 1.30 (s, 9H).

Example 62

Preparation of 4-(6-(4-(3-(5-tert-butylisoxazol-3-yl)ureido)phenylcarbamoyl)pyridin-3-yloxy)-1,2,2,4,6,6-hexamethylpiperidinium methanesulfonate

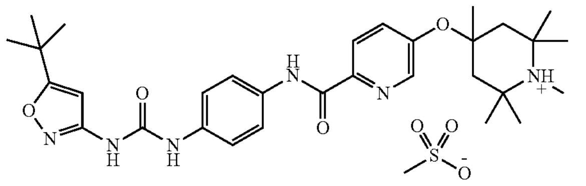

Step 1: To a stirred solution of 1,2,2,6,6-pentamethylpiperidin-4-one (1.5 g, 8.88 mmol) in diethyl ether (25 mL) at rt was added MeLi (1.6 M, 5.5 mL, 8.88 mmol) slowly. The resulting mixture was stirred at rt for 30 min before it was quenched with sat. $NH_4Cl$ (15 mL). The mixture was then partitioned between EtOAc (35 mL) and sat. $NaHCO_3$ (25 mL). The organic layer was dried over $Na_2SO_4$, filtered, and concentrated under reduced pressure to give crude 1,2,2,4,6,6-hexamethylpiperidin-4-ol (1.51 g) as an oil. LC-MS (ESI) m/z 186 $(M+H)^+$.

Step 2: 5-(1,2,2,4,6,6-hHexamethylpiperidin-4-yloxy)picolinonitrile (540 mg, 21% over two steps) was prepared using a procedure analogous to that described in Step 1 of Example 1, substituting the crude 1,2,2,4,6,6-hexamethylpiperidin-4-ol from Step 1 of this example for tert-butyl 4-hydroxypiperidine-1-carboxylate, and 5-fluoro-2-cyanopyridine for 4-chlorocyanopicoline used in Example 1. LC-MS (ESI) m/z 288 $(M+H)^+$.

During this step of transformation, 5-(1,2,2,6,6-pentamethyl-4-oxopiperidin-3-yl)picolinonitrile (670 mg, 28% over two steps) was also isolated from the unreacted 1,2,2,6,6-pentamethylpiperidin-4-one used in Step 1 of this example. LC-MS (ESI) m/z 272 $(M+H)^+$.

Step 3: 5-(1,2,2,4,6,6-Hexamethylpiperidin-4-yloxy)picolinic acid (500 mg, 87%) was prepared using a procedure analogous to that described in Step 2 of Example 1, substituting 5-(1,2,2,4,6,6-hexamethylpiperidin-4-yloxy)picolinonitrile from Step 2 of this example for tert-butyl 4-(2-cyanopyridin-4-yloxy)piperidine-1-carboxylate used in Step 2 of Example 1. LC-MS (ESI) m/z 307 $(M+H)^+$.

Step 4: N-(4-(3-(5-tert-Butylisoxazol-3-yl)ureido)phenyl)-5-(1,2,2,4,6,6-hexamethylpiperidin-4-yloxy)picolinamide (140 mg, 77%) was prepared using a procedure analogous to that described in Step 3 of Example 1, substituting 5-(1,2,2,4,6,6-hexamethylpiperidin-4-yloxy)picolinic acid from Step 3 of this example for 4-(1-(tert-butoxycarbonyl)piperidin-4-yloxy)picolinic acid used in Step 3 of Example 1. LC-MS (ESI) m/z 563 $(M+H)^+$.

Step 5: 4-(6-(4-(3-(5-tert-Butylisoxazol-3-yl)ureido)phenylcarbamoyl)pyridin-3-yloxy)-1,2,2,4,6,6-hexamethylpiperidinium methanesulfonate (135 mg, 100%) was prepared using a procedure analogous to that described in Example 27, substituting N-(4-(3-(5-tert-butylisoxazol-3-yl)ureido)phenyl)-5-(1,2,2,4,6,6-hexamethylpiperidin-4-yloxy)picolinamide from Step 4 of this example for N-(4-(3-(5-tert-butylisoxazol-3-yl)ureido)phenyl)-5-(1-isopropylpiperidin-4-yloxy)picolinamide used in Step 2 of Example 27. LC-MS (ESI) m/z 563 $(M+H)^+$; $^1H$ NMR (300 MHz, DMSO-$d_6$) δ 10.40 (s, 1H), 9.50 (s, 1H), 8.82 (s, 1H), 8.67 (br. s., 1H), 8.40 (d, J=2.64 Hz, 1H), 8.09 (d, J=8.85 Hz, 1H), 7.83 (d, J=2.83 Hz, 1H), 7.76-7.82 (m, 2H), 7.43 (d, J=9.04 Hz, 2H), 6.50 (s, 1H), 2.82 (d, J=4.90 Hz, 3H), 2.61 (d, J=15.26 Hz, 2H), 2.36 (s, 3H), 2.00 (d, J=15.26 Hz, 2H), 1.51 (s, 6H), 1.46 (s, 6H), 1.36 (s, 3H), 1.30 (s, 9H).

Example 63

Preparation of 3-(6-(4-(3-(5-tert-butylisoxazol-3-yl)ureido)phenylcarbamoyl)pyridin-3-yloxy)-1-azoniabicyclo[2.2.2]octane methanesulfonate

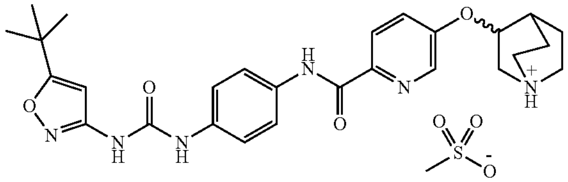

Step 1: 5-(Quinuclidin-3-yloxy)picolinic acid (1.0 g) was prepared using procedures analogous to those described in Steps 1-2 of Example 1, substituting quinuclidin-3-ol for tert-butyl 4-hydroxypiperidine-1-carboxylate, and 5-fluoropicolinonitrile for 4-chlorocyanopicoline used in Example 1. LC-MS (ESI) m/z 249 $(M+H)^+$.

Step 2: N-(4-(3-(5-tert-butylisoxazol-3-yl)ureido)phenyl)-5-(quinuclidin-3-yloxy)picolinamide (164 mg, 81%) was prepared using a procedure analogous to that described in Step 3 of Example 1, substituting 5-(quinuclidin-3-yloxy)picolinic acid from Step 1 of this example for 4-(1-(tert-butoxycarbonyl)piperidin-4-yloxy)picolinic acid used in Step 3 of Example 1. LC-MS (ESI) m/z 505 $(M+H)^+$.

Step 3: 3-(6-(4-(3-(5-tert-Butylisoxazol-3-yl)ureido)phenylcarbamoyl)pyridin-3-yloxy)-1-azoniabicyclo[2.2.2]octane methanesulfonate (175 mg, 100%) was prepared using a procedure analogous to that described in Example 27, substituting N-(4-(3-(5-tert-butylisoxazol-3-yl)ureido)phenyl)-5-(quinuclidin-3-yloxy)picolinamide from Step 2 of this example for N-(4-(3-(5-tert-butylisoxazol-3-yl)ureido)phenyl)-5-(1-isopropylpiperidin-4-yloxy)picolinamide used in Step 2 of Example 27. LC-MS (ESI) m/z 505 $(M+H)^+$; $^1H$ NMR (300 MHz, DMSO-$d_6$) δ 10.41 (s, 1H), 9.65 (br. s., 1H), 9.50 (s, 1H), 8.82 (s, 1H), 8.41 (d, J=2.83 Hz, 1H), 8.14 (d, J=8.67 Hz, 1H), 7.81 (d, J=9.04 Hz, 2H), 7.68 (dd, J=2.83, 8.85 Hz, 1H), 7.43 (d, J=8.85 Hz, 2H), 6.50 (s, 1H), 3.84 (dd, J=8.19, 13.66 Hz, 1H), 3.08-3.41 (m, 5H), 2.45 (br. s., 1H), 2.34 (s, 3H), 1.68-2.18 (m, 4H), 1.30 (s, 9H).

Example 64

Preparation of (1S,9aS)-1-((6-(4-(3-(5-tert-butylisoxazol-3-yl)ureido)phenylcarbamoyl)pyridin-3-yloxy)methyl)decahydroquinolizinium methanesulfonate

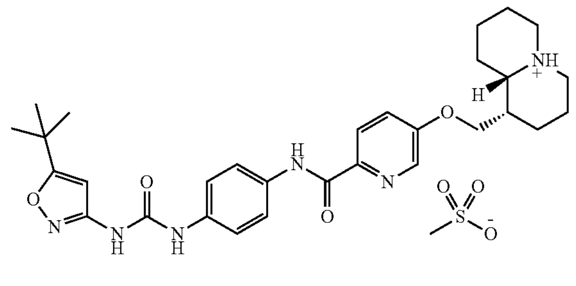

Step 1: 5-(((1S,9aS)-Octahydro-1H-quinolizin-1-yl)methoxy)picolinic acid (750 mg) was prepared using procedures analogous to those described in Steps 1-2 of Example 1, substituting (−)-lupinine for tert-butyl 4-hydroxypiperidine-1-carboxylate, and 5-fluoropicolinonitrile for 4-chlorocyanopicoline used in Example 1. LC-MS (ESI) m/z 291 $(M+H)^+$.

Step 2: N-(4-(3-(5-tert-Butylisoxazol-3-yl)ureido)phenyl)-5-(((1S,9aS)-octahydro-1H-quinolizin-1-yl)methoxy)picolinamide (170 mg, 92%) was prepared using a procedure analogous to that described in Step 3 of Example 1, substituting 5-(((1S,9aS)-octahydro-1H-quinolizin-1-yl)methoxy)picolinic acid from Step 1 of this example for 4-(1-(tert-butoxycarbonyl)piperidin-4-yloxy)picolinic acid used in Step 3 of Example 1. LC-MS (ESI) m/z 547 $(M+H)^+$.

Step 3: (1S,9aS)-1-((6-(4-(3-(5-tert-Butylisoxazol-3-yl)ureido)phenylcarbamoyl)pyridin-3-yloxy)methyl)decahydroquinolizinium methanesulfonate (180 mg, 100%) was prepared using a procedure analogous to that described in Example 27, substituting N-(4-(3-(5-tert-butylisoxazol-3-yl)ureido)phenyl)-5-(((1S,9aS)-octahydro-1H-quinolizin-1-yl)methoxy)picolinamide from Step 2 of this example for N-(4-(3-(5-tert-butylisoxazol-3-yl)ureido)phenyl)-5-(1-isopropylpiperidin-4-yloxy)picolinamide used in Step 2 of Example 27. LC-MS (ESI) m/z 547 $(M+H)^+$; $^1H$ NMR (300 MHz, DMSO-$d_6$) δ 10.40 (br. s., 1H), 9.50 (s, 1H), 8.81 (s, 1H), 8.28-8.52 (m, 1H), 8.14 (t, J=9.51 Hz, 1H), 7.81 (d, J=8.67 Hz, 2H), 7.66 (d, J=8.67 Hz, 1H), 7.43 (d, J=8.67 Hz, 2H), 6.50 (s, 1H), 4.25-4.57 (m, 1H), 4.10 (d, J=6.97 Hz, 2H), 3.50-3.77 (m, 1H), 3.19-3.47 (m, 2H), 2.83-3.16 (m, 1H), 2.45 (br. s., 1H), 2.34 (s, 3H), 1.37-2.09 (m, 10H), 1.30 (s, 9H).

Example 65

Preparation of N-(4-(3-(3-tert-butyl-1-methyl-1H-pyrazol-5-yl)ureido)phenyl)-5-(1,2,2,6,6-pentamethylpiperidin-4-yloxy)picolinamide

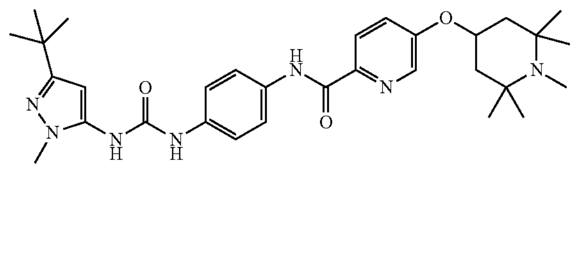 [SMILES: CN1C(C)(C)CC(Oc2ccc(C(=O)Nc3ccc(NC(=O)Nc4cc(C(C)(C)C)nn4C)cc3)nc2)CC1(C)C]

Step 1: To a suspension of 3-tert-butyl-1-methyl-1H-pyrazol-5-amine (0.75 g, 9.8 mmol) and potassium carbonate (1.76 g, 12.7 mmol) in THF (20 mL) at 0° C. was added dropwise phenyl chloroformate (0.7 mL, 10.8 mmol). The mixture was stirred at rt for 16 h. The mixture was then filtered through celite and solvent was removed under reduced pressure. The crude residue was purified by silica gel flash chromatography, eluting with 0% to 100% EtOAc in hexanes, to afford phenyl 3-tert-butyl-1-methyl-1H-pyrazol-5-ylcarbamate (1.05 g, 39% yield). LCMS (ESI) m/z 348 $(M+H)^+$; $^1H$ NMR (300 MHz, DMSO-$d_6$) δ 10.11 (br s, 1H), 7.45-7.40 (m, 2H), 7.29-7.21 (m, 3H), 6.04 (s, 1H), 3.58 (s, 3H), 1.20 (s, 9H).

Step 2: A mixture of 3-tert-butyl-1-methyl-1H-pyrazol-5-ylcarbamate from Step 1 of this example (65 mg, 0.24 mmol), N-(4-aminophenyl)-5-(1,2,2,6,6-pentamethylpiperidin-4-yloxy)picolinamide dihydrochloride from Example 49 (90 mg, 0.20 mmol), triethylamine (92 μL, 0.66 mmol), and N,N-dimethylpyridin-4-amine (2 mg, 0.02 mmol) in THF (3 mL) was stirred at rt for 2 d. The solvent was removed under reduced pressure. The crude residue was purified by silica gel flash chromatography, eluting with 9% MeOH/1% $NH_3$ in DCM. The resulting compound was then purified by reverse phase HPLC to afford N-(4-(3-(3-tert-butyl-1-methyl-1H-pyrazol-5-yl)ureido)phenyl)-5-(1,2,2,6,6-pentamethylpiperidin-4-yloxy)picolinamide (7 mg, 6% yield). LCMS (ESI) m/z 562 $(M+H)^+$; $^1H$ NMR (300 MHz, DMSO-$d_6$) δ 10.32 (s, 1H), 9.76 (br s, 1H), 9.47 (br s, 1H), 8.35-8.34 (d, 1H), 8.11-8.08 (d, 1H), 7.78-7.75 (d, 2H), 7.63-7.59 (d, 1H), 7.47-7.44 (d, 2H), 6.02 (s, 1H), 4.87 (t, 1H), 3.6 (s, 3H), 2.2 (s, 3H), 2.04-1.99 (d, 2H), 1.49-1.42 (t, 2H), 1.21 (s, 9H), 1.13-1.12 (m, 12H).

Example 66

Preparation of N-(4-(3-(1-methyl-5-(trifluoromethyl)-1H-pyrazol-3-yl)ureido)phenyl)-5-(1,2,2,6,6-pentamethylpiperidin-4-yloxy)picolinamide

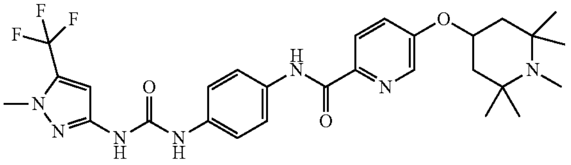

Step 1: Phenyl 1-methyl-5-(trifluoromethyl)-1H-pyrazol-3-ylcarbamate (0.13 g, 76%) was prepared using a procedure analogous to that described in Step 1 of Example 65, substituting 1-methyl-5-(trifluoromethyl)-1H-pyrazol-3-amine (Ref Hartfiel, U, Dorfineister, G.; Franke, H.; Geisler, J.; Johann, G.; Rees, R. U.S. Pat. No. 5,405,829, 1995) for 3-tert-butyl-1-methyl-1H-pyrazol-5-amine used in Example 65. LCMS (ESI) m/z 286 $(M+H)^+$; $^1H$ NMR (300 MHz, DMSO-$d_6$) δ 10.88 (br s, 1H), 7.45-7.4 (m, 2H), 7.29-7.19 (m, 3H), 6.8 (s, 1H), 3.88 (s, 3H).

Step 2: N-(4-(3-(1-methyl-5-(trifluoromethyl)-1H-pyrazol-3-yl)ureido)phenyl)-5-(1,2,2,6,6-pentamethylpiperidin-4-yloxy)picolinamide (9 mg, 9% yield) was prepared using a procedure analogous to that described in Step 2 of Example 65, substituting phenyl 1-methyl-5-(trifluoromethyl)-1H-pyrazol-3-ylcarbamate from Step 1 of this example for 3-tert-butyl-1-methyl-1H-pyrazol-5-ylcarbamate used in Example 65. LCMS (ESI) m/z 574 $(M+H)^+$; $^1H$ NMR (300 MHz, DMSO-$d_6$) δ 10.36 (s, 1H), 9.17 (s, 1H), 8.77 (s, 1H), 8.35 (s, 1H), 8.11-8.09 (d, 1H), 7.81-7.78 (d, 2H), 7.64-7.61 (d, 1H), 7.43-7.40 (d, 2H), 6.84 (s, 1H), 4.89 (t, 1H), 3.85 (s, 3H), 2.22 (s, 3H), 2.03-2.01 (d, 2H), 1.57-1.47 (t, 2H), 1.14 (s, 12H).

Example 67

Preparation of 4-(6-(4-(3-(5-tert-butylisoxazol-3-yl)ureido)phenylcarbamoyl)pyridin-3-yloxy)-2,2,6,6-tetramethylpiperidinium methanesulfonate

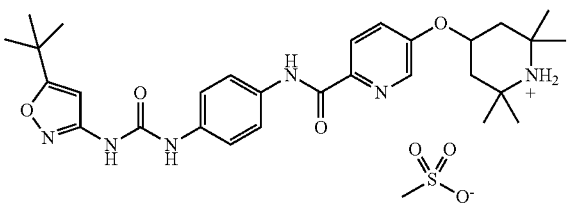

Step 1: 5-(2,2,6,6-Tetramethylpiperidin-4-yloxy)picolinic acid was prepared as a white solid using procedures analogous to those described in Steps 1-2 of Example 1, substituting 2,2,6,6-tetramethylpiperidin-4-ol for tert-butyl 4-hydroxypiperidine-1-carboxylate, and 5-fluoropicolinonitrile for 4-chlorocyanopicoline used in Example 1. LC-MS (ESI) m/z 279 $(M+H)^+$.

Step 2: N-(4-(3-(5-tert-Butylisoxazol-3-yl)ureido)phenyl)-5-(2,2,6,6-tetramethylpiperidin-4-yloxy)picolinamide (41 mg, 24%) was prepared using a procedure analogous to that described in Step 3 of Example 1, substituting 5-(2,2,6,6-tetramethylpiperidin-4-yloxy)picolinic acid from Step 1 of this example for 4-(1-(tert-butoxy carbonyl)piperidin-4-yloxy)picolinic acid used in Example 1. LC-MS (ESI) m/z 535 $(M+H)^+$.

Step 3: 4-(6-(4-(3-(5-tert-Butylisoxazol-3-yl)ureido)phenylcarbamoyl)pyridin-3-yloxy)-2,2,6,6-tetramethylpiperidinium methanesulfonate (46 mg, 98%) was prepared using a procedure analogous to that described in Example 27, substituting N-(4-(3-(5-tert-butylisoxazol-3-yl)ureido)phenyl)-5-(2,2,6,6-tetramethylpiperidin-4-yloxy)picolinamide from Step 2 of this example for N-(4-(3-(5-tert-butylisoxazol-3-yl)ureido)phenyl)-5-(1-isopropylpiperidin-4-yloxy)picolinamide used in Step 2 of Example 27. LC-MS (ESI) m/z 535 $(M+H)^+$; $^1$H NMR (300 MHz, DMSO-$d_6$) δ 10.39 (s, 1H), 9.50 (s, 1H), 8.84 (s, 1H), 8.41 (d, J=2.83 Hz, 1H), 8.13 (d, J=8.85 Hz, 1H), 7.81 (d, J=9.04 Hz, 2H), 7.73 (dd, J=2.83, 8.85 Hz, 1H), 7.43 (d, J=9.04 Hz, 2H), 6.50 (s, 1H), 2.36 (s, 3H), 2.24 (dd, J=3.01, 13.56 Hz, 2H), 1.59-1.75 (m, 2H), 1.51 (s, 6H), 1.45 (s, 6H), 1.30 (s, 12H).

Example 68

Preparation of N-(trans-4-(3-(5-(tert-butyl)isoxazol-3-yl)ureido)cyclohexyl)-5-(piperidin-4-yloxy)picolinamide hydrochloride

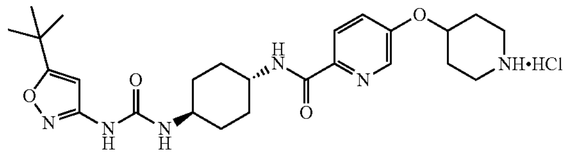

Step 1: 1-(trans-4-aminocyclohexyl)-3-(5-(tert-butyl)isoxazol-3-yl)urea hydrochloride was prepared as a white solid (350 mg, 79% over two steps) using procedures analogous to those described in Steps 1-2 of Example 17, substituting phenyl (5-(tert-butyl)isoxazol-3-yl)carbamate for phenyl 5-(1,3-difluoro-2-methylpropan-2-yl)isoxazol-3-ylcarbamate, and tert-butyl (trans-4-aminocyclohexyl)carbamate for tert-butyl 4-aminophenylcarbamate used in Example 17. LC-MS (ESI) m/z 281 $(M+H)^+$.

Step 2: N-(trans-4-(3-(5-(tert-butyl)isoxazol-3-yl)ureido)cyclohexyl)-5-(piperidin-4-yloxy)picolinamide hydrochloride was prepared as a white solid (240 mg, 94% over two steps) using procedures analogous to those described in Steps 3-4 of Example 1, substituting 1-(trans-4-aminocyclohexyl)-3-(5-(tert-butyl)isoxazol-3-yl)urea hydrochloride from Step 1 of this example for 1-(4-aminophenyl)-3-(5-tert-butylisoxazol-3-yl)urea, and 5-(1-(tert-butoxycarbonyl)piperidin-4-yloxy)picolinic acid from Step 1 of Example 6 for 4-(1-(tert-butoxycarbonyl)piperidin-4-yloxy)picolinic acid used in Example 1. LC-MS (ESI) m/z 485 $(M+H)^+$. $^1$H NMR (300 MHz, DMSO-$d_6$) δ 9.23 (s, 1H), 8.24-8.41 (m, 2H), 7.99 (d, J=8.85 Hz, 1H), 7.64 (dd, J=2.83, 8.85 Hz, 1H), 6.55 (d, J=7.54 Hz, 1H), 6.32 (s, 1H), 4.84 (br. s., 1H), 3.67-3.87 (m, 1H), 3.24 (br. s., 2H), 3.09 (br. s., 2H), 2.05-2.23 (m, 2H), 1.71-1.97 (m, 6H), 1.42-1.64 (m, 2H), 1.14-1.39 (m, 13H).

Example 69

Preparation of N-(trans-4-(3-(5-(tert-butyl)isoxazol-3-yl)ureido)cyclohexyl)-5-((1-ethylpiperidin-4-yl)oxy)picolinamide

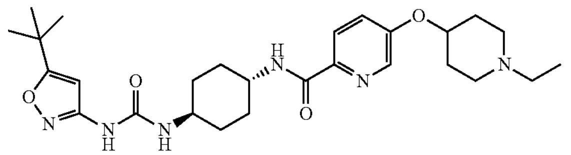 [SMILES: CCN1CCC(Oc2ccc(C(=O)N[C@H]3CC[C@H](NC(=O)Nc4cc(C(C)(C)C)on4)CC3)nc2)CC1]

N-(trans-4-(3-(5-(tert-butyl)isoxazol-3-yl)ureido)cyclohexyl)-5-((1-ethylpiperidin-4-yl)oxy)picolinamide was prepared as a white powder (65 mg, 68% yield) using a procedure analogous to that described in Example 2, substituting N-(trans-4-(3-(5-(tert-butyl)isoxazol-3-yl)ureido)cyclohexyl)-5-(piperidin-4-yloxy)picolinamide hydrochloride from Example 68 for N-(4-(3-(5-tert-butylisoxazol-3-yl)ureido)phenyl)-4-(piperidin-4-yloxy)picolinamide hydrochloride from Step 4 of Example 1. LC-MS (ESI) m/z 513 $(M+H)^+$; $^1$H NMR (300 MHz, DMSO-$d_6$) δ 9.18 (s, 1H), 8.21-8.35 (m, 2H), 7.97 (d, J=8.85 Hz, 1H), 7.52-7.65 (m, 1H), 6.46 (d, J=7.54 Hz, 1H), 6.32 (s, 1H), 3.77 (d, J=8.29 Hz, 1H), 3.43 (d, J=7.54 Hz, 1H), 2.02 (br. s., 2H), 1.72-1.95 (m, 5H), 1.41-1.63 (m, 2H), 1.19-1.38 (m, 15H), 1.07 (br. s., 3H).

Example 70

Preparation of N-(4-(3-(5-(tert-butyl)isoxazol-3-yl)ureido)phenyl)-6-(4-methylpiperazin-1-yl)picolinamide

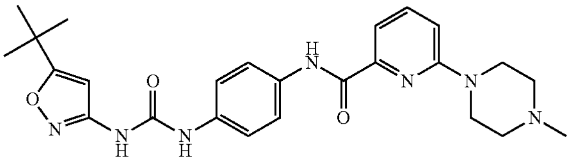 [SMILES: CN1CCN(c2cccc(C(=O)Nc3ccc(NC(=O)Nc4cc(C(C)(C)C)on4)cc3)n2)CC1]

N-(4-(3-(5-(tert-butyl)isoxazol-3-yl)ureido)phenyl)-6-(4-methylpiperazin-1-yl)picolinamide was prepared as a white powder (20 mg) using procedures analogous to those described in Steps 1-3 of Example 1, substituting N-methylpiperazine for tert-butyl 4-hydroxypiperidine-1-carboxylate, and 6-chloropicolinonitrile for chlorocyanopicoline used in Example 1. LC-MS (ESI) m/z 478 $(M+H)^+$.

Example 71

Preparation of N-(4-(3-(5-(tert-butyl)isoxazol-3-yl)ureido)phenyl)-6-(2-morpholinoethoxy)picolinamide

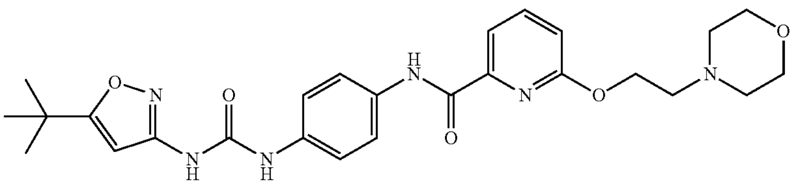 [SMILES: CC(C)(C)c1cc(NC(=O)Nc2ccc(NC(=O)c3cccc(OCCN4CCOCC4)n3)cc2)no1]

N-(4-(3-(5-(tert-butyl)isoxazol-3-yl)ureido)phenyl)-6-(2-morpholinoethoxy)picolinamide was prepared as a white powder (50 mg) using procedures analogous to those described in Steps 1-3 of Example 1, substituting 2-morpholinoethanol for tert-butyl 4-hydroxypiperidine-1-carboxylate, and 6-chloropicolinonitrile for chlorocyanopicoline used in Example 1. LC-MS (ESI) m/z 509 $(M+H)^+$.

Example 72

Preparation of N-(4-(3-(5-(tert-butyl)isoxazol-3-yl)ureido)phenyl)-6-(piperidin-4-yloxy)picolinamide

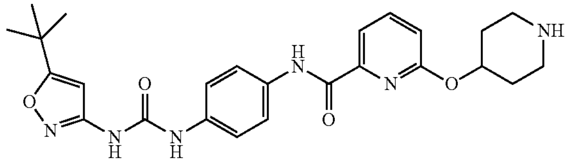 [SMILES: CC(C)(C)c1cc(NC(=O)Nc2ccc(NC(=O)c3cccc(OC4CCNCC4)n3)cc2)no1]

N-(4-(3-(5-(tert-butyl)isoxazol-3-yl)ureido)phenyl)-6-(piperidin-4-yloxy)picolinamide was prepared as a white powder (30 mg) using procedures analogous to those described in Steps 1-4 of Example 1, substituting 6-chloropicolinonitrile for chlorocyanopicoline used in Example 1. LC-MS (ESI) m/z 479 $(M+H)^+$.

Example 73

Preparation of N-(4-(3-(5-(tert-butyl)isoxazol-3-yl)ureido)phenyl)-6-((diethylamino)methyl)picolinamide Step 1: To a suspension of ethyl 6-(chloromethyl)picolinate (200 mg, 1.00 mmol) and KI (166 mg, 1.00 mmol) in DMF was added N,N-diethyl amine (73 mg, 1.00 mmol) and $K_2CO_3$ (304 mg, 2.20 mmol). The reaction mixture was stirred at rt for 5 h. LC-MS indicated the presence of product. The solvent was evaporated under reduced pressure and the residue was partitioned between EtOAc (20 mL) and water (20 mL). The organic layer was washed with water (15 mL) and dried over $Na_2SO_4$. The solvent was evaporated under reduced pressure to give ethyl 6-((diethylamino)methyl)picolinate (150 mg, 64%) as an oil. LC-MS (ESI) m/z 237 $(M+H)^+$.

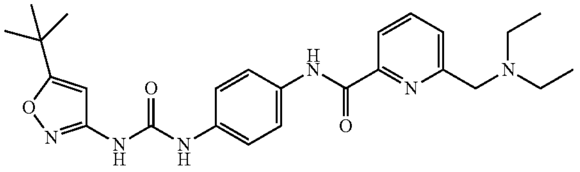 [SMILES: CCN(CC)Cc1cccc(C(=O)Nc2ccc(NC(=O)Nc3cc(C(C)(C)C)on3)cc2)n1]

Step 2: N-(4-(3-(5-(tert-butyl)isoxazol-3-yl)ureido)phenyl)-6-((diethylamino)methyl)picolinamide was prepared as a white powder (30 mg) using procedures analogous to those described in Steps 2-3 of Example 1, substituting ethyl 6-((diethylamino)methyl)picolinate from Step 1 of this Example for tert-butyl 4-(2-cyanopyridin-4-yloxy)piperidine-1-carboxylate from Step 1 of Example 1. LC-MS (ESI) m/z 465 $(M+H)^+$.

Example 74

Preparation of N-(4-(3-(5-(tert-butyl)isoxazol-3-yl)ureido)phenyl)-6-(morpholinomethyl)picolinamide

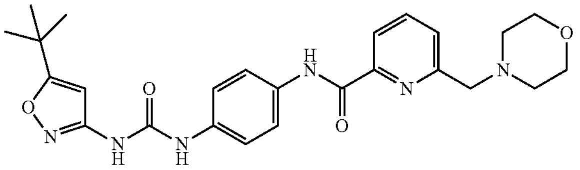 [SMILES: CC(C)(C)c1cc(NC(=O)Nc2ccc(NC(=O)c3cccc(CN4CCOCC4)n3)cc2)no1]

N-(4-(3-(5-(tert-butyl)isoxazol-3-yl)ureido)phenyl)-6-(morpholinomethyl)picolinamide was prepared as a white powder (60 mg) using procedures analogous to those described in Steps 1-2 of Example 73, substituting morpholine for N,N-diethyl amine used in Example 73. LC-MS (ESI) m/z 479 $(M+H)^+$.

Example 75

Preparation of 6-(aminomethyl)-N-(4-(3-(5-(tert-butyl)isoxazol-3-yl)ureido)phenyl)picolinamide hydrochloride Step 1: N-(4-(3-(5-(tert-butyl)isoxazol-3-yl)ureido)phenyl)-6-((1,3-dioxoisoindolin-2-yl)methyl)picolinamide was prepared using a procedure analogous to that described in Step 3 of Example 1, substituting 6-((1,3-dioxoisoindolin-2-yl)methyl)picolinic acid (Ref: Kyne, G. M. et al. Journal of the Chemical Society, Perkin Transactions 1, 2001, p. 1258-1263) for 4-(1-(tert-butoxycarbonyl)piperidin-4-yloxy)picolinic acid used in Example 1. LC-MS (ESI) m/z 539 $(M+H)^+$.

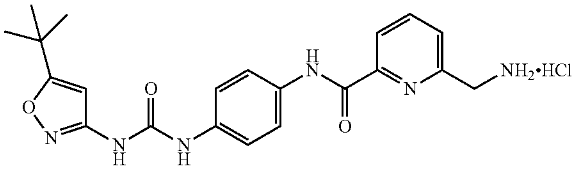

Step 2: A suspension of N-(4-(3-(5-(tert-butyl)isoxazol-3-yl)ureido)phenyl)-6-((1,3-dioxoisoindolin-2-yl)methyl)picolinamide (60 mg, 0.11 mmol) from Step 1 of this example in ethanol was heated at 70° C. until a clear solution was observed. Hydrazine hydrate (0.1 mL) was then added, the resulting mixture was heated at 70° C. for 1 h. The reaction mixture was cooled to 0° C. and filtered through celite. The filtrate was concentrated under reduced pressure, and the crude residue was purified by preparative TLC, eluting with MeOH in DCM (10:1, v:v). The compound obtained was treated with 2N HCl in $Et_2O$ to form the corresponding hydrochloric acid salt. The salt was washed with cold water and dried in a vacuum oven to afford 6-(aminomethyl)-N-(4-(3-(5-(tert-butyl)isoxazol-3-yl)ureido)phenyl)picolinamide hydrochloride (8 mg, 16%). LC-MS (ESI) m/z 409 $(M+H)^+$.

Example 76

M-NFS-60 Cell Proliferation Assay

The compounds disclosed herein were tested in an M-NFS-60 cell proliferation assay to determine their cellular potency against CSF1R. M-NFS-60s are mouse monocytic cells that depend on the binding of the ligand M-CSF to its receptor, CSF1R, to proliferate Inhibition of CSF1R kinase activity will cause reduced growth and/or cell death. This assay assesses the potency of compounds as CSF1R inhibitors by measuring the reduction of Alamar Blue reagent by viable cells.

On day one of the experiment, M-NFS-60 cells were maintained in RPMI complete medium (Omega Scientific) plus 10% FBS supplemented with 20 ng/mL of M-CSF (R&D Systems). 96-well TC-treated, flat bottom plates were seeded at 10,000 cell/well at a volume of 100 μL per well. The cells were cultured overnight at 37° C. under 5% $CO_2$.

On day two, compounds were added to the cells at 9 different concentrations, with half-log intervals alongside a control reference compound serving as a positive control. Final DMSO concentration was kept at 0.5% for a final volume of 200 μL. The compounds were allowed to incubate with the cells for 72 hours at 37° C. under 5% $CO_2$.

On day five of the experiment, 40 μl of Alamar Blue reagent was added to each well and allowed to incubate for 3 hours. Alamar Blue fluorescence was read using SoftMax Pro software at 560 nm (excitation) and 590 nm (emission). $IC_{50}$s were generated as an average of duplicates and represents the concentration of test compound that achieves 50% inhibition of cellular proliferation compared to control.

In one embodiment, the compounds provided herein were found to have $IC_{50}$ of about or less than about 5, 4, 3, 2, 1, 0.5, 0.1, 0.05 or 0.01 μM. In another embodiment, the compounds provided herein were found to have activity IC50 of about or less than about 2000, 1000, 500, 300, 100, 50, 40, 30 or 20 nM. In another embodiment, the compounds provided herein were found to have activity IC50 of less than about 200 or 100 nM.

Example 77

Competition Binding Assay to Determine Selectivity Scores and Binding Constants (Kd) of the Compounds against a Panel of Kinases Competition binding assays used herein were developed, validated and performed as described in Fabian et al., *Nature Biotechnology* 2005, 23, 329-336. Kinases were produced as fusions to T7 phage (See, Fabian et al. or WO04/015142) or alternatively, the kinases were expressed in HEK-293 cells and subsequently tagged with DNA for PCR detection (See, WO08/005,310). For the binding assays, streptavidin-coated magnetic beads were treated with biotinylated affinity ligands for 30 min at room temperature to generate affinity resins. The liganded beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining kinase, liganded affinity beads, and test compounds in 1× binding buffer (20% SeaBlock, 0.17× PBS, 0.05% Tween 20, 6 mM DTT). Test compounds were prepared as 100× stocks in DMSO and diluted into the aqueous environment. Kds were determined using an eleven point threefold serial dilutions. DMSO or control compounds were was added to control assays lacking a test compound. Primary screen assays were performed in polypropylene 384-well plates in a final volume of 20-40 μL, while $K_d$ determinations were performed in polystyrene 96-well plates in a final volume of 135 pt. The assay plates were incubated at room temperature with shaking for 1 hour to allow the binding reactions to reach equilibrium, and the affinity beads were washed extensively with wash buffer (1×PBS, 0.05% Tween 20) to remove unbound protein. The beads were then resuspended in elution buffer (1×PBS, 0.05% Tween 20, 0.5 μM non-biotinylated affinity ligand) and incubated at room temperature with shaking for 30 min. The kinase concentration in the eluates was measured by quantitative PCR.

A selectivity score (S10) is a quantitative measure of selectivity of a compound against a panel of kinases. An S10 was calculated for a compound by dividing the number of kinases found to have a percent of control (DMSO) less than 10 by the total number of distinct kinases tested (excluding mutant variants). Percent of control (POC) is calculated by subtracting the signal of the control compound (POC=0) from the signal of the test compound and dividing the outcome by the signal of DMSO (POC=100) minus the signal of the control compound. For the compounds disclosed herein, S10 scores were obtained by testing the compounds at 10 μM concentration in a kinase panel containing either 359 or 386 distinct kinases.

In one embodiment, the compounds provided herein were found to have S10 score of about or less than about 0.1, 0.08, 0.06, 0.04, 0.03, or 0.02.

Example 78

Rat Toxicity Study

The potential toxicity of a compound of Formula I was assessed in rats administered by oral gavage, 60 mg/kg of a compound of Formula I in 1% hydropropyl cellulose (Klucell®) QD, either once weekly, twice weekly or three times weekly, for up to 21 days. A fourth dosing group was administered 20 mg/kg of a compound of Formula I in 1% hydroxypropyl cellulose (Klucell®) QD three times weekly by oral gavage for up to 21 days.

The animals were evaluated for the following: clinical signs (daily), body weight (weekly), food consumption (weekly), hematology (pre-treatment and at necropsy), coagulation (at necropsy), serum chemistry (pre-treatment and at necropsy), urinalysis (end of dosing and end of recovery), macroscopic observations at necropsy, organ weights and histopathology (on selected tissues). No statistically significant changes were seen in the clinical pathology parameters in the dosing group receiving a compound of Formula I at 60 mg/kg once weekly.

A separate group of animals across the four dosing groups were evaluated solely for toxicokinetics. For the toxicokinetic study, blood was collected by jugular venipuncture at the beginning of dosing (day 1) and at the end of the study (end of week 3). Samples were collected from subgroups so that both male and female subgroups were available for sample collection at the following time points of 0 hour, 0.5 hour, 1 hour, 2 hours, 4 hours, 8 hours and 24 hours after dosing. Toxicokinetic parameters were estimated using WinNonlin pharmacokinetic software (Pharsight Corp., Mountain View, Calif., USA.). A non-compartmental approach consistent with the oral route of administration was used for parameter estimation. All parameters were generated from mean concentrations of the compound of Formula I in plasma from Days 1 and Week 3 unless otherwise stated. Mean concentrations were derived from 3 animals/sex/group/time point/TK sampling occasion for the four dosing groups. The parameters C. (the maximum observed concentration of the compound of Formula I and its metabolite measured after dosing), $C_{max}$/D ($C_{max}$ divided by the dose administered), $T_{max}$ (time after dosing at which the maximum observed concentration of the compound of Formula I was observed), $AUC_{(0-t)}$ (area under the concentration (of the compound of Formula I) versus time curve from time zero to the time after dosing at which the last quantifiable concentration of the drug was observed or imputed estimated by the linear or linear/log trapezoidal method), $AUC_{(0-t)}$/D ($AUC_{(0-t)}$ divided by the dose administered) were estimated using sampling times relative to the start of each dose administration.

When data permitted, the slope of the terminal elimination phase of each arithmetic mean concentration versus time curve was determined by log-linear regression, and the following additional parameters were also estimated: $T_{1/2}$ (apparent terminal eliminate half life), $AUC_{(0-inf)}$(area under the concentration versus time curve from time zero to infinity) and $AUC_{(0-inf)}$/D (the $AUC_{(0-inf)}$ divided by the dose administered). In addition to parameter estimates for individual animals, descriptive statistics (arithmetic and geometric means, ranges, standard deviations and coefficient of variance [%]) by dose group, day and sex (as appropriate) were generated using WinNonlin. For T., median values were reported. In addition to parameter estimates from mean concentration vs. time curves, the standard error of the AUC(0-t) and $C_{max}$ by dose group, day and sex (as appropriate) were generated using WinNonlin.

Example 79

Rat MRMT-1 Bone Metastasis Model

A rat mammary MRMT-1 bone metastasis model was performed by Ricerca Biosciences, LLC. Female Sprague-Dawley rats (Harlan Sprague-Dawley; ~125-150 g) were acclimated for 1 wk. The animals were randomized into six treatment groups (n=10). On day 1 of the study, $3\times10^4$ MRMT-1 rat mammary gland carcinoma cells were injected into the medullary cavity of the left proximal tibia of each rat. Groups of inoculated rats received a dose of compound having the Formula I at 120 mg/kg p.o. QD on a once weekly dosing schedule (on days 3 and 10 of the study) or at a dose of 60 mg/kg p.o. QD on a once weekly dosing schedule (on days 3 and 10 of the study). Another group of inoculated rats received a dose of compound having the Formula I at 60 mg/kg p.o. QD on a twice weekly dosing schedule (on days 3, 7, 10 and 14 of the study). The positive control group was given 0.03 mg/kg zoledronate in calcium and magnesium-free PBS by s.c. injection every other day beginning on day 3. Rats were sacrificed on day 17.

The left tibia from each animal was excised and the distal end was severed to expose the marrow cavity. The microradiographs were prepared using high resolution microradiograph (Faxitron X-ray Corporation). Tibiae microradiographs were evaluated for the extent of tumor-induced osteolysis at the end of the study using the scoring criteria outlined in Table A:

TABLE A

| Score | Descriptive Criteria |
|---|---|
| 0 | Normal bone with no signs of destruction |
| 1 | Small radiolucent lesions indicative of bone destruction (one to three lesions) |
| 2 | Increased number of lesions (three to six lesions) and loss of medullary bone |
| 3 | Loss of medullary bone and erosion of cortical bone |
| 4 | Full thickness unicortical bone loss |
| 5 | Full thickness bicortical bone loss and/or displaced skeletal fractures |

All hind limbs were fixed in 10% neutral buffered formalin and decalcified for tartrate-resistant alkaline phosphate-positive ($TRAP^+$) staining and for evaluation of bone structure, tumor osteolysis and osteoclast activity. The summary of the microradiographic score is shown in FIG. 1. Both once weekly dose and twice weekly dose showed to be as protective against bone destruction as the positive control, zoledronate.

The compounds provided herein were found to have the following activity shown in Table 1:

| CHEMISTRY | CSF1R (human) $K_d$ (nM) | CSF1R (mouse) $K_d$ (nM) | CSF1R Cell Proliferation (M-NFS-60) $IC_{50}$ (nM) | Kinase Specificity (S10) |
|---|---|---|---|---|
| 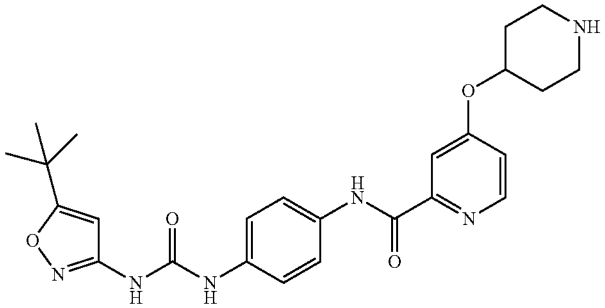 [SMILES: CC(C)(C)c1cc(NC(=O)Nc2ccc(NC(=O)c3cc(OC4CCNCC4)ccn3)cc2)no1] | A | A | B | B |

-continued
| CHEMISTRY | CSF1R (human) $K_d$ (nM) | CSF1R (mouse) $K_d$ (nM) | CSF1R Cell Proliferation (M-NFS-60) $IC_{50}$ (nM) | Kinase Specificity (S10) |
|---|---|---|---|---|
| 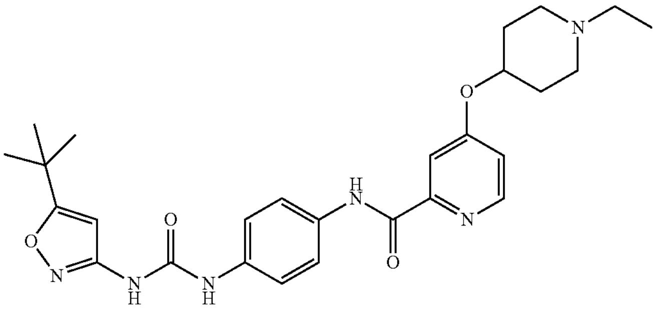 [SMILES: CCN1CCC(Oc2ccnc(C(=O)Nc3ccc(NC(=O)Nc4cc(C(C)(C)C)on4)cc3)c2)CC1] | B | B | C | B |
| 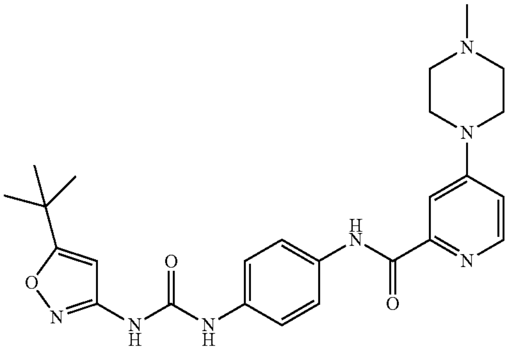 [SMILES: CN1CCN(c2ccnc(C(=O)Nc3ccc(NC(=O)Nc4cc(C(C)(C)C)on4)cc3)c2)CC1] | B | B | B | B |
| 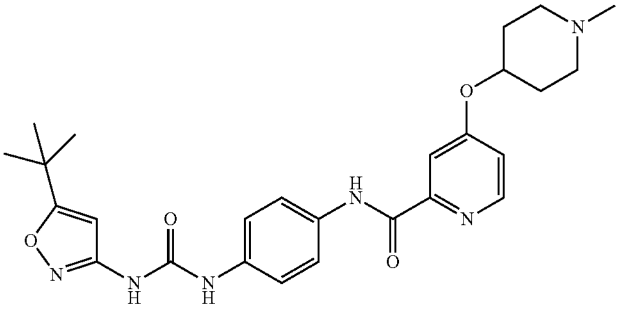 [SMILES: CN1CCC(Oc2ccnc(C(=O)Nc3ccc(NC(=O)Nc4cc(C(C)(C)C)on4)cc3)c2)CC1] | B | B | C | B |
| 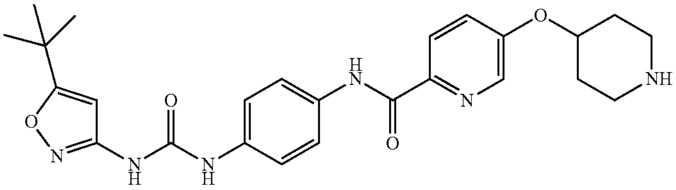 [SMILES: CC(C)(C)c1cc(NC(=O)Nc2ccc(NC(=O)c3ccc(OC4CCNCC4)cn3)cc2)no1] | A | A | A | C |
| 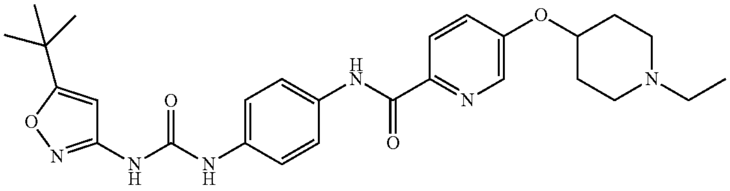 [SMILES: CCN1CCC(Oc2ccc(C(=O)Nc3ccc(NC(=O)Nc4cc(C(C)(C)C)on4)cc3)nc2)CC1] | A | A | A | C |

-continued
| CHEMISTRY | CSF1R (human) $K_d$ (nM) | CSF1R (mouse) $K_d$ (nM) | CSF1R Cell Proliferation (M-NFS-60) $IC_{50}$ (nM) | Kinase Specificity (S10) |
|---|---|---|---|---|
| 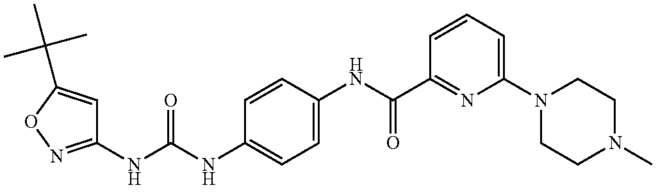 [SMILES: CN1CCN(c2cccc(C(=O)Nc3ccc(NC(=O)Nc4cc(C(C)(C)C)on4)cc3)n2)CC1] | B | B | D | B |
| 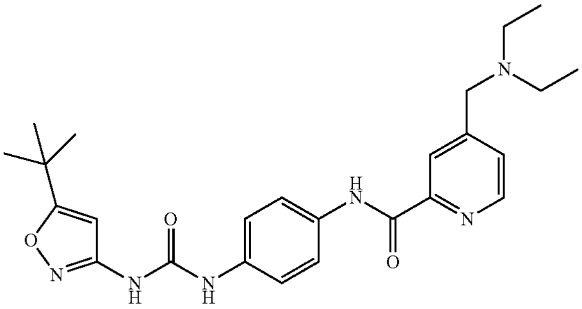 [SMILES: CCN(CC)Cc1ccnc(C(=O)Nc2ccc(NC(=O)Nc3cc(C(C)(C)C)on3)cc2)c1] | B | B | C | A |
| 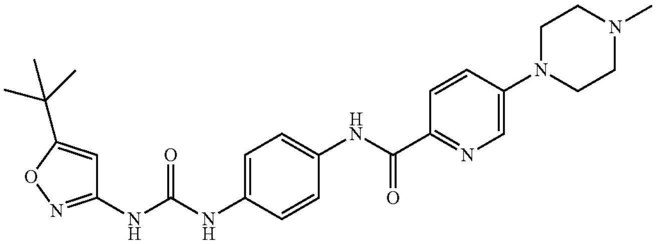 [SMILES: CN1CCN(c2ccc(C(=O)Nc3ccc(NC(=O)Nc4cc(C(C)(C)C)on4)cc3)nc2)CC1] | A | A | A | C |
| 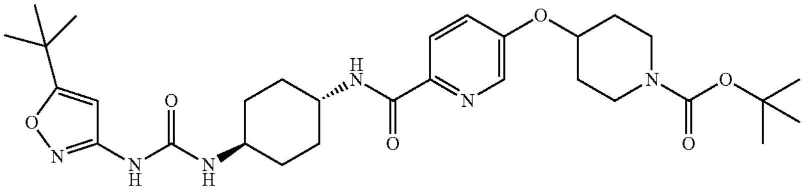 [SMILES: CC(C)(C)OC(=O)N1CCC(Oc2ccc(C(=O)N[C@H]3CC[C@H](NC(=O)Nc4cc(C(C)(C)C)on4)CC3)nc2)CC1] | C | B | C | A |
| 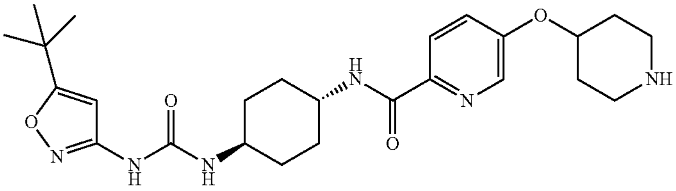 [SMILES: CC(C)(C)c1cc(NC(=O)N[C@H]2CC[C@H](NC(=O)c3ccc(OC4CCNCC4)cn3)CC2)no1] | B | B | D | A |
| 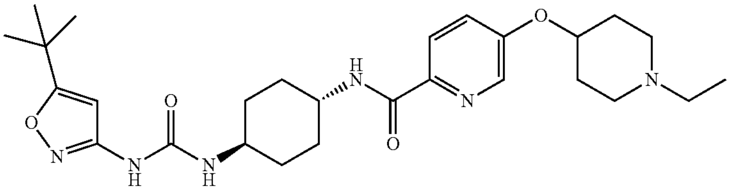 [SMILES: CCN1CCC(Oc2ccc(C(=O)N[C@H]3CC[C@H](NC(=O)Nc4cc(C(C)(C)C)on4)CC3)nc2)CC1] | B | B | C | A |

-continued
| CHEMISTRY | CSF1R (human) $K_d$ (nM) | CSF1R (mouse) $K_d$ (nM) | CSF1R Cell Proliferation (M-NFS-60) $IC_{50}$ (nM) | Kinase Specificity (S10) |
|---|---|---|---|---|
| 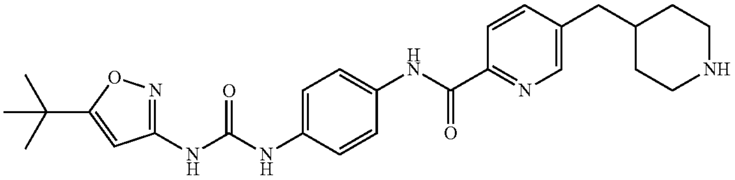 [SMILES: CC(C)(C)c1cc(NC(=O)Nc2ccc(NC(=O)c3ccc(CC4CCNCC4)cn3)cc2)no1] | A | A | B | A |
| 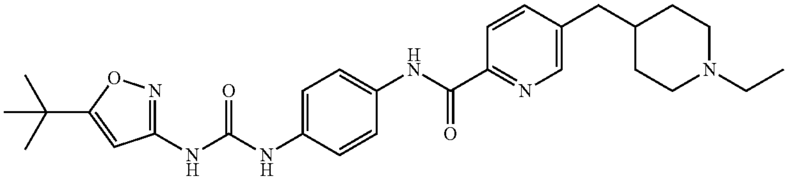 [SMILES: CCN1CCC(Cc2ccc(C(=O)Nc3ccc(NC(=O)Nc4cc(C(C)(C)C)on4)cc3)nc2)CC1] | A | A | A | B |
| 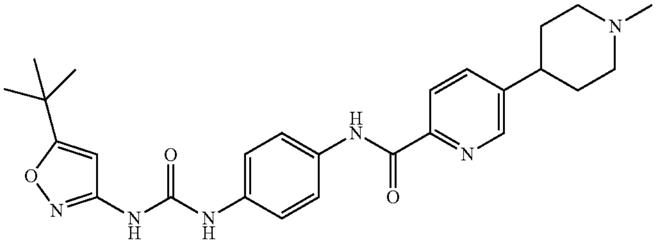 [SMILES: CN1CCC(c2ccc(C(=O)Nc3ccc(NC(=O)Nc4cc(C(C)(C)C)on4)cc3)nc2)CC1] | B | B | A | B |
| 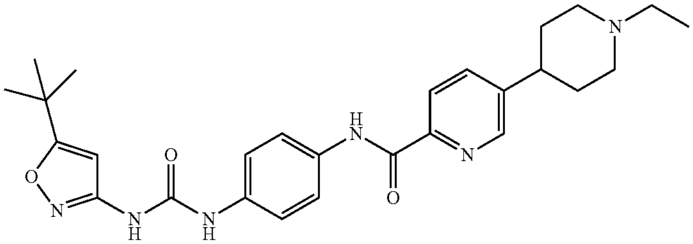 [SMILES: CCN1CCC(c2ccc(C(=O)Nc3ccc(NC(=O)Nc4cc(C(C)(C)C)on4)cc3)nc2)CC1] | B | B | A | B |
| 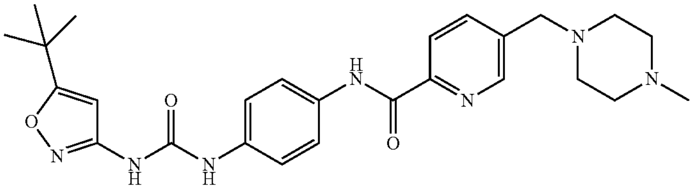 [SMILES: CN1CCN(Cc2ccc(C(=O)Nc3ccc(NC(=O)Nc4cc(C(C)(C)C)on4)cc3)nc2)CC1] | B | B | A/B | A |
| 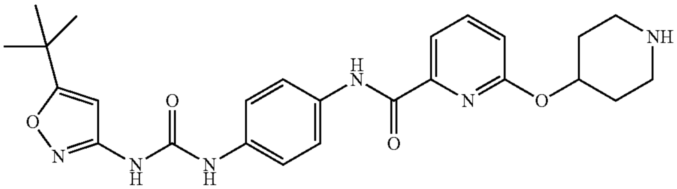 [SMILES: CC(C)(C)c1cc(NC(=O)Nc2ccc(NC(=O)c3cccc(OC4CCNCC4)n3)cc2)no1] | C | C | D | B |
| 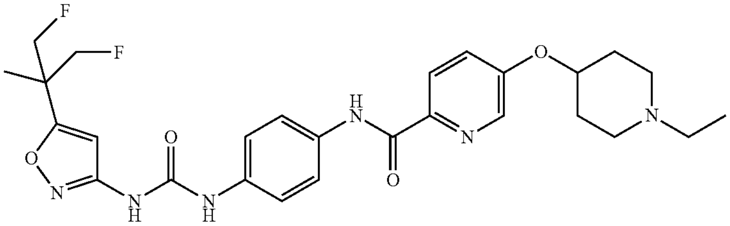 [SMILES: CCN1CCC(Oc2ccc(C(=O)Nc3ccc(NC(=O)Nc4cc(C(C)(CF)CF)on4)cc3)nc2)CC1] | A | A | A | B |

-continued
| CHEMISTRY | CSF1R (human) $K_d$ (nM) | CSF1R (mouse) $K_d$ (nM) | CSF1R Cell Proliferation (M-NFS-60) $IC_{50}$ (nM) | Kinase Specificity (S10) |
|---|---|---|---|---|
| 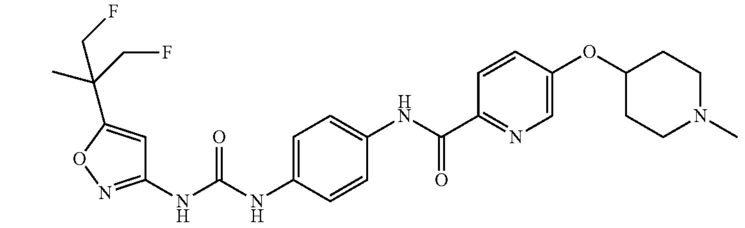 [SMILES: CN1CCC(Oc2ccc(C(=O)Nc3ccc(NC(=O)Nc4cc(C(C)(CF)CF)on4)cc3)nc2)CC1] | A | A | A | B |
| 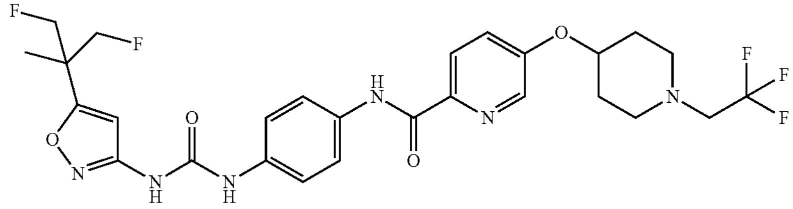 [SMILES: CC(CF)(CF)c1cc(NC(=O)Nc2ccc(NC(=O)c3ccc(OC4CCN(CC(F)(F)F)CC4)cn3)cc2)no1] | A | A | B | A |
| 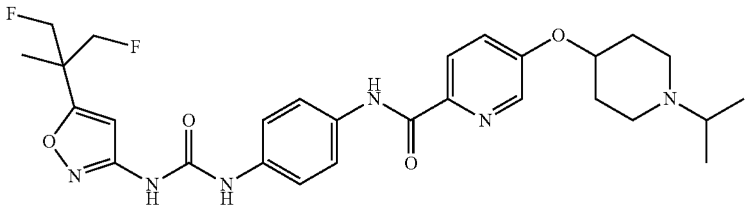 [SMILES: CC(C)N1CCC(Oc2ccc(C(=O)Nc3ccc(NC(=O)Nc4cc(C(C)(CF)CF)on4)cc3)nc2)CC1] | A | A | A | B |
| 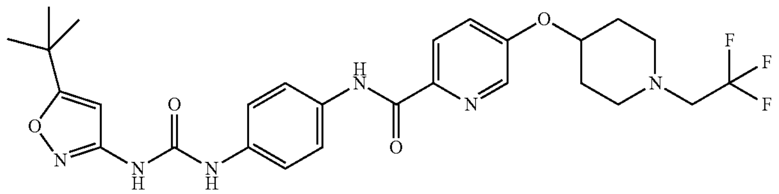 [SMILES: CC(C)(C)c1cc(NC(=O)Nc2ccc(NC(=O)c3ccc(OC4CCN(CC(F)(F)F)CC4)cn3)cc2)no1] | B | A | B | A |
| 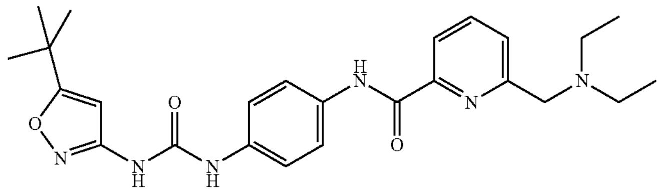 [SMILES: CCN(CC)Cc1cccc(C(=O)Nc2ccc(NC(=O)Nc3cc(C(C)(C)C)on3)cc2)n1] | C | C | D | A |
| 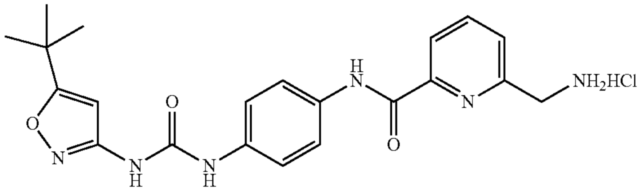 | C | C | C | A |
| 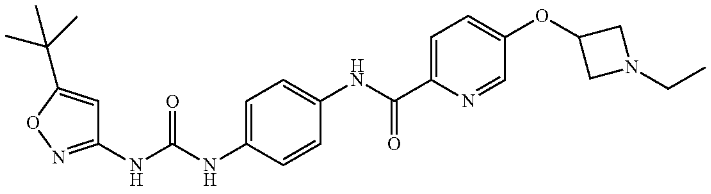 [SMILES: CCN1CC(Oc2ccc(C(=O)Nc3ccc(NC(=O)Nc4cc(C(C)(C)C)on4)cc3)nc2)C1] | A | ND | B | B |

-continued
| CHEMISTRY | CSF1R (human) $K_d$ (nM) | CSF1R (mouse) $K_d$ (nM) | CSF1R Cell Proliferation (M-NFS-60) $IC_{50}$ (nM) | Kinase Specificity (S10) |
|---|---|---|---|---|
| 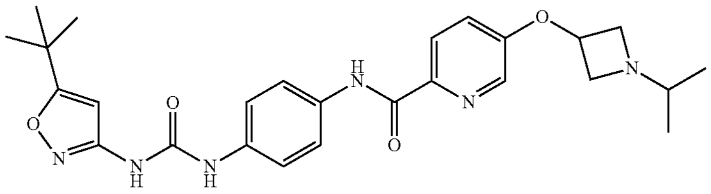 [SMILES: CC(C)N1CC(Oc2ccc(C(=O)Nc3ccc(NC(=O)Nc4cc(C(C)(C)C)on4)cc3)nc2)C1] | A | ND | A | B |
| 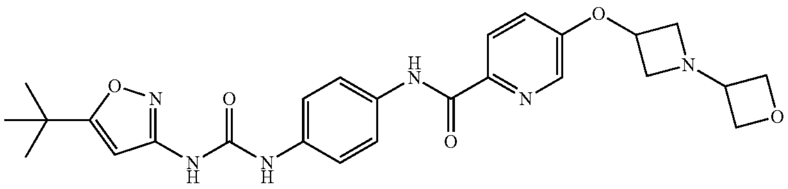 [SMILES: CC(C)(C)c1cc(NC(=O)Nc2ccc(NC(=O)c3ccc(OC4CN(C5COC5)C4)cn3)cc2)no1] | A | ND | A | C |
| 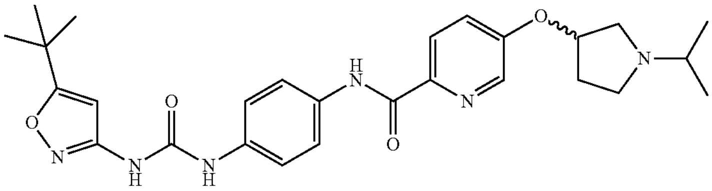 [SMILES: CC(C)N1CCC(Oc2ccc(C(=O)Nc3ccc(NC(=O)Nc4cc(C(C)(C)C)on4)cc3)nc2)C1] | A | ND | A | B |
| 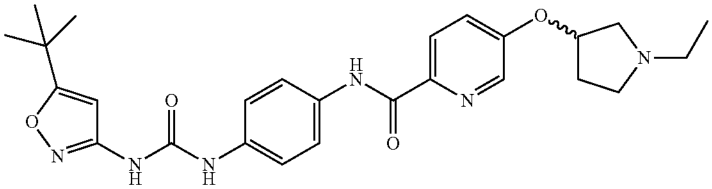 [SMILES: CCN1CCC(Oc2ccc(C(=O)Nc3ccc(NC(=O)Nc4cc(C(C)(C)C)on4)cc3)nc2)C1] | A | ND | A | B |
| 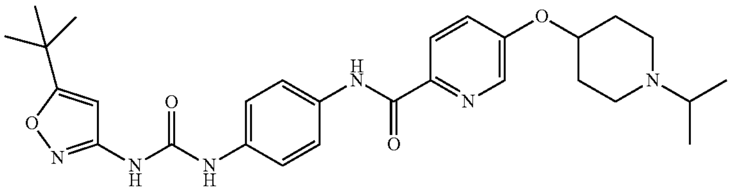 [SMILES: CC(C)N1CCC(Oc2ccc(C(=O)Nc3ccc(NC(=O)Nc4cc(C(C)(C)C)on4)cc3)nc2)CC1] | A | ND | A | B |
| 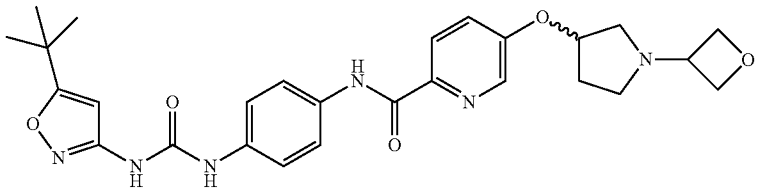 [SMILES: CC(C)(C)c1cc(NC(=O)Nc2ccc(NC(=O)c3ccc(OC4CCN(C5COC5)C4)cn3)cc2)no1] | A | ND | A | B |
| 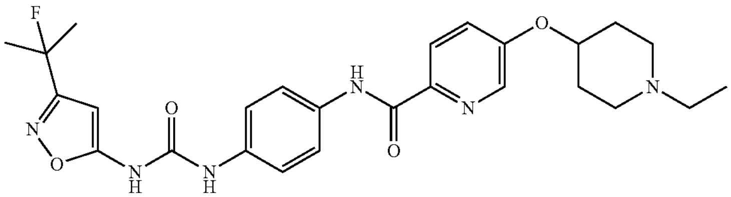 [SMILES: CCN1CCC(Oc2ccc(C(=O)Nc3ccc(NC(=O)Nc4cc(C(C)(C)F)no4)cc3)nc2)CC1] | A | ND | A/B | A |

-continued
| CHEMISTRY | CSF1R (human) $K_d$ (nM) | CSF1R (mouse) $K_d$ (nM) | CSF1R Cell Proliferation (M-NFS-60) $IC_{50}$ (nM) | Kinase Specificity (S10) |
|---|---|---|---|---|
| 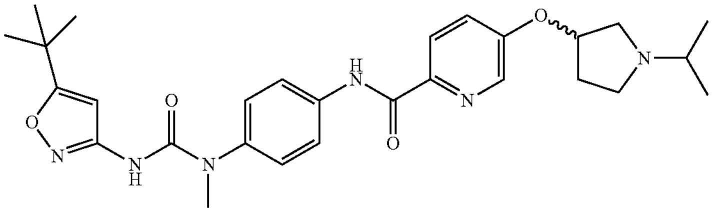 [SMILES: CC(C)N1CCC(Oc2ccc(C(=O)Nc3ccc(N(C)C(=O)Nc4cc(C(C)(C)C)on4)cc3)nc2)C1] | A | ND | B | C |
| 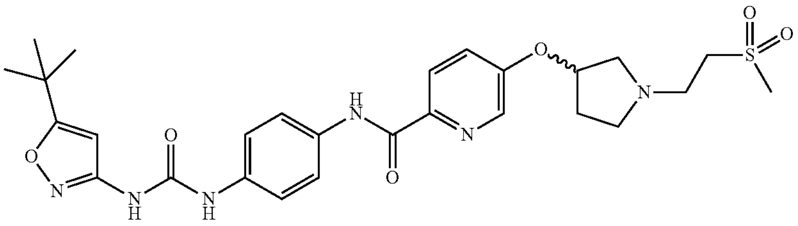 [SMILES: CC(C)(C)c1cc(NC(=O)Nc2ccc(NC(=O)c3ccc(OC4CCN(CCS(C)(=O)=O)C4)cn3)cc2)no1] | A | ND | A | C |
| 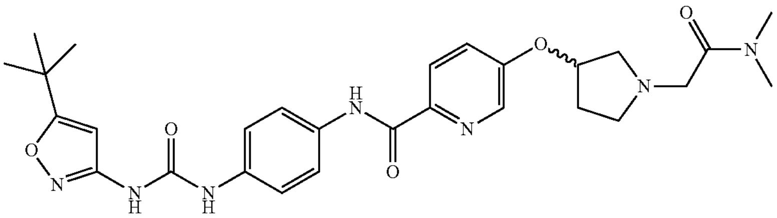 [SMILES: CN(C)C(=O)CN1CCC(Oc2ccc(C(=O)Nc3ccc(NC(=O)Nc4cc(C(C)(C)C)on4)cc3)nc2)C1] | A | ND | A | B |
| 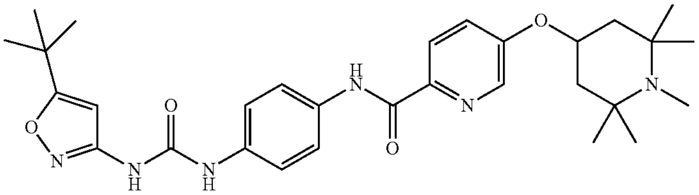 [SMILES: CN1C(C)(C)CC(Oc2ccc(C(=O)Nc3ccc(NC(=O)Nc4cc(C(C)(C)C)on4)cc3)nc2)CC1(C)C] | A | ND | A | C |
| 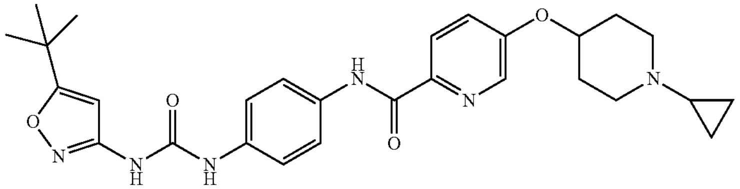 [SMILES: CC(C)(C)c1cc(NC(=O)Nc2ccc(NC(=O)c3ccc(OC4CCN(C5CC5)CC4)cn3)cc2)no1] | A | ND | B | A |
| 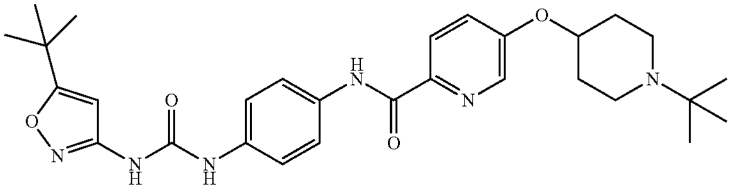 [SMILES: CC(C)(C)c1cc(NC(=O)Nc2ccc(NC(=O)c3ccc(OC4CCN(C(C)(C)C)CC4)cn3)cc2)no1] | A | ND | A | B |
| 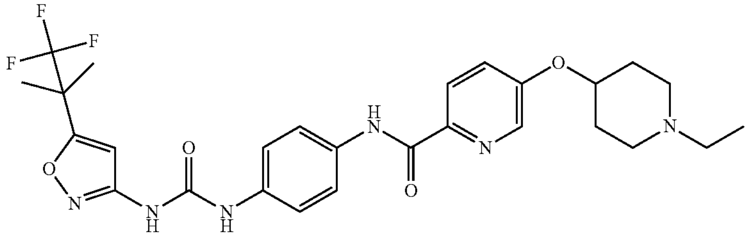 [SMILES: CCN1CCC(Oc2ccc(C(=O)Nc3ccc(NC(=O)Nc4cc(C(C)(C)C(F)(F)F)on4)cc3)nc2)CC1] | A | ND | A | C |

-continued
| CHEMISTRY | CSF1R (human) $K_d$ (nM) | CSF1R (mouse) $K_d$ (nM) | CSF1R Cell Proliferation (M-NFS-60) $IC_{50}$ (nM) | Kinase Specifi-city (S10) |
|---|---|---|---|---|
| 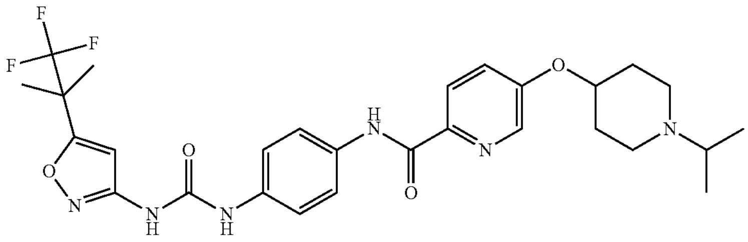 [SMILES: CC(C)N1CCC(Oc2ccc(C(=O)Nc3ccc(NC(=O)Nc4cc(C(C)(C)C(F)(F)F)on4)cc3)nc2)CC1] | A | ND | A | C |
| 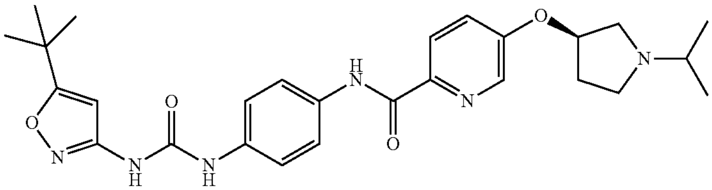 [SMILES: CC(C)N1CC[C@@H](Oc2ccc(C(=O)Nc3ccc(NC(=O)Nc4cc(C(C)(C)C)on4)cc3)nc2)C1] | A | ND | A | C |
| 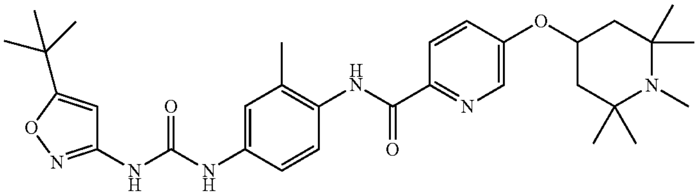 [SMILES: Cc1cc(NC(=O)Nc2cc(C(C)(C)C)on2)ccc1NC(=O)c1ccc(OC2CC(C)(C)N(C)C(C)(C)C2)cn1] | B | ND | D | C |
| 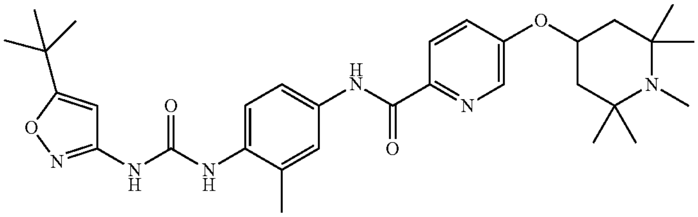 [SMILES: Cc1cc(NC(=O)c2ccc(OC3CC(C)(C)N(C)C(C)(C)C3)cn2)ccc1NC(=O)Nc1cc(C(C)(C)C)on1] | A | ND | B | B |
| 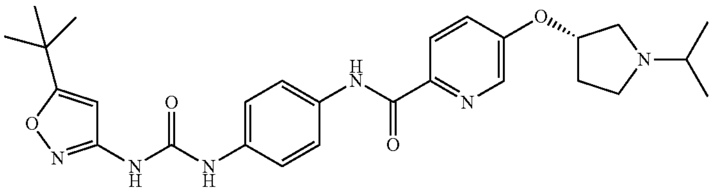 [SMILES: CC(C)N1CC[C@H](Oc2ccc(C(=O)Nc3ccc(NC(=O)Nc4cc(C(C)(C)C)on4)cc3)nc2)C1] | A | ND | A | C |
| 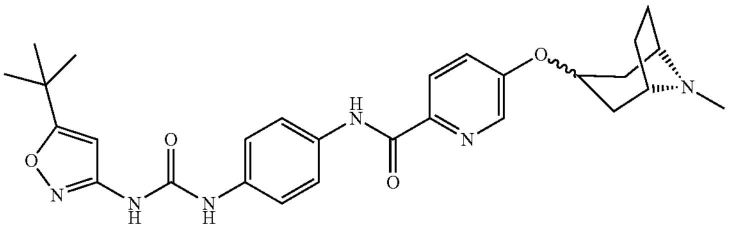 | A | ND | A | C |

-continued
| CHEMISTRY | CSF1R (human) $K_d$ (nM) | CSF1R (mouse) $K_d$ (nM) | CSF1R Cell Proliferation (M-NFS-60) $IC_{50}$ (nM) | Kinase Specificity (S10) |
|---|---|---|---|---|
| 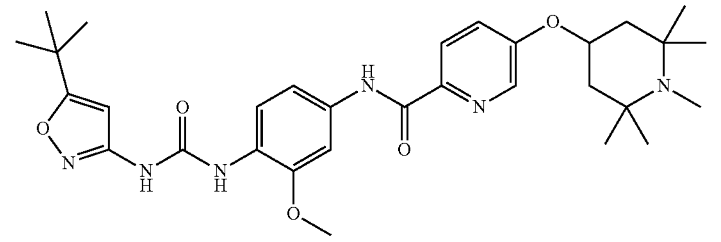 [SMILES: COc1cc(NC(=O)c2ccc(OC3CC(C)(C)N(C)C(C)(C)C3)cn2)ccc1NC(=O)Nc1cc(C(C)(C)C)on1] | B | ND | D | A |
| 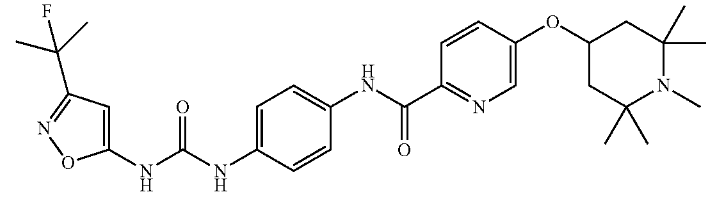 [SMILES: CN1C(C)(C)CC(Oc2ccc(C(=O)Nc3ccc(NC(=O)Nc4cc(C(C)(C)F)no4)cc3)nc2)CC1(C)C] | A | ND | A | A |
| 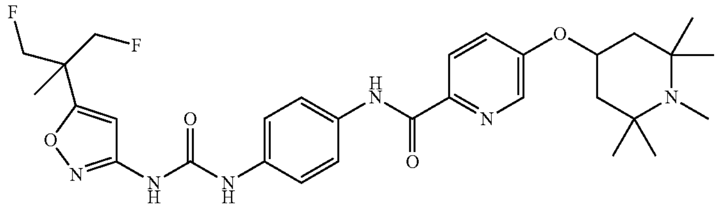 [SMILES: CN1C(C)(C)CC(Oc2ccc(C(=O)Nc3ccc(NC(=O)Nc4cc(C(C)(CF)CF)on4)cc3)nc2)CC1(C)C] | A | ND | A | B |
| 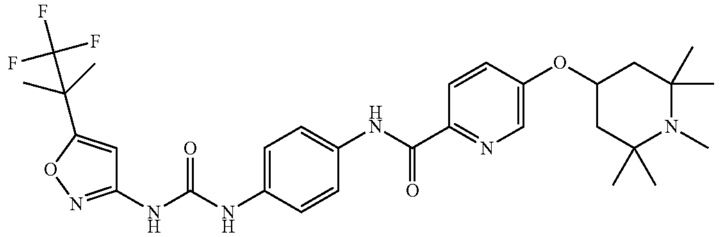 [SMILES: CN1C(C)(C)CC(Oc2ccc(C(=O)Nc3ccc(NC(=O)Nc4cc(C(C)(C)C(F)(F)F)on4)cc3)nc2)CC1(C)C] | B | ND | A | B |
| 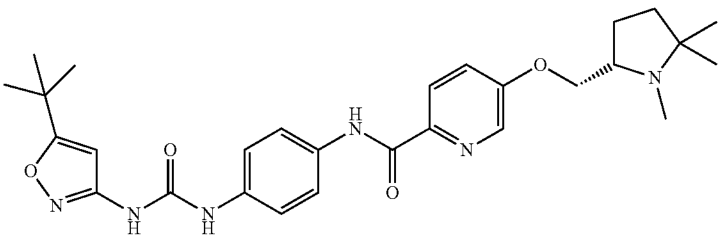 | B | ND | A | B |
| 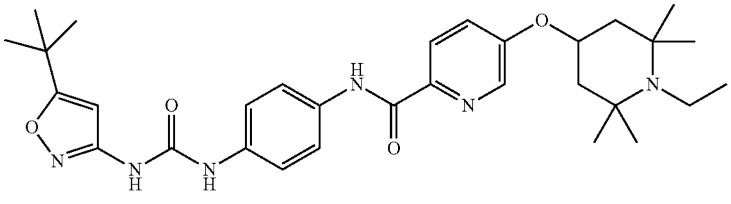 [SMILES: CCN1C(C)(C)CC(Oc2ccc(C(=O)Nc3ccc(NC(=O)Nc4cc(C(C)(C)C)on4)cc3)nc2)CC1(C)C] | A | ND | A | A |

-continued
| CHEMISTRY | CSF1R (human) $K_d$ (nM) | CSF1R (mouse) $K_d$ (nM) | CSF1R Cell Proliferation (M-NFS-60) $IC_{50}$ (nM) | Kinase Specificity (S10) |
|---|---|---|---|---|
| 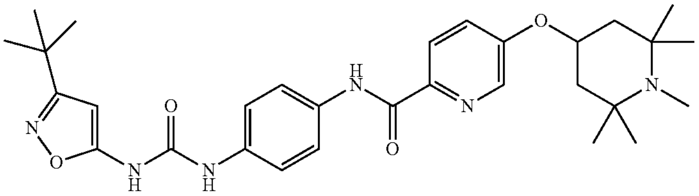 | B | ND | A | B |
| 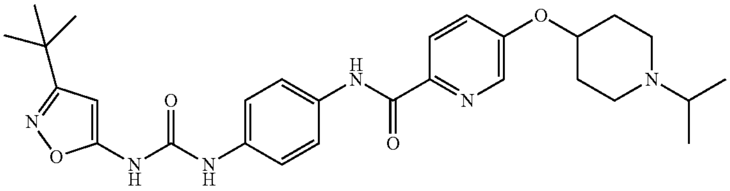 | B | ND | A | B |
| 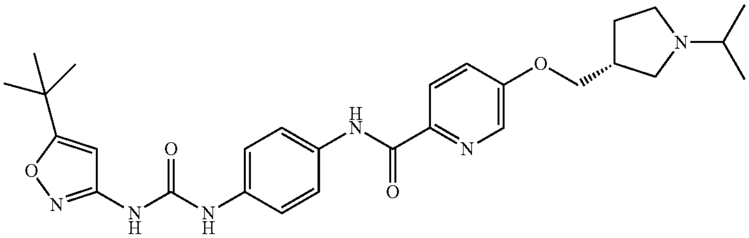 [SMILES: CC(C)N1CC[C@@H](COc2ccc(C(=O)Nc3ccc(NC(=O)Nc4cc(C(C)(C)C)on4)cc3)nc2)C1] | A | ND | A | C |
| 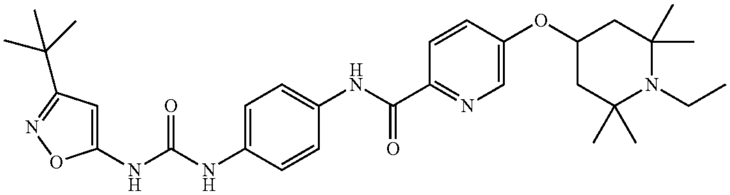 [SMILES: CCN1C(C)(C)CC(Oc2ccc(C(=O)Nc3ccc(NC(=O)Nc4cc(C(C)(C)C)no4)cc3)nc2)CC1(C)C] | C | ND | A | B |
| 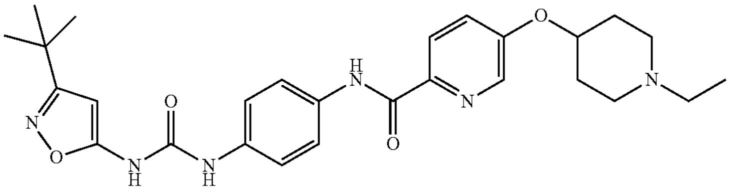 [SMILES: CCN1CCC(Oc2ccc(C(=O)Nc3ccc(NC(=O)Nc4cc(C(C)(C)C)no4)cc3)nc2)CC1] | B | ND | A | B |
| 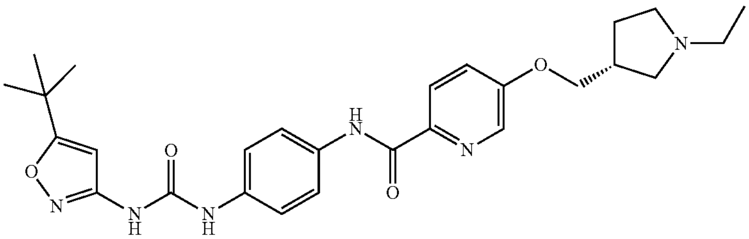 [SMILES: CCN1CC[C@@H](COc2ccc(C(=O)Nc3ccc(NC(=O)Nc4cc(C(C)(C)C)on4)cc3)nc2)C1] | C | ND | A | C |

-continued
| CHEMISTRY | CSF1R (human) $K_d$ (nM) | CSF1R (mouse) $K_d$ (nM) | CSF1R Cell Proliferation (M-NFS-60) $IC_{50}$ (nM) | Kinase Specificity (S10) |
|---|---|---|---|---|
| 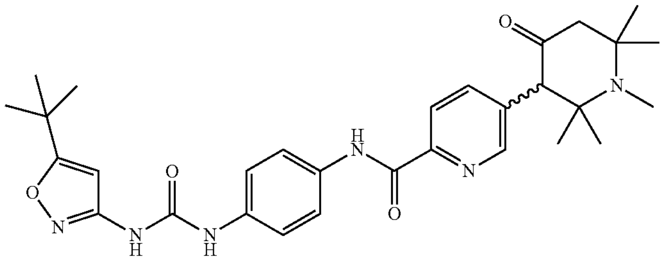 [SMILES: CN1C(C)(C)CC(=O)C(c2ccc(C(=O)Nc3ccc(NC(=O)Nc4cc(C(C)(C)C)on4)cc3)nc2)C1(C)C] | A | ND | B | A |
| 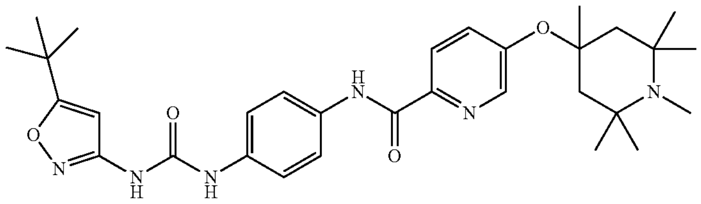 [SMILES: CN1C(C)(C)CC(C)(Oc2ccc(C(=O)Nc3ccc(NC(=O)Nc4cc(C(C)(C)C)on4)cc3)nc2)CC1(C)C] | A | ND | A | C |
| 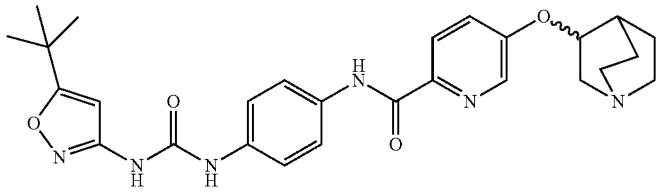 [SMILES: CC(C)(C)c1cc(NC(=O)Nc2ccc(NC(=O)c3ccc(OC4CN5CCC4CC5)cn3)cc2)no1] | A | ND | A | C |
| 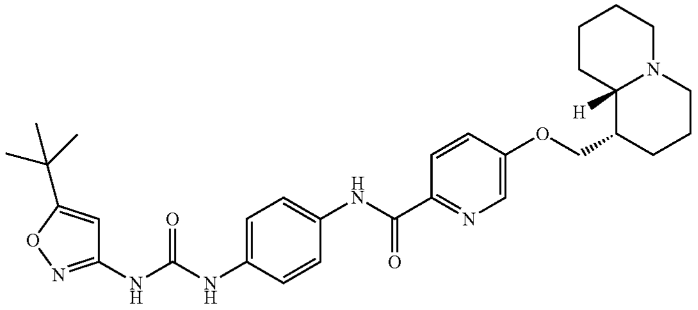 [SMILES: CC(C)(C)c1cc(NC(=O)Nc2ccc(NC(=O)c3ccc(OC[C@H]4CCCN5CCCC[C@@H]45)cn3)cc2)no1] | A | ND | A | C |
| 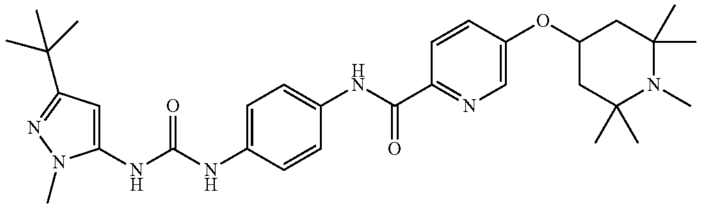 [SMILES: CN1C(C)(C)CC(Oc2ccc(C(=O)Nc3ccc(NC(=O)Nc4cc(C(C)(C)C)nn4C)cc3)nc2)CC1(C)C] | B | ND | B | B |
| 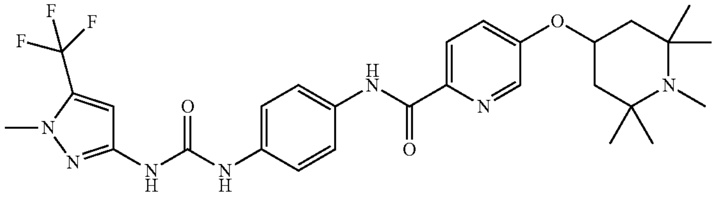 | A | ND | C | C |

-continued
| CHEMISTRY | CSF1R (human) $K_d$ (nM) | CSF1R (mouse) $K_d$ (nM) | CSF1R Cell Proliferation (M-NFS-60) $IC_{50}$ (nM) | Kinase Specificity (S10) |
|---|---|---|---|---|
| 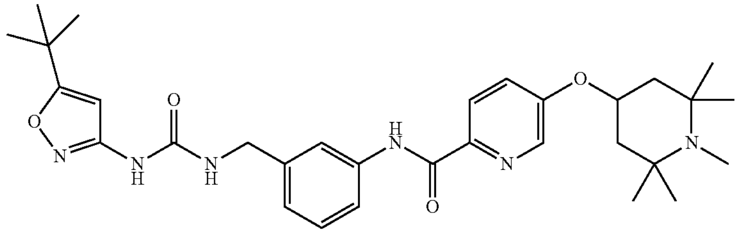 [SMILES: CN1C(C)(C)CC(Oc2ccc(C(=O)Nc3cccc(CNC(=O)Nc4cc(C(C)(C)C)on4)c3)nc2)CC1(C)C] | C | ND | D | C |
| 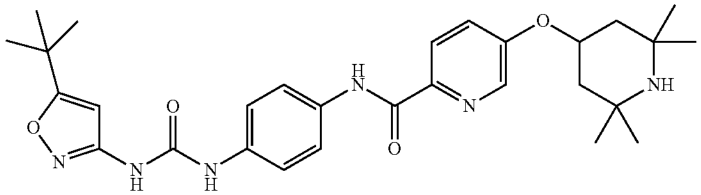 [SMILES: CC1(C)CC(Oc2ccc(C(=O)Nc3ccc(NC(=O)Nc4cc(C(C)(C)C)on4)cc3)nc2)CC(C)(C)N1] | A | ND | A | C |
| 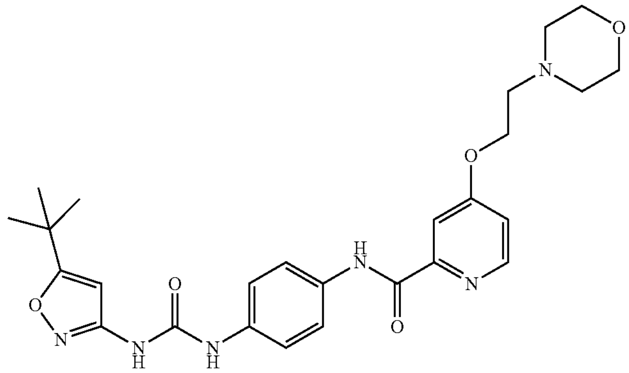 [SMILES: CC(C)(C)c1cc(NC(=O)Nc2ccc(NC(=O)c3cc(OCCN4CCOCC4)ccn3)cc2)no1] | B | A | B/C | A |
| 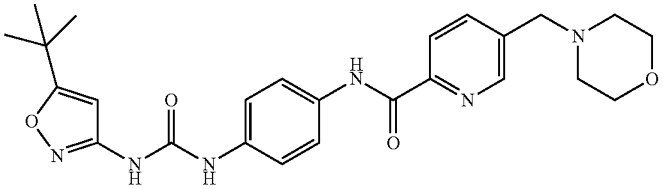 [SMILES: CC(C)(C)c1cc(NC(=O)Nc2ccc(NC(=O)c3ccc(CN4CCOCC4)cn3)cc2)no1] | B | B | B | A |
| 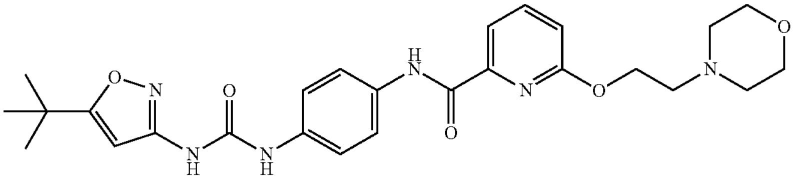 [SMILES: CC(C)(C)c1cc(NC(=O)Nc2ccc(NC(=O)c3cccc(OCCN4CCOCC4)n3)cc2)no1] | C | C | D | A |
| 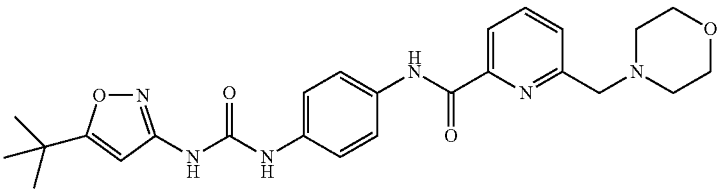 [SMILES: CC(C)(C)c1cc(NC(=O)Nc2ccc(NC(=O)c3cccc(CN4CCOCC4)n3)cc2)no1] | C | C | D | B |

-continued

| CHEMISTRY | CSF1R (human) $K_d$ (nM) | CSF1R (mouse) $K_d$ (nM) | CSF1R Cell Proliferation (M-NFS-60) $IC_{50}$ (nM) | Kinase Specificity (S10) |
|---|---|---|---|---|
| 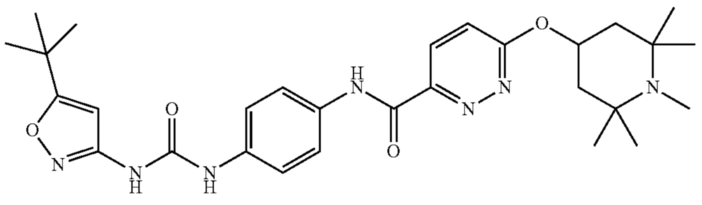 [SMILES: CN1C(C)(C)CC(Oc2ccc(C(=O)Nc3ccc(NC(=O)Nc4cc(C(C)(C)C)on4)cc3)nn2)CC1(C)C] | A | ND | C | C |
| 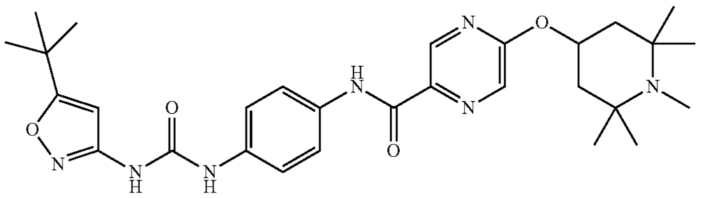 | B | ND | B | B |

In Table 1,
CSF1R (human) Kd (nM): A ≤ 3, 3 < B ≤ 10, C > 10; and ND = no data;
CSF1R (mouse) Kd (nM): A ≤ 3, 3 < B ≤ 10, C> 10; and ND = no data;
CSF1R Cell Proliferation Assay (M-NSF-60) $IC_{50}$ (nM): A ≤ 100, 100 < B ≤ 250, 250 < C ≤ 1000, D > 1000; and ND = no data; and S score: A ≤ 0.03, 0.03 < B ≤ 0.05, C > 0.05; and ND = no data.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the claimed subject matter and are encompassed by the appended claims.

Since modifications will be apparent to those of skill in the art, it is intended that the claimed subject matter be limited only by the scope of the appended claims.

What is claimed is:

1. A compound having formula

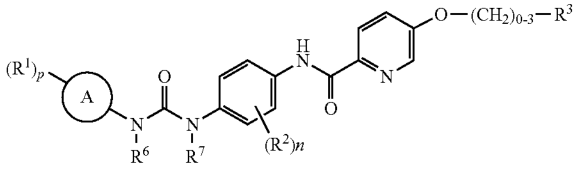

or a pharmaceutically acceptable salt, solvate, hydrate or clathrate thereof, wherein $R^1$ is tert-butyl;

A is azolyl, $R^6$ and $R^7$ are each independently hydrogen or alkyl;

$R^2$ is alkyl;

$R^3$ is selected as follows:

i) $R^3$ is —$NR^{3a}R^{3b}$, or ii) $R^3$ is optionally substituted heterocyclyl containing at least one nitrogen atom, such that the heterocyclyl ring is connected on the carbon atom of the ring, and wherein the substituents, when present are selected from one or more $Q^1$ groups, $R^{3a}$ and $R^{3b}$ are selected as follows:

i) $R^{3a}$ and $R^{3b}$ are each independently alkyl, alkenyl, alkynyl, cycloalkyl, or haloalkyl; or ii) $R^{3a}$ and $R^{3b}$ together form optionally substituted heterocyclyl, wherein the substituents when present are selected from one, two or three $Q^1$ groups, each $Q^1$ is independently selected from alkyl, haloalkyl, cycloalkyl, —$R^uC(J)OR^x$, —$R^uS(O)_tR^w$, —$R^uC(J)N(R^y)(R^z)$, and heterocyclyl, each $R^u$ is independently alkylene or a direct bond;

$R^W$ is alkyl;

each $R^x$ is alkyl;

$R^y$ and $R^z$ are each hydrogen or alkyl;

J is O;

p is 0, 1 or 2;

n is 0 or 1; and t is 0-2.

2. The compound of claim 1, where A is:

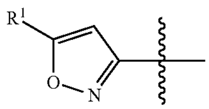 or 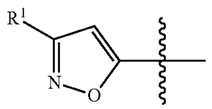 .

3. The compound of claim 1, wherein each $Q^1$ is independently selected from —$CH_3$, —$CH_2$—$CH_3$, —$CH_2CF_3$, —CH—$(CH_3)_2$, —C(O)O$(CH_3)_3$, —$(CH_2)_2S(O)_2CH_3$, —$CH_2C(O)N(CH_3)_2$, —$C(CH_3)_3$, cyclopropyl and oxetanyl.

4. The compound of claim 1, where $R^3$ is optionally substituted piperidinyl, piperazinyl, azetidinyl, morpholinyl, pyrrolidinyl, quinuclidine, octahydroquinolizinyl or azabicyclo[3.2.1]octanyl, and wherein the substituents, when present are selected from 1-5 $Q^1$ groups, each independently selected from —$CH_3$, —$CH_2$—$CH_3$, —$CH_2CF_3$, —CH—$(CH_3)_2$—C(O)O$(CH_3)_3$, —$(CH_2)_2S(O)_2CH_3$, —$CH_2C(O)N(CH_3)_2$, —$C(CH_3)_3$, cyclopropyl and oxetanyl.

5. The compound of claim 1 having formula XIII

XIII

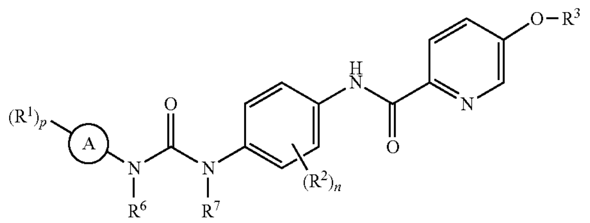

or pharmaceutically acceptable salts, solvates, hydrates or clathrates thereof, wherein $R^3$ is optionally substituted piperidinyl, piperazinyl, azetidinyl, pyrrolidinyl, quinuclidine, octahydroquinolizinyl or azabicyclo[3.2.1]octanyl, where the substituents, when present are selected from one, two or three $Q^1$ groups, each independently selected from $—CH_3$, $—CH_2—CH_3$, $—CH_2CF_3$, $—CH—(CH_3)_2$, $—C(O)O(CH_3)_3$, $—(CH_2)_2S(O)_2CH_3$, $—CH_2C(O)N(CH_3)_2$, $—C(CH_3)_3$, cyclopropyl and oxetanyl.

6. The compound of claim 1 having formula XIVa or XIVb

XIVa

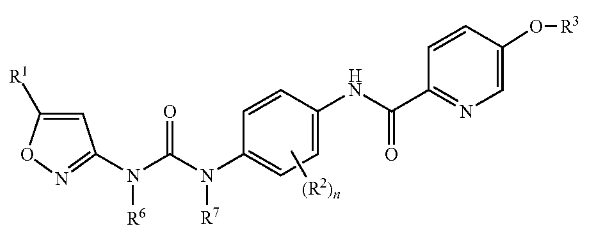

or

XIVb

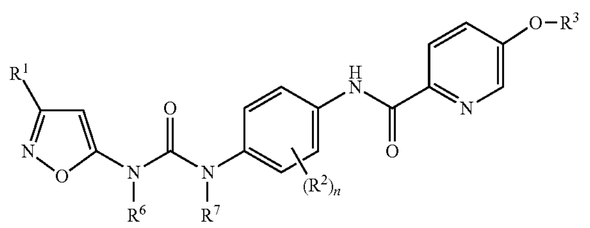

or pharmaceutically acceptable salts, solvates, hydrates or clathrates thereof, wherein $R^3$ is optionally substituted piperidinyl, piperazinyl, azetidinyl, pyrrolidinyl, quinuclidine, octahydroquinolizinyl or azabicyclo[3.2.1]octanyl, where the substituents, when present are selected from one, two or three $Q^1$ groups, each independently selected from $—CH_3$, $—CH_2—CH_3$, $—CH_2CF_3$, $—CH—(CH_3)_2$, $—C(O)O(CH_3)_3$, $—(CH_2)_2S(O)_2CH_3$, $—CH_2C(O)N(CH_3)_2$, $—C(CH_3)_3$, cyclopropyl and oxetanyl.

7. The compound of claim 1 having formula XV

XV

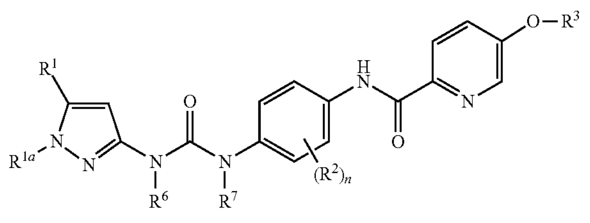

or pharmaceutically acceptable salts, solvates, hydrates or clathrates thereof, wherein $R^{1a}$ is hydrogen, $R^3$ is optionally substituted piperidinyl, piperazinyl, azetidinyl, pyrrolidinyl, quinuclidine, octahydroquinolizinyl or azabicyclo[3.2.1]octanyl, and wherein the substituents, when present are selected from one, two or three $Q^1$ groups, each independently selected from $—CH_3$, $—CH_2—CH_3$, $—CH_2CF_3$, $—CH-(CH_3)_2$, $—C(O)O(CH_3)_3$, $—(CH_2)_2S(O)_2CH_3$, $—CH_2C(O)N(CH_3)_2$, $—C(CH_3)_3$, cyclopropyl and oxetanyl.

8. The compound of claim 1 having formula XVI

XVI

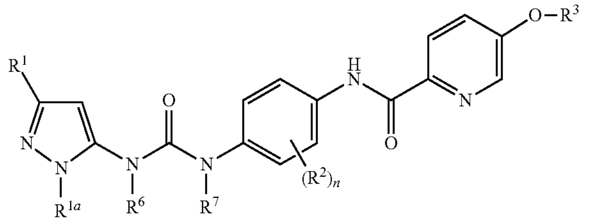

or pharmaceutically acceptable salts, solvates, hydrates or clathrates thereof, wherein $R^{1a}$ is hydrogen, $R^3$ is optionally substituted piperidinyl, piperazinyl, azetidinyl, pyrrolidinyl, quinuclidine, octahydroquinolizinyl or azabicyclo[3.2.1]octanyl, and wherein the substituents, when present are selected from one, two or three $Q^1$ groups, each independently selected from $—CH_3$, $—CH_2—CH_3$, $—CH_2CF_3$, $—CH—(CH_3)_2$, $—C(O)O(CH_3)_3$, $—(CH_2)_2S(O)_2CH_3$, $—CH_2C(O)N(CH_3)_2$, $—C(CH_3)_3$, cyclopropyl and oxetanyl.

9. The compound of claim 1, wherein the compound is selected from:

N-(4-(3-(5-tert-butylisoxazol-3-yl)ureido)phenyl)-5-(piperidin-4-yloxy)picolinamide hydrochloride, N-(4-(3-(5-tert-butylisoxazol-3-yl)ureido)phenyl)-5-(1-ethylpiperidin-4-yloxy)picolinamide, N-(4-(3-(5-tert-butylisoxazol-3-yl)ureido)phenyl)-5-(1-(2,2,2-trifluoroethyl)piperidin-4-yloxy)picolinamide, N-(4-(3-(5-tert-butylisoxazol-3-yl)ureido)phenyl)-5-(1-ethylazetidin-3-yloxy)picolinamide, N-(4-(3-(5-tert-butylisoxazol-3-yl)ureido)phenyl)-5-(1-isopropylazetidin-3-yloxy)picolinamide, N-(4-(3-(5-tert-butylisoxazol-3-yl)ureido)phenyl)-5-(1-(oxetan-3-yl)azetidin-3-yloxy)picolinamide, N-(4-(3-(5-tert-butylisoxazol-3-yl)ureido)phenyl)-5-(1-isopropylpyrrolidin-3-yloxy)picolinamide, N-(4-(3-(5-tert-butylisoxazol-3-yl)ureido)phenyl)-5-(1-ethylpyrrolidin-3-yloxy)picolinamide, 4-(6-(4-(3-(5-tert-butylisoxazol-3-yl)ureido)phenylcarbamoyl)pyridin-3-yloxy)-1-isopropylpiperidinium methanesulfonate, 3-(6-(4-(3-(5-tert-butylisoxazol-3-yl)ureido)phenylcarbamoyl)pyridin-3-yloxy)-1-(oxetan-3-yl)pyrrolidinium methanesulfonate, 1-ethyl-4-(6-(4-(3-(3-(2-fluoropropan-2-yl)isoxazol-5-yl)ureido)phenylcarbamoyl)pyridin-3-yloxy)piperidinium methanesulfonate, N-(4-(3-(5-(tert-butyl)isoxazol-3-yl)ureido)phenyl)-5-((1-methylpyrrolidin-3-yl)oxy)picolinamide, N-(4-(3-(5-(tert-butyl)isoxazol-3-yl)ureido)phenyl)-5-((1-isobutylpyrrolidin-3-yl)oxy)picolinamide, 3-(6-(4-(3-(5-tert-butylisoxazol-3-yl)-1-methylureido)phenylcarbamoyl)pyridin-3-yloxy)-1-isopropylpyrrolidinium methanesulfonate, 3-(6-(4-(3-(5-tert-butylisoxazol-3-yl)ureido)phenylcarbamoyl)pyridin-3-yloxy)-1-(2-(methylsulfonyl)ethyl)pyrrolidinium methanesulfonate, 3-(6-(4-(3-(5-tert-butylisoxazol-3-yl)ureido)phenylcarbamoyl)pyridin-3-yloxy)-1-(2-(dimethylamino)-2-oxoethyl)pyrrolidinium methanesulfonate, 4-(6-(4-(3-(5-tert-butylisoxazol-3-yl)ureido)phenylcarbamoyl)pyridin-3-yloxy)-1-cyclopropylpiperidinium methanesulfonate, 1-tert-butyl-4-(6-(4-(3-(5-tert-butylisoxazol-3-yl)ureido)phenylcarbamoyl)pyridin-3-yloxy)piperidinium methanesulfonate, (3R)-3-(6-(4-(3-(5-tert-butylisoxazol-3-yl)ureido)phenylcarbamoyl)pyridin-3-yloxy)-1-isopropylpyrrolidinium methanesulfonate, 4-(6-(4-(3-(5-tert-butylisoxazol-3-yl)ureido)phenylcarbamoyl)pyridazin-3-yloxy)-1,2,2,6,6-pentamethylpiperidinium methanesulfonate, 4-(6-(4-(3-(5-tert-butylisoxazol-3-yl)ureido)-2-methylphenylcarbamoyl)pyridin-3-yloxy)-1,2,2,6,6-pentamethylpiperidinium methanesulfonate, 4-(6-(4-(3-(5-tert-butylisoxazol-3-yl)ureido)-3-methylphenylcarbamoyl)pyridin-3-yloxy)-1,2,2,6,6-pentamethylpiperidinium methanesulfonate, (3S)-3-(6-(4-(3-(5-tert-butylisoxazol-3-yl)ureido)phenylcarbamoyl)pyridin-3-yloxy)-1-isopropylpyrrolidinium methanesulfonate, (1R,5S)-3-(6-(4-(3-(5-tert-butylisoxazol-3-yl)ureido)phenylcarbamoyl)pyridin-3-yloxy)-8-methyl-8-azoniabicyclo[3.2.1]octane methanesulfonate, N-(4-(3-(5-(tert-butyl)isoxazol-3-yl)ureido)phenyl)-5-((1-isopropyl-2,2,6,6-tetramethylpiperidin-4-yl)oxy)picolinamide, (5S)-5-((6-(4-(3-(5-tert-butylisoxazol-3-yl)ureido)phenylcarbamoyl)pyridin-3-yloxy)methyl)-1,2,2-trimethylpyrrolidinium methanesulfonate, 4-(6-(4-(3-(5-tert-butylisoxazol-3-yl)ureido)phenylcarbamoyl)pyridin-3-yloxy)-1-ethyl-2,2,6,6-tetramethylpiperidinium methanesulfonate, 4-(6-(4-(3-(3-tert-butylisoxazol-5-yl)ureido)phenylcarbamoyl)pyridin-3-yloxy)-1,2,2,6,6-pentamethylpiperidinium methanesulfonate, 4-(6-(4-(3-(3-tert-butylisoxazol-5-yl)ureido)phenylcarbamoyl)pyridin-3-yloxy)-1-isopropylpiperidinium methanesulfonate, (3R)-3-((6-(4-(3-(5-tert-butylisoxazol-3-yl)ureido)phenylcarbamoyl)pyridin-3-yloxy)methyl)-1-isopropylpyrrolidinium methanesulfonate, 4-(6-(4-(3-(3-tert-butylisoxazol-5-yl)ureido)phenylcarbamoyl)pyridin-3-yloxy)-1-ethyl-2,2,6,6-tetramethylpiperidinium methanesulfonate, 4-(6-(4-(3-(3-tert-butylisoxazol-5-yl)ureido)phenylcarbamoyl)pyridin-3-yloxy)-1-ethylpiperidinium methanesulfonate, (3R)-3-((6-(4-(3-(5-tert-butylisoxazol-3-yl)ureido)phenylcarbamoyl)pyridin-3-yloxy)methyl)-1-ethylpyrrolidinium methanesulfonate, 3-(6-(4-(3-(5-tert-butylisoxazol-3-yl)ureido)phenylcarbamoyl)pyridin-3-yl)-1,2,2,6,6-pentamethyl-4-oxopiperidinium methanesulfonate, 4-(6-(4-(3-(5-tert-butylisoxazol-3-yl)ureido)phenylcarbamoyl)pyridin-3-yloxy)-1,2,2,4,6,6-hexamethylpiperidinium methanesulfonate, 3-(6-(4-(3-(5-tert-butylisoxazol-3-yl)ureido)phenylcarbamoyl)pyridin-3-yloxy)-1-azoniabicyclo[2.2.2]octane methanesulfonate, (1S,9aS)-1-((6-(4-(3-(5-tert-butylisoxazol-3-yl)ureido)phenylcarbamoyl)pyridin-3-yloxy)methyl)decahydroquinolizinium methanesulfonate, N-(4-(3-(3-tert-butyl-1-methyl-1H-pyrazol-5-yl)ureido)phenyl)-5-(1,2,2,6,6-pentamethylpiperidin-4-yloxy)picolinamide, 4-(6-(4-(3-(5-tert-butylisoxazol-3-yl)ureido)phenylcarbamoyl)pyridin-3-yloxy)-2,2,6,6-tetramethylpiperidinium methanesulfonate, N-(4-(3-(5-(tert-butyl)isoxazol-3-yl)ureido)phenyl)-6-(2-morpholinoethoxy)picolinamide, and N-(4-(3-(5-(tert-butyl)isoxazol-3-yl)ureido)phenyl)-6-(piperidin-4-yloxy)picolinamide.

10. A pharmaceutical composition comprising a compound of claim 1 and a pharmaceutically acceptable carrier.

11. A method for treatment of a disease selected from an inflammatory disease, an inflammatory condition, an autoimmune disease and cancer comprising administering a therapeutically effective amount of a compound of claim 1.

12. The method of claim 11, wherein the disease is modulated by CSF-1R kinase.

13. The method of claim 12, wherein the disease is modulated by wild type or mutant CSF-1R kinase.

14. A method for the treatment of a disease comprising administering a therapeutically effective amount of a compound of claim 1, wherein the disease is selected from myeloproliferative disorder (MPD), myelodysplastic syndrome (MDS), polycythemia vera (PCV), essential thrombocythemia (ET), primary myelofibrosis (PMF), chronic eosinophilic leukemia (CEL), chronic myelomonocytic leukemia (CMML), systemic mastocytosis (SM), idiopathic myelofibrosis (IMF), myeloid leukemia, chronic myeloid leukemia (CML), imatinib-resistant CML, acute myeloid leukemia (AML), acute megakaryoblastic leukemia (AMKL), lymphoma, lymphoblastic leukemia, myeloma, cancer of the head and neck, prostate cancer, breast cancer, ovarian cancer, endometrial cancer, melanoma, lung cancer, brain cancer, thyroid cancer, stomach cancer, gastrointestinal stromal tumor, colorectal cancer, pancreatic cancer, renal cancer, non-small cell lung cancer, idiopathic hypereosinophilic syndrome, chronic eosinophilic syndrome, systemic mastocytosis, Langerhans cell histiocytosis, Kaposi's sarcoma, multiple endocrine neoplasia, immunodeficiency, autoimmune diseases, tissue transplant rejection, graft-versus-host disease, wound, kidney disease, multiple sclerosis, thyroiditis, type 1 diabetes, sarcoidosis, psoriasis, allergic rhinitis, inflammatory bowel disease including Crohn's disease and ulcerative colitis (UC), systemic lupus erythematosis (SLE), arthritis, osteoarthritis, rheumatoid arthritis, osteoporosis, asthma and chronic obstructive pulmonary disease (COPD).

15. The method of claim 14 further comprising administering a second pharmaceutical agent selected from anti-proliferative agent, anti-inflammatory agent, immunomodulatory agent and immunosuppressive agent.

16. A method of modulating CSF-1R kinase by administering a compound of claim 1.

* * * * *